United States Patent
Low et al.

(10) Patent No.: US 12,397,059 B2
(45) Date of Patent: Aug. 26, 2025

(54) COMPOUNDS AND METHODS FOR THE TREATMENT AND PREVENTION OF FIBROTIC DISEASE STATES AND CANCER

(71) Applicant: Purdue Research Foundation, West Lafayette, IN (US)

(72) Inventors: Philip Stewart Low, West Lafayette, IN (US); Fenghua Zhang, West Lafayette, IN (US); John Victor Napoleon, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 757 days.

(21) Appl. No.: 17/625,461

(22) PCT Filed: Jul. 8, 2020

(86) PCT No.: PCT/US2020/041120
§ 371 (c)(1),
(2) Date: Jan. 7, 2022

(87) PCT Pub. No.: WO2021/007277
PCT Pub. Date: Jan. 14, 2021

(65) Prior Publication Data
US 2022/0331434 A1    Oct. 20, 2022

Related U.S. Application Data

(60) Provisional application No. 62/872,146, filed on Jul. 9, 2019, provisional application No. 62/871,686, filed on Jul. 8, 2019.

(51) Int. Cl.
| | |
|---|---|
| *A61K 47/55* | (2017.01) |
| *A61K 45/06* | (2006.01) |
| *A61K 47/54* | (2017.01) |
| *A61K 47/60* | (2017.01) |
| *A61P 11/00* | (2006.01) |

(52) U.S. Cl.
CPC .............. *A61K 47/55* (2017.08); *A61K 45/06* (2013.01); *A61K 47/545* (2017.08); *A61K 47/60* (2017.08); *A61P 11/00* (2018.01)

(58) Field of Classification Search
CPC .................................................... A61K 47/55
See application file for complete search history.

(56) References Cited

U.S. PATENT DOCUMENTS

| | | |
|---|---|---|
| 2006/0142202 A1 | 6/2006 | Alkan et al. |
| 2010/0093998 A1 | 4/2010 | Isobe et al. |
| 2015/0174268 A1 | 6/2015 | Li |

FOREIGN PATENT DOCUMENTS

| | | |
|---|---|---|
| WO | 2003028634 A2 | 4/2003 |
| WO | 2007093901 A1 | 8/2007 |
| WO | 2016085967 A1 | 6/2016 |
| WO | 2017205661 A1 | 11/2017 |

OTHER PUBLICATIONS

Pubchem, Compound Summary, PubChem CID: 56675929, Create Date: Mar. 6, 2012, US.
International Searching Authority, International Search Report, PCT Application No. PCT/US2020/041120, dated Dec. 2, 2020, US.
International Searching Authority, Written Opinion of the International Searching Authority, PCT Application No. PCT/US2020/041120, dated Dec. 2, 2020, US.
Jones et al., Discovery of a Highly Potent Series of TLR7 Agonists, Biorganic & Medical Chemistry Letters, 21: 5939-5943 (2011).
Zhang et al., Macrophages: Friend or For in Idiopathic Pulmonary Fibrosis? Respiratory Research, 19: 170 (2018).

*Primary Examiner* — Golam M Shameem
(74) *Attorney, Agent, or Firm* — Reichel Stohry Dean LLP; Natalie J. Dean

(57) ABSTRACT

Compounds, pharmaceutical compositions and methods are provided for reprogramming M2-like macrophages to M1-like macrophages, which reverses the antifibrotic to profibrotic shift observed during the course of fibrotic diseases and certain cancers. The compounds comprise an immune modulator that targets a pattern recognition receptor of a cell and are specific to the cells of interest through the incorporation of a targeting moiety (e.g., folate or a functional fragment or analog thereof). Releasable and/or non-releasable linkers can be included and engineered to facilitate the optimal delivery of the immune modulator. The compounds and compositions can be employed in one or more methods of treatment for fibrotic diseases and/or cancers.

14 Claims, 57 Drawing Sheets

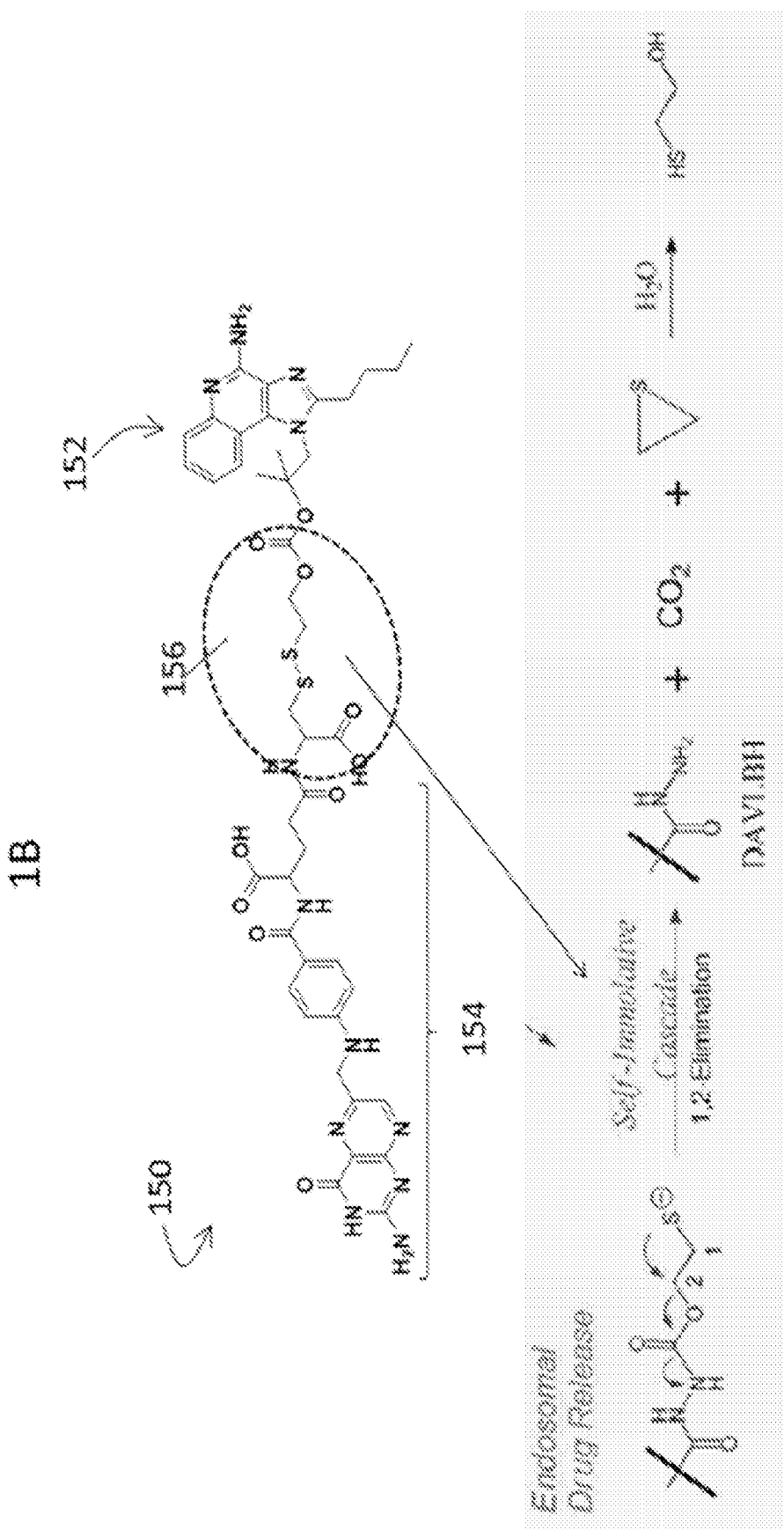
FIG. 1 con't

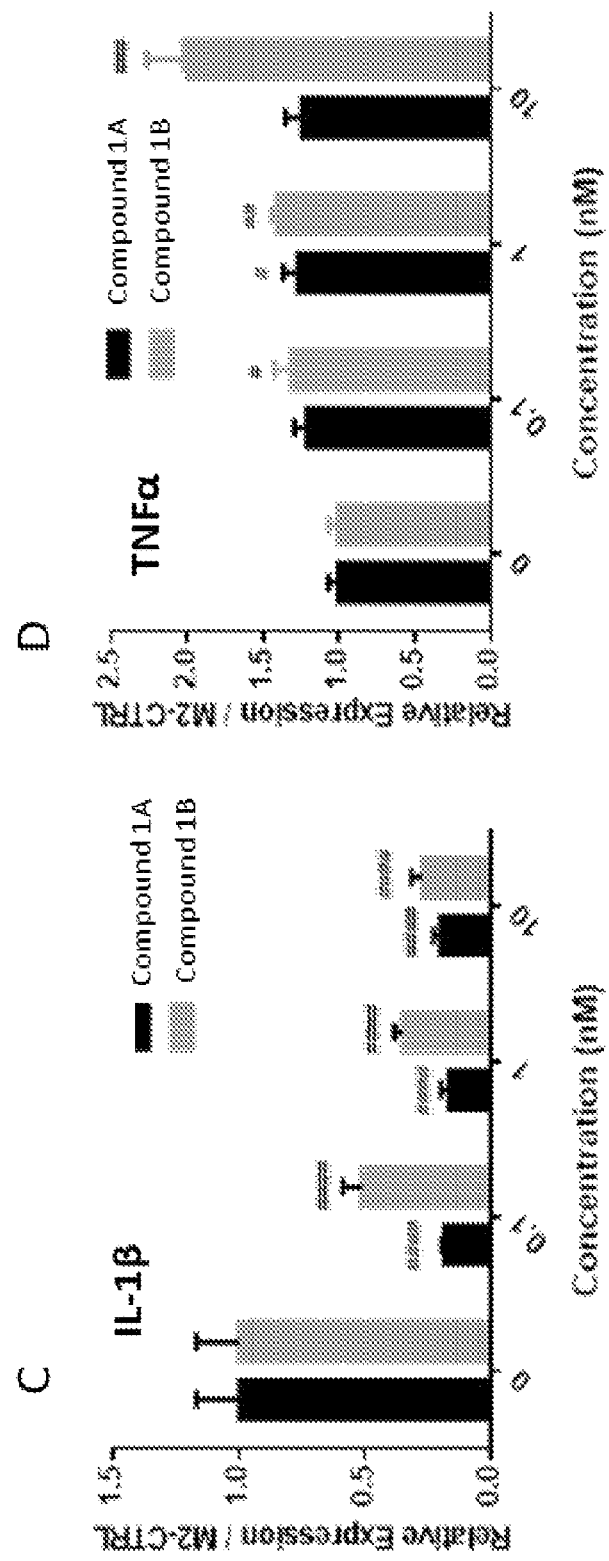
FIG. 3 con't

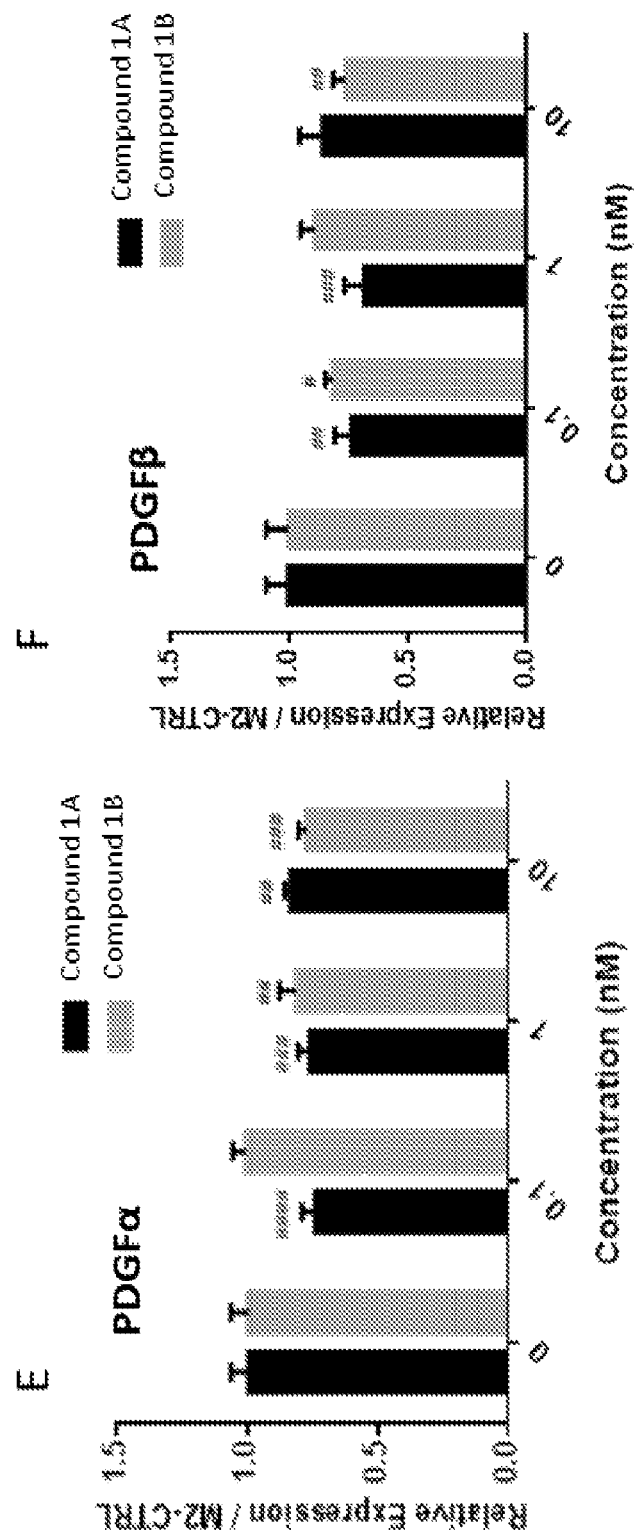
FIG. 3 con't

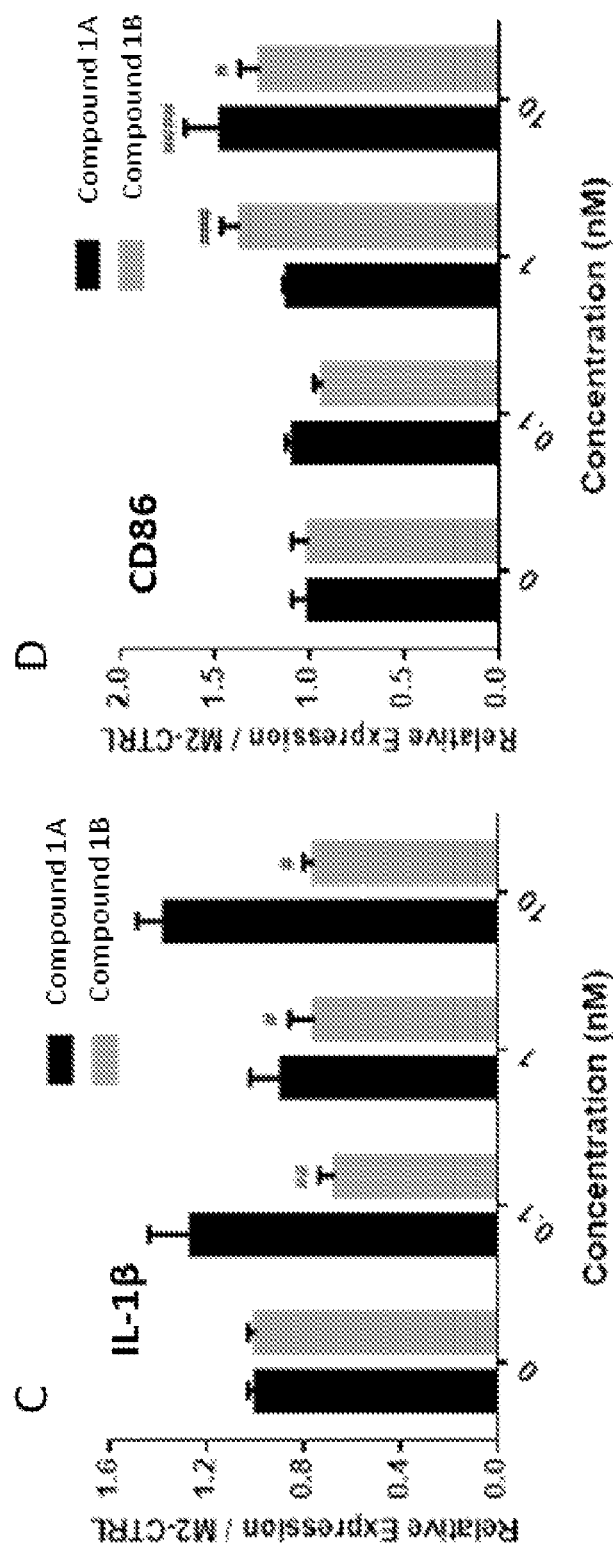
FIG. 4 con't

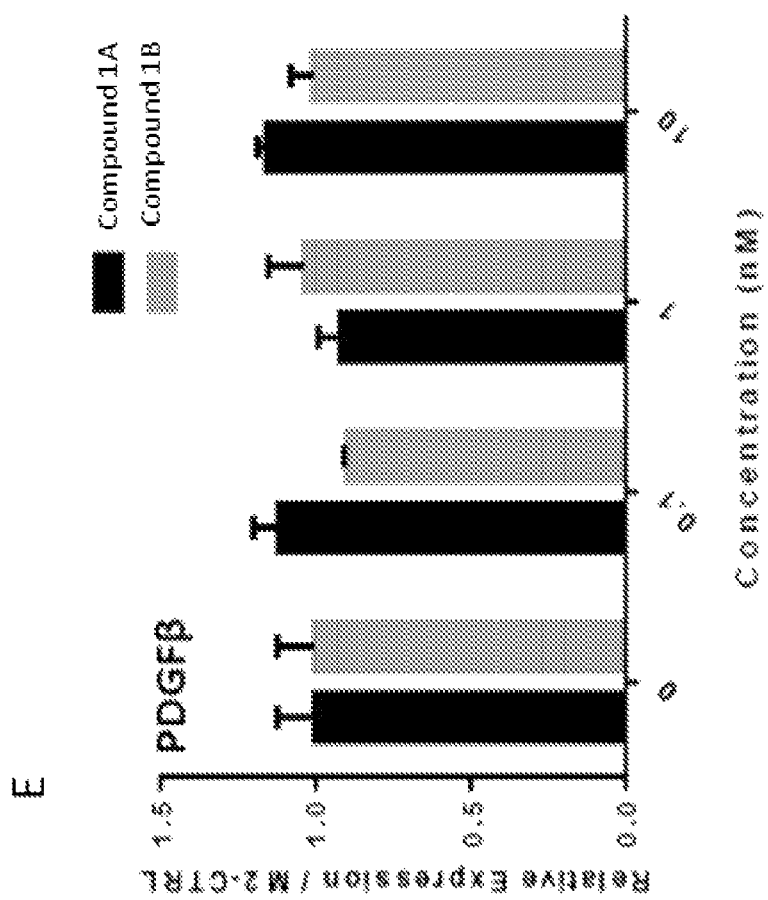
FIG. 4 con't

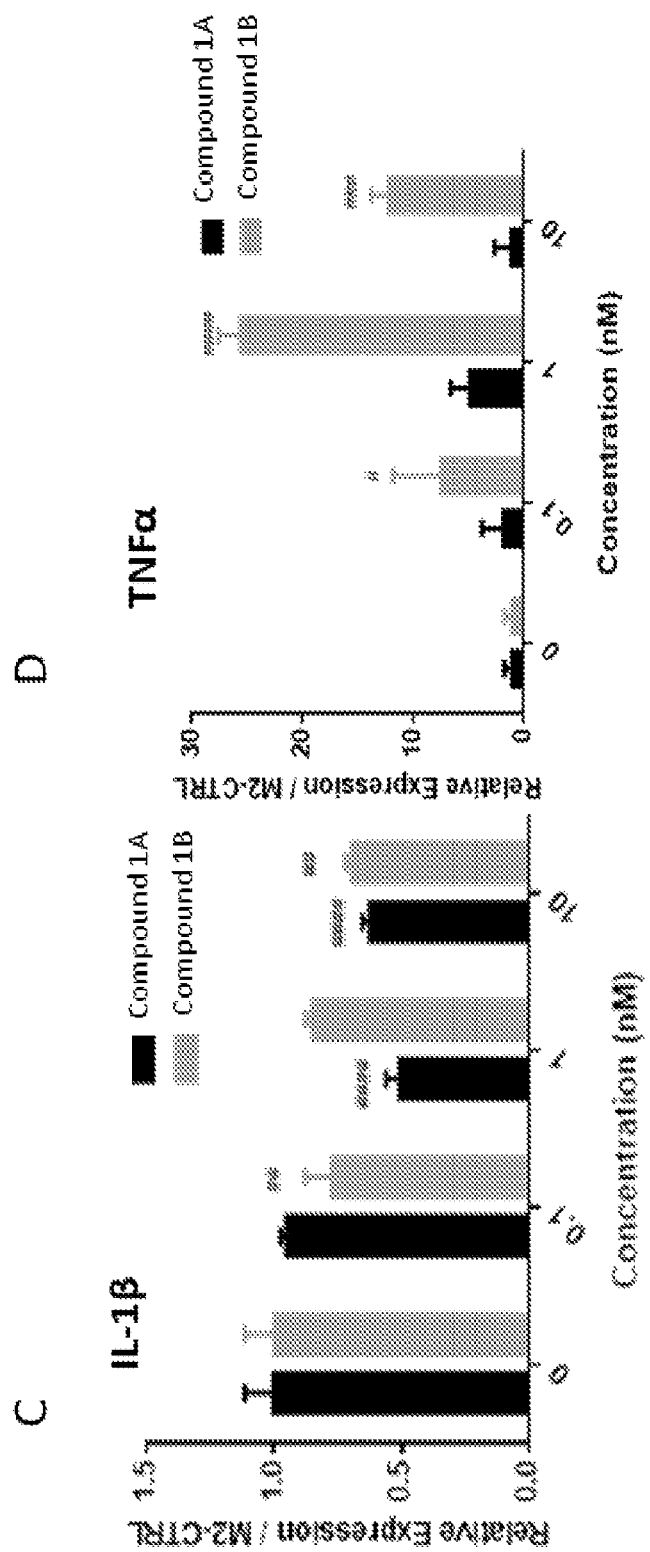
FIG. 5 con't

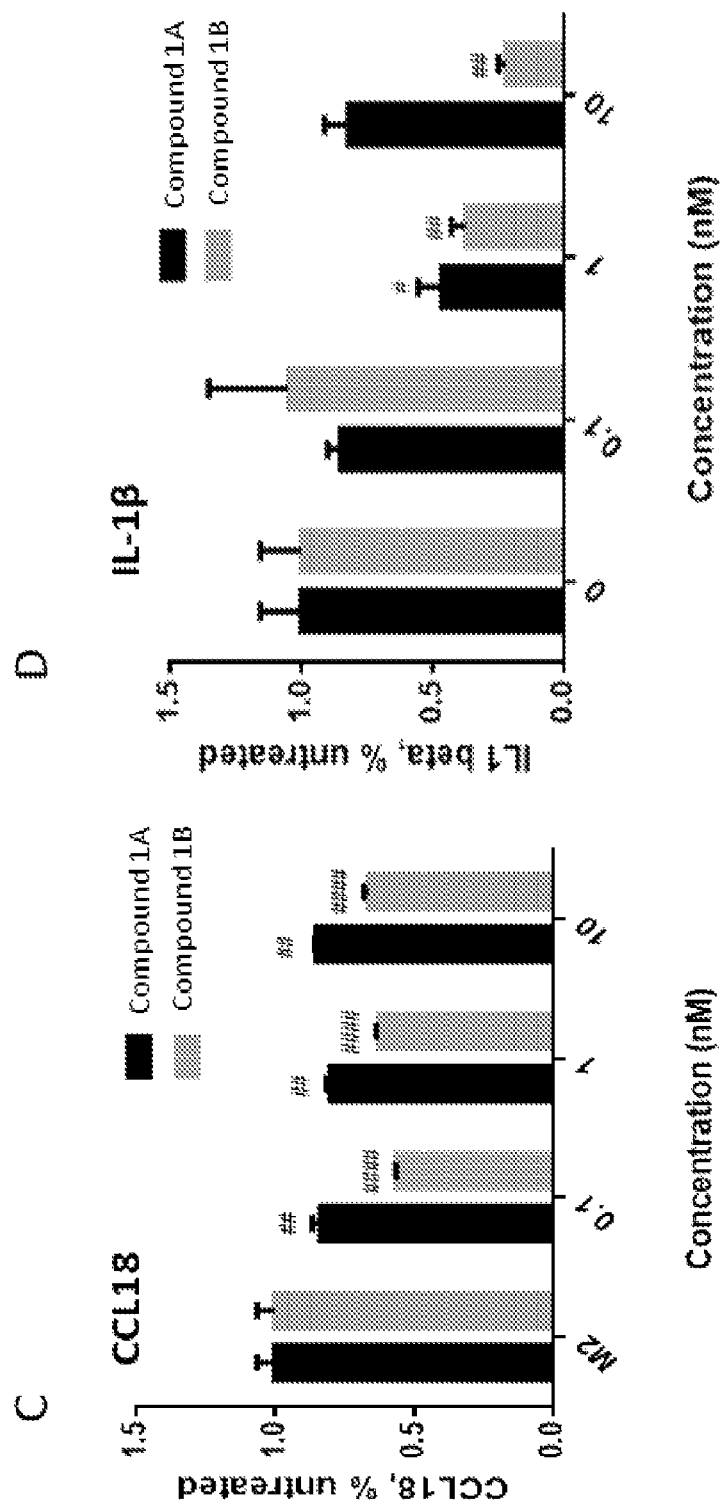
FIG. 6 con't

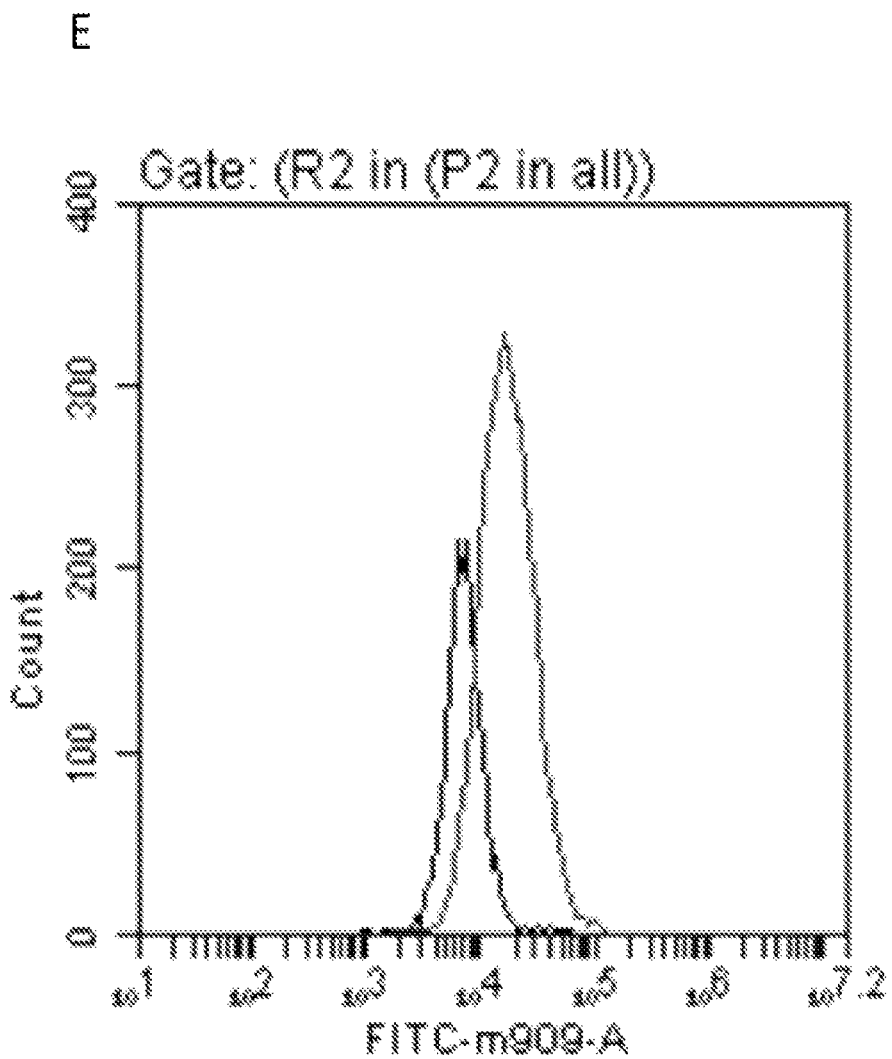
FIG. 6 con't

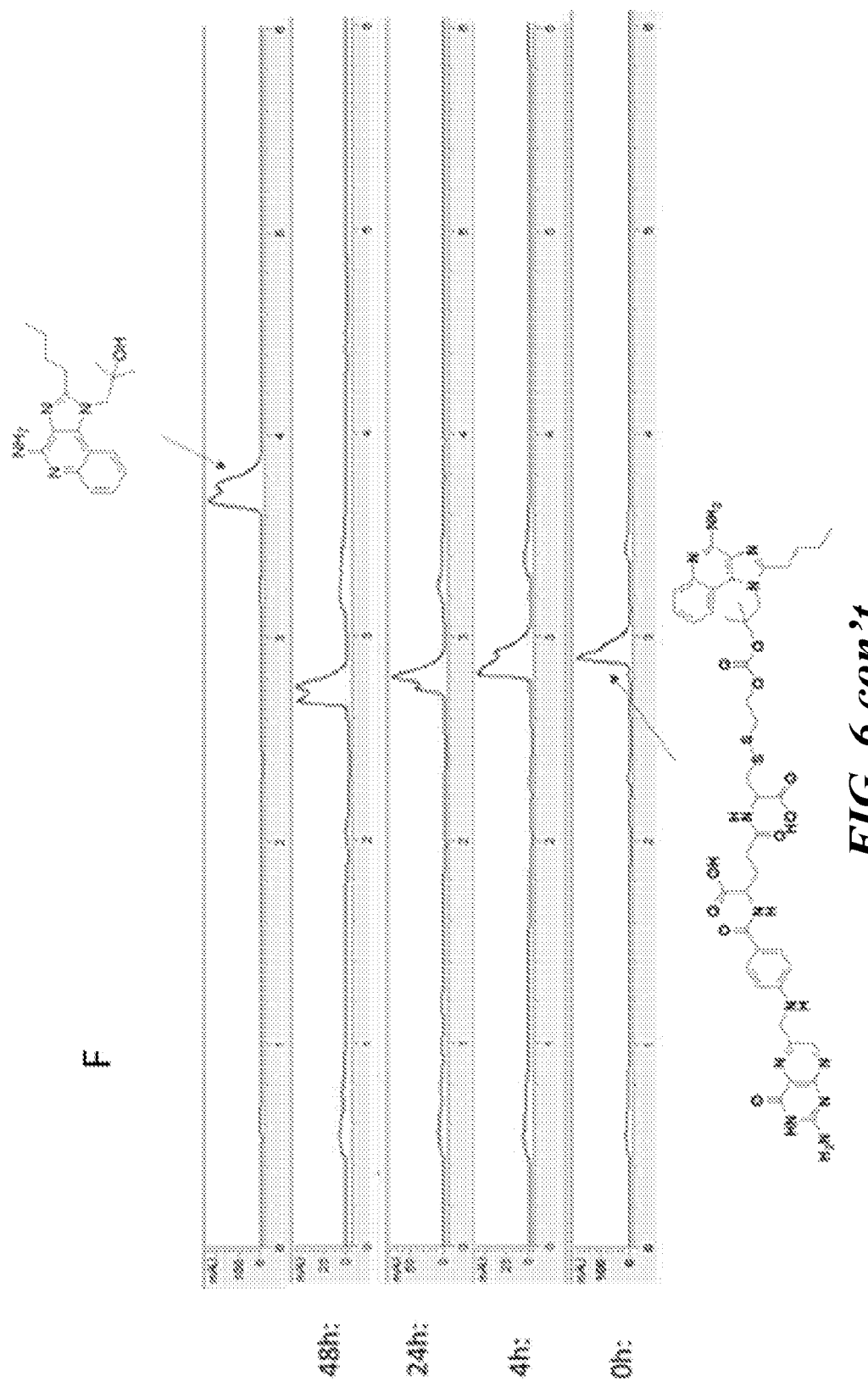
FIG. 6 con't

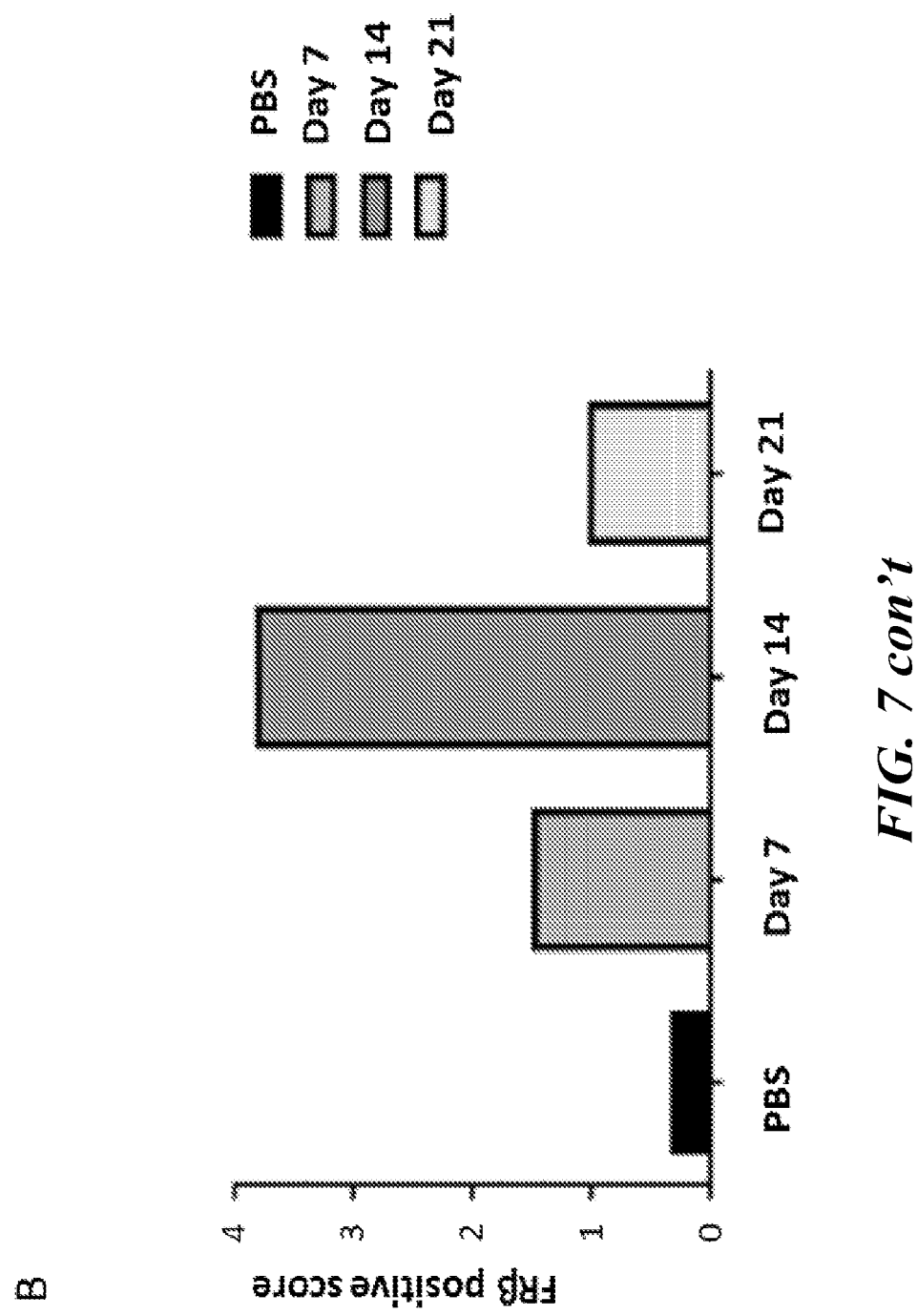
FIG. 7 con't

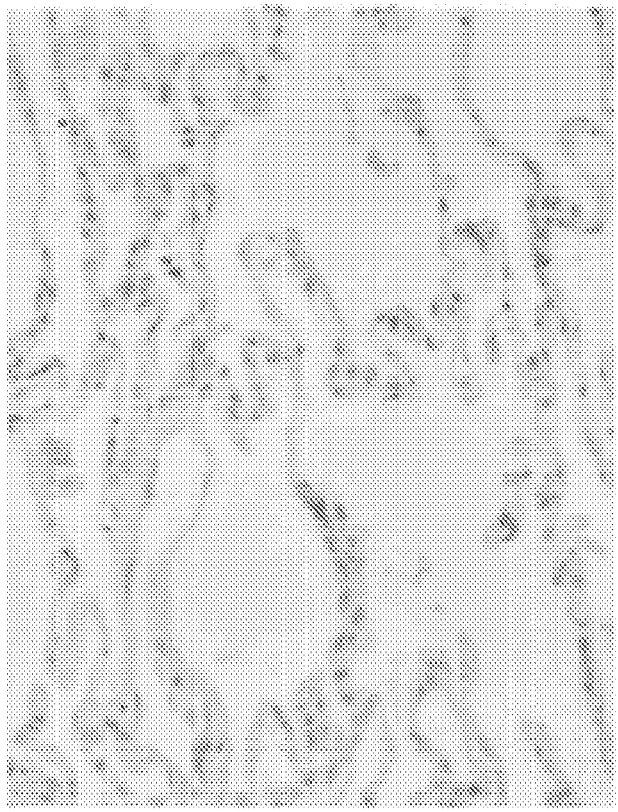
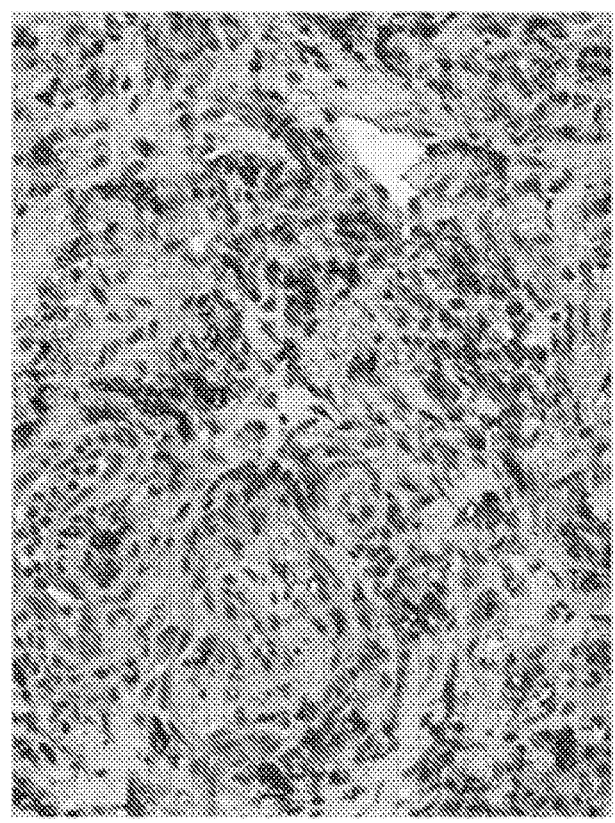
FIG. 7 con't

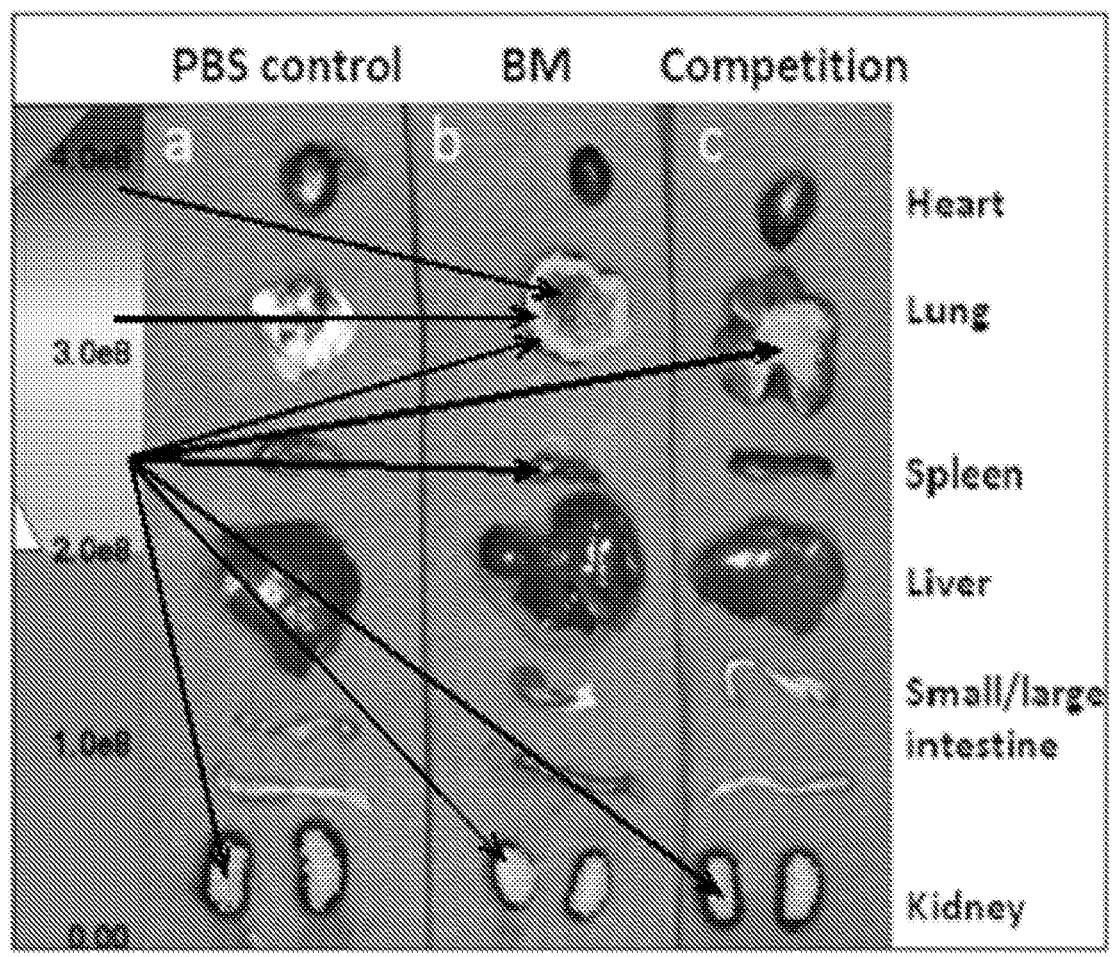
FIG. 7 con't

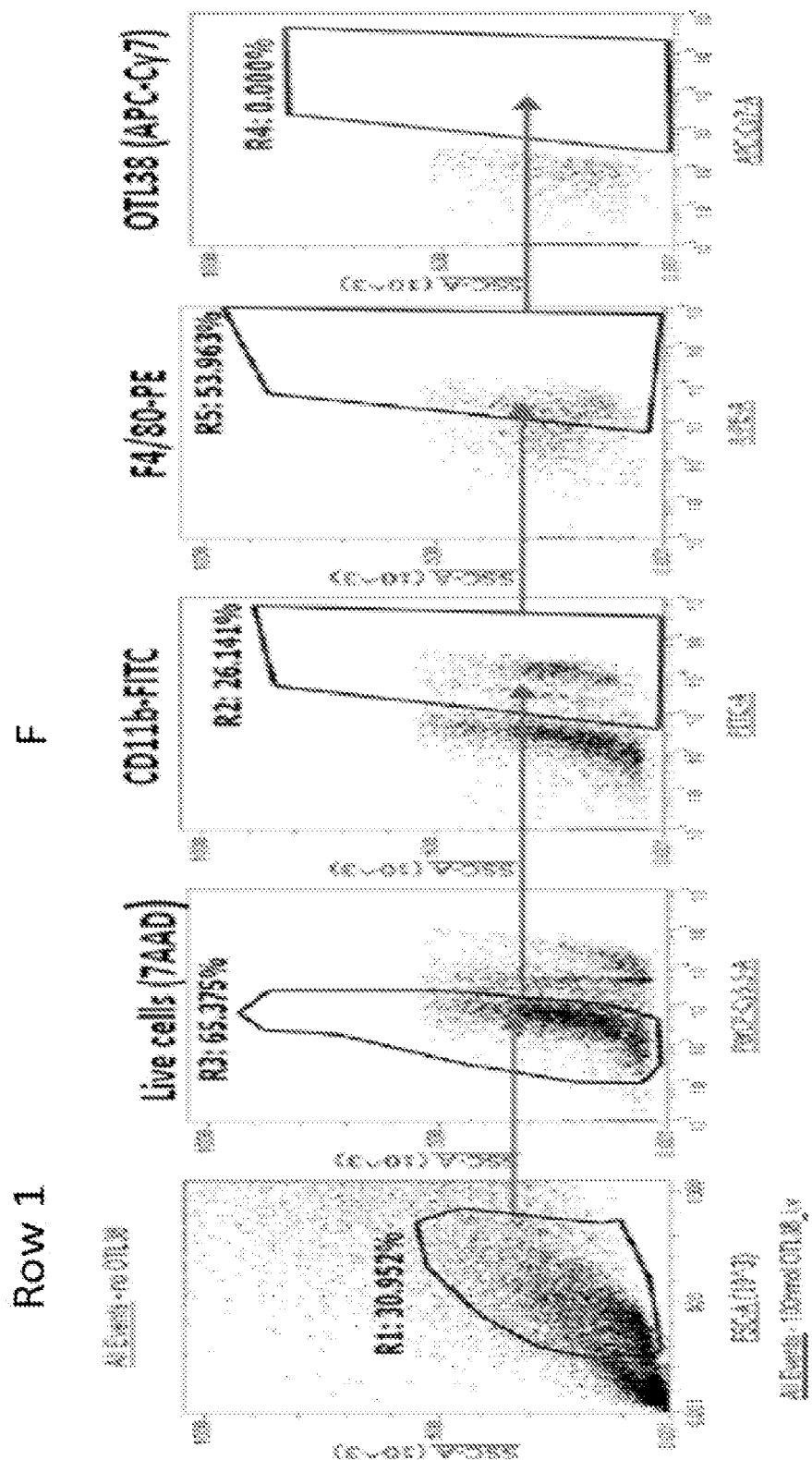
FIG. 7 con't

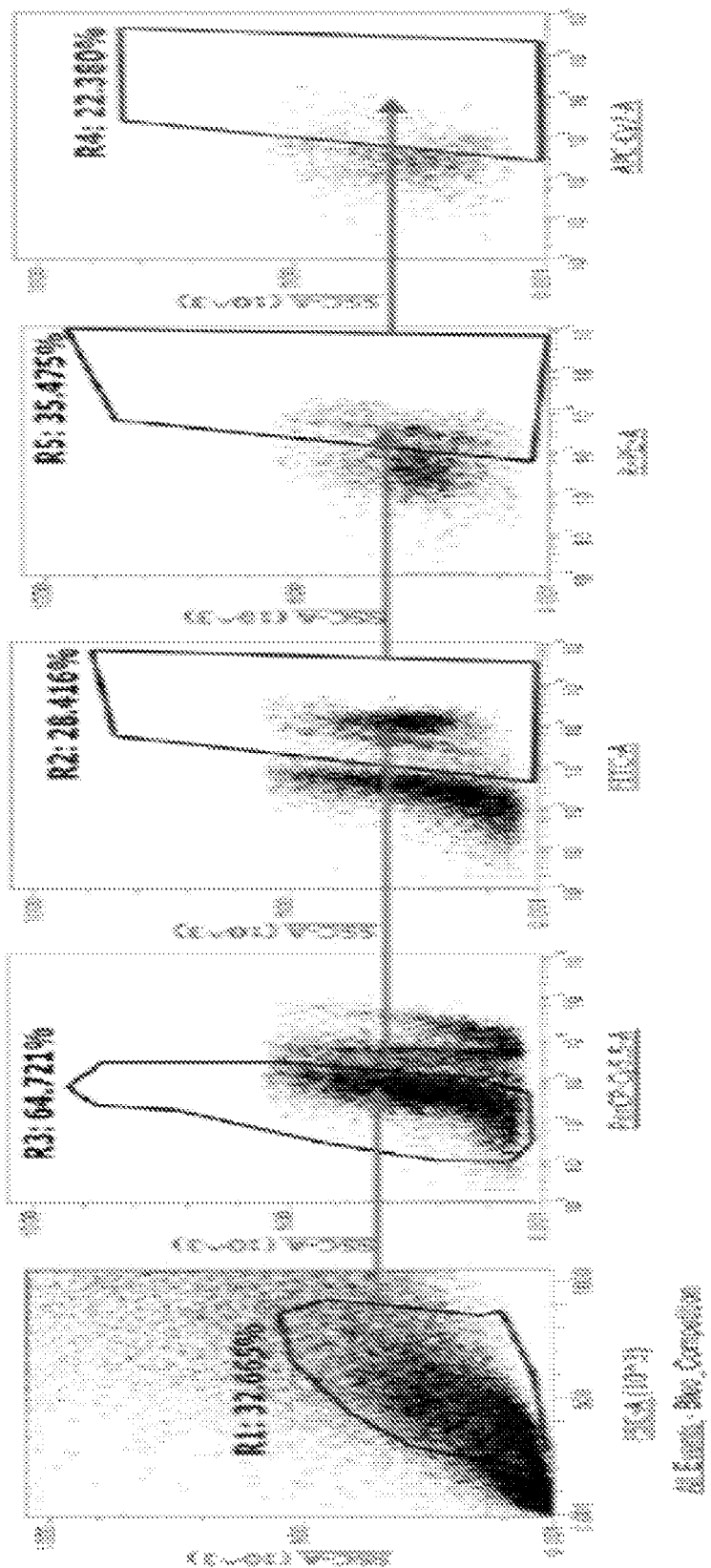
FIG. 7 con't

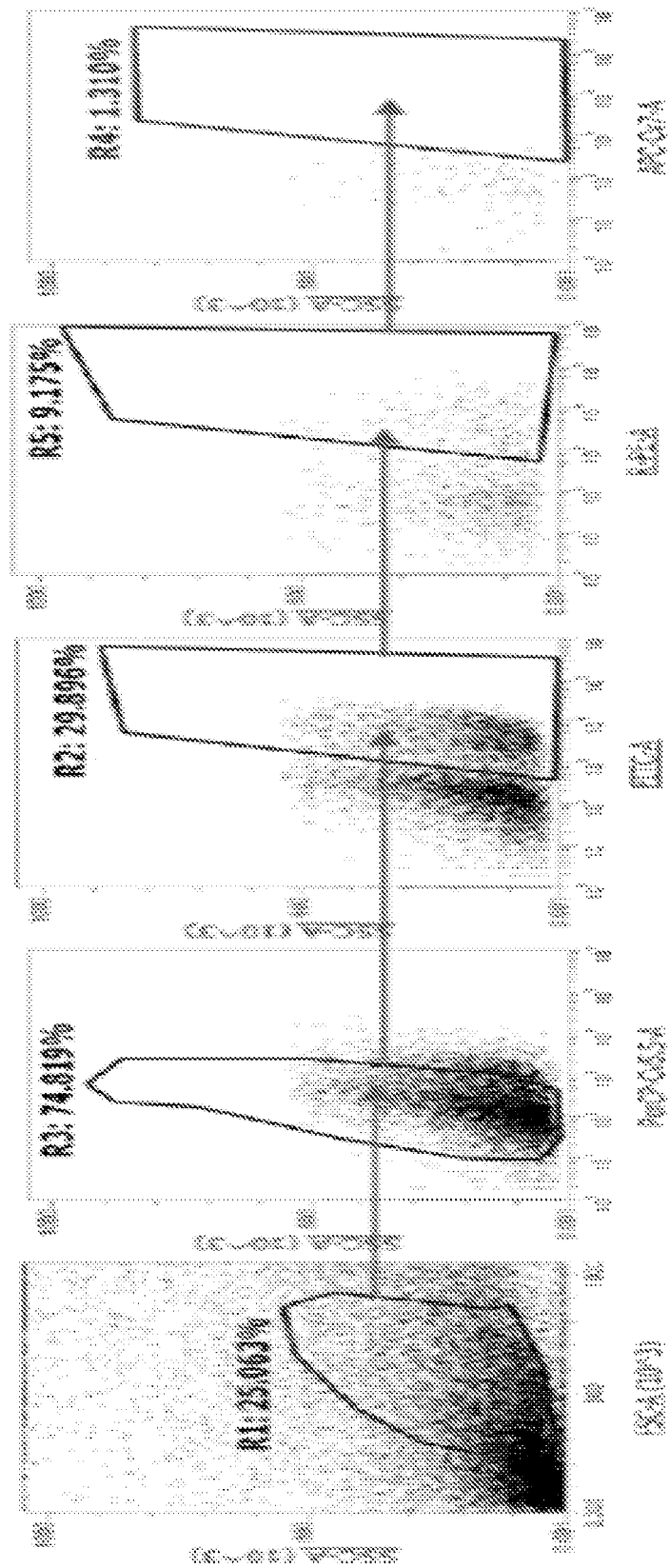
FIG. 7 con't

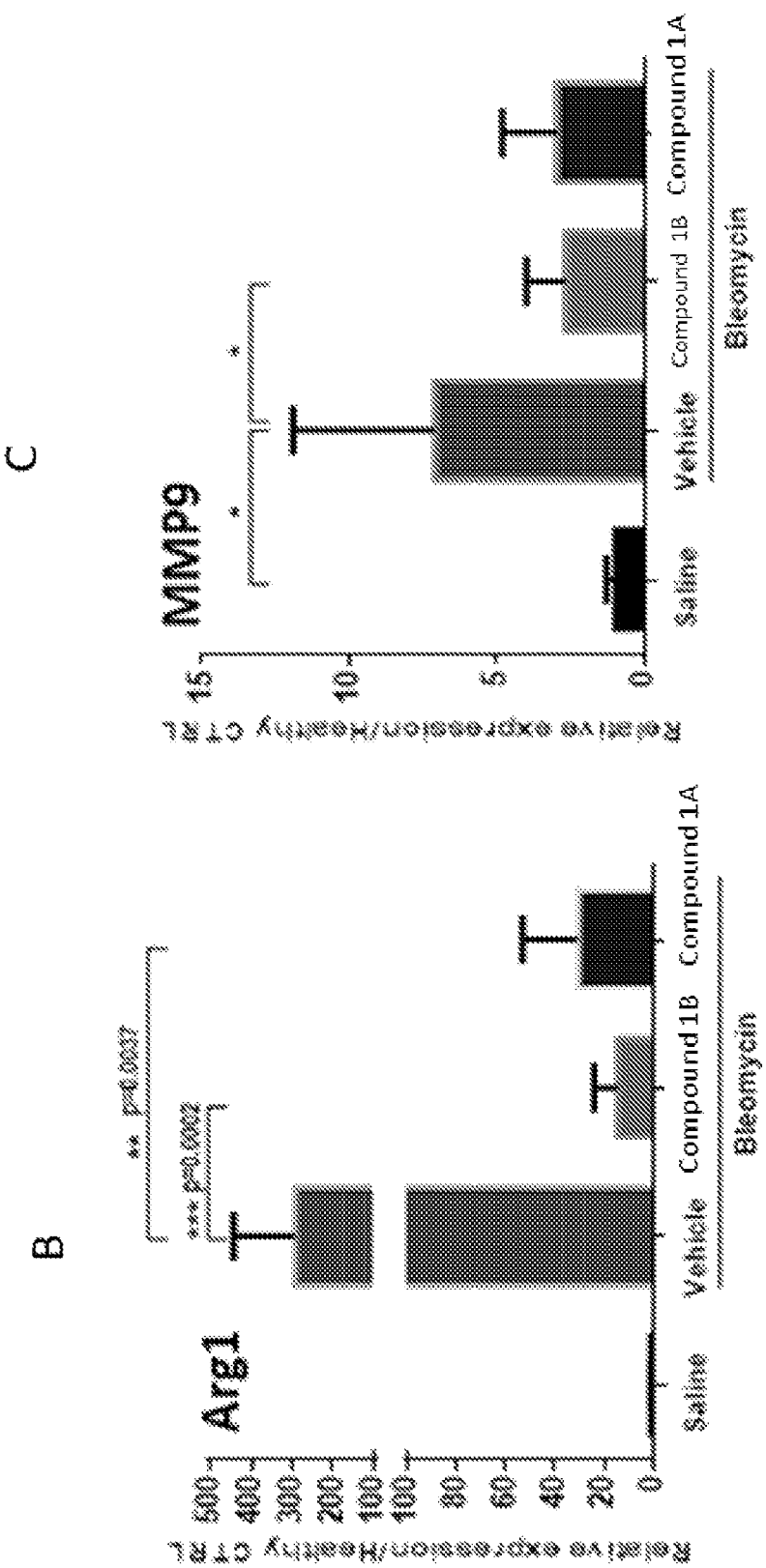
FIG. 8 con't

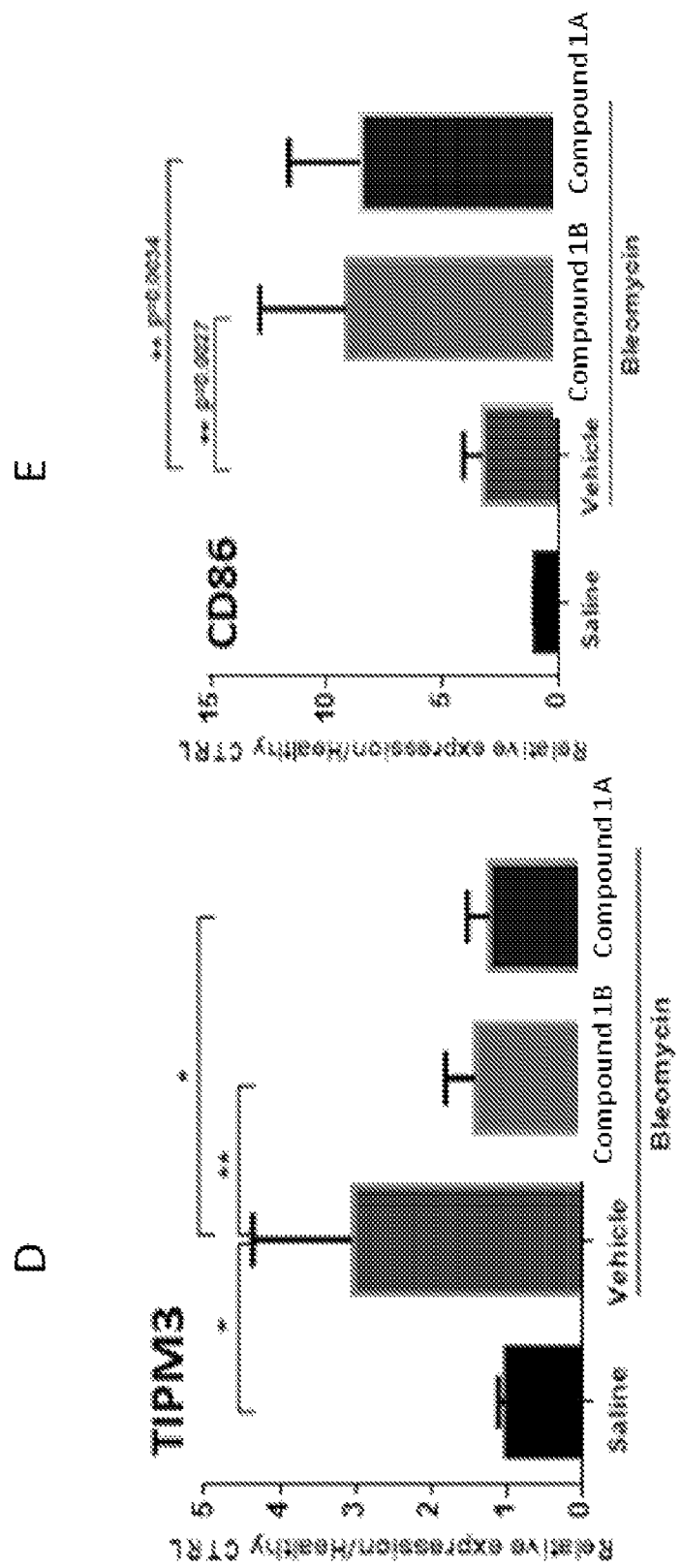
FIG. 8 con't

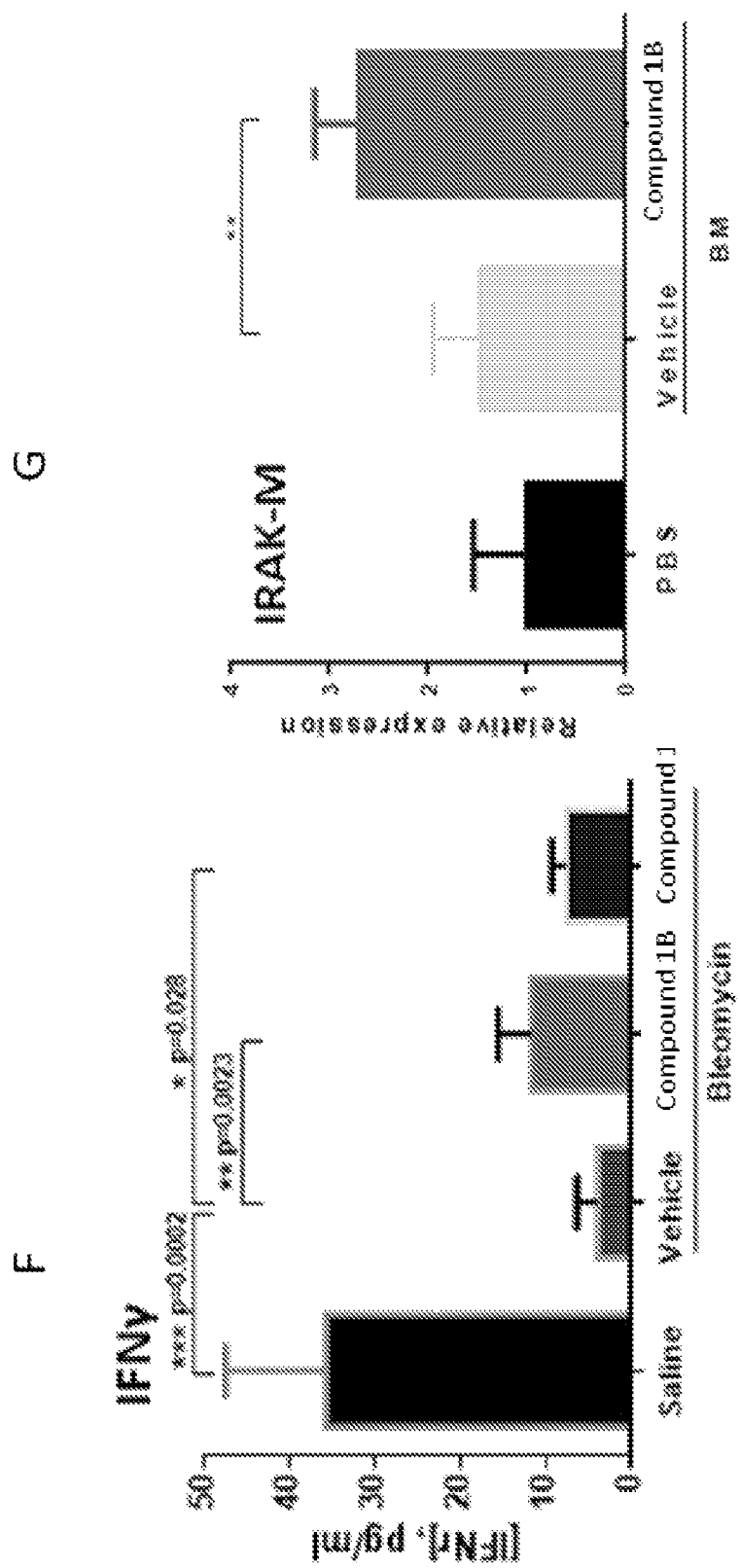
FIG. 8 con't

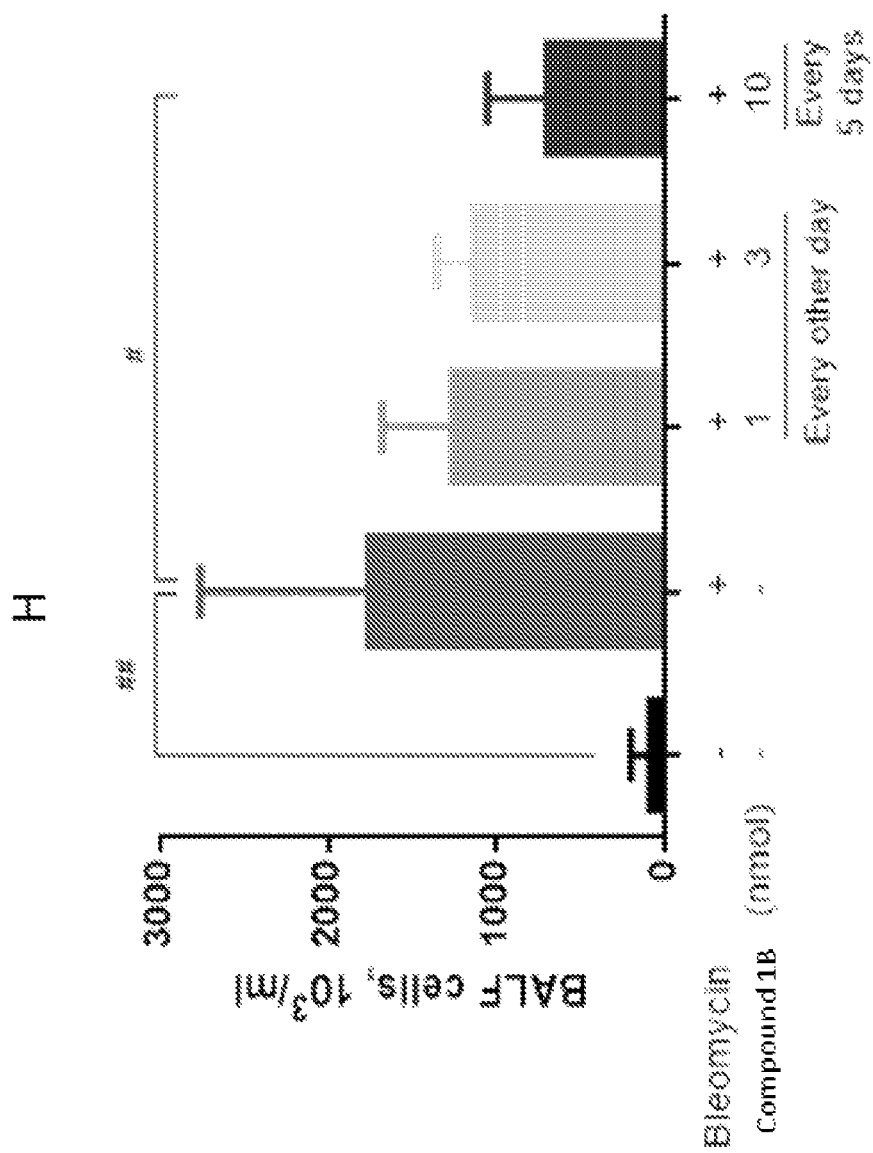
FIG. 8 con't

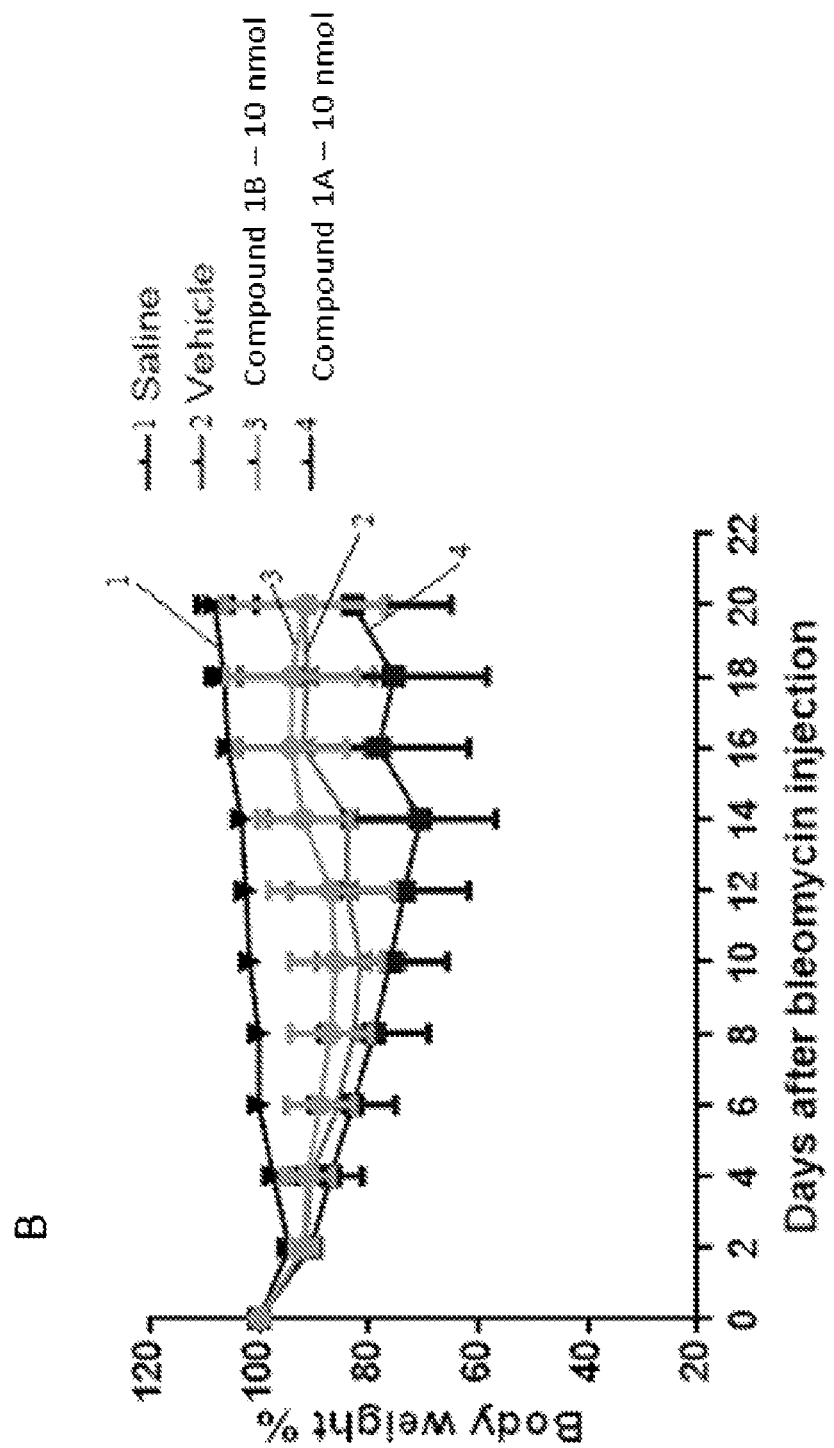
FIG. 9 con't

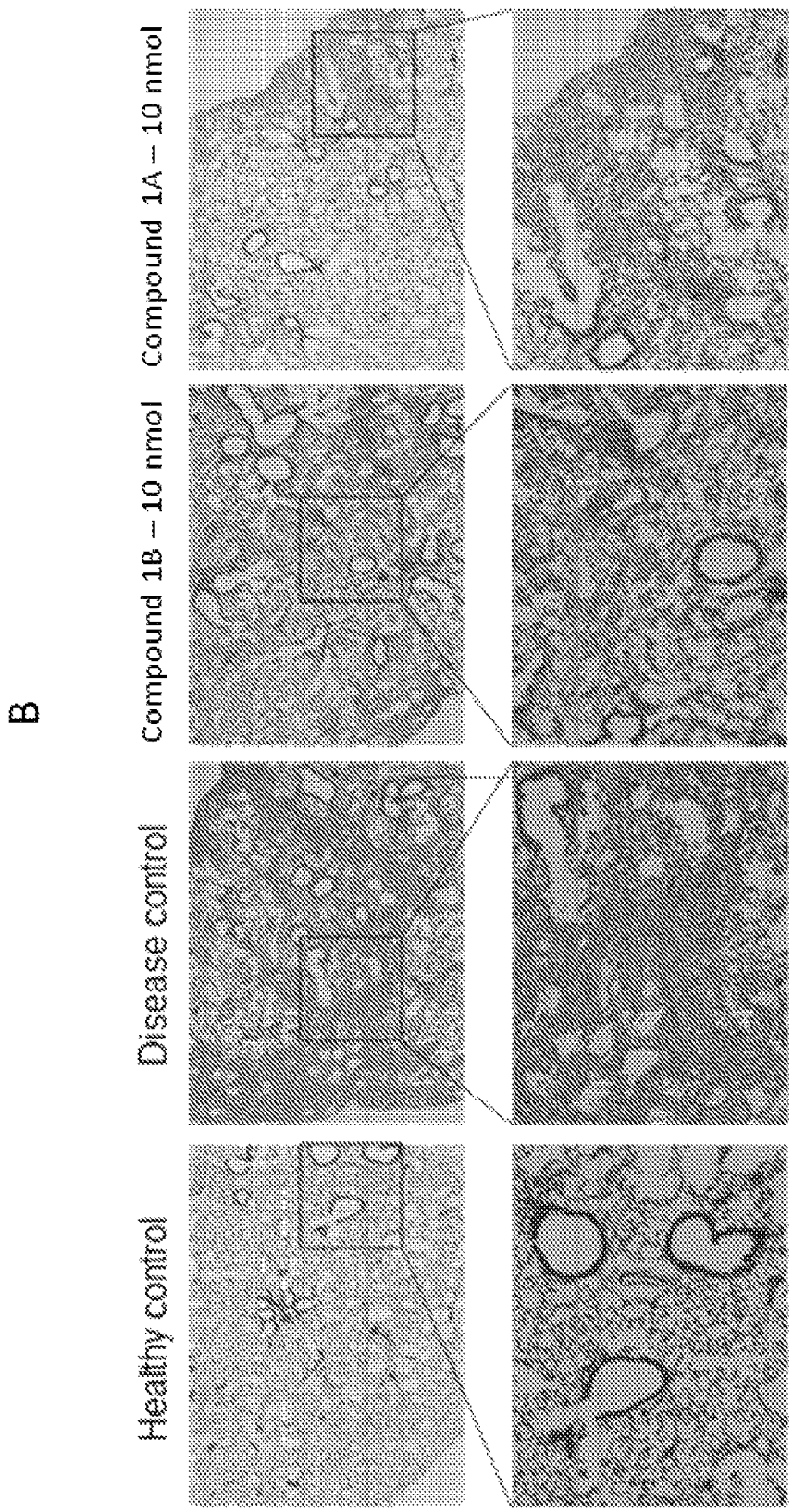
FIG. 10 con't

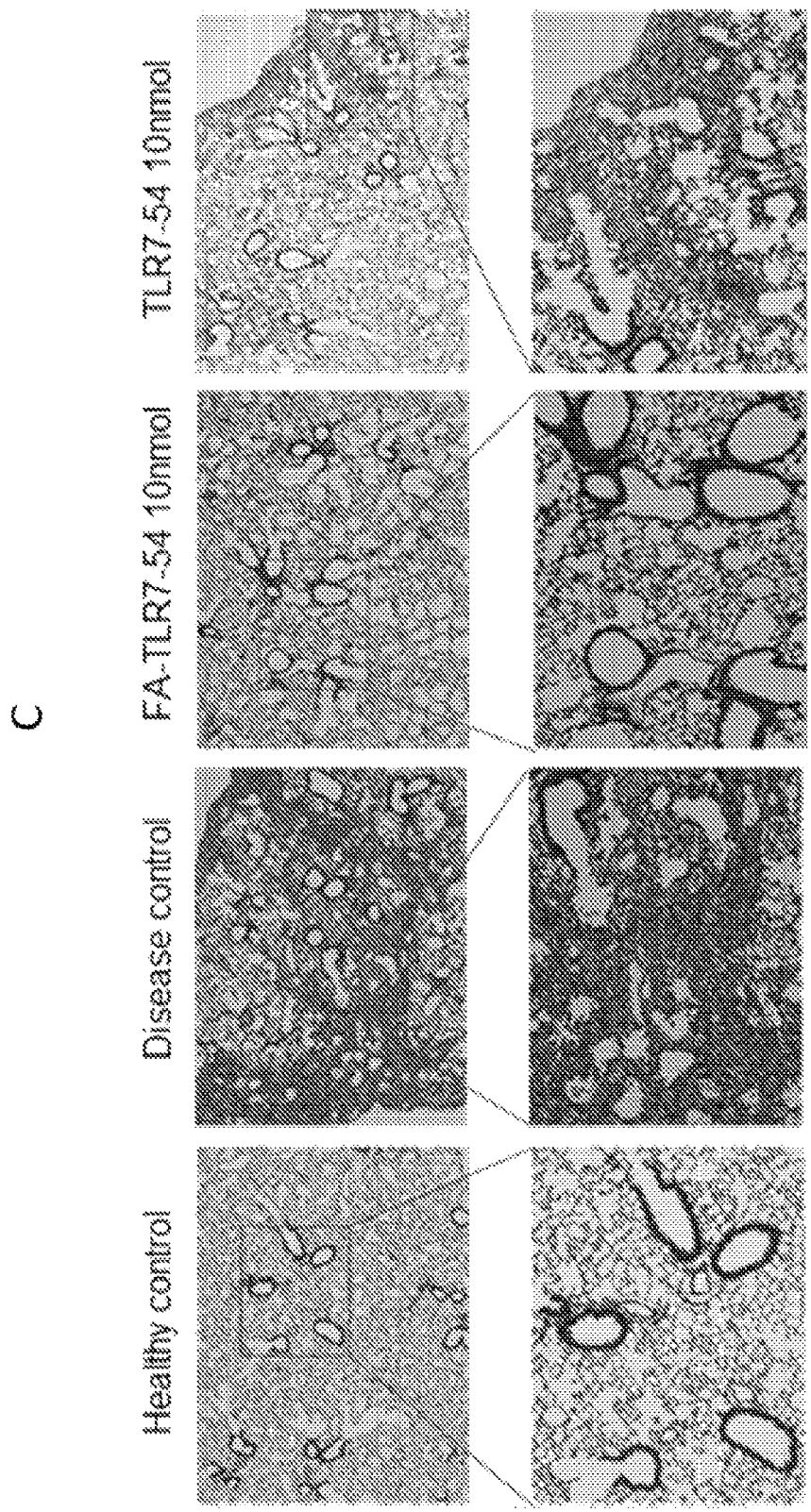
FIG. 10 con't

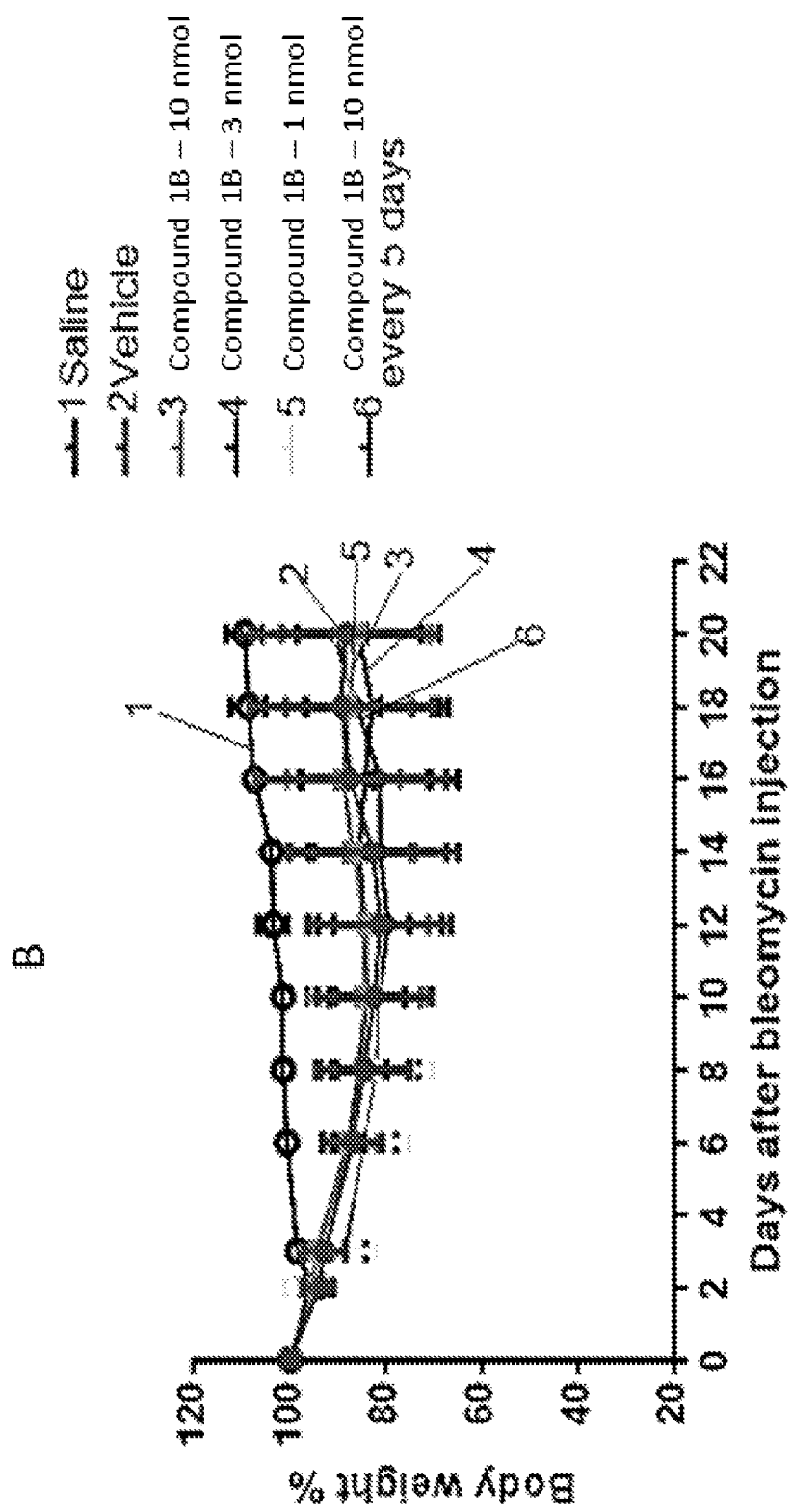
FIG. 11 con't

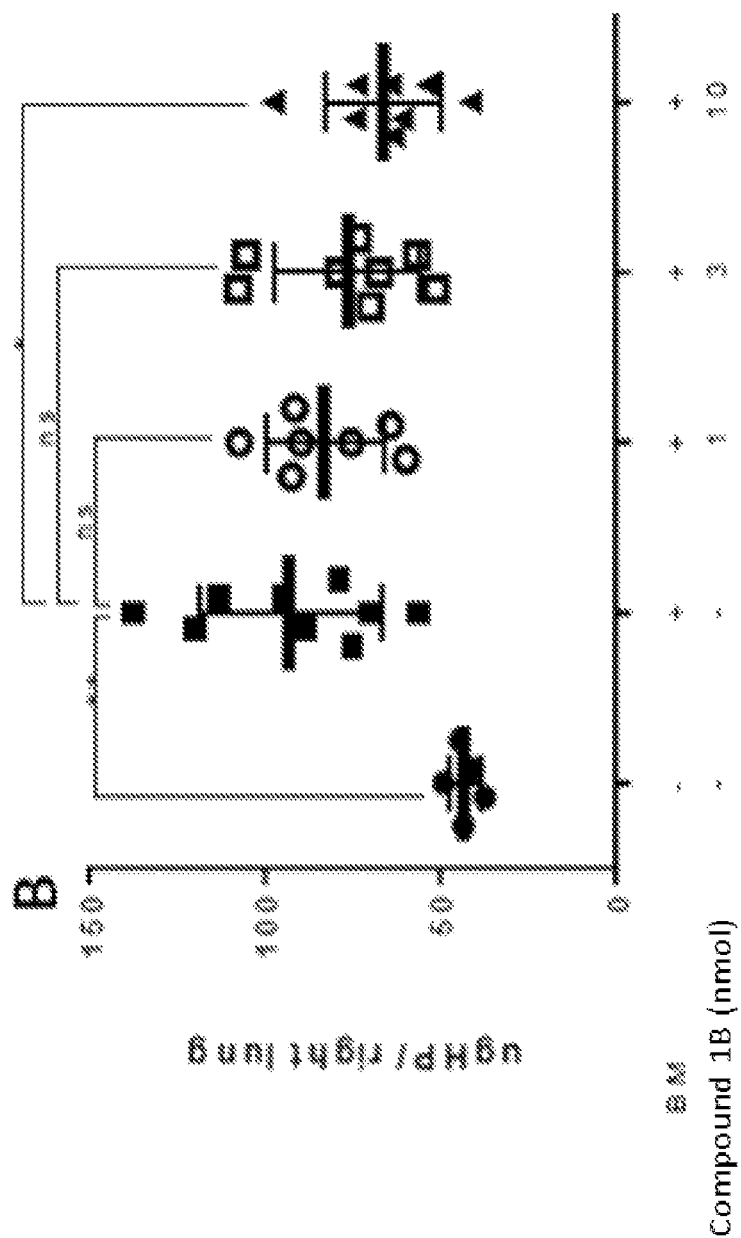
FIG. 12 con't

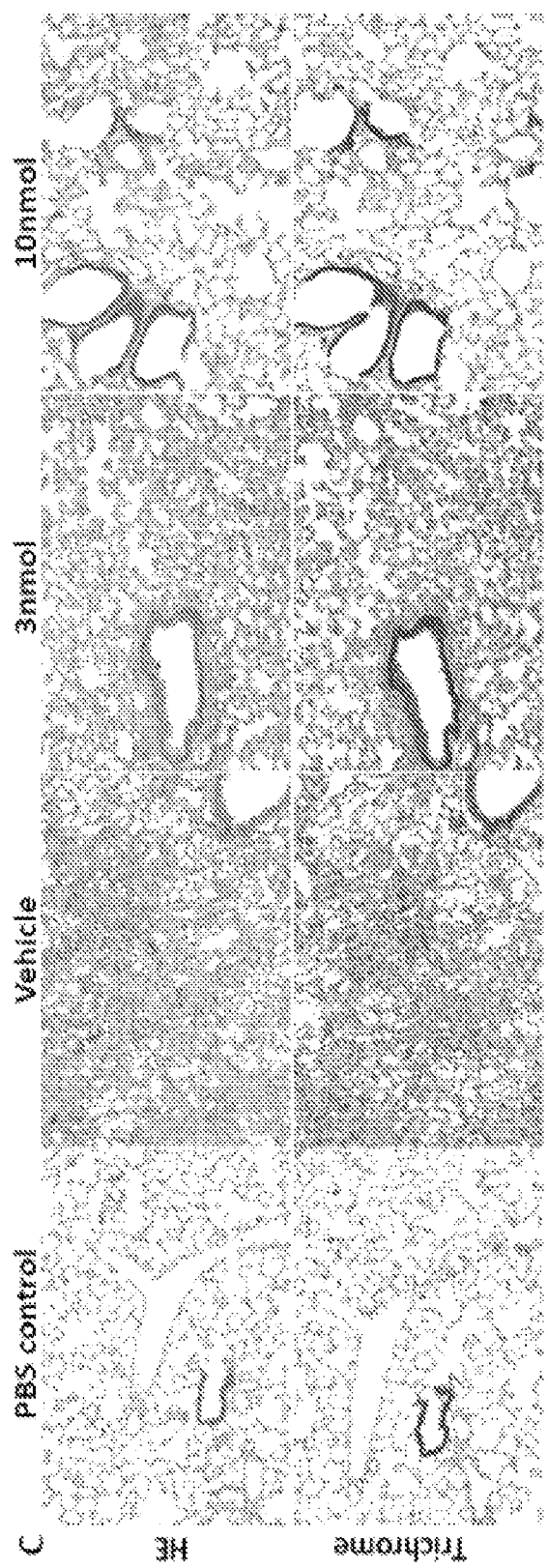
FIG. 12 con't

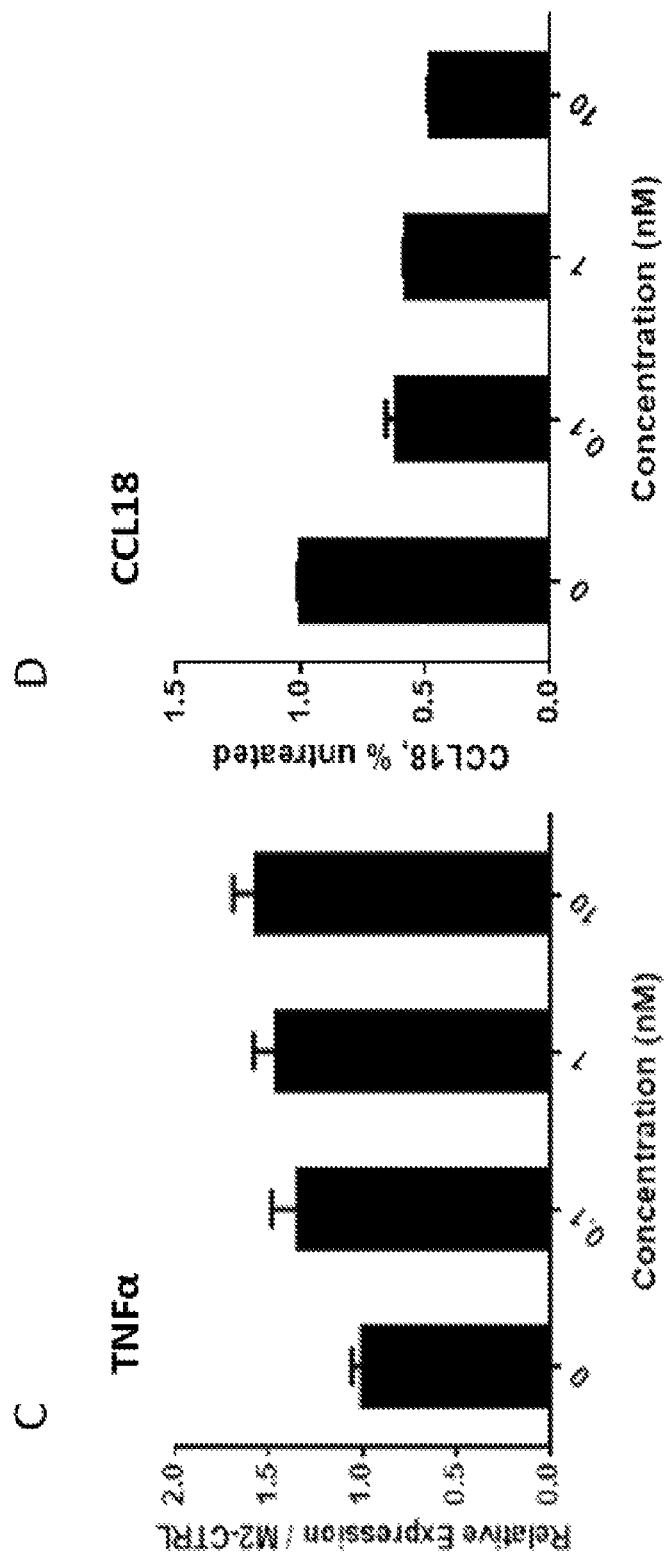
FIG. 13 con't

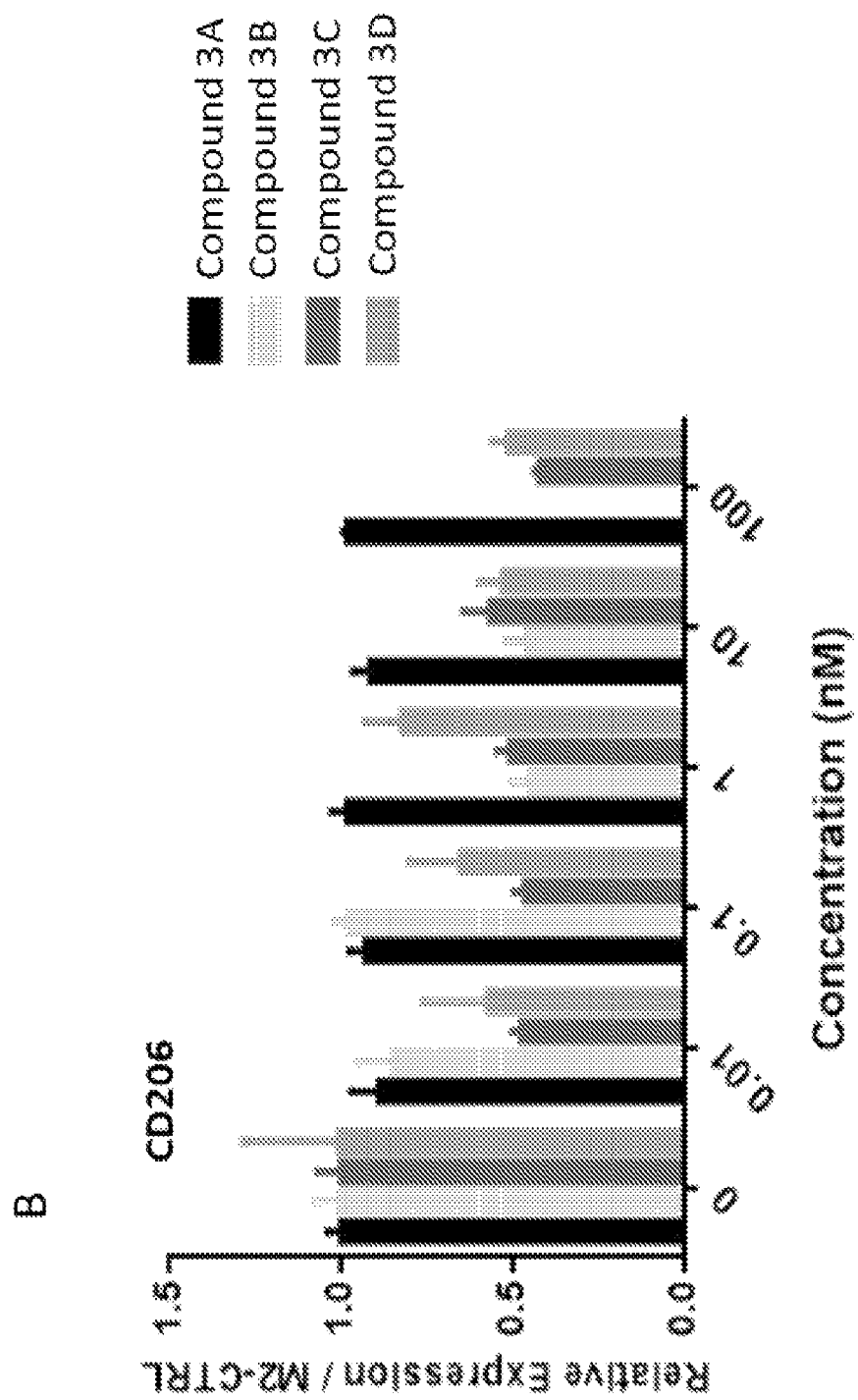
FIG. 14 con't

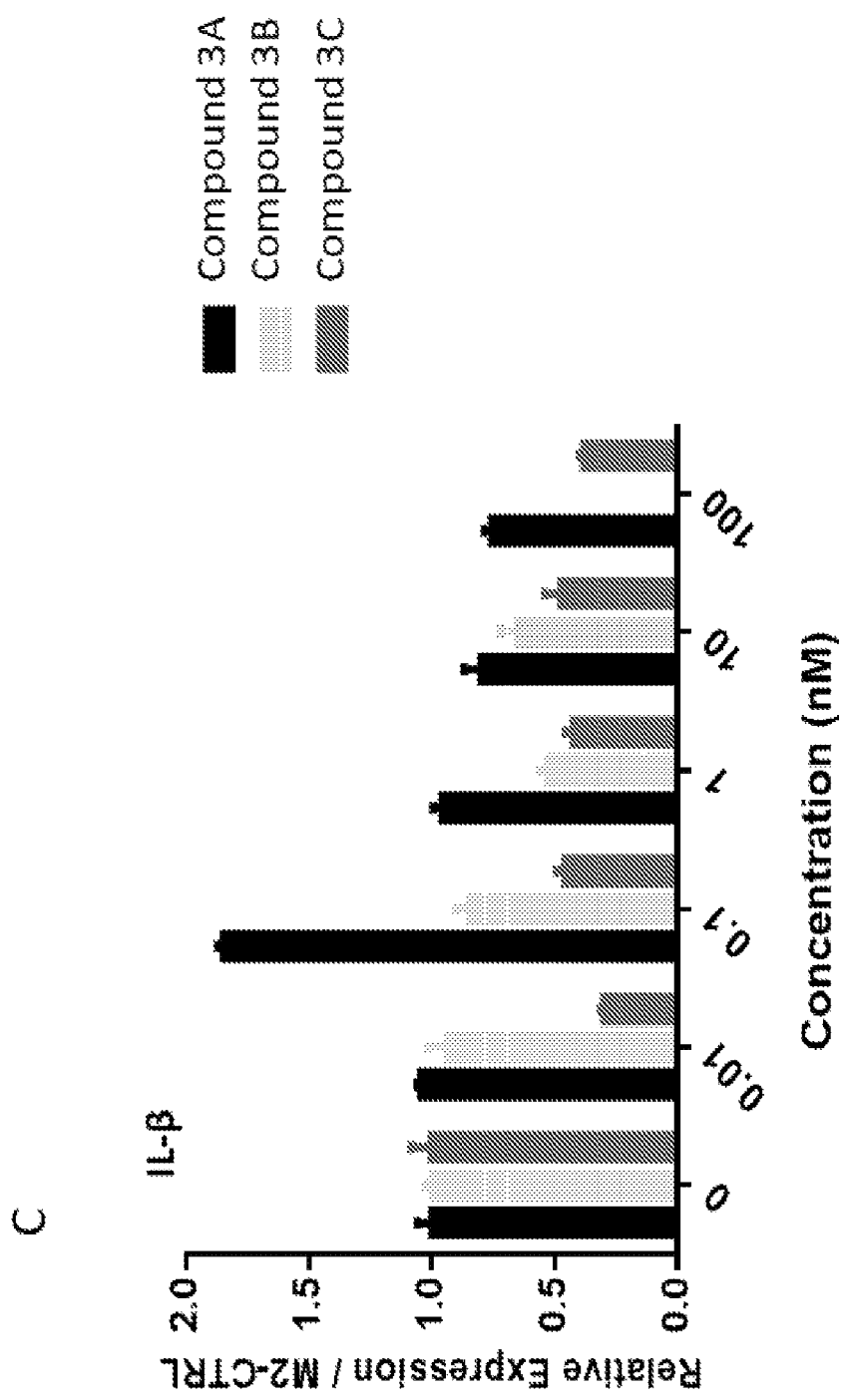
FIG. 14 con't

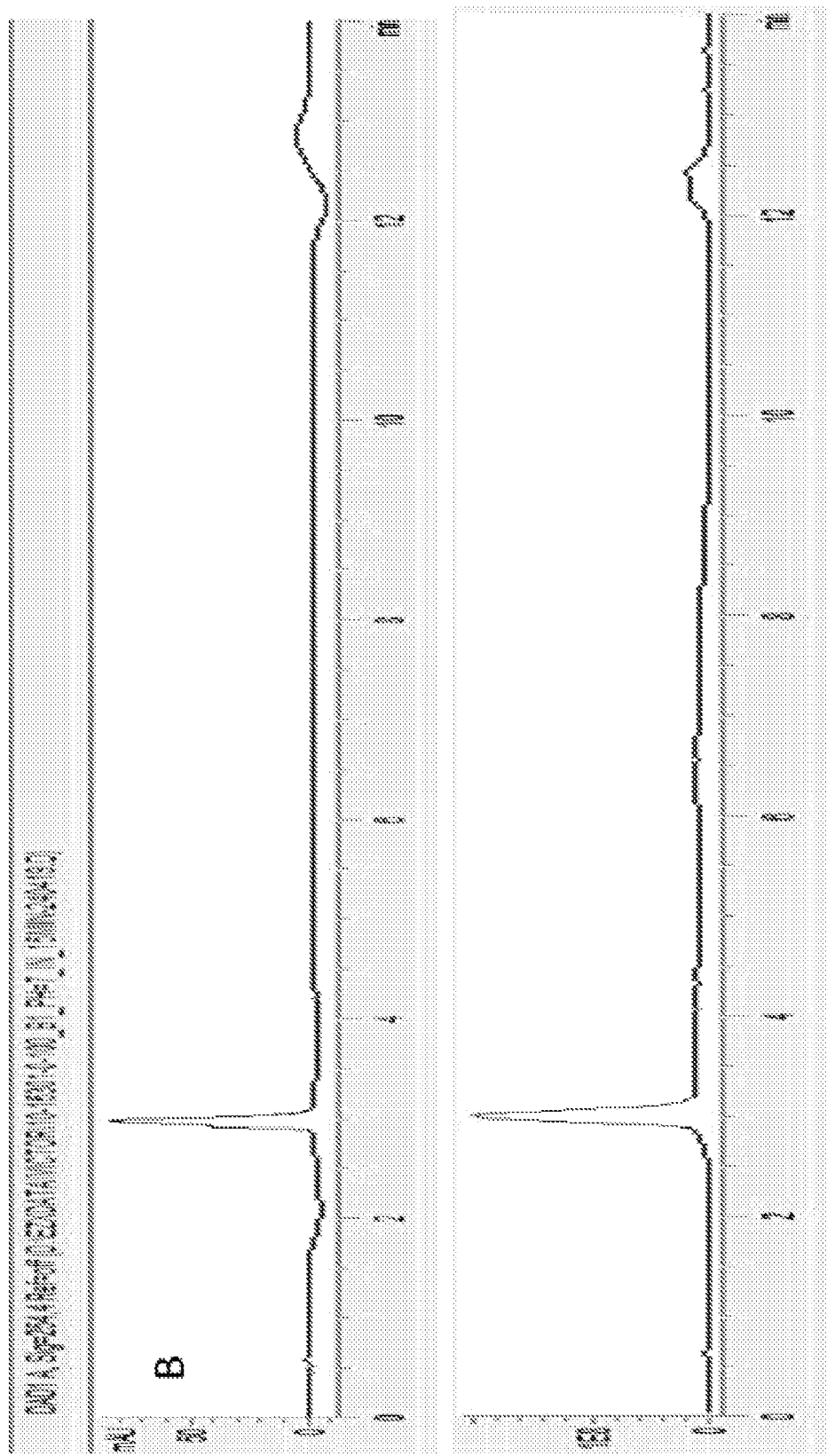
FIG. 17 con't

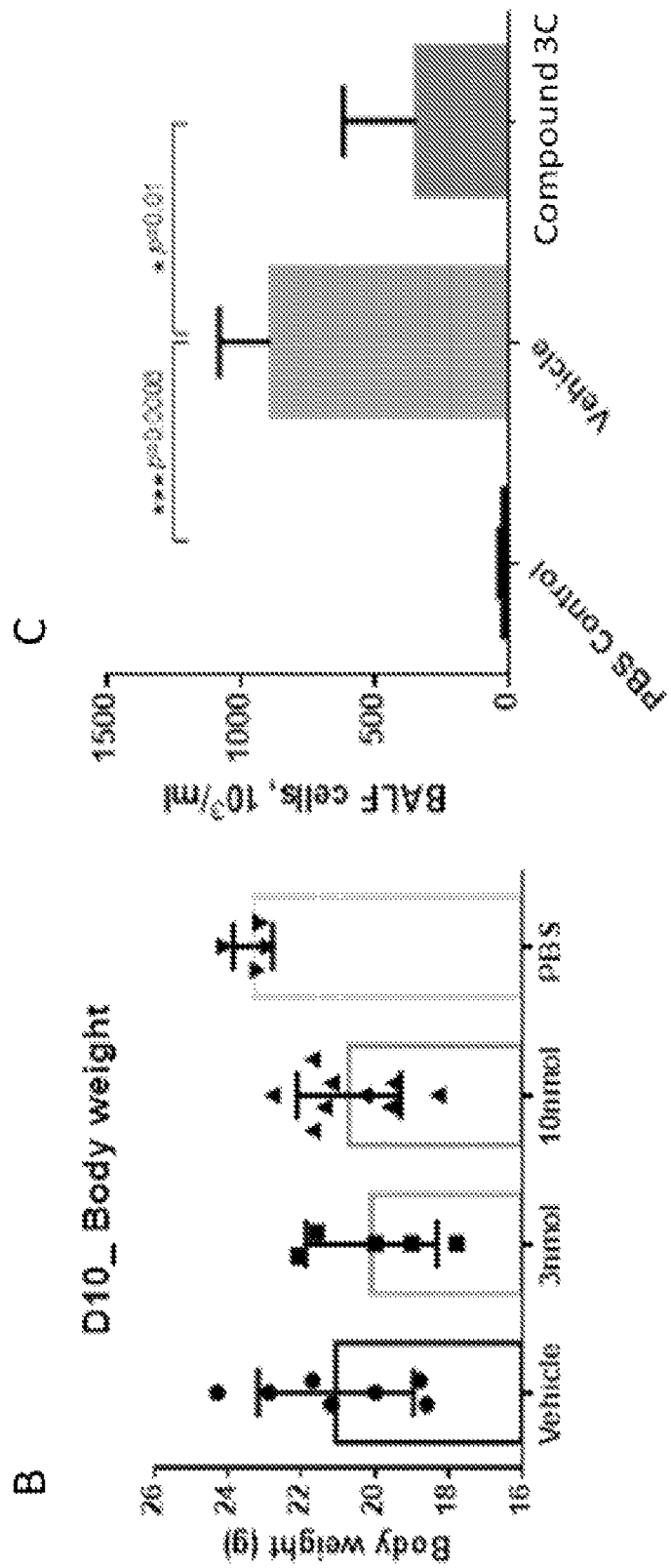
FIG. 18 con't

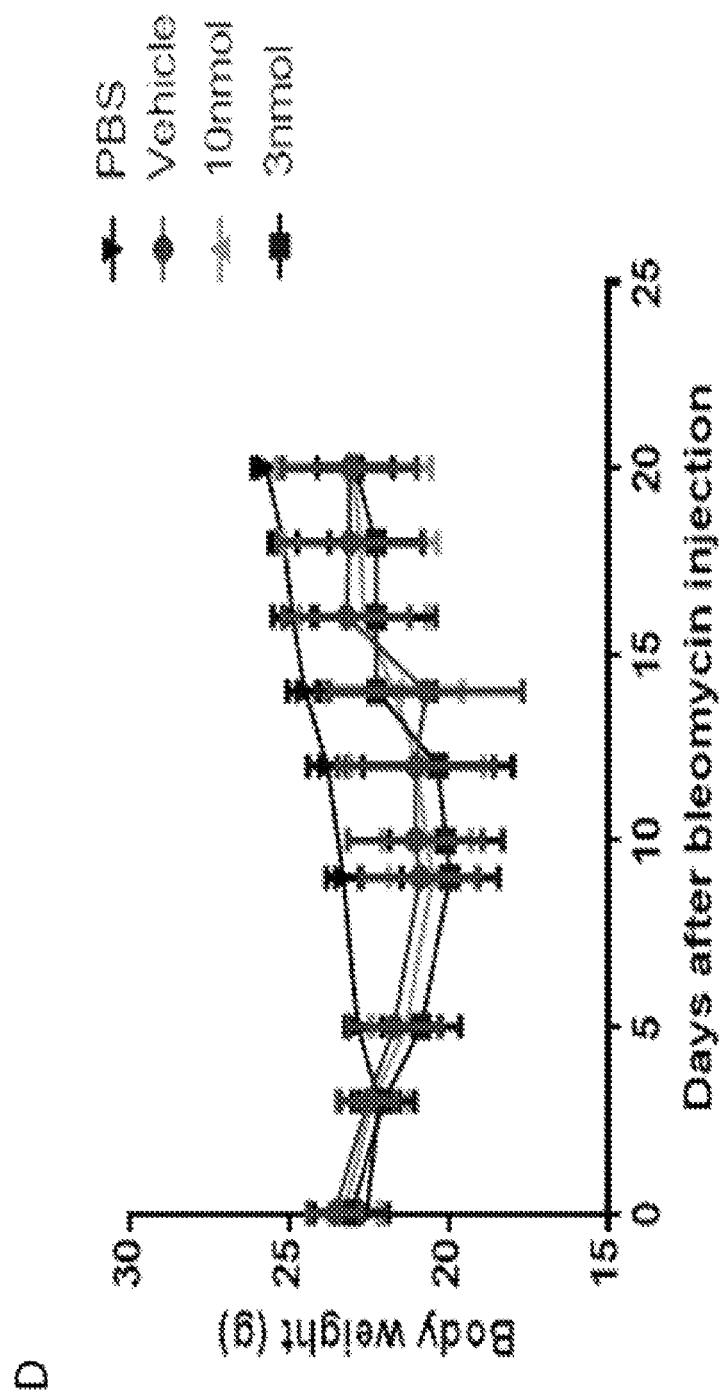
FIG. 18 con't

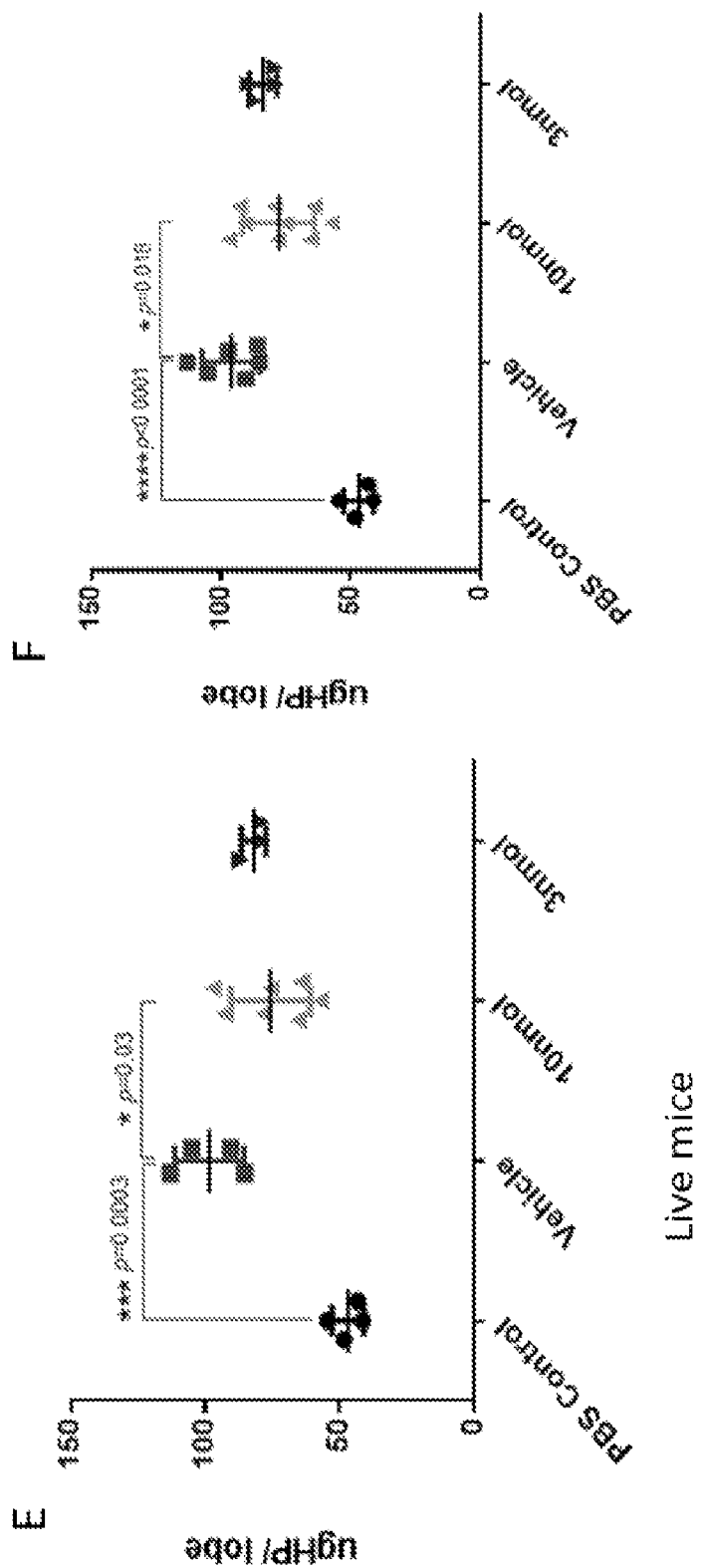
FIG. 18 con't

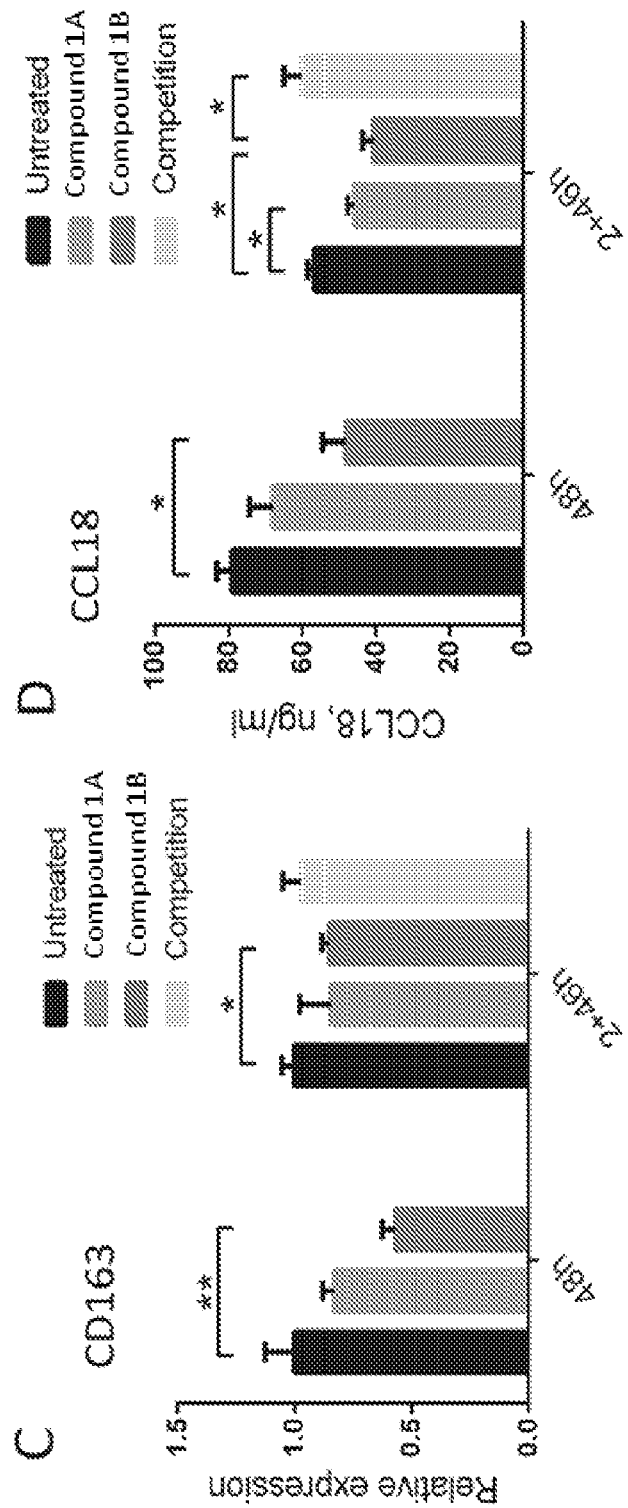
FIG. 19 con't

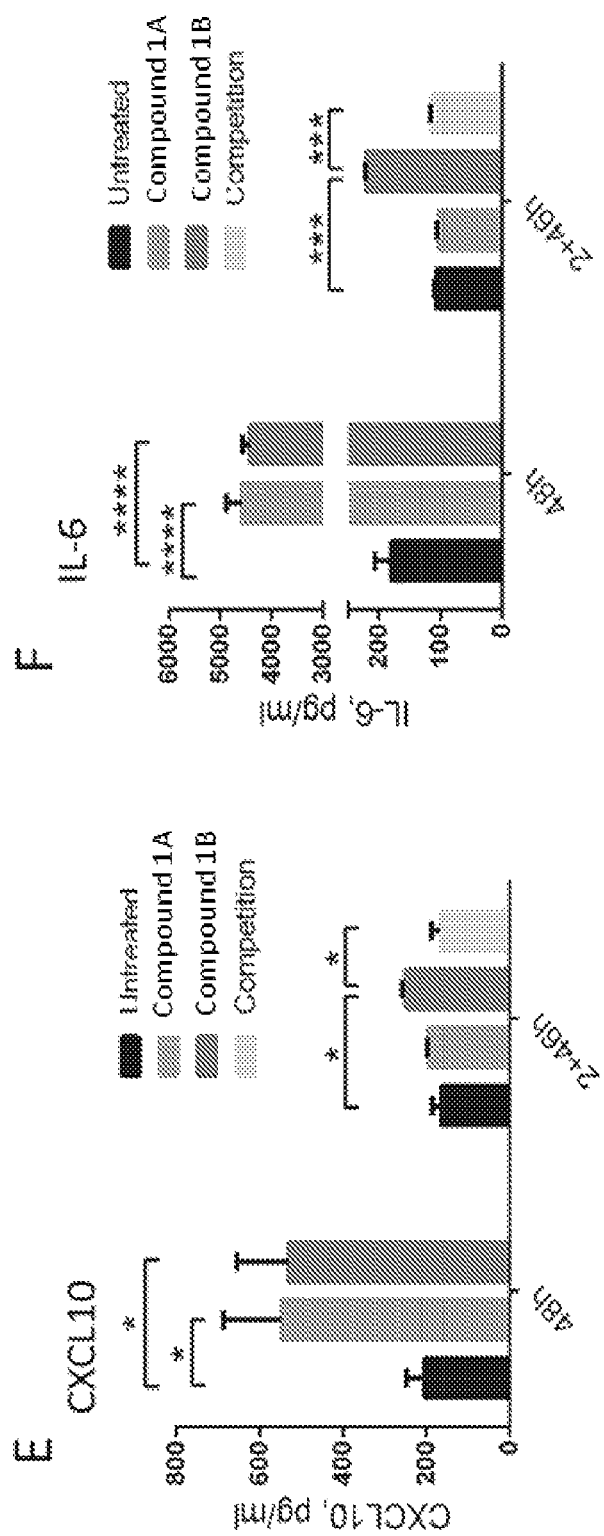
FIG. 19 con't

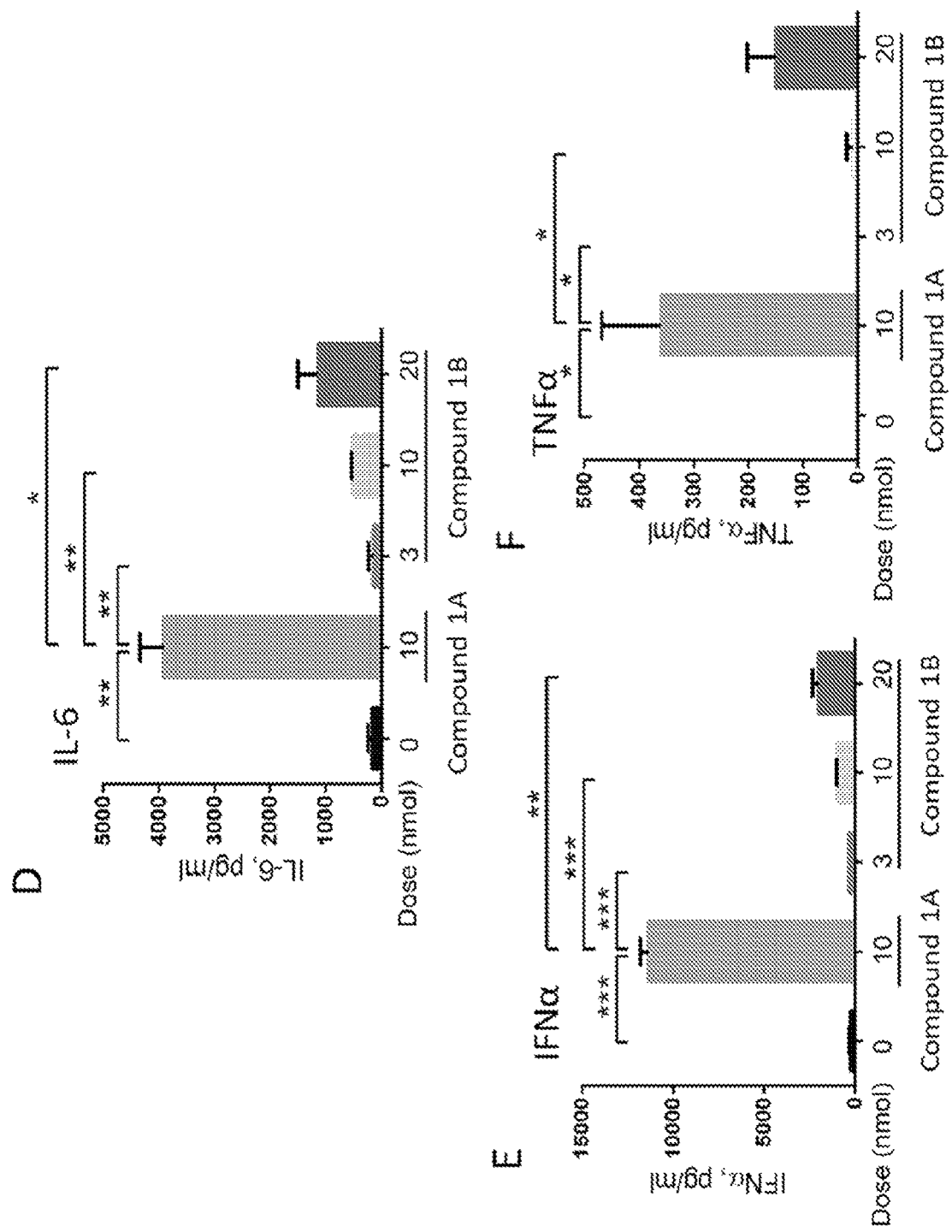
FIG. 20 con't

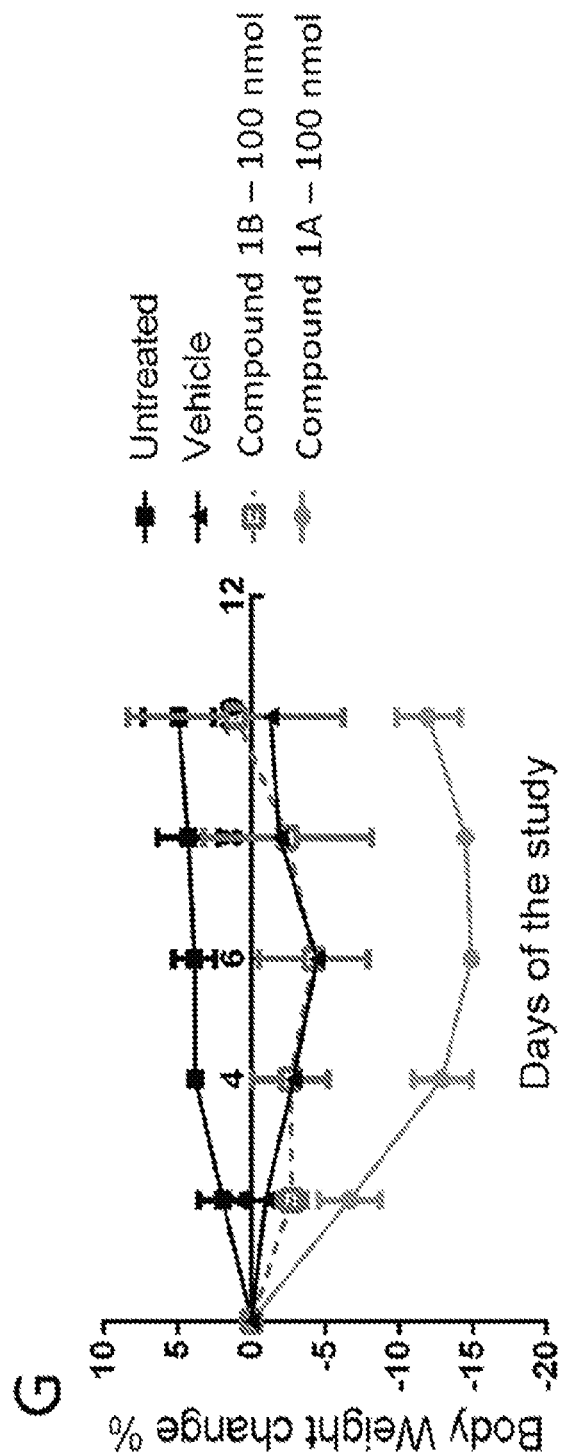
FIG. 20 con't

COMPOUNDS AND METHODS FOR THE TREATMENT AND PREVENTION OF FIBROTIC DISEASE STATES AND CANCER

PRIORITY

This application is related to and claims priority benefit of, and is a 35 U.S.C. 371 national stage application of International Patent Application No. PCT/US2020/041120, filed Jul. 8, 2020, which is related to and claims the priority benefit of: a) U.S. Provisional Patent Application No. 62/871,686 filed Jul. 8, 2019; and b) U.S. Provisional Patent Application No. 62/872,146 filed Jul. 9, 2019. The contents of the aforementioned applications are hereby incorporated by reference in their entireties into this disclosure.

TECHNICAL FIELD

This disclosure relates to compounds, pharmaceutical compositions, and methods for treating and preventing fibrotic disease states and/or a cancer using one or more compounds that comprise a targeting moiety and reprogram M2-type macrophages to M1-type macrophages.

BACKGROUND

Despite the seriousness of numerous fibrotic diseases like idiopathic pulmonary fibrosis (IPF), few options exist for successful treatment and nearly all that are conventionally available are designed to mitigate symptoms and retard progression, not cure the underlying disease. For example, with IPF, oxygen therapy can improve comfort and lifestyle, but has little effect on disease progression. Similarly, while two FDA-approved drugs, pirfenidone and nintedanib, may slow advancement of the disease, neither can reverse existing fibrosis or halt production of further fibrosis. Given the high probability of mortality associated with many fibrotic diseases such as IPF, there is a major need to identify new strategies to slow and perhaps even halt progression of the disease.

Moreover, cancer is treated with chemotherapy utilizing highly potent drugs such as mitomycin, paclitaxel and camptothecin. In many cases these chemotherapeutic agents show a dose responsive effect, and tumor inhibition is proportional to the drug dosage. Thus, an aggressive dosing regime is used to treat neoplasms; however, high-dose chemotherapy is hindered by poor selectivity for cancer cells and toxicity to normal cells. A lack of tumor specificity is one of the many hurdles that need to be overcome by conventional chemotherapies.

Despite the clear need for the prevention and treatment of both fibrotic diseases and cancers, these conditions remain significant causes of death and/or suffering worldwide because no effective therapeutic options presently exist that can cure the conditions. Further, where drugs or other therapies are available, such treatments typically employ highly potent drugs that risk systemic toxicity in the underlying subject as they are poorly selective for the fibrotic and/or cancer cells of interest. What is needed is a treatment effective to not only disrupt the profibrotic and/or pro-growth factor cycle initiated by activated M2-type (alternatively activated) macrophages, but also that can do so with very high specificity to the cells at issue (whether that be cancer cells or other cells experiencing a fibrotic disease).

SUMMARY

In some instances, activated M2 phenotype macrophages play a role in fibrotic diseases, such as by secreting profibrotic cytokines that activate fibroblasts to synthesize collagen and other extracellular matrix proteins. In certain instances, these macrophages similarly cause the release of growth factors that are problematic in subjects experiencing cancer. For example, such growth factors can promote growth of cancerous tumors. Moreover, in some instances, macrophages (e.g., concurrently) release immune suppression cytokines. As such, macrophages can play an important role in facilitating the establishment and growth of fibrotic disease and/or cancer.

Idiopathic pulmonary fibrosis (IPF) is one such fibrotic disease, e.g., that is an interstitial lung disease resulting from excessive deposition of collagen. In some instances, this type of fibrosis leads to progressive rigidification of the lung and, in some instances, to a consequent loss of the lung's ability to mediate gas exchange. Due to this progressive decline in vital capacity, median survival following diagnosis of IPF is estimated at only 2.5-5 years. In some instances, severe associated morbidities (e.g. chronic hypoxia, fatigue, weight loss, muscle and joint pain, persistent coughing, and loss of mobility, etc.) increase continuously during the later stages of the pathology. About 40,000 new cases of IPF are diagnosed per year in the United States and most end in death.

In some instances, activated macrophages, which derive from tissue-resident macrophages or peripheral blood monocytes, induce activation of fibroblasts via secretion of chemokine (C—C motif) ligand 18 (CCL18), transforming growth factor-β1 (TGFβ1) and/or platelet derived growth factor (PDGF). This activation, in some instances, promotes the secretion of collagen by the fibroblasts, which can cause fibrotic disease and cancer associated therewith to advance. In later stages of many fibrotic diseases, the activated macrophages and myofibroblasts can cross-stimulate each other, resulting in a vicious cycle that assures propagation of fibrosis throughout the lung or other relevant portion of the body.

Similar pathologies are observed in other fibrotic diseases as well. Cancers may also involve a similar immune response, such that promotes the growth of cancerous tumors (e.g., owing to the growth factors secreted by the activated macrophages) and/or promotes collagen formation in cancerous tumors (e.g., through downstream fibrotic collagen production, which can result in a cancerous tumor that is more difficult to treat by blocking drug penetrability thereof).

Provided herein in some embodiments is a compound represented by the formula Q-L-T. In some embodiments, Q is a radical of a folate receptor binding ligand. In some embodiments, L is a linker. In some embodiments, T is a radical of a toll-like receptor (TLR) agonist. In some embodiments, Q-L-T is a pharmaceutically acceptable salt thereof.

In some embodiments, the linker is a non-releasable linker. In some embodiments, the non-releasable linker is represented by the formula:

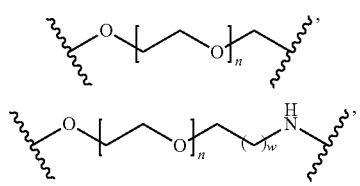

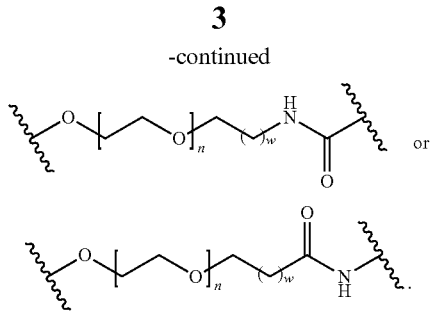 or

In some embodiments, n is 1-30. In some embodiments, n is 1-24. In some embodiments, n is 1-12. In some embodiments, n is 1-3. In some embodiments, n is 12. In some embodiments, n is 3.

In some embodiments, w is 0-5. In some embodiments, w is 0-2. In some embodiments w is 1.

In some embodiments, the TLR agonist is a toll-like receptor 7 (TLR7) agonist. In some embodiments, the radical of the TLR agonist has a structure represented by Formula X:

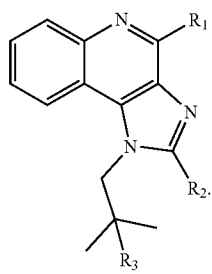

(X)

In some embodiments, $R_1$ is —$NH_2$ or —NH—$R_{1X}$. In some embodiments, $R_2$ is an H, an alkyl, an alkenyl, an alkynyl, an alicyclic, an aryl, a biaryl, a heteroaryl, —NH—$R_{2X}$, —O—$R_{2X}$, —S—$R_{2X}$,

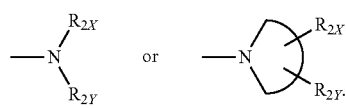

In some embodiments, each of $R_{1X}$, $R_{2X}$, and $R_{2Y}$ is independently selected from the group consisting of a hydrogen (H), an alkyl, an alkenyl, an alkynyl, an alicyclic, an aryl, a biaryl, and a heteroaryl. In some embodiments,

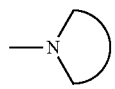

is a 3-10 membered nitrogen (N)-containing non-aromatic mono- or bicyclic heterocycle. In some embodiments, $R_3$ is —OH, —SH, —$NH_2$ or —NH—$R_{1X}$. In some embodiments, $R_1$ is —$NH_2$ or —NH—$R_{1X}$; $R_2$ is an H, an alkyl, an alkenyl, an alkynyl, an alicyclic, an aryl, a biaryl, a heteroaryl, —NH—$R_{2X}$, —O—$R_{2X}$, —S—$R_{2X}$,

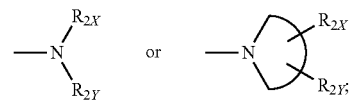

each of $R_{1X}$, $R_{2X}$, and $R_{2Y}$ is independently selected from the group consisting of an H, an alkyl, an alkenyl, an alkynyl, an alicyclic, an aryl, a biaryl and a heteroaryl;

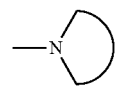

is a 3-10 membered N-containing non-aromatic mono- or bicyclic heterocycle; and $R_3$ is —OH, —SH, —$NH_2$ or —NH—$R_{1X}$.

In some embodiments, the radical of the TLR agonist has a structure represented by Formula XX:

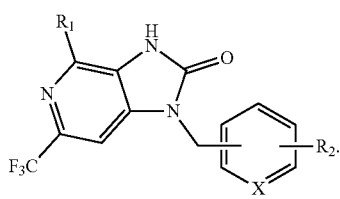

(XX)

In some embodiments, $R_1$ is —$NH_2$ or —NH—$R_{1X}$. In some embodiments, $R_2$ is an H, an alkyl, an alkenyl, an alkynyl, an alicyclic, an aryl, a biaryl, a heteroaryl, —NH—$R_{2X}$, —O—$R_{2X}$, —S—$R_{2X}$,

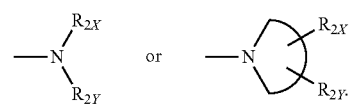

In some embodiments, each of $R_{1X}$, $R_{2X}$, and $R_{2Y}$ are independently selected from the group consisting of an H, an alkyl, an alkenyl, an alkynyl, an alicyclic, an aryl, a biaryl, and a heteroaryl. In some embodiments,

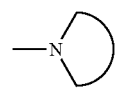

is a 3-10 membered N-containing non-aromatic mono- or bicyclic heterocycle. In some embodiments, X is CH, $CR_2$, or N. In some embodiments, $R_1$ is —$NH_2$ or —NH—$R_{1X}$; $R_2$ is an H, an alkyl, an alkenyl, an alkynyl, an alicyclic, an aryl, a biaryl, a heteroaryl, —NH—$R_{2X}$, —O—$R_{2X}$, —S—$R_{2X}$,

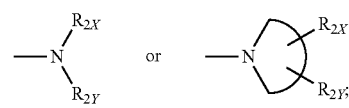

each of $R_{1X}$, $R_{2X}$, and $R_{2Y}$ is independently selected from the group consisting of an H, an alkyl, an alkenyl, an alkynyl, an alicyclic, an aryl, a biaryl and a heteroaryl;

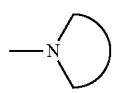

is a 3-10 membered N-containing non-aromatic mono- or bicyclic heterocycle; and X is CH, CR$_2$, or N.

In some embodiments, the radical of the TLR7 agonist has a structure represented by Formula XXX:

(XXX)

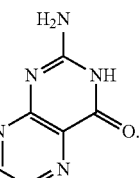

In some embodiments, the compound further comprises a linker L$_n$ between the targeting moiety and the immune modulator or the pharmaceutically acceptable salt thereof, wherein the linker L$_n$ is configured to avoid release of a free form of the TLR7 agonist, and n is an integer equal to or less than 50. In some embodiments, the linker L$_n$ comprises polyethylene glycol (PEG) or a PEG derivative, n is an integer selected from the range 1-32, and the radical of folate receptor binding ligand is a folate receptor β (FBβ) binding ligand.

In some embodiments, the compound has a structure represented by:

In some embodiments, the compound has a structure represented by:

In some embodiments, the compound has a structure represented by:

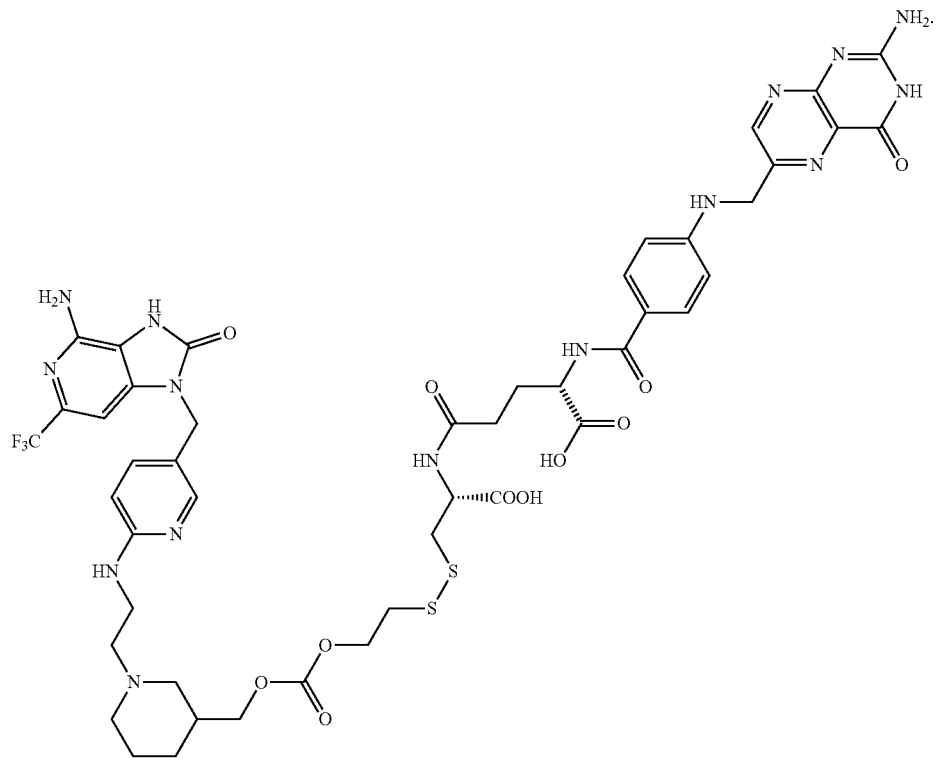 [SMILES: Nc1nc2ncc(CNc3ccc(C(=O)N[C@@H](CCC(=O)N[C@@H](CSSCCOC(=O)OCC4CCCN(CCNc5ccc(Cn6c(=O)[nH]c7c(N)nc(C(F)(F)F)cc76)cn5)C4)C(=O)O)C(=O)O)cc3)nc2c(=O)[nH]1]

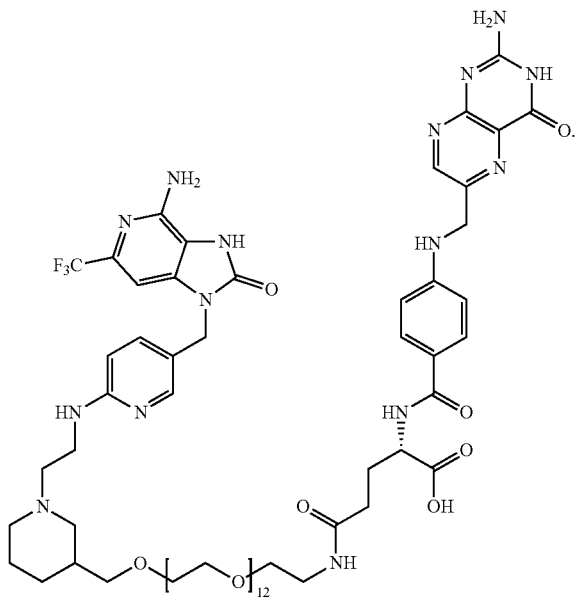

In some embodiments, the compound has a structure represented by:

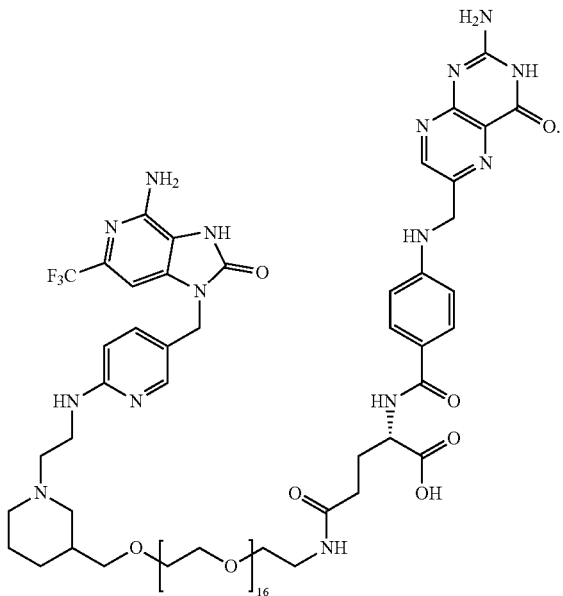

In some embodiments provided herein is a pharmaceutical composition comprising one or more of the compounds of the present disclosure, wherein the TLR7 agonist has a structure represented by Formula XX.

In certain instances, provided herein is a method of treating a subject suffering from a fibrotic disease state or a cancer, the method comprising contacting a cell of the subject with at least one compound comprising a compound described herein wherein the immune modulator comprises an agonist of TLR 7, 8, or 9.

In some embodiments, provided herein is a compound comprising a folate ligand or a functional fragment or analog thereof attached to a TLR agonist via a linker, the TLR agonist having the following formula or a pharmaceutically acceptable salt thereof:

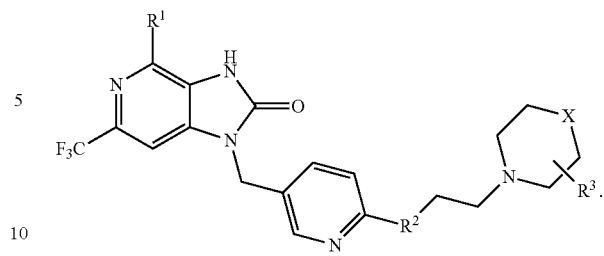

In some embodiments, $R^1$ is an amine group, $R^2$ is a single bond —NH—, and $R^3$ is an H, an alkyl, a hydroxy group, or any other substituted group thereof, X is a $CH_2$, NH, oxygen (O), or sulfur (S), and the linker is attached at $R^1$, $R^2$ or $R^3$.

Provided in some embodiments herein is a pharmaceutical composition comprising the compound of any one of the formulas provided herein, wherein the linker comprises a PEG linker or a PEG derivative linker and is either a non-releasable linker attached at $R^3$ or is a releasable linker attached at $R^1$, $R^2$ or $R^3$.

In some embodiments, the pharmaceutically acceptable salt is selected from hydrobromide, citrate, trifluoroacetate, ascorbate, hydrochloride, tartrate, triflate, maleate, mesylate, formate, acetate or fumarate.

Provided in some embodiments herein is a method of preventing or treating a fibrotic disease state comprising contacting a cell with at least one compound (e.g., any compound provided by a formula provided herein) comprising an immune modulator or pharmaceutically acceptable salt thereof attached, via a linker, to a folate ligand or functional fragment or analog thereof, wherein the immune modulator or pharmaceutically acceptable salt thereof targets a pattern recognition receptor. In some embodiments, the cell comprises a cell of a subject experiencing, or at risk for experiencing, a fibrotic disease state and contacting the cell with at least one compound further comprises administering or applying to the subject a therapeutically effective amount of the at least one compound. In some embodiments, the subject is a patient experiencing IPF and the at least one compound is administered to the subject intravenously, intramuscularly, intraperitoneally, topically or by inhalation. In some embodiments, the fibrotic disease state comprises IPF or a fibrotic disease of a liver, skin, bladder, heart, pancreas, prostate, or kidneys.

In some embodiments, the method further comprises obtaining, or having obtained, a sample from the subject; quantifying a level of expression of one or more biomarkers in the sample, each of the one or more biomarkers selected from the group consisting of CCL18, Arginase 1 (Arg1), matrix metallopeptidase 9 (MMP9), metalloproteinase 3 (TIMP3), interleukin 1 β (IL-1β), hydroxyproline, collagen, PDGF, TGFβ, folate receptor β (FRβ), tumor necrosis F-α (TNFα), interferon gamma (IFN-γ), mannose receptor (CD206), cluster of differentiation 163 (CD163), cluster of differentiation 86 (CD86), interleukin 6 (IL-6), chemokine 10 (CXCL10), and immune interferon (IFNα); comparing the level of expression of each of the one or more biomarkers in the sample to an expression level of such biomarker in a control; and administering or having administered to the subject a therapeutically effective amount of an unconjugated agonist or inhibitor if CCL18, Arg1, MMP9, TIMP 3, IL-1β, PDGF, TGFβ, FRβ, CD206, CD163, hydroxyproline, or collagen is unregulated relative to the expression level of the control or TNFα, IFN-γ, IL-6, CXCL10, IFNα or CD86 is downregulated or not expressed relative to the expression level of the control.

In some embodiments, the folate ligand or functional fragment or analog thereof is specific for FRβ and binds to a FRβ on the cell.

Provided in some embodiments herein is a compound comprising a targeting moiety attached to an immune modulator or a pharmaceutically acceptable salt thereof that targets a pattern recognition receptor of a cell, the targeting moiety comprising a folate ligand or a functional fragment or analog thereof.

DESCRIPTION OF THE DRAWINGS

The disclosed embodiments and other features, advantages, and aspects contained herein, and the matter of attaining them, will become apparent in light of the following detailed description of various exemplary embodiments of the present disclosure. Such detailed description will be better understood when taken in conjunction with the accompanying drawings, wherein:

FIGS. 4A-4E and FIGS. 5A-5D support that the M2-type profibrotic phenotype was downregulated following administration of the free and targeted TLR7 agonist. Each value represents the mean±S.D. for each group; #P<0.05, ##P<0.01, ###P<0.005, ####P<0.0001; Compound 1A and Compound 1B treated groups in FIGS. 4A-5D versus M2-untreated group by Dunnett's multiple comparison test.

FIG. 12A shows graphical data related to the body weight of the BM-induced mice over time. FIG. 12B shows measurement of hydroxyproline content of the lung tissue treated with various doses of exemplary conjugates provided herein (e.g., Compound 1B). FIG. 12C shows images for histological analysis of lung tissue with various stains. Each value represents the mean±S.D. for each group; *P<0.05, P<0.005, *<0.0005; saline versus vehicle group, the treated groups versus vehicle group by Student's t test.

FIG. 20G shows the change in body weight after treatment of mice with exemplary compounds provided herein, with change in body weight as a measure of systemic toxicity during alternate day dosing (n=2); mean±SD. Statistical significance between groups was compared using unpaired two-tailed t-test (*P<0.05, P<0.01, *P<0.001).

Figure 1:
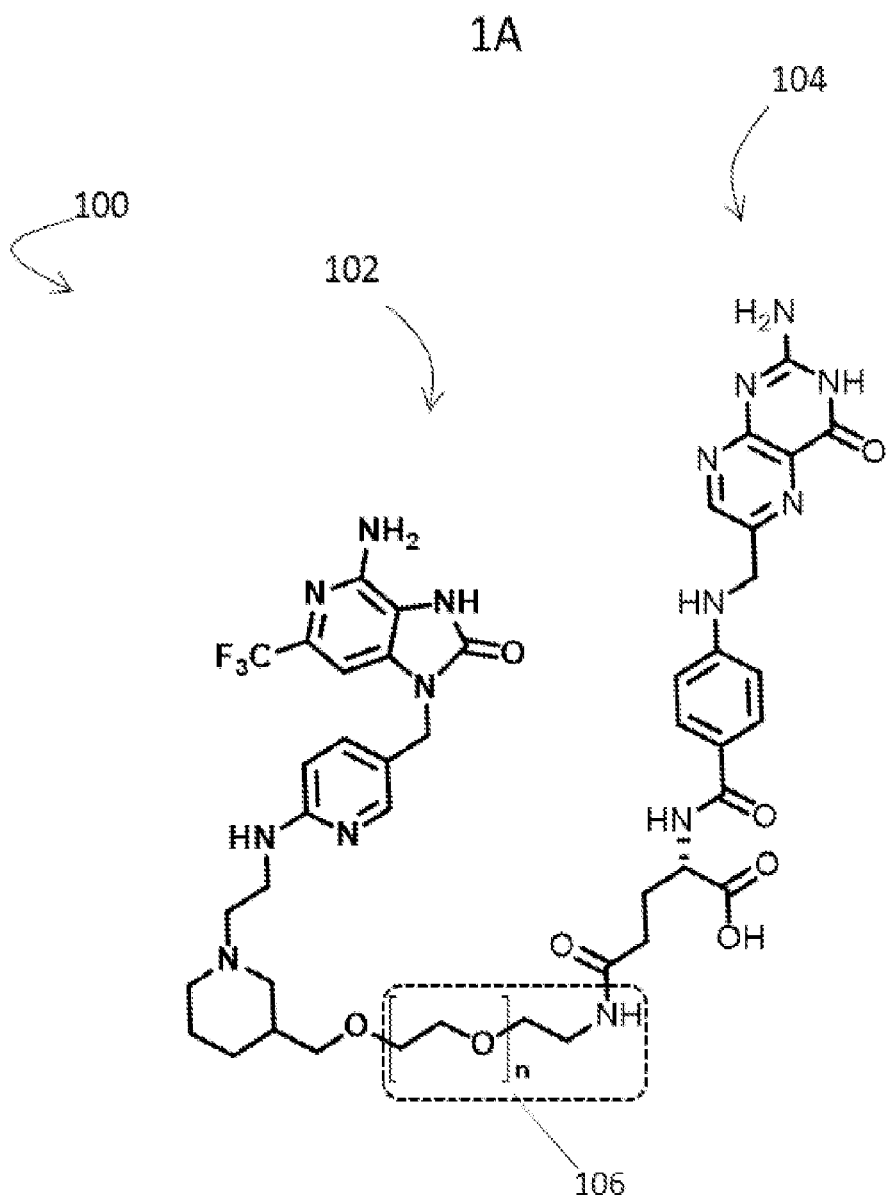
FIG. 1A shows the chemical structure of an exemplary compound having a targeting moiety (folate receptor ligand) attached to an immune modulator (toll-like receptor 7 (TLR7) agonist radical) via a non-releasable linker (e.g., comprising a polyethylene glycol (PEG) backbone portion).
FIG. 1B shows the chemical structure of an exemplary compound having a targeting moiety (folate receptor ligand) attached to an immune modulator (TLR7 agonist radical) via a releasable linker (e.g., comprising a disulfide portion in the backbone thereof), as well as an exemplary drug release mechanism.

While the present disclosure is susceptible to various modifications and alternative forms, exemplary embodiments thereof are shown by way of example in the drawings and are herein described in detail.

DETAILED DESCRIPTION

For the purposes of promoting an understanding of the principles of the present disclosure, reference will now be made to the embodiments illustrated in the drawings and specific language will be used to describe the same. It will nevertheless be understood that no limitation of scope is intended by the description of these embodiments. On the contrary, this disclosure is intended to cover alternatives, modifications, and equivalents as may be included within the spirit and scope of this application as defined by the appended claims. As previously noted, while this technology may be illustrated and described in one or more preferred embodiments, the compositions, compounds and methods hereof may comprise many different configurations, forms, materials, and accessories.

In the following description, numerous specific details are set forth to provide a thorough understanding of the present disclosure. Particular examples may be implemented without some or all of these specific details and it is to be understood that this disclosure is not limited to particular biological systems, particular fibrotic diseases or cancers, or particular organs or tissues, which can, of course, vary, but remain applicable in view of the data provided herein.

Various techniques and mechanisms of the present disclosure will sometimes describe a connection or link between two components. Words such as attached, linked, coupled, connected, and similar terms with their inflectional morphemes are used interchangeably, unless the difference is noted or made otherwise clear from the context. These words and expressions do not necessarily signify direct connections but include connections through mediate components. It should be noted that a connection between two components does not necessarily mean a direct, unimpeded connection, as a variety of other components may reside between the two components of note. Consequently, a connection does not necessarily mean a direct, unimpeded connection unless otherwise noted.

Further, wherever feasible and convenient, like reference numerals are used in the figures and the description to refer to the same or like parts or steps. The drawings are in a simplified form and not to precise scale. It is understood that the disclosure is presented in this manner merely for explanatory purposes and the principles and embodiments described herein may be applied to compounds and/or composition components that have configurations other than as specifically described herein. Indeed, it is expressly contemplated that the components of the composition and compounds of the present disclosure may be tailored in furtherance of the desired application thereof.

Unless defined otherwise, all technical and scientific terms used herein have the same meaning as commonly understood by one of skill in the chemical and biological arts. Although any methods and materials similar to or equivalent to those described herein can be used in the practice or testing of the subject of the present application, the preferred methods and materials are described herein. Additionally, as used in this specification and the appended claims, the singular forms "a", "an" and "the" include plural referents unless the content clearly dictates otherwise. Thus, for example, where a compound/composition is substituted with "an" alkyl or aryl, the compound/composition is optionally substituted with at least one alkyl and/or at least one aryl. Further, unless specifically stated otherwise, the term "about" refers to a range of values plus or minus 10% for percentages and plus or minus 1.0 unit for unit values; for example, "about 1.0" refers to a range of values from 0.9 to 1.1.

In certain embodiments, the compounds, compositions and methods of the present disclosure are useful for the prevention and/or treatment of fibrotic diseases. In certain embodiments, the compounds and/or compositions provided are also useful for the prevention and/or treatment of cancer. In some embodiments, the compounds, compositions and methods provided herein leverage strategies to (e.g., selectively) target the innate immune system and reprogram the polarization of a macrophage from M2 to M1 and, for example, leverage the antifibrotic properties thereof.

Generally and without any intended limitation, the novel compounds, compositions, and methods of the present disclosure target the innate immune system of a subject and reprogram the polarization of a macrophage from M2-type to M1-type in favor of the antifibrotic properties of the M1-type phenotype. For example, in at least one exemplary embodiment, such compounds and compositions comprise a targeting moiety to target folate receptor β (FRβ), such as a folate receptor binding ligand or a radical thereof, coupled with an immune modulator or a pharmaceutically acceptable salt thereof. As is described in detail below, such embodiments utilize the limited expression of FRβ to localize systemically administered compounds directly to FRβ expressing cells (e.g., those of fibrotic and/or cancerous tissue) such that the immune modulator component can then convert—e.g., reprogram—activated myeloid cells (e.g., M2-like macrophages) into an antifibrotic M1 polarization. This targeting design advantageously prevents the systemic activation of the immune system and, thus, avoids toxicity.

Further exemplary embodiments may comprise a linker disposed between the targeting moiety and the immune modulator. Such linkers can be releasable or non-releasable. As is described herein, a compound/composition of the present disclosure that comprises a releasable linker will, when administered, result in the targeting moiety and immune modulator being released from each other on or about the time the immune modulator becomes active. Additionally or alternatively, in embodiments where a compound/composition of the present disclosure comprises a non-releasable linker, when administered the targeting moiety and immune modulator do not release quickly under physiological conditions. In this way, the components remain together following uptake by a targeted cell and/or activation of the immune modulator.

Various embodiments of the present disclosure will now be described, as well as data relating to examples that support the same. Primarily, there are two main immunity strategies found in vertebrates: the innate immune system and the adaptive immune system. The innate, or non-specific, immune response is the first line of defense against non-self pathogens and consists of physical, chemical and cellular defenses. The adaptive immune system, on the other hand, is called into action against pathogens that evade or overcome the primary innate immune defenses.

Inflammatory response plays a critical role in immunity. When tissues are damaged or a pathogen is detected, for example, an inflammatory response is initiated, and the immune system is mobilized. The immune cells of the innate immune system (i.e., neutrophils and eosinophils) are the first recruited to the site of tissue injury or damage or pathogen location via blood vessels and the lymphatic system, followed by macrophages.

The cells of the innate immune system can express special pattern recognition receptors that sense and bind with specific protein sequences present in microbial pathogens or other non-self molecules. As used herein, "pattern recognition receptors" means and includes any immune receptors that are expressed on the membranes of leukocytes—e.g., at least macrophages—and can bind specific ligands that activate the receptor and ultimately lead to an innate immune response (and, in certain cases, eventually the development of antigen-specific acquired immunity).

Examples of two classes of molecules that can bind to pattern recognition receptors include pathogen-associated molecular patterns associated with microbial pathogens and damage-associated molecular patterns associated with components of the host's cells that are released during cell damage or death. Recognition of these protein sequences by the pattern recognition receptors can initiate signal transduction pathways that trigger the expression of certain genes whose products control innate immune responses (e.g., in some cases, instructing the development of antigen-specific acquired immunity). Accordingly, the pattern recognition receptors mediate these signaling pathways and, in certain cases, can be used to positively or negatively control innate—and even adaptive—immune response.

Macrophages are a diverse group of white blood cells known for eliminating pathogens through phagocytosis and are broadly classified as either having an M1 or M2 phenotype depending on which specific differentiation they undergo in response to the local tissue environment. In some instances, macrophages are polarized towards the M1 phenotype by exposure to interferon gamma (IFN-γ), lipopolysaccharide (LPS), and/or granulocyte-macrophage colony stimulating factor (GM-CSF). In certain instances, the M1 phenotype is characterized by the production of high levels of pro-inflammatory cytokine(s) (such as interleukin 1 β (IL-1β), tumor necrosis factor (TNF), interleukin 12 (IL-12), interleukin 18 (IL-18), and/or interleukin 23 (IL-23)), an ability to mediate resistance to pathogens, strong microbicidal properties, high production of reactive nitrogen and oxygen intermediates, and/or promotion of T helper type 1 (Th1) responses. In some instances, M1 polarization is associated with the "attack and kill" phase of the innate immune response. In certain instances, M1 polarization operates to inhibit or prevent initial establishment of infection and/or remove damaged tissue.

In certain instances, after the innate immune system performs this "attack and kill" phase, a macrophage may reprogram itself to become a healing system (i.e. M2-type) and, for example, release growth factors to promote healing. Such growth factors may include (without limitation) certain cytokines such as interleukin 4 (IL-4), interleukin 10 (IL-10), platelet-derived growth factor (PDGF), transforming growth factor-β1 (TGFβ), chemokine (C—C motif) ligand 18 (CCL18), and/or interleukin 13 (IL-13). In certain instances, exposure to such cytokines/growth factors alternatively activates the M2 macrophage phenotype.

In contrast to M1, M2 macrophages can be associated with wound healing and tissue repair. In some instances, M2 macrophages are characterized by their involvement in tissue remodeling, immune regulation/suppression, and/or tumor promotion. In specific instances, M2 macrophages produce polyamines to induce cell proliferation and/or proline to induce collagen production. While this healing response is beneficial in a healthy subject, the presence of M2 macrophages can have significantly detrimental effects through immune suppression and/or the promotion of tumor growth and fibrosis for those subjects suffering from a fibrotic disease or cancer.

For example, fibrotic pathologies can begin with an unknown trauma or insult to the epithelium. In response to the resulting tissue damage, chemokines and other factors can be released to promote the infiltration of immune cells to the damaged tissue (e.g., an innate immune response), which, for example, include monocytes and macrophages that assume an M2-like phenotypes and, for example, release profibrotic cytokines. The chronic secretion of these cytokines can then activate tissue-resident and infiltrating fibroblasts/fibrocytes to become myofibroblasts that, in turn, secret collagen and other extracellular matrix proteins that can stiffen the surrounding tissue. In some instances, these M2 macrophages exacerbate the disease by promoting fibrosis. For example, with idiopathic pulmonary fibrosis (IPF) subjects, for example, the M2 macrophages can infiltrate the lungs and promote fibrosis therein, which further reduces their functionality. In some instances, the growth factors and other cytokines produced by the M2 phenotype drive cancerous tumor growth through similar pathways.

Reprogramming M2-Like Macrophages to M1-Like Macrophages

In certain cancers and fibrotic diseases, macrophages can be disproportionately biased towards the anti-inflammatory (M2-like) phenotype. In certain instances, immune modulators can convert—e.g., reprogram—activated myeloid cells (e.g., M2-like macrophages) into an antifibrotic M1 polarization (e.g., where they produce little or no growth factors and/or related cytokines and, for example, slow or even eliminate the progression of the disease state). In certain instances, the compositions and methods provided herein reverse the antifibrotic to profibrotic shift observed during the course of the development of fibrotic diseases (for example, IPF and certain cancers). In some embodiments, the compositions and methods provided herein decrease the amount/expression of fibrotic biomarkers (e.g., those associated with profibrotic activity (e.g., CCL18, hydroxyproline, and collagen)) in an individual or a sample taken from a subject. An "individual," "subject" or "patient," as used herein, is a mammal, preferably a human, but can also be an animal.

A "marker" or "biomarker" as the terms are used herein may be described as being differentially expressed when the level of expression in a subject who is experiencing an active disease state is significantly different from that of a subject or sample taken from a healthy subject or one not experiencing the disease state. A differentially expressed marker may be overexpressed or underexpressed as compared to the expression level of a normal or control sample, or subjects' baseline (in the embodiment mentioned in the immediately preceding paragraph, the biomarker is decreased or underexpressed). The increase or decrease, or quantification of the markers in a biological sample, may be determined by any of the several methods known in the art for measuring the presence and/or relative abundance of a gene product or transcript. The level of markers may be determined as an absolute value, or relative to a baseline value, and the level of the subject's markers compared to a cutoff index. Alternatively, the relative abundance of the marker or markers may be determined relative to a control, which may be a clinically normal subject. Further, as used herein, the terms "gene overexpression" and "overexpression" (when used in connection with a gene) and their formatives have the meaning ascribed thereto by one of ordinary skill in the relevant arts, which includes (without limitation) the overexpression or misexpression of a wild-type gene product that may cause mutant phenotypes and/or lead to abundant target protein expression.

In some embodiments, the compositions and methods provided herein increase anti-fibrotic biomarkers (e.g., TNFα and IFN-γ). In some embodiments, compositions are provided that reverse the M2-like phenotypic shift (e.g., providing provide an effective treatment to fibrotic diseases, disorders, or conditions thereof.

In at least one embodiment, a drug comprising an immune modulator is used to make the compounds used in the methods described herein. As used herein, "immune modulator" means any drug, warhead, or other composition or compound that stimulates or otherwise affects a subject's immune system by inducing activation or increasing activity of one or more of the components of the immune system. For example, and without limitation, immune modulators may include a compound or composition that targets one or more pattern recognition receptors in addition to, or in lieu of, targeting signaling pathways in immune cells.

Exemplary examples of immune modulators of the present disclosure include, without limitation, agonists of toll-like receptors (TLRs), stimulator of interferon genes (STINGs), nucleotide-binding oligomerization domain (NOD)-like receptors (NLRs), retinoic acid-inducible gene-I (RIG-I)-like receptors (RLRs), absent in melanoma 2 (AIM2)-like receptors (ALRs), the receptor for advanced glycation end products (RAGE), or any other pattern recognition receptor that is located in the endosome or cytoplasm of a cell. The immune modulators of the present disclosure may additionally or alternatively comprise a nuclear factor kappa-light-chain-enhancer of activated B cells (NFκβ) activator or an Iκβ kinase inhibitor, which work farther downstream in the pathway. Table 1 provides examples of such NFκβ activators or Iκβ kinase inhibitor that may be employed as the immune modulators of the present disclosure.

TABLE 1

| NFκβ Activators/Inducers | |
|---|---|
| Compound | Structure |
| AA | 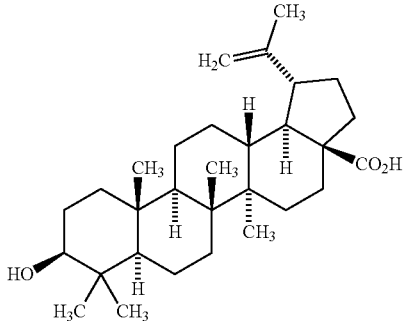 |

TABLE 1-continued
NFκβ Activators/Inducers
| Compound | Structure |
|---|---|
| BB | 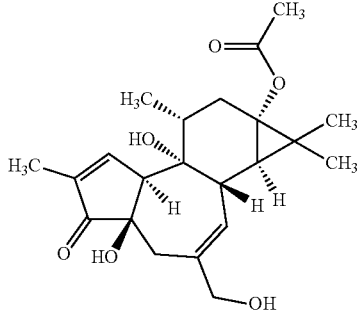 |
| CC | 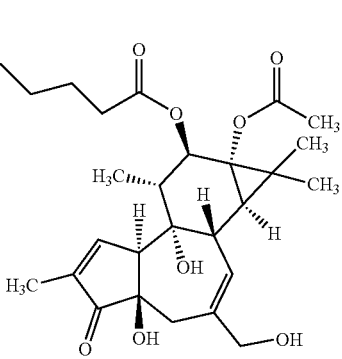 |
| DD | 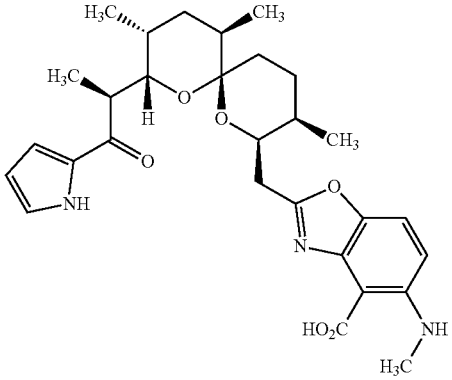 [SMILES: CNc1ccc2oc(C[C@H]3O[C@@]4(CC[C@H]3C)O[C@H]([C@H](C)C(=O)c3ccc[nH]3)[C@H](C)C[C@H]4C)nc2c1C(=O)O] |
| EE | 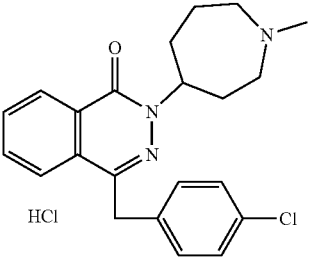 [SMILES: CN1CCCC(n2nc(Cc3ccc(Cl)cc3)c3ccccc3c2=O)CC1 ; Cl] |

TABLE 1-continued

NFκβ Activators/Inducers

| Compound | Structure |
|---|---|
| FF | (5-fluoro-1-methyl pyrimidine nucleoside structure) |
| GG | (sodium 2-hydroxyglutarate structure) |

As used herein, "TLRs" are a class of proteins that play a role in the innate immune system and are an example of pattern recognition receptors. TLRs can be single, membrane-spanning receptors that recognize structurally conserved molecules derived from microbes. TLRs can be expressed on the membranes of leukocytes including, for example, dendritic cells, macrophages, natural killer cells, cells of adaptive immunity (e.g., T and B lymphocytes) and non-immune cells (epithelial and endothelial cells and fibroblasts). Non-limiting examples of TLRs include TLR1, TLR2, TLR3, TLR4, TLR5, TLR6, TLR7, TLR8, TLR9, TLR10, TLR11, TLR12, and TLR13. In some embodiments, a TLR agonist provided herein binds to one or more TLR. In some embodiments, a TLR agonist provided herein binds to TLR7, TLR8, or TLR9. In some embodiments, a TLR agonist provided herein binds to TLR7. In some embodiments, a TLR agonist provided herein binds to TLR7 and TLR8. In some embodiments, an agonist is a ligand that binds to and activates a receptor.

Any therapeutic agent (e.g., drug) suitable for reprogramming activated macrophages (M2-like phenotype) to an M1-like phenotype can be used and the drug (or warhead) may operate in the endosome and/or cytoplasm of the cell (e.g., depending on its structure). In at least one embodiment, the therapeutic agent comprises an immune modulator (e.g., one that positively controls a pattern recognition receptor and/or its downstream signaling pathways (in each case, part of the innate immune system), such as, for example, TLR, NLR, RLR, ALR, RAGE, and/or STING agonists and/or a kinase of the Pelle/interleukin-1 receptor-associated kinase (IRAK) family, such as an IRAK-M inhibitor). In other embodiments, the compound provided herein comprises a phosphoinositide 3-kinase (PI3K) kinase inhibitor or other inhibitor that negatively controls the adaptive immune system (e.g., which may be employed alone or in conjunction with an immune modulator that targets a pattern recognition receptor). In some embodiments, especially when used in the treatment of IPF or other fibrotic conditions, the composition or compound (e.g., drug) comprises a combination of (a) an immune modulator that targets a pattern recognition receptor and/or is an agonist of its downstream signaling pathways of the innate immune system, and (b) a mammalian target of rapamycin (mTOR) inhibitor (ATP-competitive or otherwise) such as, for example, rapamycin or CZ415.

In certain embodiments, provided herein is a compound comprising a targeting moiety (or a radical thereof) attached to an immune modulator (or a radical thereof) that targets a pattern recognition receptor of a cell, the targeting moiety comprising a folate ligand or a functional fragment or analog thereof "Folate" means a folate receptor-binding molecule, including for example folic acid and analogs and derivatives of folic acid such as, without limitation, folinic acid, pteroylpolyglutamic acid, pteroyl-D-glutamic acid, and folate receptor-binding pterdines such as tetrahydropterins, dihydrofolates, tetrahydrofolates, and their deaza and dideaza analogs.

The terms "deaza" and "dideaza" analogs refer to the art-recognized analogs having a carbon atom substituted for one or two nitrogen atoms in the naturally occurring folic acid structure, or analog or derivative thereof. For example, the deaza analogs may include the 1-deaza, 3-deaza, 5-deaza, 8-deaza, and 10-deaza analogs of folate, folinic acid, pteropolyglutamic acid, and folate receptor-binding pteridines such as tetrahydropterins, dihydrofolates, and tetrahydrofolates. The dideaza analogs include, for example, 1,5-dideaza, 5,10-dideaza, 8,10-dideaza, and 5,8-dideaza analogs of folate. Other folates useful as complex forming ligands in the context of the present disclosure are the folate receptor-binding analogs pemetrexed, proguanil, pyrimethamine, trimethoprim, pralatrexed, raltitrexed, aminopterin, amethopterin (also known as methotrexate), $N^{10}$-methylfolate, 2-deamino-dydroxyfolate, deaza analogs such as 1-deazamethopterin or 3-deazamethopterin, and 3',5'-dichloro-4-amino-4-deoxy-$N^{10}$-methylpteroylglutamic acid (dichloromethotrexate).

Folic acid and the foregoing analogs and/or derivatives are also termed "a folate," "the folate," or "folates" reflecting their ability to bind to folate-receptors. As described herein, such molecules, when conjugated with exogenous molecules, are effective to enhance transmembrane transport, such as via folate-mediated endocytosis. The foregoing can be used in the folate receptor-binding ligands described herein. As used herein, the term "ligand" is a molecule, ion, or atom that is attached to the central atom or ion (e.g., a drug) of a compound.

Certain embodiments of novel compounds of the present disclosure will now be provided. It will be appreciated by those of skill in the art that compounds of the present disclosure may exhibit polymorphism. Indeed, the compounds of the present disclosure may comprise any racemic, optically-active, polymorphic, or stereoisomeric form, or mixtures thereof, of a compound described herein that exhibits the useful properties described, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine antitumor activity using the standard tests described herein, or using other similar tests which are well known in the art. Further, unless otherwise expressly stated, structures depicted herein are also meant to include all stereochemical forms of the structure, i.e., the right hand (R) and left hand (S) configurations of each asymmetric center. Therefore, single stereochemical isomers as well as enantiomeric and diasteromeric mixtures of the present compositions are within the scope of the present disclosure.

Specific values listed herein for radicals, substituents, and ranges are for illustration purposes only unless otherwise specified; such examples do not exclude other defined values or other values within defined ranges for the radicals and substituents. For example, $(C_1-C_6)$alkyl can be methyl, ethyl, propyl, isopropyl, butyl, iso-butyl, sec-butyl, pentyl, 3-pentyl, or hexyl; $(C_1-C_3)$alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; $(C_1-C_3)$alkoxy can be methoxy, ethoxy, or propoxy; and $(C_2-C_6)$alkanoyloxy can be acetoxy, propanoyloxy, butanoyloxy, isobutanoyloxy, pentanoyloxy, or hexanoyloxy.

Further, where a moiety is substituted with an R substituent or a substituted group, the group may be referred to as "R-substituted." Where a moiety is R-substituted or is otherwise described as generally comprising a substituted group, the moiety is substituted with at least one R substituent and each substituent is optionally different. It will be appreciated that the substituted group (or R substituent) may comprise any molecule or combination molecules provided the inclusion thereof does not substantially affect the overall structure and shape of the compound, nor alters any hydrogen bonds that are essential to the underlying compound achieving its intended purpose (e.g., binding to a targeted pattern recognition receptor).

Where substituent groups are specified by the conventional chemical formulae, written from left to right, they equally encompass the chemically identical substituents that would results from writing the structure from right to left, e.g., —CH$_2$O— is equivalent to —OCH$_2$—.

In some embodiments, the immune modulator (e.g., TLR7 agonist) group of a compound provided herein is a radical having a structure of Formula XX, and more specifically Formula XX':

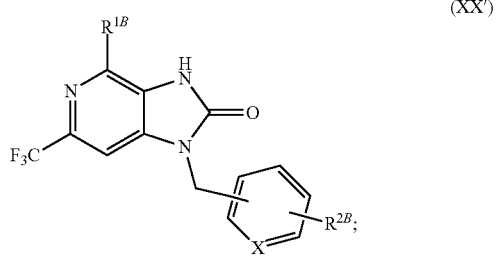

(XX')

wherein, $R^{1B}$ is —NH$_2$ or —NH—R$^{1X}$, $R^{2B}$ is a hydrogen (H), an alkyl, an alkenyl, an alkynyl, an alicyclic, an aryl, a biaryl, a heteroaryl, —NH—R$_{2X}$, —O—R$^{2X}$, —S—R$^{2X}$, $$\begin{array}{c}\xi\\\xi\end{array}-N\begin{array}{c}R^{2X}\\R^{2Y}\end{array} \text{ or } \begin{array}{c}\xi\\\xi\end{array}-N\begin{array}{c}R^{2X}\\R^{2Y}\end{array},$$

each of R$^{1X}$, R$^{2X}$, and R$^{2Y}$ are independently selected from the group consisting of an H, an alkyl, an alkenyl, an alkynyl, an alicyclic, an aryl, a biaryl, and a heteroaryl, and $$\begin{array}{c}\xi\\\xi\end{array}-N\bigcirc$$

is a 3-10 membered N-containing non-aromatic mono- or bicyclic heterocycle, and

X is CH or nitrogen (N).

Alkyl, alkoxy, etc. as used herein denote a straight (i.e., unbranched) or branched chain, or a combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, without limitation, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, without limitation, vinyl, 2-propenyl, crotyl-2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). In some embodiments, alkoxy refers to a radical bonded through an oxygen atom of the formula —O-alkyl.

In general, the term "acyl" or "acyl substituent" refers to a derived by the removal of one or more hydroxyl groups from an oxoacid, including inorganic acids, and contains a double-bonded oxygen atom and an alkyl group. Further, reference to an individual radical such as "propyl" embraces only the straight chain radical, a branched chain isomer such as "isopropyl" being specifically referenced.

In some embodiments, the TLR7 agonist has Formula X, the TLR7 agonist is conjugated to the targeting moiety at any one of R$^{1A}$, R$^{1B}$, R$^{3A}$, or R$^{3B}$ through a linker; and where the TLR7 agonist has Formula XX', the TLR7 agonist is conjugated to the targeting moiety at one of R$^{1A}$, R$^{1B}$, R$^{3A}$, or R$^{3B}$ through a linker.

As used herein, the term "linker" includes a chain of atoms that is bio-functionally adapted to form a chemical bond with an A, B, or S and connects two or more functional parts of a molecule to form a compound of the present disclosure. Illustratively, the chain of atoms may be selected from carbon (C), N, oxygen (O), sulfur (S), silicon (Si), and phosphorus (P), or C, N, O, S, and P, C, N, O, and S. The chain of atoms may covalently connect different functional capabilities of the compound, such as the folate and the drug. The linker may comprise a wide variety of links, such as in the range from about 2 to about 100 atoms in the contiguous backbone, and may comprise a releasable or non-releasable linker. In some embodiments, the immune modulator (e.g., TLR7 agonist) group of a compound provided herein is a radical having a structure of Formula XXX, and more specifically of Formula XXX':

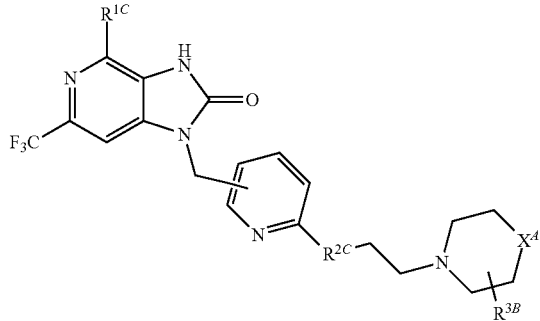

(XXX')

wherein,
$R^{1C}$ is —$NH_2$ or —NH—$R^{1X}$,
$R^{2C}$ is a bond, NH, —$NR^{1X}$, or $CH_2$,
and
if applicable,

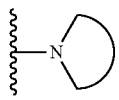

is a 3-10 membered N-containing non-aromatic mono- or bicyclic heterocycle;
$X^A$ is $CH_2$, $NH_2$, or —NH—$R^{1X}$; and
each $R^{1X}$ is independently selected from the group consisting of an H, an alkyl, an alkenyl, an alkynyl, an alicyclic, an aryl, a biaryl, and a heteroaryl,
where the TLR7 agonist is conjugated to the targeting moiety at one of $R^{1C}$, $R^{2C}$, or $R^{3B}$ through a linker.

In some embodiments, the compound further comprises a linker ("L" or "$L_n$") between or otherwise connecting the targeting moiety and the immune modulator. In some embodiments, the linker $L_n$ is configured to avoid release of the immune modulator and n is an integer equal to or less than 50. In some embodiments, the linker $L_n$ comprises a polyethylene glycol (PEG) linker or a PEG derivative linker, n is an integer selected from the range 1-32, and the targeting moiety is specific for folate receptor β. In some embodiments, n is 1-50, 1-10, 2-8, or 2-4.

In some embodiments, L is a hydrolyzable linker. In some embodiments, L is a non-hydrolyzable linker. In some embodiments, L is an optionally substituted heteroalkyl.

The term "alkylene," by itself or as part of another substituent means, unless otherwise stated, a divalent radical derived from an alkyl, as exemplified, but not limited to, —$CH_2CH_2CH_2CH_2$—. Typically, an alkyl (or alkylene) group will have from 1 to 24 carbon atoms. A "lower alkyl" or "lower alkylene" is a shorter chain alkyl or alkylene group, generally having eight or fewer carbon atoms.

The term "heteroalkyl" by itself or in combination with another term means, unless otherwise stated, a stable straight or branched chain, or combination(s) thereof, consisting of at least one carbon atom and at least one heteroatom selected from the group consisting of O, N, P, Si, and S, and wherein the nitrogen and sulfur atoms may optionally be oxidized, and the nitrogen heteroatom may optionally be quarternized. The heteroatom(s) O, N, P, S, and Si may be placed at any interior position of the heteroalkyl group or at the position at which the alkyl group is attached to the remainder of the molecule. Examples include, without limitation, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —$CH_2$—CH—O—$CH_3$, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two heteroatoms may be consecutive, such as, for example, —$CH_2$—NH—$OCH_3$.

Similarly, the term "heteroalkylene" by itself or as part of another substituent, means (unless otherwise stated) a divalent radical derived from heteroalkyl, as exemplified, but not limited by, —$CH_2$—$CH_2$—S—$CH_2$—$CH_2$ and —$CH_2$—S—$CH_2$—$CH_2$—NH—$CH_2$. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —$SO_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

In some embodiments, L is a substituted heteroalkyl comprising at least one substituent selected from the group consisting of alkyl, hydroxyl, oxo, PEG, carboxylate, and halo. "Halo" or "halogen" by itself or as part of another substituent means, unless otherwise stated, a fluorine, chlorine, bromine, or iodine atom.

In some embodiments, L comprises a spacer (e.g., as described elsewhere herein). In some embodiments, the spacer comprises a peptidoglycan or a sugar.

In some embodiments, L is substituted heteroalkyl with at least one disulfide bond in the backbone thereof. In some embodiments, L is a peptide with at least one disulfide bond in the backbone thereof.

The terms "polypeptide," "peptide," and "protein" are used interchangeably herein to refer to a polymer of amino acid residues, a polypeptide, or a fragment of a polypeptide, peptide, or fusion polypeptide. The terms apply to amino acid polymers in which one or more amino acid residue is an artificial chemical mimetic of a corresponding naturally occurring amino acid, as well as to naturally occurring amino acid polymers and non-naturally occurring amino acid polymers.

In some embodiments, L comprises —CONH—CH(COOH)—$CH_2$—S—S—$CH_2$—CR$_a$R$_b$—O—CO—, —CONH—CH(COOH)CR$_a$R$_b$—O—CO—, —C(O)NHCH(COOH) (CH$_2$)$_2$—CONH—CH(COOH)CR$_a$R$_b$—O—CO— or —C(O)NHCH(COOH) (CH$_2$)$_2$—CONH—CH(COOH)—$CH_2$—S—S—$CH_2$—CR$_a$R$_b$—O—CO—,
wherein R$_a$ and R$_b$ are independently H, alkyl, or heteroalkyl (e.g., PEG).

In some embodiments, L comprises a structure of:

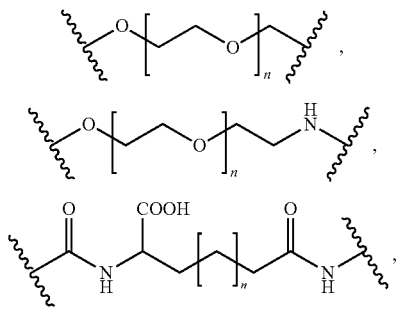

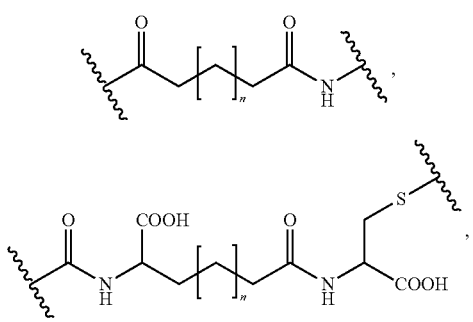

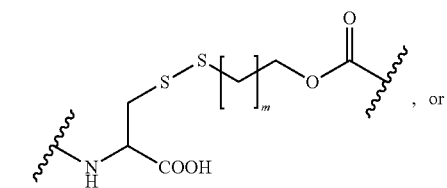

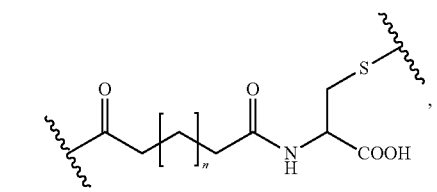

wherein n and m are each independently 0 to 10.

In some embodiments, the L comprises a structure of:

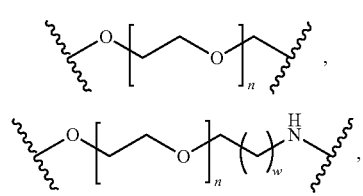

-continued

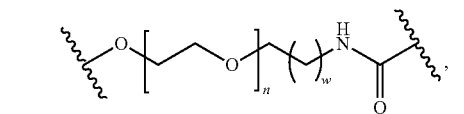

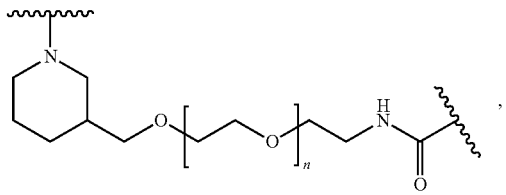

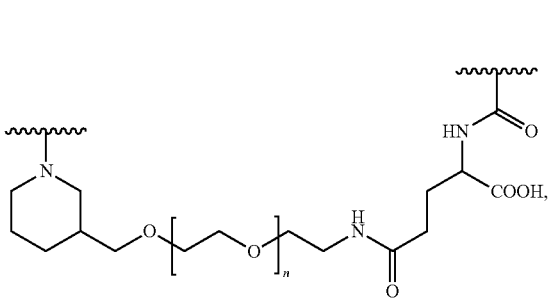

wherein n is 1 to 32. In at least one exemplary embodiment, n is 1 to 30 and w is 0 to 5.

In some embodiments, the L comprises the structure of:

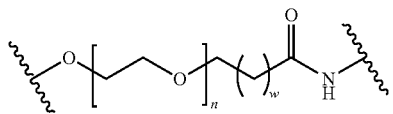

wherein n is 1 to 30 and w is 0 to 5.

In some embodiments, the compound has a structure represented by the formula:

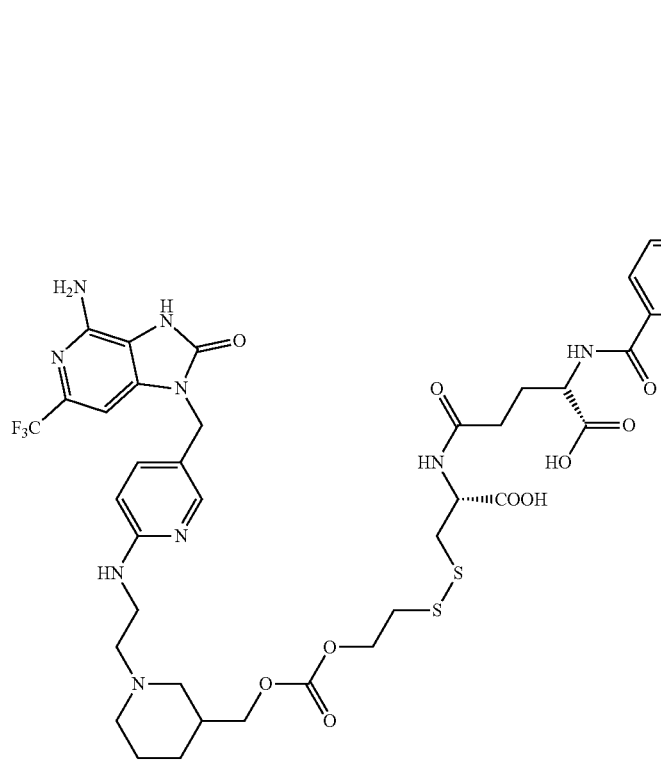
In some embodiments, the compound has a structure represented by the formula:
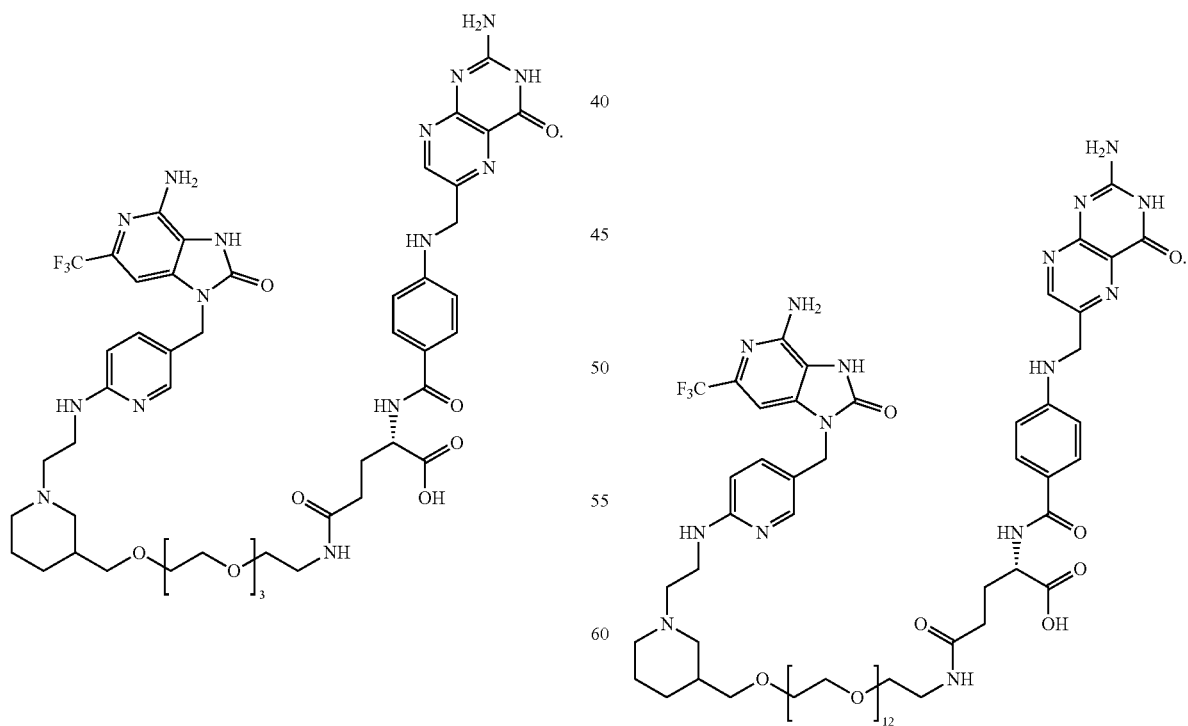
In some embodiments, the compound has a structure represented by the formula:
In some embodiments, the compound has a structure represented by the formula:

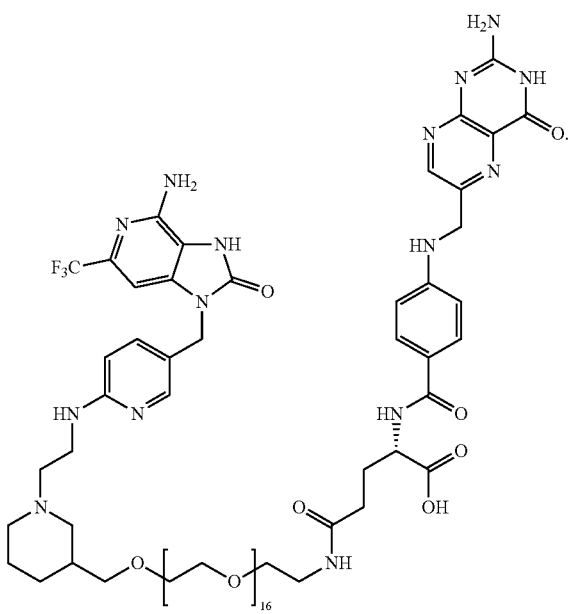

In certain embodiments, provided herein is a compound comprising a targeting moiety comprising a folate ligand or a functional fragment or analog thereof attached to an immune modulator comprising a TLR agonist via a linker, the TLR agonist having the following structure represented by formula XXX:

(XXX)

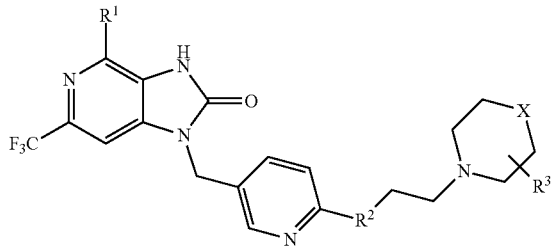

wherein $R^1$ is an amine group, $R^2$ is a single bond —NH—, and $R^3$ is an H, an alkyl, a hydroxy group, or any other substituted group thereof, X is a $CH_2$, NH, O, or S, and the linker is attached at $R^1$, $R^2$ or $R^3$. Additionally or alternatively, $R_1$ may be —$NH_2$ or —NH—$R_{1X}$; $R_2$ may be an H, an alkyl, an alkenyl, an alkynyl, an alicyclic, an aryl, a biaryl, a heteroaryl, —NH—$R_{2X}$, —O—$R_{2X}$, —S—$R_{2X}$,

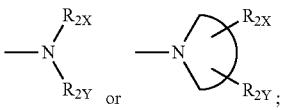

each of $R_{1X}$, $R_{2X}$, and $R_{2Y}$ may be independently selected from the group consisting of an H, an alkyl, an alkenyl, an alkynyl, an alicyclic, an aryl, a biaryl, and a heteroaryl;

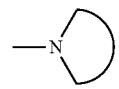

may be a 3-10 membered N-containing non-aromatic mono- or bicyclic heterocycle; and/or X may be CH, $CR_2$, or N.

In some embodiments, provided herein is a pharmaceutical composition comprising any formula or compound provided herein, wherein the linker comprises PEG or a PEG derivative and, in some instances, is either a non-releasable linker attached at $R^3$ or is a releasable linker attached at $R^1$, $R^2$ or $R^3$.

In some embodiments, the pharmaceutically acceptable salt is selected from hydrobromide, citrate, trifluoroacetate, ascorbate, hydrochloride, tartrate, triflate, maleate, mesylate, formate, acetate or fumarate.

In some embodiments, the compound comprises a TLR agonist (e.g., a radical thereof), for example and without limitation, a TLR3 agonist, a TLR7 agonist, a TLR7/8 agonist, a TLR8 agonist, or a TLR9 agonist (e.g., all of which bind with a toll-like receptors present within the endosome of a cell). For example, and without limitation, in at least one exemplary embodiment, the immune modulator of the drug/compound may be selected from the compounds listed in Table 2 below.

TABLE 2

| | TLR agonists. | |
|---|---|---|
| Compound | Structure/Description | Type |
| A | (structure shown) | TLR7 agonist |

TABLE 2-continued

TLR agonists.

| Compound | Structure/Description | Type |
|---|---|---|
| B | 4-amino-1-isobutyl-1H-imidazo[4,5-c]quinoline | TLR7 agonist |
| C | 4-amino-2-ethyl-1-[4-(methylsulfonamido)butyl]-1H-imidazo[4,5-c]quinoline | TLR7 agonist |
| D | 2-[4-[(6-amino-2-(butylamino)-8-hydroxy-9H-purin-9-yl)methyl]benzamido]acetic acid | TLR7 agonist |
| E | 6-amino-2-(butylamino)-9-[[4-[[[2-[[3-[[4-[(3-aminopropyl)amino]butyl]amino]propyl]amino]-2-oxoethyl]carbamoyl]phenyl]methyl]-8-hydroxy-9H-purine | TLR7 agonist |
| F | 4-amino-2-[(ethylamino)methyl]-1-(2-hydroxy-2-methylpropyl)-1H-imidazo[4,5-c]quinoline | TLR7 agonist |

TABLE 2-continued

TLR agonists.

| Compound | Structure/Description | Type |
|---|---|---|
| G | [chemical structure: 7-allyl-8-oxo-guanosine derivative] | TLR7 agonist |
| H | [chemical structure: 5-bromo-6-phenyl-2-amino-pyrimidin-4(1H)-one] | TLR7 agonist |
| I | [chemical structure: long-chain fatty amide linked to butyl-imidazoquinoline amine] | TLR7 agonist |
| J | [chemical structure: 6-amino-2-butylamino-8-oxo-purine with pyridyl-oxyethyl-dimethylamine substituent] | TLR7 agonist |
| K | [chemical structure: 6-amino-2-ethoxy-8-oxo-purine with pyridyl-oxyethyl-dimethylamine substituent] | TLR7 agonist |
| L | [chemical structure: 2-(2-methoxyethoxy)-6-amino-8-hydroxy-purine with benzyl-amide-succinic acid linker] | TLR7 agonist |

TABLE 2-continued
TLR agonists.
| Compound | Structure/Description | Type |
|---|---|---|
| M | 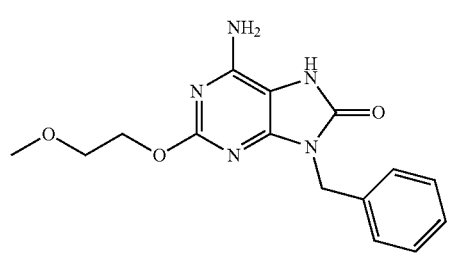 [SMILES: COCCOc1nc(N)c2[nH]c(=O)n(Cc3ccccc3)c2n1] | TLR7 agonist |
| N | 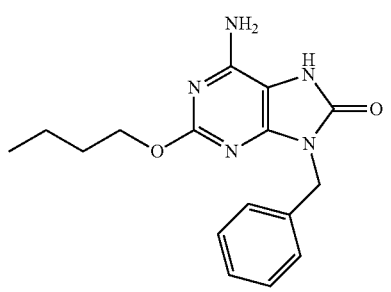 [SMILES: CCCCOc1nc(N)c2[nH]c(=O)n(Cc3ccccc3)c2n1] | TLR7 agonist |
| O | 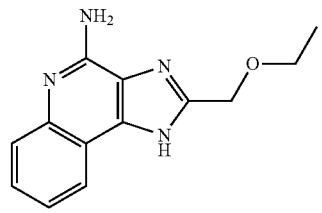 [SMILES: CCOCc1nc2c(N)nc3ccccc3c2[nH]1] | TLR7/8 agonist |
| P | 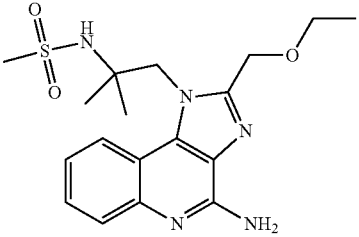 [SMILES: CCOCc1nc2c(N)nc3ccccc3c2n1CC(C)(C)NS(C)(=O)=O] | TLR7/8 agonist |
| Q | See, e.g., Lipanov et al., "The structure of poly(dA): poly(dT) in a condensed state and in solution," Nucleic Acids Research 15 (14): 5833-5844 (1987). | TLR7/8 agonist |
| R | 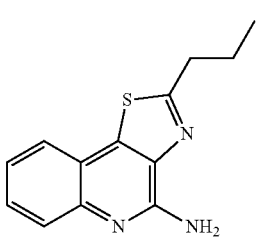 | TLR8 agonist |

TABLE 2-continued

TLR agonists.

| Compound | Structure/Description | Type |
|---|---|---|
| S | [Chemical structure] | TLR8 agonist |
| T | [Chemical structure] | TLR8 agonist |
| U | Short synthetic single-stranded DNA molecules containing unmethylated CpG dinucleotides in particular sequence contexts (CpG motifs) (CpG ODN) | TLR9 agonist |
| V | Synthetic oligonucleotide containing unmethylated CpG dinucleotides with potential immuno-potentiating activity (IMO 2005) | TLR9 agonist |
| W | Short, synthetic, unmethylated CpG oligodeoxynucleotide (CpG ODN) with immunostimulatory activity (1018-ISS) | TLR9 agonist |
| X | Comprises a strand of inosine poly(I) homopolymer annealed to a strand of cytidine (poly(I:C)) | TLR3 agonist |
| Y | Poly(C)homopolymer | TLR3 agonist |
| Z | [Chemical structure] | TLR7 agonist |

In some embodiments, a compound provided herein is or comprises a compound (or radical) (e.g., TLR7 agonist) of formula I:

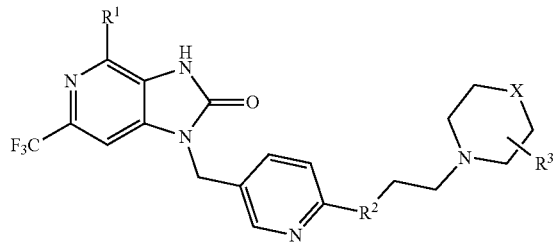

(I)

or a pharmaceutically acceptable salt thereof. In some embodiments, $R^1$ is an amine. In some embodiments, $R^2$ is a (e.g., single) bond, or an amine (e.g., —NH—). In certain embodiments, $R^3$ is an H, an alkyl, a hydroxy group, or any other suitable substituent (e.g., as described herein). In some embodiments, X is $CH_2$, NH, O, or S. In some embodiments wherein a compound provided herein comprises a radical of formula I, a targeting moiety is conjugated or connected thereto at any suitable location, such as at or through $R^1$, $R^2$, and/or $R^3$ (e.g., through a linker and/or directly).

In at least one exemplary embodiment, a compound described herein is or comprises a compound (or radical) (e.g., TLR7 agonist) of formula Ia:

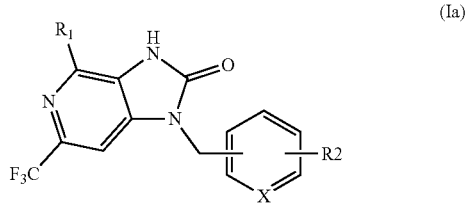

(Ia)

or a pharmaceutically acceptable salt thereof. In some embodiments, X is a CH or an N. In some embodiments, $R_1$ is —$NH_2$ or —NH—$R_{1X}$. In some embodiments, $R_2$ is H, alkyl, alkenyl, alkynyl, alicyclic, aryl, biaryl, heteroaryl, —NH—$R_{2X}$, —O—$R_{2X}$, —S—$R_{2X}$,

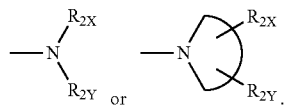

In specific embodiments, each of $R_{1X}$, $R_{2X}$, and $R_{2Y}$ are independently selected from the group consisting of H, alkyl, alkenyl, alkynyl, alicyclic, aryl, biaryl, and heteroaryl. In some embodiments,

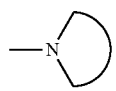

is a 3-10 membered N-containing non-aromatic mono- or bicyclic heterocycle. In some embodiments wherein a compound provided herein comprises a radical of formula Ia, a targeting moiety is conjugated or connected thereto at any suitable location, such as at or through $R^1$, $R^2$, and/or $R^3$ (e.g., through a linker and/or directly).

In some embodiments, a compound provided herein is or comprises a compound (or radical) (e.g., TLR7 agonist) of formula II:

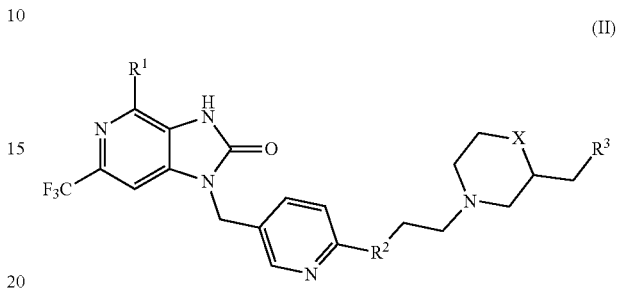

(II)

or a pharmaceutically acceptable salt thereof. In some embodiments, $R^1$ is an amine. In some embodiments, $R^2$ is a (e.g., single) bond or —NH—. In some embodiments, $R^3$ is H, alkyl, hydroxy group, or any other substituent, such as described herein. In some embodiments, X is a $CH_2$, NH, O, or S. In some embodiments wherein a compound provided herein comprises a radical of formula II, a targeting moiety is conjugated or connected thereto at any suitable location, such as at or through $R^1$, $R^2$, and/or $R^3$ (e.g., through a linker and/or directly).

In other embodiments, compounds of the present disclosure may include a drug comprising the TLR agonist (e.g., or a radical thereof) of formula III or a pharmaceutically acceptable salt thereof:

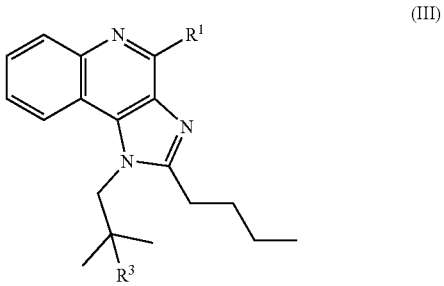

(III)

wherein, $R^1$ is an amine group and $R^3$ is a hydroxy group. Further, if desired, a targeting moiety (e.g., or a radical thereof) or other ligand may be conjugated to the agonist of formula III at $R^1$ or $R^3$ (through a linker or directly). The TLR agonist (e.g., or radical thereof) of formula III is a TLR7 agonist and at least ten times (10×) as potent as the TLR7 agonists conventionally available.

Provided in some embodiments herein is a TLR7 agonist (e.g., or radical thereof) of formula IV or a pharmaceutically acceptable salt thereof:

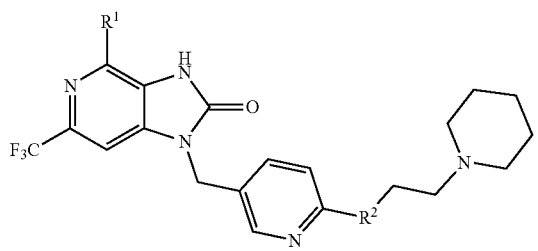

(IV)

wherein R¹ is an amine group and R² is a single bond —NH—.

In some embodiments, administration of the compounds provided herein (e.g., to an individual) convert a macrophage in fibrotic tissue from an M2-like phenotype to an M1-like phenotype. In some embodiments, a decrease in cytokines that stimulate collagen synthesis (i.e., CCL18, PDGF, and IL-1β) occurs after administration of a compound provided herein, as well as the concurrent increase in cytokines that inhibit collagen production (e.g., IFN-γ). Notably, in at least one embodiment, after administration of a compound provided herein the cytokine profiles are consistent with the reprogramming of the M2-like phenotype to the M1-like phenotype. As used herein, a "profile" or "assay" is a set of one or more markers and their presence, absence, and/or relative level or abundance (relative to one or more controls). For example, a cytokine profile is a dataset of the presence, absence, relative level or abundance of cytokines present within a sample. A genomic or nucleic acid profile is a dataset of the presence, absence, relative level or abundance of expressed nucleic acids (e.g., transcripts, mRNA, or the like). A profile may alternatively be referred to as an expression profile.

In some embodiments, the net consequences of the reprogramming is an increase in alveolar air sacs, a decrease in extracellular matrix deposition, and a reduction in hydroxyproline/collagen biosynthesis; an effective reversal of the disease (e.g., see Example 4).

It is to be understood that while particular drugs and formulae are described herein, any compound (e.g., drug) useful for reprogramming activated myeloid cells into an antifibrotic M1-like phenotype may be used in the novel compounds and methods hereof (for example, any compound (e.g., drug) capable of binding with a pattern recognition receptor and inhibiting at least a portion of the innate immune system response downstream thereof). In some embodiments, analogs and/or derivatives a compound described herein may be used in the targeting compounds provided herein.

Further, more than one compound can be administered and, in some instances, the compounds can comprise different drugs. For example, the different drugs can be selected from a TLR7 agonist and a TLR9 agonist. In yet another embodiment, one or more compounds can be administered in a composition along with one or more conjugated and/or unconjugated drugs (e.g., conjugated embodiments described below). In some embodiments, any of the compounds and drugs described herein may be used in accordance with the methods described herein and, in some instances, depending on the desired application, may be combined with other drugs that deplete or inhibit myeloid-derived suppressor cells (e.g., in connection with treatment for cancer), downregulate the production of growth factors (e.g., pirfenidone in connection with treatment of IPF), directly modifies the fibroblasts via inhibiting mammalian target of rapamycin complex 1 (mTORC1) signaling (e.g., CZ415 in connection with treatment of IPF or other fibrotic disease states), and/or any other antifibrotic and/or anticancer drugs and therapies. As used herein, "downregulation" and its formatives (such as "down-regulation" or "down-regulated," for example) may be used interchangeably and refer to a decrease in the level of a marker, such as a gene, nucleic acid, metabolite, transcript, protein, or polypeptide. Similarly, "upregulation" and its formatives ("p-regulation" or "up-regulated," for example) may also be used interchangeably and refer to an increase in the level of a marker, such as a gene, nucleic acid, metabolite, transcript, protein, or polypeptide. Also, a pathway, such as a signal transduction or metabolic pathway may be up- or down-regulated.

Targeting Moieties

In some instances, toxicities associated with systemic administration of at least the conventional drugs identified herein has precluded their practical application with respect to treating fibrotic diseases, cancers, or any other disease state. For example, TLR agonists may not be tolerated by an individual and, in some instances, can result in the death of a subject (e.g., if administered systemically via conventional modalities). In some embodiments, the compounds provided herein, such as, for example, those having formulas I and/or II, are significantly more potent than the conventional drugs that can be used with the compounds of the present disclosure, and, in some instances, a mechanism for circumventing systemic toxicity is preferable.

In certain embodiments, provided herein is a therapeutic agent (e.g., a drug (as previously described)) conjugated to a targeting moiety. In some embodiments, the targeting moiety comprises a ligand or other atom or molecule that targets a particular area or tissue of an individual (e.g., with high specificity) and, in certain instances, may, for example, comprise hormones, antibodies, and/or vitamins. As described in further detail below, in at least one embodiment, the targeting moiety comprises a molecule that has (e.g., a high) affinity for FRβ. In some instances, the targeting moiety has a specific affinity for any receptor that is particular to cells or tissues of a fibrotic disease or a cancer, as appropriate.

In some instances, FRβ is significantly upregulated in activated myeloid cells (e.g., predominantly activated monocytes and M2-like macrophages), for example, with all recorded data to date supporting that FRβ is only induced in cells of myelogenous origin following exposure to anti-inflammatory or proinflammatory stimuli. The folate receptor can be upregulated in (e.g., more than 90%) of non-mucinous ovarian carcinomas. In certain instances, the folate receptor is present in kidney, brain, lung, and breast carcinoma. For example, although there are a number of cancers that do not themselves express the folate receptor in sufficient numbers to provide the desired specificity, cancerous tumors do express myeloid-derived suppressor cells (MDSCs), for example, which do express FRβ and, for example, can be targeted by a targeting moiety provided herein. In some embodiments, folate receptors are not substantially present (e.g., present only at extremely low levels) in healthy (non-myeloid) tissues (e.g., whether lungs, liver, spleen, heart, brain, muscle, intestines, pancreas, bladder, etc.). In some instances, even quiescent tissue-resident macrophages that are abundant throughout the body are predominantly FRβ-negative. In some instances, uptake of folate-targeted imaging agents is in, for example, inflamed tissues, malignant lesions, and the kidneys. In certain instances, subjects devoid of cancer only retain folate-targeted drugs in the kidneys and sites of inflammation. In some instances, the discrepancy in folate receptor expression provides a mechanism for selectively targeting fibrotic cancer cells.

In some embodiments, the compounds and methods provided herein leverage the limited expression of FRβ to target/localize systemically administered potent compounds (e.g., conjugates or drugs) to fibrotic and/or cancerous tissue. In some instances, the compounds provided herein are delivered directly to FRβ expressing cells, for example, which advantageously prevents the systemic activation of the immune system and, for example, can avoid (e.g., at least a portion of) the toxicity that has heretofore prevented systemic use of non-targeting compounds (e.g., drugs) described herein. In some embodiments, the methods described herein are used to treat fibrotic diseases and/or cancers, for example, regardless of if the cancer expresses the folate receptor. In some embodiments, folic acid and other folate receptor binding ligands (or radicals thereof), such as, for example folate, are used as targeting moieties, since for example, they have affinity for FRβ.

Folic acid is a member of the B family of vitamins and can play an essential role in cell survival, for example, by participating in the biosynthesis of nucleic and amino acids. Folic acid can enhance the specificity of conjugated immune modulator drugs by targeting activated myeloid cells and conjugated anti-cancer drugs by targeting folate receptor-positive cancer cells. Provided herein in some instances are compounds comprising a folate ligand (or radical thereof), or a functional fragment or analog thereof, as a targeting moiety and an immune modulator (e.g., TLR7, TLR8, TLR 7/8, TLR9, or TLR3 agonist). In some instances, TLR7, TLR8, TLR 7/8, TLR9, and TLR3 are present in the endosome. In some embodiments, the compound, or radical thereof, binds to a TLR. In some embodiments, the TLR is TLR7.

A pyrido[2,3-d]pyrimidine analog ligand (e.g., or radical thereof), a functional fragment or analog thereof, or any other molecule, fragment or atom with a affinity (for example, and without limitation, a high specificity) for FRβ may alternatively be used as the targeting moiety (or radical thereof). For example, such folate analog molecules may have a relative affinity for binding FRβ of about 0.01 or greater as compared to folic acid at a temperature about 20° C./25° C./30° C./physiological. Similarly, a Galectin-3 ligand, a translocator protein (TSPO) ligand, and any other ligand or targeting moiety with a highly specific affinity for fibrotic and/or cancerous cells or tissue may be employed.

Specific examples of suitable targeting moieties (or radicals thereof) will now be provided; however, it will be understood that the targeting moiety (or radical thereof) of the present disclosure may comprise any ligand (or radical thereof) useful to target FRβ and is not limited to the structures specified herein. The ligand (or radical thereof) may bind to FRβ.

In at least one embodiment, compounds provided herein include a targeting moiety (or radical thereof) has a structure of formula V or a functional fragment or analog thereof:

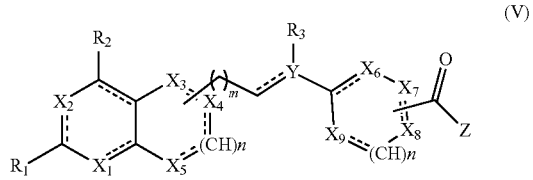

(V)

wherein
$X_1$, $X_2$, $X_3$, $X_4$, $X_5$, $X_6$, $X_7$, $X_8$, and $X_9$ are each independently N, NH, CH, $CH_2$, O, or S;
Y is C, CH, $CH_2$, N, NH, O, or S;
Z is glutamic acid, valine, or a substrate;
$R_1$ and $R_2$ are each independently $NH_2$, OH, SH, $CH_3$, or H;
$R_3$ is hours or an alkyl;
m and n are each independently 0, 1, or between 0 and 1; and
⤳ is representative of either a single or double bond C—C.

In a further aspect, by way of nonlimiting example, the targeting moiety (or radical thereof) of formula V has a structure of VI (or a functional fragment or analog thereof):

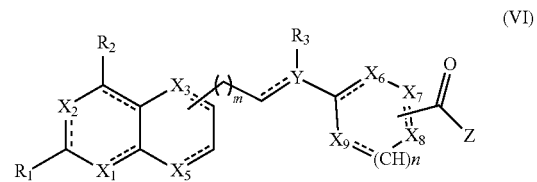

(VI)

wherein
$X_1$, $X_2$, $X_3$, $X_5$, $X_6$, $X_7$, $X_8$, and $X_9$ are each independently N, NH, CH, $CH_2$, O, or S;
Y is C, CH, $CH_2$, N, NH, O, or S;
Z is glutamic acid, valine, or a substrate;
$R_1$ and $R_2$ are each independently $NH_2$, OH, SH, $CH_3$, or H;
$R_3$ is hours or an alkyl;
m and n are each independently 0, 1, or between 0 and 1; and
⤳ is representative of either a single or double bond C—C.

Another specific targeting moiety (or radical thereof) of formula V (or a functional fragment or analog thereof) has a structure of formula VII:

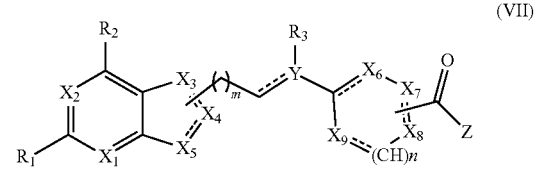

(VII)

wherein
$X_1$, $X_2$, $X_3$, $X_4$, $X_5$, $X_6$, $X_7$, $X_8$, and $X_9$ are each independently N, NH, CH, $CH_2$, O, or S;
Y is C, CH, $CH_2$, N, NH, O, or S;
Z is glutamic acid, valine, or a substrate;
$R_1$ and $R_2$ are each independently $NH_2$, OH, SH, $CH_3$, or H;
$R_3$ is hours or an alkyl;
m and n are each independently 0, 1, or between 0 and 1; and
⤳ is representative of either a single or double bond C—C.

In some embodiments, the targeting moiety (or radical thereof) of formula VI has the structure of formula VIII:

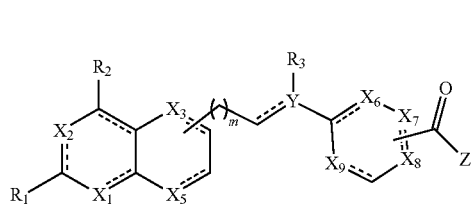

(VIII)

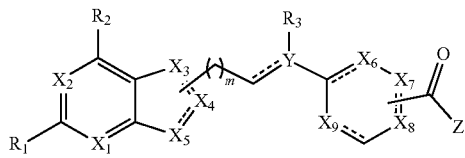

(X)

wherein $X_1, X_2, X_3, X_5, X_6, X_7, X_8$, and $X_9$ are each independently N, NH, CH, $CH_2$, O, or S;

Y is C, CH, $CH_2$, N, NH, O, or S;

Z is glutamic acid, valine, or a substrate;

$R_1$ and $R_2$ are each independently $NH_2$, OH, SH, $CH_3$, or H;

$R_3$ is hours or an alkyl;

m is 0, 1, or between 0 and 1; and

⇜ is representative of either a single or double bond C—C.

In some embodiments, the targeting moiety (or radical thereof) of formula VI has the structure of formula IX:

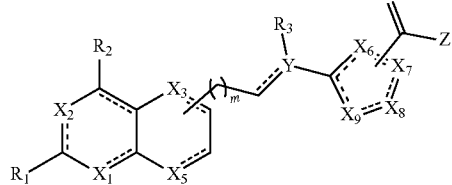

(IX)

wherein $X_1, X_2, X_3, X_5, X_6, X_7, X_8$, and $X_9$ are each independently N, NH, CH, $CH_2$, O, or S;

Y is C, CH, $CH_2$, N, NH, O, or S;

Z is glutamic acid, valine, or a substrate;

$R_1$ and $R_2$ are each independently $NH_2$, OH, SH, $CH_3$, or H;

$R_3$ is hours or an alkyl;

m is 0, 1, or between 0 and 1; and

⇜ is representative of either a single or double bond C—C.

In some embodiments, the targeting moiety (or radical thereof) of formula VII has the structure of formula X or XI:

wherein $X_1, X_2, X_3, X_4, X_5, X_6, X_7, X_8$, and $X_9$ are each independently N, NH, CH, $CH_2$, O, or S;

Y is C, CH, $CH_2$, N, NH, O, or S;

Z is glutamic acid, valine, or a substrate;

$R_1$ and $R_2$ are each independently $NH_2$, OH, SH, $CH_3$, or H;

$R_3$ is hours or an alkyl;

m is 0, 1, or between 0 and 1; and

⇜ is representative of either a single or double bond C—C; or

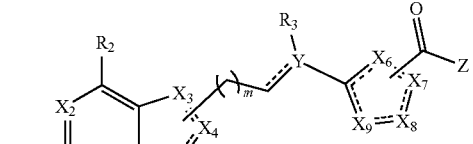

(XI)

wherein $X_1, X_2, X_3, X_4, X_5, X_6, X_7, X_8$, and $X_9$ are each independently N, NH, CH, $CH_2$, O, or S;

Y is C, CH, $CH_2$, N, NH, O, or S;

Z is glutamic acid, valine, or a substrate;

$R_1$ and $R_2$ are each independently $NH_2$, OH, SH, $CH_3$, or H;

$R_3$ is hours or an alkyl;

m is 0, 1, or between 0 and 1; and

⇜ is representative of either a single or double bond C—C.

The chemical structures and spectroscopic data of some additional embodiments of a targeting moiety (e.g., or radicals thereof) of the present disclosure are provided in the following Table 3, Table 4, Table 5 and Table 6.

Table 3 provides non-limiting examples of additional embodiments of a targeting moiety (e.g., or radicals thereof) having the structure of formula VIII.

TABLE 3

| Ligand | Structure |
|---|---|
| a | (folic acid structure) |
| b | (methotrexate structure) |
| c | (5-formyl tetrahydrofolate/folinic acid structure) |
| d | (5-formyl tetrahydrofolate isomer structure) |
| e | (aminopterin-alkyne analog structure) |

TABLE 3-continued
Formula VIII
| Ligand | Structure |
|---|---|
| f | 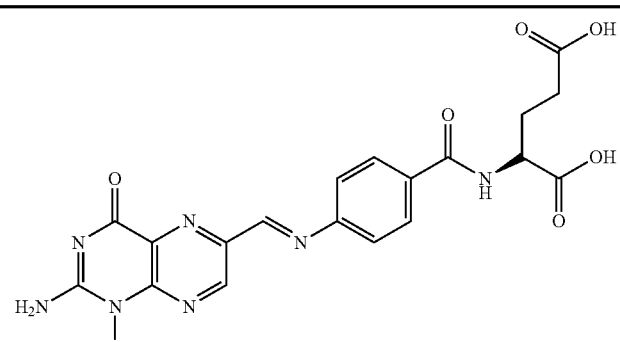 |
| g | 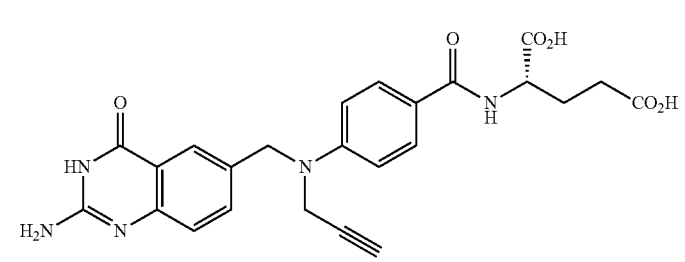 [SMILES: C#CCN(Cc1ccc2nc(N)[nH]c(=O)c2c1)c1ccc(C(=O)N[C@@H](CCC(=O)O)C(=O)O)cc1] |
| h | 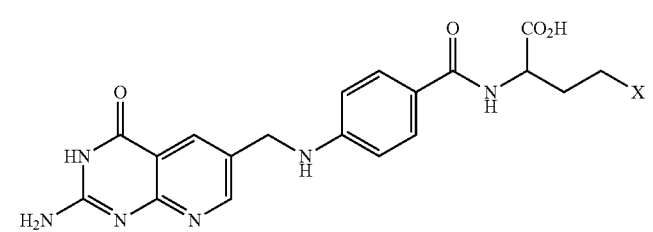
wherein X is PO(OH)$_2$, CH$_2$NH$_2$, or SO$_2$OH |
| i | 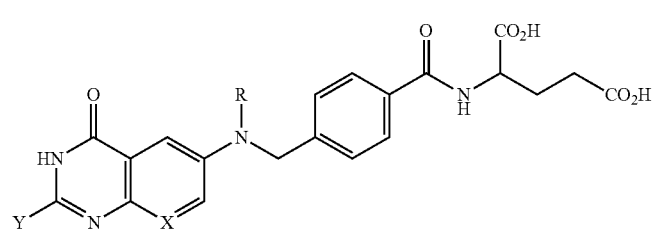
wherein X is N or CH; Y is NH$_2$, H, or CH$_3$; and R is H, CH$_3$, or CHO |
| j | 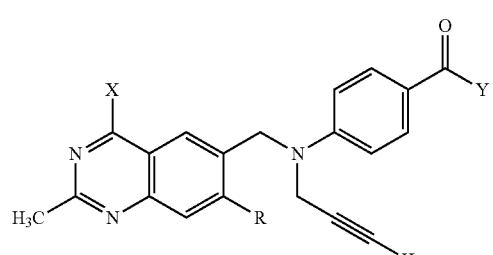
wherein X is OH or OCH$_3$; R is hours or CH$_3$; and
Y is glutamic acid, valine, or a substrate. |

Table 4 provides non-limiting examples of additional embodiments of a targeting moiety (e.g., or radicals thereof) having the structure of formula IX.

TABLE 4

Formula IX

| Ligand | Structure |
|---|---|
| aa | *(structure: pterin-CH=N-imidazole-C(O)NH-glutamate)* |
| bb | *(structure: pterin-CH=N-oxazole-C(O)NH-glutamate)* |
| cc | *(structure: pterin-CH=N-thiazole-C(O)NH-glutamate)* |
| dd | *(structure: pterin-CH=N-indole-C(O)NH-glutamate)* |
| ee | *(structure: pterin-CH=N-benzofuran-C(O)NH-glutamate)* |
| ff | *(structure: pterin-CH=N-benzothiophene-C(O)NH-glutamate)* |

Table 5 provides non-limiting examples of additional embodiments of a targeting moiety having the structure of formula X.

TABLE 5

Formula X

| Ligand | Structure |
| --- | --- |
| aaa | 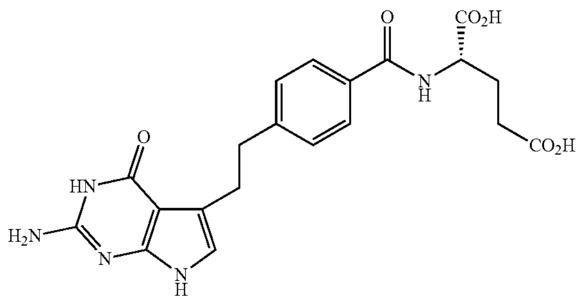 [SMILES: Nc1nc2[nH]cc(CCc3ccc(C(=O)N[C@@H](CCC(=O)O)C(=O)O)cc3)c2c(=O)[nH]1] |
| bbb | 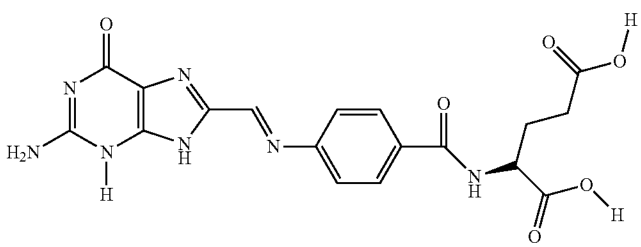 |
| ccc | 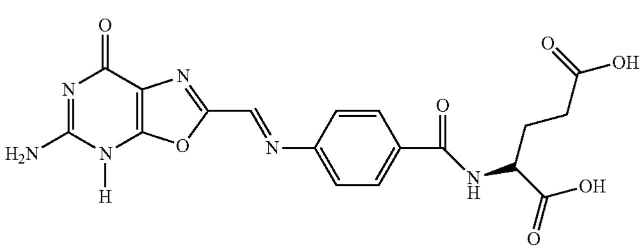 |
| ddd | 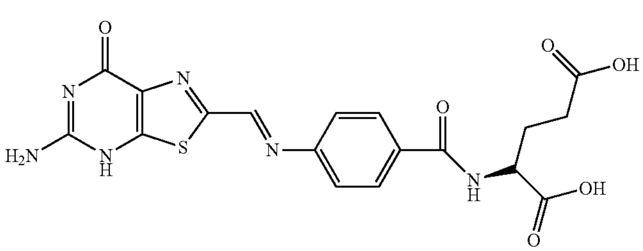 |

As previously noted, instead of a folate, the targeting moiety (e.g., a radical thereof) may be one or more nonclassical antifolate analogs such as, for example, pyrido[2,3-d]pyrimidine or similar analogs (or radicals thereof) having the formulas (e.g., radicals of the formulas) set forth in Table 6 below (or an analog or functional fragment thereof):

TABLE 6

Nonclassical antifolate analogs

| Ligand | Formula |
|---|---|
| aaaa | [structure with pyrimidine, NH2, NO2, Et, R groups]<br>wherein R is NH2 or NHMe or NHCH(CO2Et)(CH2)2CO2Et or NHCH(CO2Et)(CH2)2CO2H or [piperidine structure] |
| bbbb | [pyrido-pyrimidine structure with R1, R2]<br>wherein<br>R1 is 3,4,5-(OCH3)3 or 3,4-(OCH3)2 or 4-OCH3;<br>R2 is an hours or alkyl chain or CHO; and ⇌ is representative of either a single or double bond C—C. |
| cccc | [structure with R2, R3]<br>wherein n is 0 or 1;<br>R1 and R2 are each independently an hours or an alkyl; and R3 is an hours or 3',4',5'-OMe or 2',3',4'-OMe or 2',4',5'-OMe or 2',4',6'-OMe or 3',4'-OMe or 3',5'-OMe or 2',5'-OMe or 2',3'-C4H4 or 4'-OMe, 2',3'-C4H4 or 6'-OMe, 2',3'-C4H4 or 4'-O-C6H5 or 4'-CONH-L-glutamic acid. |
| dddd | [quinazoline structure with R1, R2, R3, (CH2)n, phenyl]<br>wherein n is 0 or 1; R1 is CH3, Cl or OCH3; R2 is hours or OCH3; and R3 is one of the following: |

TABLE 6-continued

Nonclassical antifolate analogs

| Ligand | Formula |
|---|---|
| | [thiazole with methyl, NH2]  [thiazole with EtOOC, methyl, NH2]<br>[pyridine with COOH]  [benzene with COOH, methyl, NO2] |
| eeee | [triazole-thiazole-thiourea structure with R groups]<br>wherein<br>R is H, 4-Cl, 2-CH3O, 4-CH3O, 2,4-(CH3O)2, 4-CH3, or 4-C6H5O. |
| ffff | [structure with thiazole, acetamide, R]<br>wherein<br>R is H, 4-Cl, 2-CH3O, 4-CH3O, 2,4-(CH3O)2, 4-CH3, or 4-C6H5O. |
| gggg | [structure with thiazole, acetamide, R]<br>wherein<br>R is H, 4-Cl, 2-CH3O, 4-CH3O, 2,4-(CH3O)2, 4-CH3, or 4-C6H5O. |
| hhhh | [triazole-thiazole structure with HS, R, NH2] |

TABLE 6-continued

Nonclassical antifolate analogs

| Ligand | Formula |
|---|---|
| | wherein R is H, 4-Cl, 2-$CH_3O$, 4-$CH_3O$, 2,4-($CH_3O)_2$, 4-$CH_3$, or 4-$C_6H_5O$. |
| iiii | 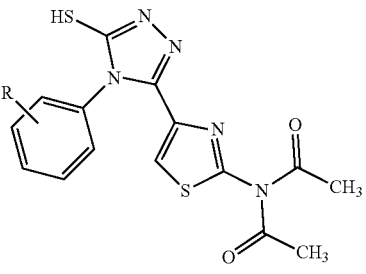 wherein R is H, 4-Cl, 2-$CH_3O$, 4-$CH_3O$, 2,4-($CH_3O)_2$, 4-$CH_3$, or 4-$C_6H_5O$. |
| jjjj | 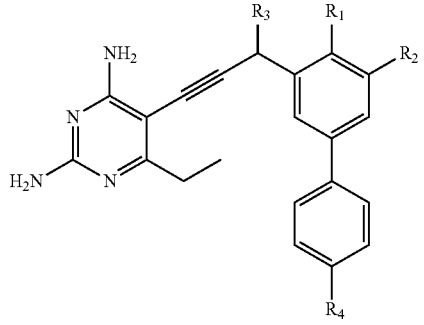 wherein $R_1$ and $R_2$ are each independently hours or OMe; $R_3$ is hours or an alkyl; and $R_4$ is o-COOH or m-COOH or p-COOH. |
| kkkk | 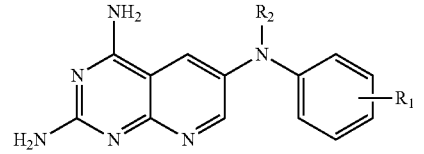 wherein $R_1$ is hours or 2'-OMe or 4'-OMe or 2',5'-diOMe or 3',4',5'-triOMe or 4'-Me or 4'-i-Pr or 3',4'-($C_4H_4$) or 2',3'-($C_4H_4$) or 4'-$NO_2$ or 2',5'-diF or 3',4,'5'-triF; and $R_2$ is hours or an alkyl. |

In some instances, the compounds provided herein comprise a drug (e.g., a radical thereof) (e.g., an immune modulator) conjugated with a targeting moiety (e.g., a radical thereof). The immune modulator (e.g., a radical thereof) may be conjugated directly to the targeting moiety (e.g., a radical thereof) or through a linker (e.g., optionally comprising a spacer). FIG. 1A shows at least one embodiment of a compound 100. Here, compound 100 comprises an immune modulator (or drug or radical thereof) 102, for example, having formula I, where $R^3$ is a hydroxy group. The immune modulator (e.g., a radical thereof) 102 is conjugated to a targeting moiety (e.g., radical thereof) 104 through a linker 106. Here, the targeting moiety (e.g., a radical thereof) 106 is a folate and the (e.g., non-releasable) linker 106 is a PEG linker repeated n times, wherein n is between 1 and 32.

In at least one embodiment, and without limitation, the compound 100 may be represented by the formula: Q-L-T, wherein Q is a radical of a folate receptor binding ligand/targeting moiety 104, L is a linker 106, and T is a radical of a TLR agonist/immune modulator 102. The linker L may comprise any of the linker formulae presented herein.

Similarly, FIG. 1B shows at least one embodiment of compound 150. Compound 150 has an immune modulator/drug (e.g., a radical thereof) 152 that is a TLR7 agonist (e.g., a radical thereof), e.g., having formula III, conjugated to a targeting moiety (e.g., a radical thereof) 154 through a (e.g., releasable) linker 156.

The linker (L or $L_n$) may be releasable or non-releasable. In some instances, the target for a compound comprising a non-releasable linker is the endosome (e.g., of the cell of interest), for example, whereas the target for a releasable linker, in some instances, the endosome, the cytoplasm, or both (e.g., of the cell of interest).

In at least one exemplary embodiment, the linker $L_n$ is disposed between the targeting moiety (e.g., a radical thereof) and the immune modulator or the pharmaceutically acceptable salt thereof, wherein the linker L or $L_n$ is configured to avoid release of a free form of the TLR7 agonist, and n is an integer equal to or less than 50. Additionally or alternatively, the compound may comprise a linker $L_n$ comprising PEG or a PEG derivative, n may be an integer selected from the range 1 to 32, and the targeting moiety (e.g., a radical thereof) may comprise a radical of folate receptor binding ligand comprising FRβ binding ligand.

The term "releasable" in the context of a linker means a linker that includes at least one bond that can be broken (e.g., chemically or enzymatically hydrolyzed) under physiological conditions, such as, for example, by reducing agent-labile, pH-labile, acid-labile, base-labile, oxidatively labile, metabolically labile, biochemically labile, enzyme-labile or p-aminobenzylic based multivalent releasable bond. It is appreciated that the physiological conditions resulting in bond breaking do not necessarily include a biological or metabolic process and instead may include a standard chemical reaction, such as a hydrolysis reaction for example, at physiological pH or as a result of compartmentalization into a cellular organelle such as an endosome having a lower pH than cytosolic pH. A cleavable bond can connect two adjacent atoms within the releasable linker and/or connect other linker portions or the targeting moiety and/or the drug, as described herein, for example, at either or both ends of the releasable linker. In some instances, the releasable linker is broken into two or more fragments. In some instances, the releasable linker is separated from the targeting moiety. In some embodiments, the targeting moiety and the immune modulator are released from each other and the immune modulator becomes active.

In contrast, the term "non-releasable" in the context of a linker means a linker that includes at least one bond that is not easily or quickly broken under physiological conditions. In some embodiments, a non-releasable linker comprises a backbone that is stable under physiological conditions (e.g., the backbone is not susceptible to hydrolysis (e.g., aqueous hydrolysis or enzymatic hydrolysis)). In some embodiments, a composition provided herein comprising a non-releasable linker does not release any component of the composition (e.g., a targeting ligand (e.g., a fully amorphous (FA)-ligand) or an immune modulator (e.g., a TLR7 agonist)). In some embodiments, the non-releasable linker lacks a disulfide bond (e.g., S—S) or an ester in the backbone. In some embodiments, the composition comprises a targeting moiety and an immune modulator connected by a backbone that is substantially stable for the entire duration of the composition's circulation (e.g., during endocytosis into the target cell endosome). In some embodiments, the composition comprising the non-releasable linker is particularly beneficial when the immune modulator targets TLRs, NOD-like receptors, and/or other pattern recognition receptors present within the endosome of a cell. The non-releasable linker can comprise: an amide, ester, ether, amine, and/or thioether (e.g., thio-maleimide). While specific examples are provided herein, it will be understood that any molecule(s) may be used in the non-releasable linker provided that at least one bond that is not easily or quickly broken under physiological conditions is formed.

Perhaps more specifically, a non-releasable linker comprises a linker that, at a neutral pH, for example, less than ten percent (10%) (e.g., less than 5%, less than 4%, less than 3%, less than 2%, less than 1%, less than 0.1%, less than 0.01%, or less than 0.001%) will hydrolyze in an aqueous (e.g., buffered (e.g., phosphate buffer) solution) within a period of time (e.g., 24 hours). In some embodiments, where a non-releasable linker is employed, less than about ten percent (10%), and preferably less than five percent (5%) or none, of the conjugate compound administered releases the free drug (e.g., in systemic circulation prior to uptake by the targeted cells/tissue). In some embodiments, within one (1) hour of administration, less than five percent (5%) of the free drug is released from the conjugate while the compound is in systemic circulation.

In some embodiments, the targeting moiety does not cleave from the drug/immune modulator for the compound to be therapeutically effective in vivo. In some embodiments, this is advantageous as it allows for the use of targeting compositions comprising potent drugs (e.g., TLR7 agonists), for example, because only a negligible amount (if any) of the drug (e.g., immune modulator, e.g., TLR7 agonist) is released (e.g., systemically) prior to the targeted delivery of the compound. In some embodiments, tuning the releasing properties of active components is a difficult aspect of the preparation of effective pharmaceutical compositions. In some embodiments, the compositions comprising the non-releasable linkers provided herein avoid the difficulties of the preparation of effective pharmaceutical compositions (e.g., by removing the necessity of timing the release). In some embodiments, the immune modulator or warhead of the compound provided herein is active when bound (e.g., conjugated to the targeting conjugate). In some embodiments, while the warhead/immune modulator is active, the non-releasable linker and the targeting moiety prevent the release of toxic cytokines (e.g., by the subject's body) that activate the immune system (such as, for example, interleukin 6 (IL-6)) (e.g., because the compound is specifically targeted (using), for example, folate or an analog thereof)). In certain instances, the immune modulator cannot access the appropriate (e.g., targeted) receptor within the endosome of the cell until the compound binds to the targeted receptor (for example, a folate receptor), for example, even though the warhead/immune modulator of the compound is active when connected to the non-releasable linker.

By way of nonlimiting examples, the linker 106 of FIG. 1A is a non-releasable PEG linker, whereas the linker 156 of FIG. 1B is a self-immolative, releasable linker (e.g., comprising a disulfide bond (e.g., S—S)). For example, the scheme shown in FIG. 1B illustrates the self-immolative cascade of compound 150 upon cleavage from the targeting moiety 154.

In some embodiments, the linker 156 is formed such that the drug is cleaved from the targeting moiety 154 only after sufficient time has passed for the compound to circulate within a subject's systemic circulation following administration (e.g., clear from non-targeted tissues, and be captured and internalized by the targeted cell and/or receptor). In some embodiments, the time period for the release will vary (e.g., from subject to subject (e.g., based on a variety of factors)). In some embodiments, a releasable linker may be engineered such that it will not cleave/release until at least 24 hours post administration or even over a period of a week. In some embodiments, the compound can safely pass through the subject's system and any amount not captured by the targeted cells (e.g., those expressing FRβ, for example) can be excreted prior to release/activation thus preventing toxicity (e.g., because the immune modulator is not active when bound to a releasable linker,).

Both releasable and non-releasable linkers may be engineered to optimize biodistribution, bioavailability, and PK/PD (e.g., of the compound) and/or to increase uptake (e.g., of the compound) into the targeted tissue pursuant to methodologies commonly known in the art or hereinafter developed such as through PEGylation and the like. In some embodiments, the linker is configured to avoid significant release of a pharmaceutically active amount of the drug in circulation prior to capture by a cell (e.g., a cell of interest (e.g., a macrophage in fibrotic or cancer tissue to be treated)).

In some embodiments, the compounds comprising releasable linkers of the present disclosure may be designed to diffuse across the membrane of the endosome and, for example, into the cytoplasm of the targeted cell. In some embodiments, releasable linkers may be designed such that the immune modulator is not released until the compound reaches the cytoplasm.

In some embodiments, a conjugate provided herein may comprise a releasable linker (e.g., to facilitate the release of the immune modulator in the cytoplasm, e.g., where the immune modulator comprises a PI3K kinase, IRAK, or an activator of 1-kappa-β (Iκβ) kinase (e.g., using Prostratin or the like) or nuclear factor kappa-light-chain-enhancer of activated B cells (NF-κβ) (see, e.g., Table 1), or an Myeloid differentiation primary response 88 (MyD88) agonist). In some embodiments, the releasable linker prevents the release of the immune modulator, for example, until after the targeting moiety binds the appropriate target (e.g., a macrophage folate receptor), is internalized into the endosome of the targeted cell, and/or diffuses into the cytoplasm (e.g., which is where the desired pattern recognition receptor is located). In some embodiments, the releasable linker releases the immune modulator within the endosome.

In some embodiments, linkers provided herein may comprise one or more spacers (e.g., to facilitate a particular release time, facilitate an increase in uptake into a targeted tissue, and/or optimize biodistribution, bioavailability, and/or PK/PD of a compound provided herein). A spacer may comprise one or more of alkyl chains, PEGs, peptides, sugars, peptidoglycans, clickable linkers (e.g., triazoles), rigid linkers such as poly prolines and poly piperidines, and the like.

In some embodiments, a linker comprising $PEG_{12}$ significantly reduces-if not altogether avoids-nonspecific uptake of the compounds provided herein (e.g., into a non-targeted organ (e.g., into the liver and/or kidneys of a subject following administration)). In some embodiments, the compounds avoid delivery to the liver and kidneys. In some embodiments, the targeting moieties (in their free form, a radical thereof, or a conjugate thereof) do not bind with uptake receptors on non-targeted cells (e.g., provided the organs are not the targeted sites, and, as such, stimulation of the immune complex in those organs can be avoided, which is highly beneficial in a clinical context).

In some embodiments, a conjugate, comprising a non-releasable linker, provided herein reduces or eliminates toxicity of a component released from the conjugate in its free form (e.g., a free form of a compound and/or ligand provided herein).

In at least one embodiment, the linker comprises a hydrophilic spacer. In some embodiments, the compound has the structure of formula XII (e.g., a sub-structure of the TLR7 agonist of formula III conjugated with folate via a releasable linker containing a first hydrophilic spacer):

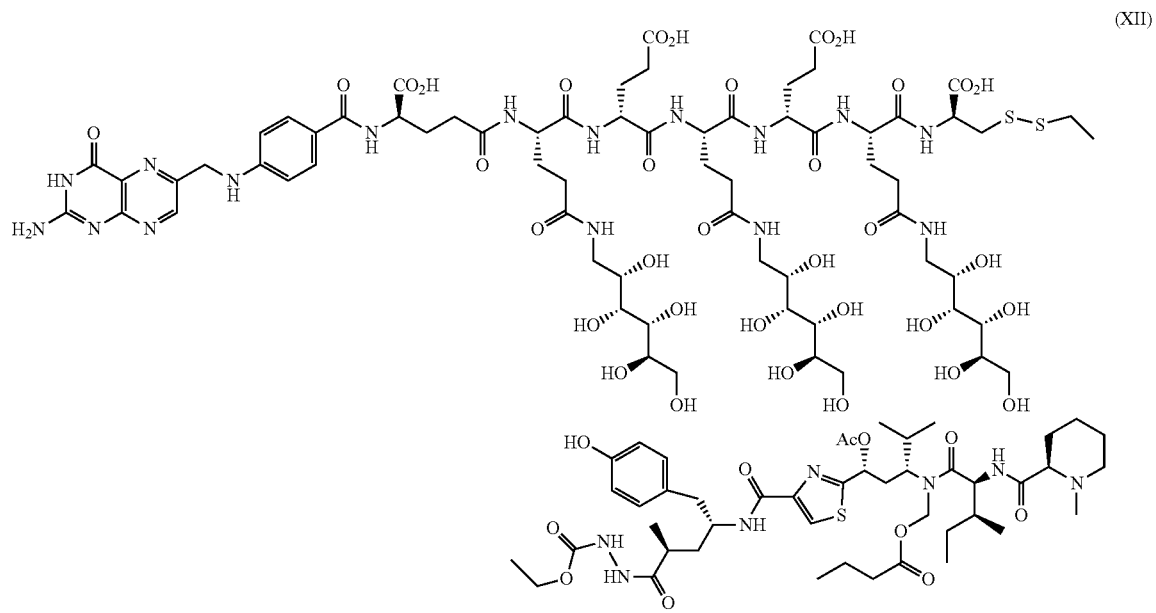

(XII)

In some embodiments, the compound has a structure of formula XIII (e.g., a substructure of the TLR7 agonist of formula III conjugated with folate via a non-releasable linker (covalent bond) comprising a second hydrophilic spacer):

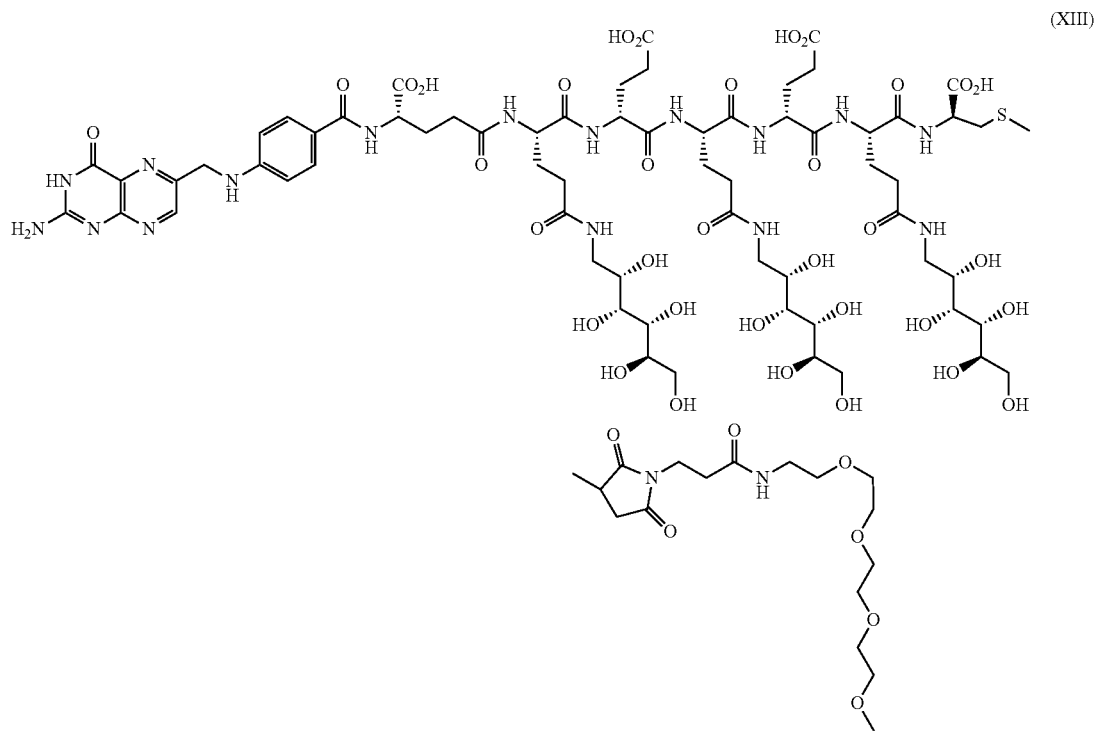

(XIII)

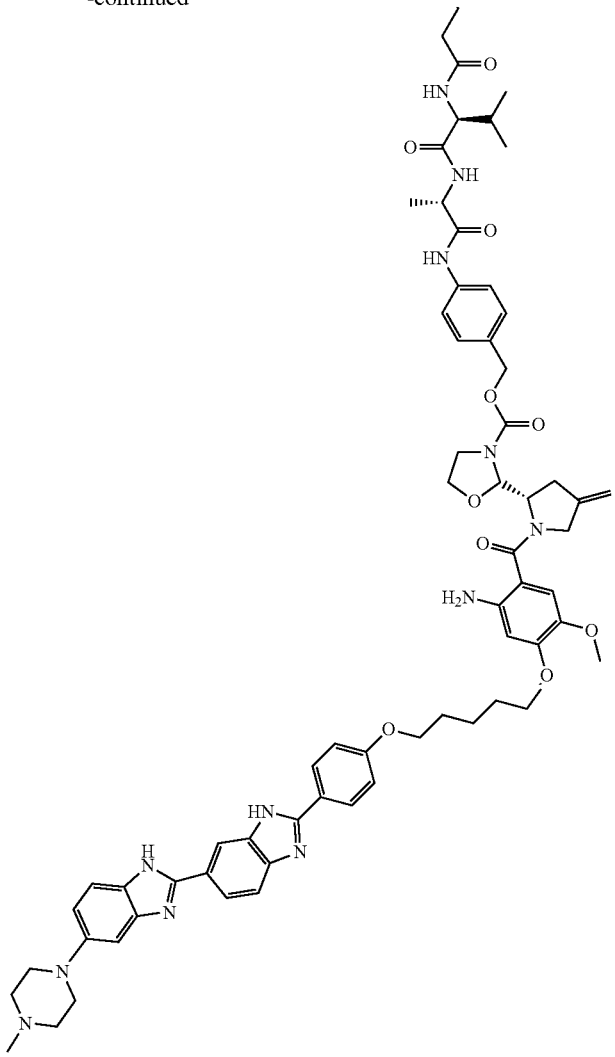

Specific examples of exemplary conjugated compounds are provided herein.

In some embodiments, a compound provided herein comprises a radical of a targeting moiety conjugated with a radical of an immune modulator or a pharmaceutically acceptable salt thereof such that the immune modulator (or radical thereof) or pharmaceutically acceptable salt thereof remains pharmaceutically active when conjugated. The targeting moiety may comprise any targeting moiety described herein and, in at least one embodiment, comprises a folate ligand, any other folate receptor-binding molecule (e.g., or a functional fragment or analog of either of the foregoing) or a pyrido[2,3-d]pyrimidine analog. In some embodiments, the targeting moiety (or conjugate or radical thereof) is specific for FRβ.

In some embodiments, a compound provided herein comprises one or more linkers, wherein a radical of the targeting moiety is conjugated to a radical of the immune modulator through the one or more linkers. For example, where the immune modulator or pharmaceutically acceptable salt thereof has formula I or II, a radical of the immune modulator may be conjugated to a radical of the targeting moiety at one of $R^1$, $R^2$, or $R^3$, through a linker or directly, Similarly, where the immune modulator or pharmaceutically acceptable salt thereof has formula III, a radical of the immune modulator may be conjugated to a radical of the targeting moiety at one of $R^1$ or $R^3$, through a linker or directly. Alternatively, where the immune modulator or pharmaceutically acceptable salt thereof has formula IV, a radical of the immune modulator may be conjugated to a radical of the targeting moiety at one of $R^1$ or $R^2$ through a linker or directly. As described herein, a linker may be releasable or non-releasable.

In some embodiments, the one or more linkers of the compound provided herein may comprise PEG, a PEG derivative, or any other linker known in the art or hereinafter developed that can achieve the purpose set forth herein. In some embodiments, the linker may be repeated n times, where n is a positive integer. For example, and without limitation, n may be any integer selected from a range of 1-16, 1-32, 1-64, or 1-96. The number of repeats in the linker (i.e., n) may be selected to achieve the desired functionality, size, and/or potency of the compound and/or in view of the desired application. In some embodiments, the one or more of the linkers comprise one or more spacers (e.g., which may also be used to specifically design characteristics of the compound).

In some embodiments, the linker is a hydrolyzable linker. In some embodiments, the linker is a non-hydrolyzable linker. In some embodiments, the linker is an optionally substituted heteroalkyl. In some embodiments, the linker is a substituted heteroalkyl comprising at least one substituent selected from the group consisting of alkyl, hydroxyl, oxo, PEG, carboxylate, and halo. In some embodiments, the linker comprises a spacer (e.g., as described elsewhere herein).

In some embodiments, the linker is substituted heteroalkyl with at least one disulfide bond in the backbone thereof. In some embodiments, the linker is a peptide with at least one disulfide bond in the backbone thereof.

In some embodiments, the linker comprises —CONH—CH(COOH)—CH$_2$—S—S—CH$_2$—CR$_a$R$_b$—O—CO—, —CONH—CH(COOH)CR$_a$R$_b$—O—CO—, —C(O)NHCH(COOH) (CH$_2$)$_2$—CONH—CH(COOH)CR$_a$R$_b$—O—CO— or —C(O)NHCH(COOH) (CH$_2$)$_2$—CONH—CH(COOH)—CH$_2$—S—S—CH$_2$—CR$_a$R$_b$—O—CO—, wherein R$_a$ and R$_b$ are independently H, alkyl, or heteroalkyl (e.g., PEG).

In some embodiments, the linker comprises a structure of:

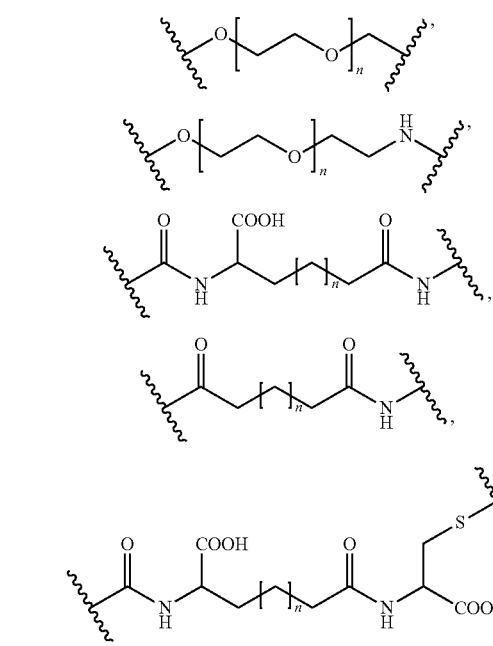

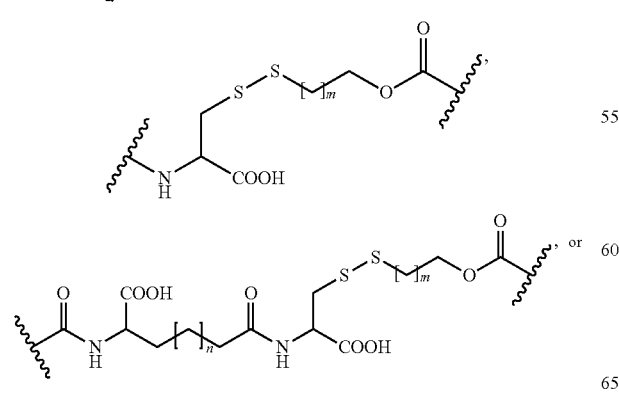

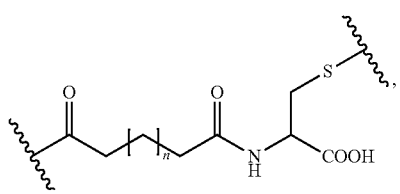

wherein n and m are each independently 0 to 10.

In some embodiments, the linker comprises a structure of:

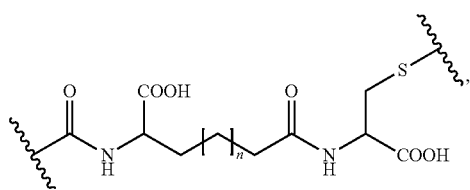

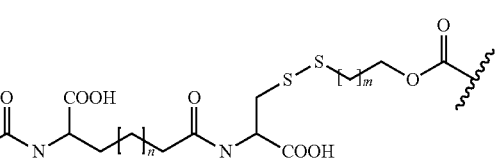

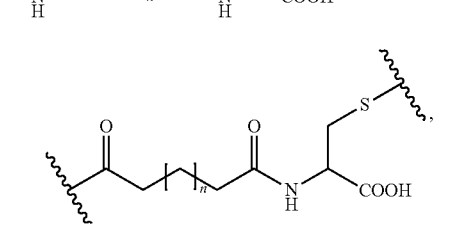

wherein n and m are each independently 0 to 10.

In some embodiments, the linker comprises a structure of:

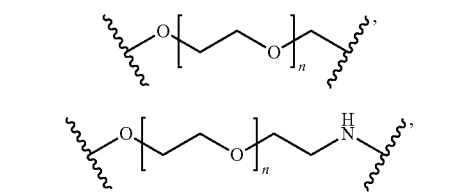

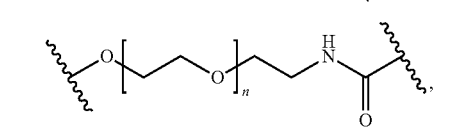

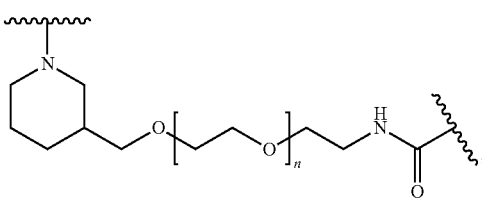

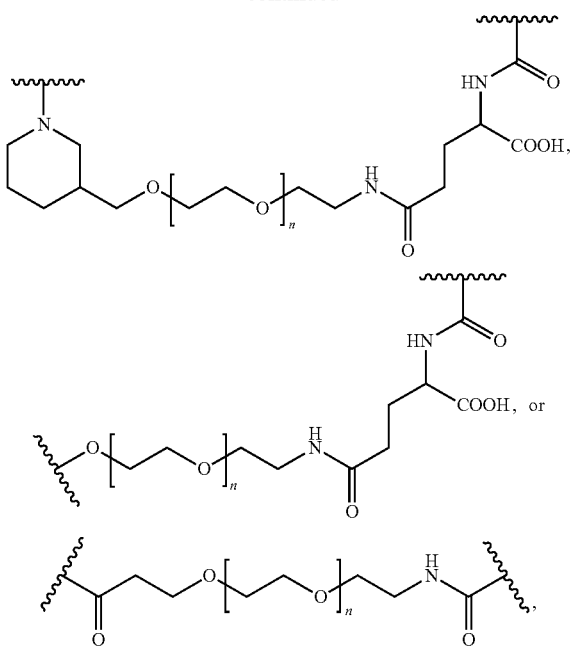

wherein n is 1 to 32.

In some embodiments, the linker comprises the structure of:

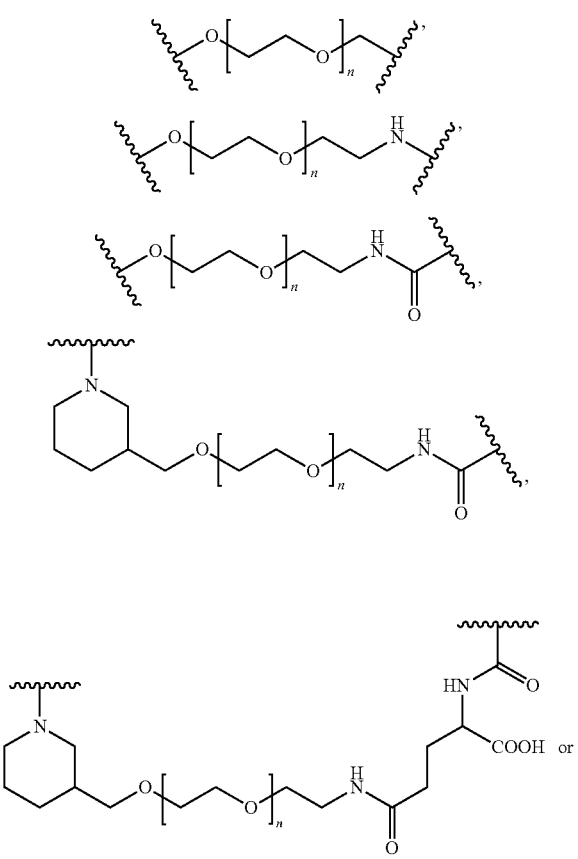

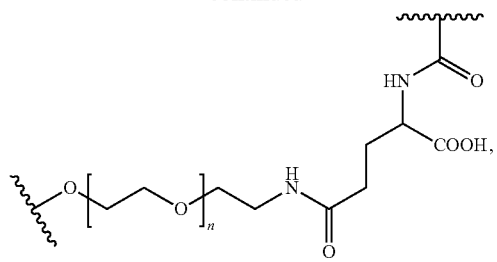

wherein n is 1 to 16.

It is understood that any combination of a radical of a compound (e.g., a radical of a compound in any one of Tables 1 or 2), a linker (e.g., as provided herein), and a radical of a ligand (e.g., a radical of a ligand in any one of Tables 3-6) can be combined to form a conjugate provided herein. In some embodiments, the radical of the compound or the radical of the ligand is a carbon atom or a heteroatom (e.g., O, S, N, etc.). In some embodiments, the radical of the compound is C or O. In some embodiments, the radical of the ligand is C or O. In some embodiments, the point of attachment of the compound and the ligand (e.g., through a linker) is determined by the placement of the radical. In some embodiments, the linkers comprise a spacer (e.g., as described elsewhere herein). It is also understood that any conjugate provided herein can be synthesized in a similar process as provided in the methods provided in the Examples.

Non-limiting examples of conjugates provided herein are provided in Table 7.

TABLE 7

Examples of Conjugates.

| Compound | Linker | Ligand |
|---|---|---|
| A• | ![structure] wherein n is 1 to 16 | a• |
| A• | ![structure] m is 1 to 5 | a• |
| Z• | ![structure] wherein n is 1 to 16 | a• |

TABLE 7-continued

Examples of Conjugates.

| Compound | Linker | Ligand |
|---|---|---|
| Z• | cysteine-disulfide-(CH₂)ₘ-O-C(=O)- linker; m is 1 to 5 | a• |
| F• | -O-(CH₂CH₂O)ₙ-CH₂CH₂-NH-C(=O)- linker; wherein n is 1 to 16 | a• |
| F• | cysteine-disulfide-(CH₂)ₘ-O-C(=O)- linker; m is 1 to 5 | a• |
| L• | -O-(CH₂CH₂O)ₙ-CH₂CH₂-NH-C(=O)- linker; wherein n is 1 to 16 | a• |
| L• | cysteine-disulfide-(CH₂)ₘ-O-C(=O)- linker; m is 1 to 5 | a• |
| D• | -O-(CH₂CH₂O)ₙ-CH₂CH₂-NH-C(=O)- linker; wherein n is 1 to 16 | a• |
| D• | cysteine-disulfide-(CH₂)ₘ-O-C(=O)- linker; m is 1 to 5 | a• |
| A• | -O-(CH₂CH₂O)ₙ-CH₂CH₂-NH-C(=O)- linker; wherein n is 1 to 16 | b• |
| A• | -O-(CH₂CH₂O)ₙ-CH₂CH₂-NH-C(=O)- linker; wherein n is 1 to 16 | f• |
| A• | -O-(CH₂CH₂O)ₙ-CH₂CH₂-NH-C(=O)- linker; wherein n is 1 to 16 | h• |
| A• | -O-(CH₂CH₂O)ₙ-CH₂CH₂-NH-C(=O)- linker; wherein n is 1 to 16 | aa• |
| A• | -O-(CH₂CH₂O)ₙ-CH₂CH₂-NH-C(=O)- linker; wherein n is 1 to 16 | bb• |
| A• | -O-(CH₂CH₂O)ₙ-CH₂CH₂-NH-C(=O)- linker; wherein n is 1 to 16 | cc• |
| A• | -O-(CH₂CH₂O)ₙ-CH₂CH₂-NH-C(=O)- linker; wherein n is 1 to 16 | aaa• |
| Z• | -O-(CH₂CH₂O)ₙ-CH₂CH₂-NH-C(=O)- linker; wherein n is 1 to 16 | b• |
| Z• | -O-(CH₂CH₂O)ₙ-CH₂CH₂-NH-C(=O)- linker; wherein n is 1 to 16 | f• |

TABLE 7-continued

Examples of Conjugates.

| Compound | Linker | Ligand |
|---|---|---|
| Z• | 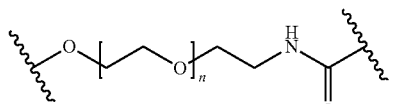 wherein n is 1 to 16 | h• |
| Z• | 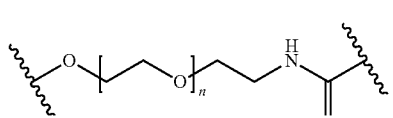 wherein n is 1 to 16 | aa• |
| Z• | 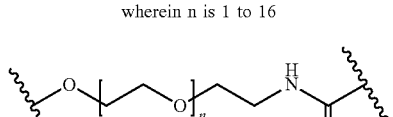 | bb• |

TABLE 7-continued

Examples of Conjugates.

| Compound | Linker | Ligand |
|---|---|---|
| | wherein n is 1 to 16 | |
| Z• | 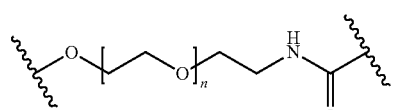 wherein n is 1 to 16 | cc• |
| Z• | 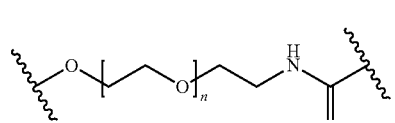 wherein n is 1 to 16 | aaa• |

Non-limiting examples of conjugates provided herein are provided in Table 8.

TABLE 8

Additional Examples of Conjugates

| Compound | Structure |
|---|---|
| 1A | 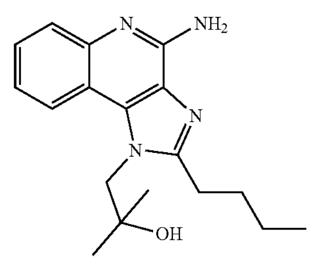 [SMILES: CCCCc1nc2c(N)nc3ccccc3c2n1CC(C)(C)O] |
| 1B | 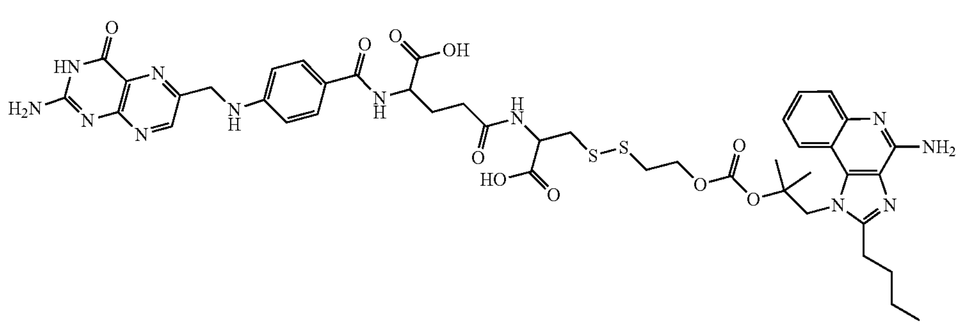 [SMILES: CCCCc1nc2c(N)nc3ccccc3c2n1CC(C)(C)OC(=O)OCCSSCC(NC(=O)CCC(NC(=O)c1ccc(NCc2cnc3nc(N)[nH]c(=O)c3n2)cc1)C(=O)O)C(=O)O] |

TABLE 8-continued
Additional Examples of Conjugates
| Compound | Structure |
| --- | --- |
| 2A | 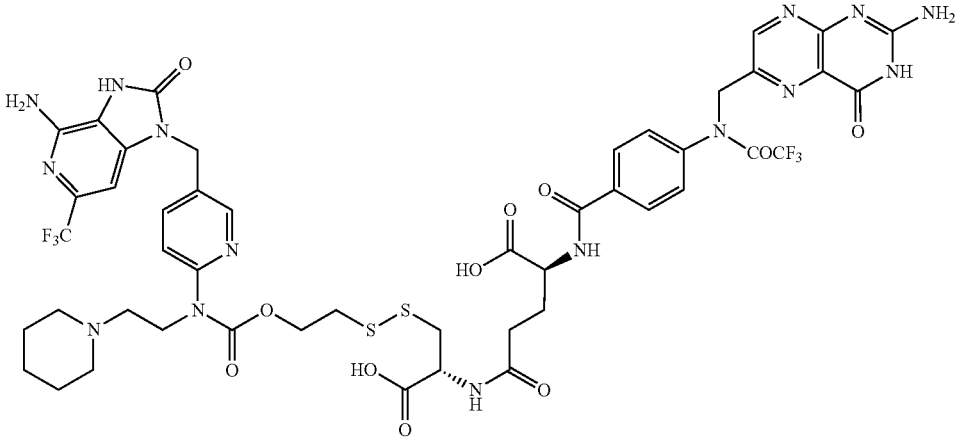 |
| 3A | 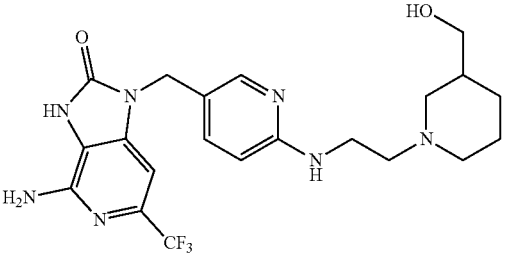 [SMILES: Nc1nc(C(F)(F)F)cc2c1[nH]c(=O)n2Cc1ccc(NCCN2CCCC(CO)C2)nc1] |
| 3B | 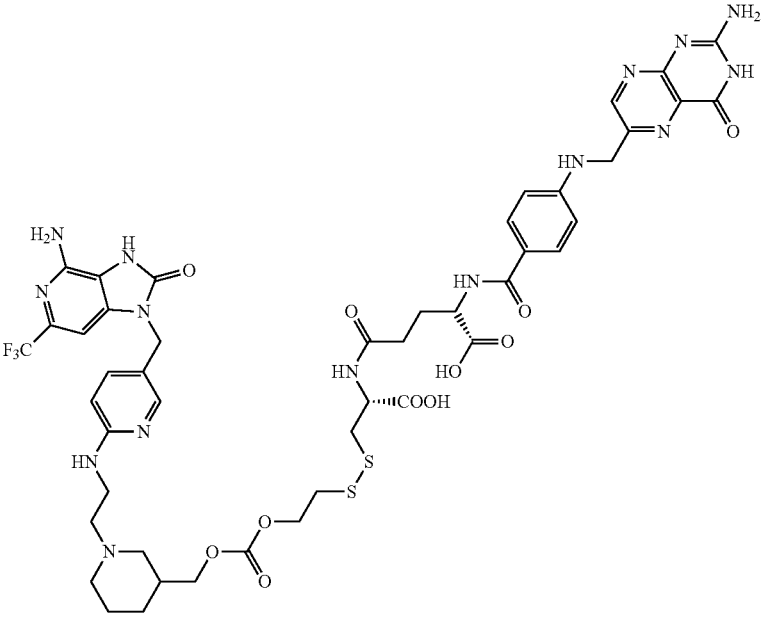 |

TABLE 8-continued
Additional Examples of Conjugates
| Compound | Structure |
|---|---|
| 3C | 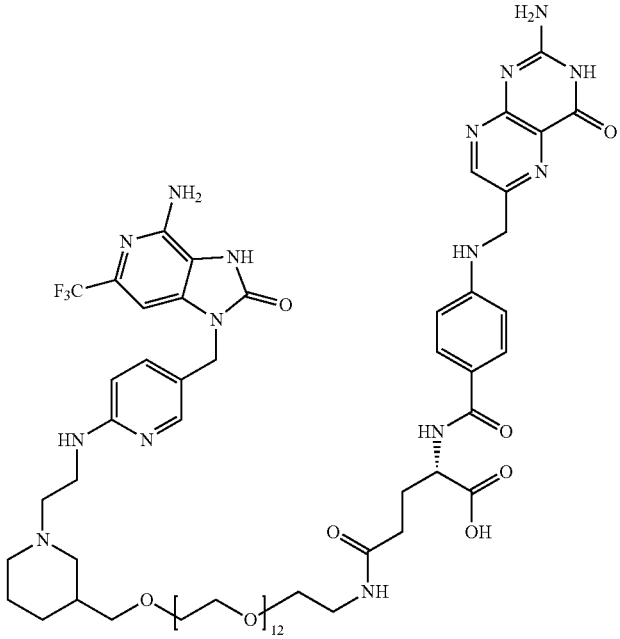 |
| 3D | 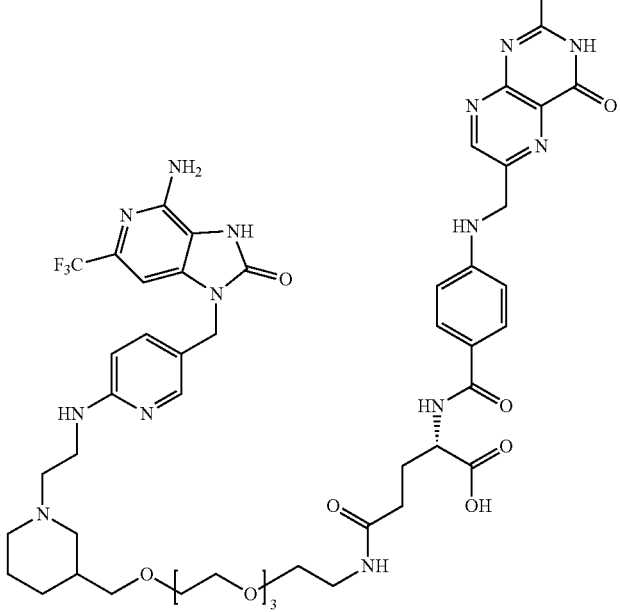 |
| 4A | 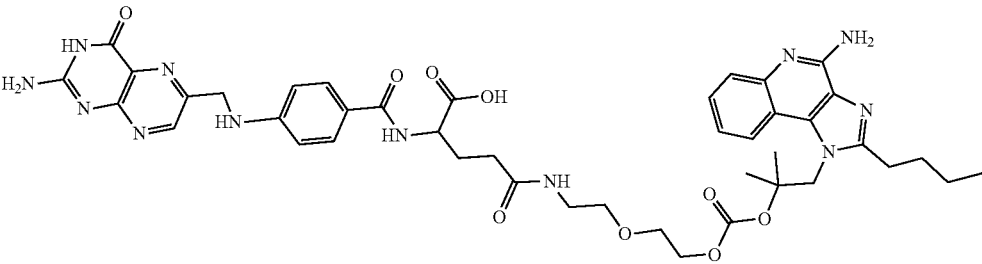 [SMILES: CCCCc1nc2c(N)nc3ccccc3c2n1CC(C)(C)OC(=O)OCCOCCNC(=O)CCC(NC(=O)c1ccc(NCc2cnc3nc(N)[nH]c(=O)c3n2)cc1)C(=O)O] |

TABLE 8-continued
Additional Examples of Conjugates
| Compound | Structure |
|---|---|
| 5A | 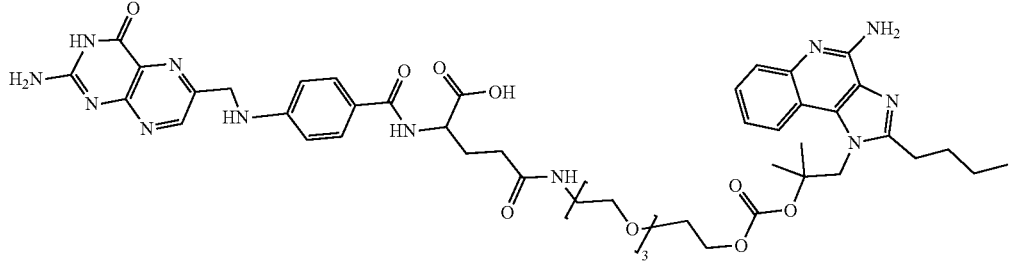 |
| 6A | 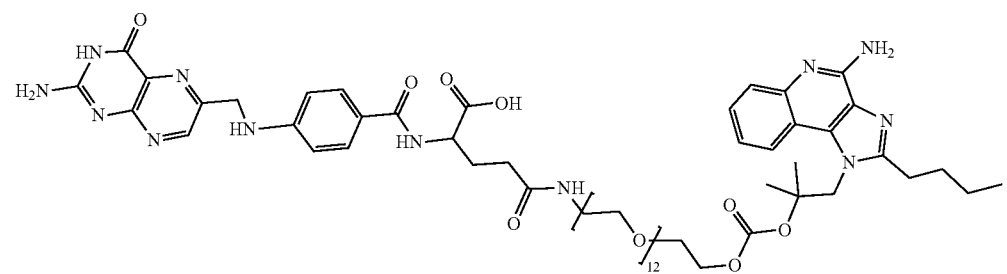 |
| 7A | 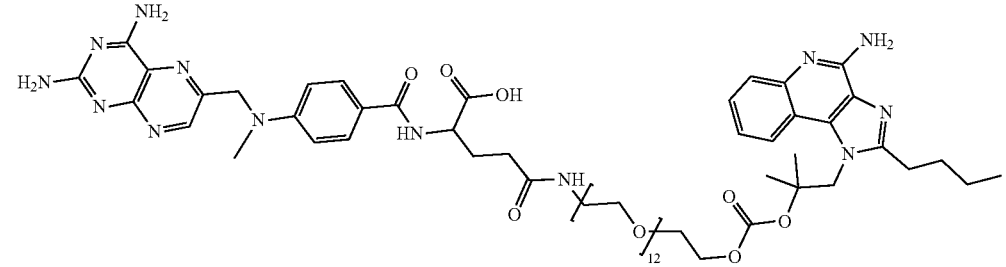 |
| 8A | 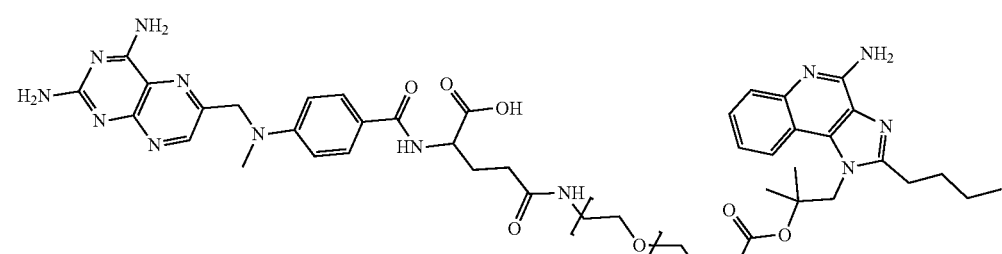 |
| 9A | 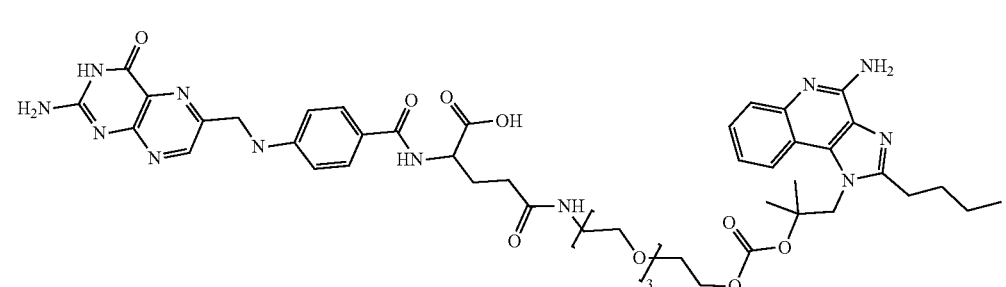 |

TABLE 8-continued

Additional Examples of Conjugates

| Compound | Structure |
|---|---|
| 10A | 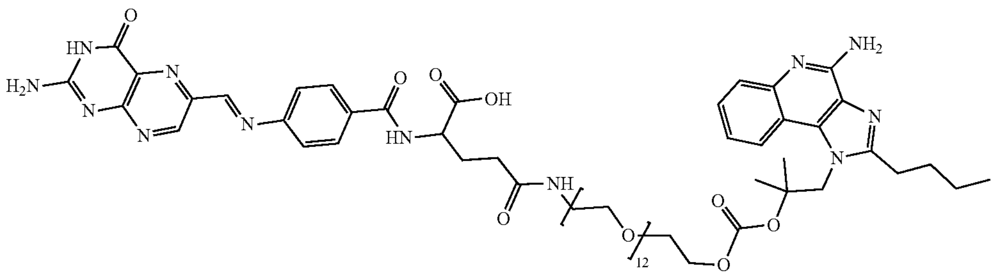 |
| 11A | 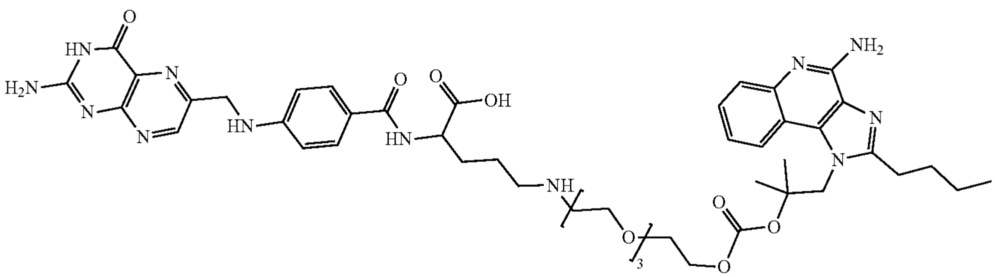 |
| 12A | 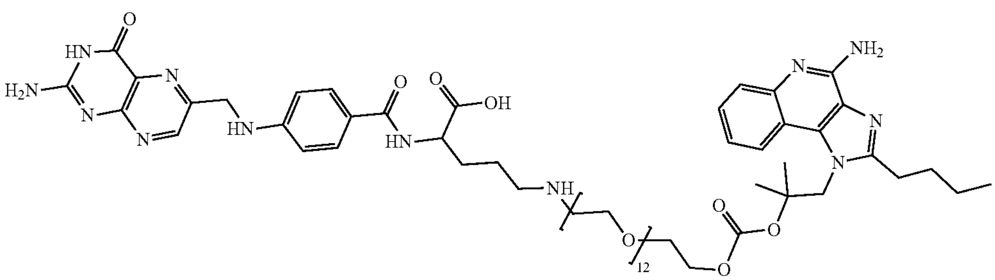 |

In some instances, a conjugated compound provided herein has the structure of formula XIV (e.g., or a functional fragment or analog thereof, which includes the TLR7 agonist of formula III conjugated with a folate via a releasable linker):

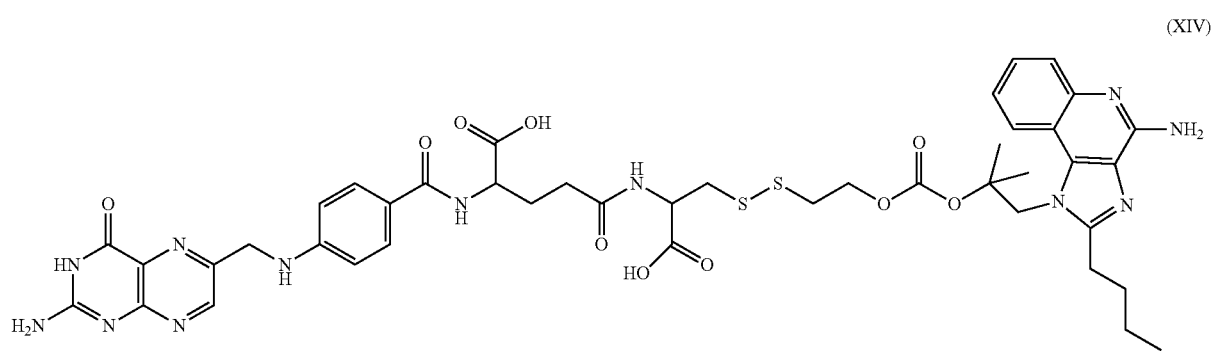 [SMILES: CCCCc1nc2c(N)nc3ccccc3c2n1CC(C)(C)OC(=O)OCCSSCC(NC(=O)CCC(NC(=O)c1ccc(NCc2cnc3nc(N)[nH]c(=O)c3n2)cc1)C(=O)O)C(=O)O]

(XIV)

In another embodiment, a conjugated compound provided herein has the structure of formula XV (e.g., or a functional fragment or analog thereof, which includes the TLR7 agonist of formula II conjugated with a folate via a releasable linker (e.g., Compound 3B)):

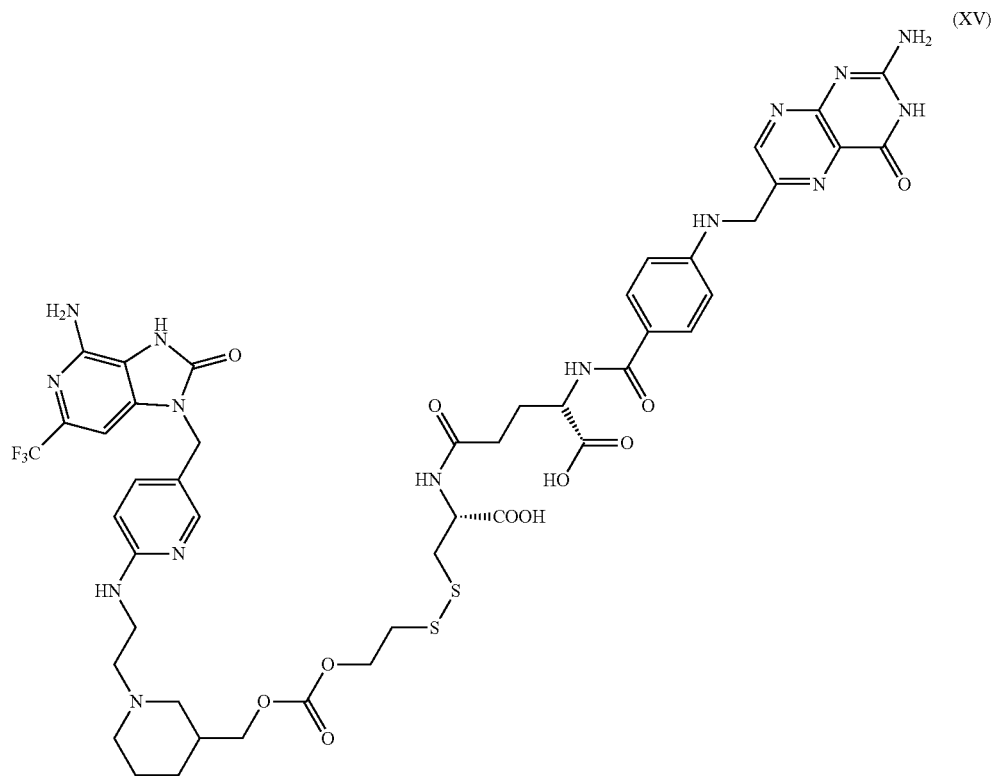
(XV)

In yet another embodiment, a conjugated compound provided herein has the structure of formula XVI (e.g., or a functional fragment or analog thereof, which includes the TLR7 agonist of formula II conjugated with a folate via a non-releasable linker comprising three PEGs (e.g., Compound 3D)):

In still another embodiment, a conjugated compound provided herein has the structure of formula XVII (e.g., or a functional fragment or analog thereof, which includes the TLR7 agonist of formula II conjugated with a folate via a non-releasable linker comprising twelve PEGs (e.g., Compound 3C)):

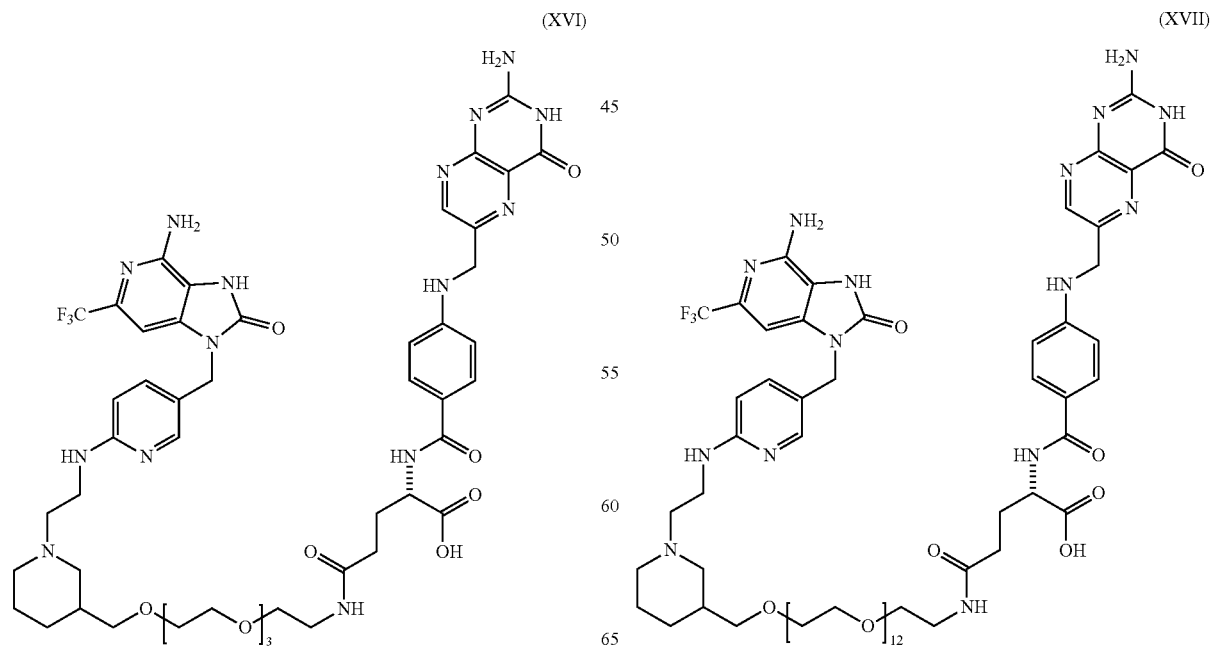
(XVI) (XVII)

Further embodiments of a conjugated compound provided herein has the structure of formula XVIII (e.g., or a functional fragment or analog thereof, which includes the TLR7 agonist of formula II conjugated with a folate via a non-releasable linker comprising sixteen PEGs (e.g., Compound 3D')):

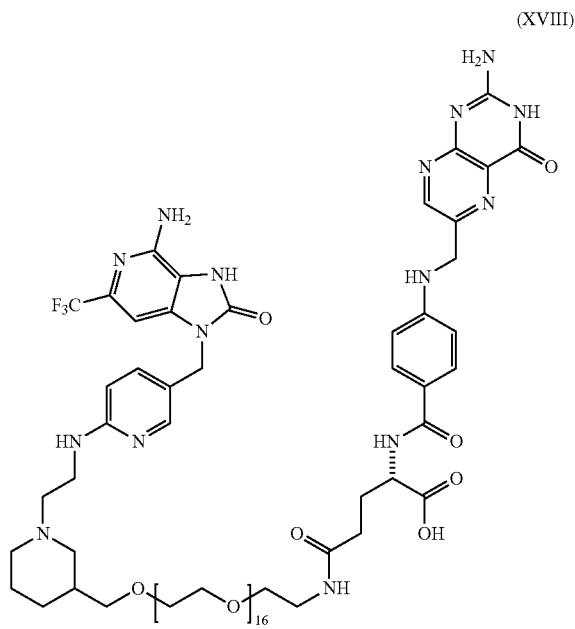

(XVIII)

Further embodiments of a conjugated compound provided herein has the structure of formula XIX (e.g., or a functional fragment or analog thereof, which includes the TLR7 agonist of formula III conjugated with a folate (Compound 1B)):

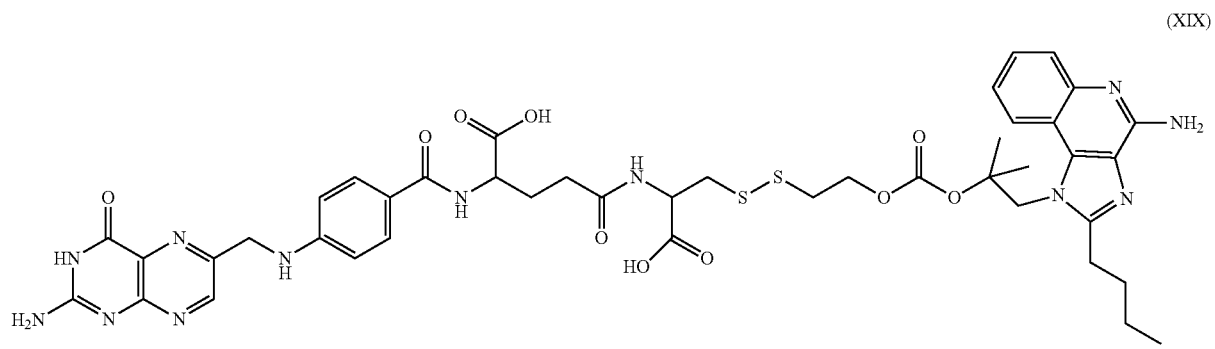 [SMILES: CCCCc1nc2c(N)nc3ccccc3c2n1CC(C)(C)OC(=O)OCCSSCC(NC(=O)CCC(NC(=O)c1ccc(NCc2cnc3nc(N)[nH]c(=O)c3n2)cc1)C(=O)O)C(=O)O]

(XIX)

The compounds described herein can be prepared by conventional methods of organic synthesis practiced by those skilled in the art. The general reaction sequences outlined below represent a general method useful for preparing the compounds of the present disclosure and are not meant to be limiting in scope or utility.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "identical" or percent "identity," in the context of two or more polypeptide sequences, refer to two or more sequences or subsequences that are the same or have a specified percentage of peptides that are the same (i.e. about 60% identity, preferably 65%, 70%, 75%, 80%, 85%, 90%, 91%, 92%, 93%, 94%, 95%, 96%, 97%, 98%, 99%, or higher identity over a specified region when compared and aligned for maximum correspondence over a comparison window or designated region such as a targeting end, folate end, linker, or warhead) as measured using sequence comparison algorithms known in the art, or by manual alignment and visual inspection. Such sequences are then said to be "substantially identical." In other words, identity exists over one or more regions of the overall sequence as long as the general shape and structure of the molecule, and hydrogen bond(s) where appropriate, are maintained such that it substantially fits into the targeted binding site and functions as an agonist thereto.

Compounds described herein may be administered in unit dosage forms and/or compositions containing one or more pharmaceutically acceptable carriers, adjuvants, diluents, excipients, and/or vehicles, and combinations thereof. As used herein, the term "administering" and its formatives generally refer to any and all means of introducing compounds described herein to the host subject including, but not limited to, by oral, intravenous, intramuscular, subcutaneous, transdermal, inhalation, buccal, ocular, sublingual, vaginal, rectal, and like routes of administration.

Administration of the compounds of the present disclosure as salts may be appropriate. Examples of acceptable salts include, without limitation, alkali metal (for example, sodium, potassium or lithium) or alkaline earth metals (for example, calcium) salts; however, any salt that is generally non-toxic and effective when administered to the subject being treated is acceptable. Similarly, "pharmaceutically acceptable salt" refers to those salts with counter ions which may be used in pharmaceuticals. Such salts may include, without limitation: (1) acid addition salts, which can be obtained by reaction of the free base of the parent compound with inorganic acids such as hydrochloric acid, hydrobromic acid, nitric acid, phosphoric acid, sulfuric acid, and perchloric acid and the like, or with organic acids such as acetic acid, oxalic acid, (D) or (L) malic acid, maleic acid, methane sulfonic acid, ethanesulfonic acid, p-toluenesulfonic acid, salicylic acid, tartaric acid, citric acid, succinic acid or malonic acid and the like; or (2) salts formed when an acidic proton present in the parent compound either is replaced by a metal ion, e.g., an alkali metal ion, an alkaline earth ion, or an aluminum ion, or coordinates with an organic base such as ethanolamine, diethanolamine, triethanolamine, trimethamine, N-m ethylglucamine, and the like. Pharmaceutically acceptable salts are well known to those skilled in the art, and any such pharmaceutically acceptable salts may be contemplated in connection with the embodiments described herein.

Acceptable salts may be obtained using standard procedures known in the art, including (without limitation) reacting a sufficiently acidic compound with a suitable base affording a physiologically acceptable anion. Suitable acid addition salts are formed from acids that form non-toxic salts. Illustrative, albeit nonlimiting, examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts. Suitable base salts of the compounds described herein are formed from bases that form non-toxic salts. Illustrative, albeit nonlimiting examples include the arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts.

As used herein, the term "composition" generally refers to any product comprising more than one ingredient, including the compounds described herein. It is to be understood that the compositions described herein may be prepared from isolated compounds described herein or from salts, solutions, hydrates, solvates, and other forms of the compounds described herein. It is appreciated that certain functional groups, such as the hydroxy, amino, and like groups may form complexes with water and/or various solvents, in the various physical forms of the compounds. It is also to be understood that the compositions may be prepared from various amorphous, non-amorphous, partially crystalline, crystalline, and/or other morphological forms of the compounds described herein, and the compositions may be prepared from various hydrates and/or solvates of the compounds described herein. Accordingly, pharmaceutical compositions that recite the compounds described herein include each of, or any combination of, or individual forms of, the various morphological forms and/or solvate or hydrate forms of the compounds described herein.

The compounds of the present disclosure can be formulated as pharmaceutical compositions and administered to a mammalian host, such as a human patient, in a variety of forms adapted to the chosen route of administration. For example, the pharmaceutical composition may be formulated for and administered via oral or parenteral, intravenous, intraarterial, intraperitoneal, intrathecal, epidural, intracerebroventricular, intraurethral, intrasternal, intracranial, intratumoral, intramuscular, topical, inhalation and/or subcutaneous routes. Indeed, in at least one embodiment, a compound and/or composition as described herein may be administered directly into the blood stream, into muscle, or into an internal organ.

For example, in at least one embodiment, the present compounds may be systemically administered (orally, for example) in combination with a pharmaceutically acceptable vehicle such as an inert diluent or an assimilable edible carrier. For oral therapeutic administration, the active compound may be combined with one or more excipients and used in the form of ingestible tablets, buccal tablets, troches, capsules, elixirs, suspensions, syrups, wafers, and the like. The percentage of the compositions and preparations may vary and may be between about 1 to about 99% weight of the active ingredient(s) and a binder, excipients, a disintegrating agent, a lubricant, and/or a sweetening agent (as are known in the art). The amount of active compound in such therapeutically useful compositions is such that an effective dosage level will be obtained.

The preparation of parenteral compounds/compositions under sterile conditions, for example, by lyophilization, may readily be accomplished using standard pharmaceutical techniques well known to those skilled in the art. In at least one embodiment, the solubility of a compound used in the preparation of a parenteral composition may be increased by the use of appropriate formulation techniques, such as the incorporation of solubility-enhancing agents.

As previously noted, the compounds/compositions of the present disclosure may also be administered via infusion or injection (e.g., using needle (including microneedle) injectors and/or needle-free injectors). Solutions of the active composition can be aqueous, optionally mixed with a nontoxic surfactant and/or may contain carriers or excipients such as salts, carbohydrates and buffering agents (preferably at a pH of from 3 to 9), but, for some applications, they may be more suitably formulated as a sterile non-aqueous solution or as a dried form to be used in conjunction with a suitable vehicle such as sterile, pyrogen-free water or phosphate-buffered saline (PBS). For example, dispersions can be prepared in glycerol, liquid PEGS, triacetin, and mixtures thereof and in oils. Under ordinary conditions of storage and use, these preparations may further contain a preservative to prevent the growth of microorganisms.

The pharmaceutical dosage forms suitable for injection or infusion can include sterile aqueous solutions or dispersions or sterile powders comprising the active ingredients that are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example and without limitation, water, ethanol, a polyol (e.g., glycerol, propylene glycol, liquid PEG(s), and the like), vegetable oils, nontoxic glyceryl esters, and/or suitable mixtures thereof. In at least one embodiment, the proper fluidity can be maintained by the formation of liposomes, by the maintenance of the required particle size in the case of dispersions or by the use of surfactants. The action of microorganisms can be prevented by the addition of various antibacterial and antifungal agents such as parabens, chlorobutanol, phenol, sorbic acid, thimerosal, and the like. In certain cases, it will be desirable to include one or more isotonic agents such as sugars, buffers, or sodium chloride. Prolonged absorption of the injectable compositions can be brought about by the incorporation of agents formulated to delay absorption, for example, aluminum monostearate and gelatin.

Sterile injectable solutions may be prepared by incorporating the active compound and/or composition in the required amount of the appropriate solvent with one or more of the other ingredients set forth above, as required, followed by filter sterilization. In the case of sterile powders for the preparation of sterile injectable solutions, the preferred methods of preparations are vacuum drying and the freeze drying techniques, which yield a powder of the active ingredient plus any additional desired ingredient present in the previously sterile-filtered solutions.

For topical administration, it may be desirable to administer the present compounds to the skin as compositions or formulations in combination with a dermatologically acceptable carrier, which may be a solid or a liquid. For example, in certain embodiments, solid carriers may include finely divided solids such as talc, clay, microcrystalline cellulose, silica, alumina and the like. Similarly, useful liquid carriers may comprise water, alcohols or glycols or water-alcohol/glycol blends, in which the present compounds can be dissolved or dispersed at effective levels, optionally with the aid of non-toxic surfactants. Additionally or alternatively, adjuvants such as fragrances and antimicrobial agents can be added to optimize the properties for a given use. The resultant liquid compositions can be applied from absorbent pads, used to impregnate bandages and/or other dressings, sprayed onto the targeted area using pump-type or aerosol sprayers, or simply applied directly to a desired area of the subject.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like for application directly to the skin of the subject.

As used herein, the terms "therapeutically effective," "therapeutically effective dose," "therapeutically effective amount," "prophylactically effective amount," or "prophylactically effective dose" mean (unless specifically stated otherwise) a quantity of a compound which, when administered either one time or over the course of a treatment cycle affects the health, wellbeing or mortality of a subject (e.g., and without limitation, delays the onset of and/or reduces the severity of one or more of the symptoms associated with a fibrotic disease or condition and/or a cancer, as applicable). Useful dosages of the compounds of the present disclosure can be determined by comparing their in vitro activity, and the in vivo activity in animal models. Methods of the extrapolation of effective dosages in mice and other animals to human subjects are known in the art. Indeed, the dosage of the compound can vary significantly depending on the condition of the host subject, the cancer or fibrotic disease being treated, how advanced the pathology is, the route of administration of the compound and tissue distribution, and the possibility of co-usage of other therapeutic treatments (such as radiation therapy or additional drugs in combination therapies). The amount of the composition required for use in treatment (e.g., the therapeutically or prophylactically effective amount or dose) will vary not only with the particular application, but also with the salt selected (if applicable) and the characteristics of the subject (such as, for example, age, condition, sex, the subject's body surface area and/or mass, tolerance to drugs) and will ultimately be at the discretion of the attendant physician, clinician, or otherwise. Therapeutically effective or prophylactically effective amounts or doses can range, for example, from about 0.05 mg/kg of patient body weight to about 30.0 mg/kg of patient body weight, or from about 0.01 mg/kg of patient body weight to about 5.0 mg/kg of patient body weight, including but not limited to 0.01 mg/kg, 0.02 mg/kg, 0.03 mg/kg, 0.04 mg/kg, 0.05 mg/kg, 0.1 mg/kg, 0.2 mg/kg, 0.3 mg/kg, 0.4 mg/kg, 0.5 mg/kg, 1.0 mg/kg, 1.5 mg/kg, 2.0 mg/kg, 2.5 mg/kg, 3.0 mg/kg, 3.5 mg/kg, 4.0 mg/kg, 4.5 mg/kg, and 5.0 mg/kg, all of which are kg of patient body weight. The total therapeutically or prophylactically effective amount of the compound may be administered in single or divided doses and may, at the practitioner's discretion, fall outside of the typical range given herein.

In another embodiment, the compound can be administered in a therapeutically or prophylactically effective amount of from about 0.5 g/m to about 500 mg/m$^2$, from about 0.5 g/m$^2$ to about 300 mg/m$^2$, or from about 100 g/m$^2$ to about 200 mg/m$^2$. In other embodiments, the amounts can be from about 0.5 mg/m$^2$ to about 500 mg/m$^2$, from about 0.5 mg/m$^2$ to about 300 mg/m$^2$, from about 0.5 mg/m$^2$ to about 200 mg/m$^2$, from about 0.5 mg/m$^2$ to about 100 mg/m$^2$, from about 0.5 mg/m$^2$ to about 50 mg/m$^2$, from about 0.5 mg/m$^2$ to about 600 mg/m$^2$, from about 0.5 mg/m$^2$ to about 6.0 mg/m$^2$, from about 0.5 mg/m$^2$ to about 4.0 mg/m$^2$, or from about 0.5 mg/m$^2$ to about 2.0 mg/m$^2$. The total amount may be administered in single or divided doses and may, at the physician's discretion, fall outside of the typical range given herein. These amounts are based on m of body surface area.

In some embodiments, in connection with measuring expression of certain biomarkers and/or analysis of cytokine levels in a sample from a subject, of significance of the present disclosure is not the particular methods used to detect the marker or set of markers, but what the markers are used to detect. There are many methods that may be used to detect the expression, quantification, or profile of one or more biomarkers. Once the marker or set of markers to be detected or quantified is identified, any of several techniques (that are now known or hereinafter developed) may be used, with the provision of appropriate reagents. One of skill in the art, when provided with the one or more biomarkers to be identified, will be capable of selecting the appropriate assay (e.g., a PCR-based or a microassay-based assay for nucleic acid markers, an enzyme-linked immunosorbent assay (ELISA), protein or antibody microarray or similar immunologic assay, etc.) for performing the methods disclosed herein.

CHEMISTRY EXAMPLES

Example A: Synthesis of Compound 1A

Compound 1A was synthesized according to scheme 1 below and as reported by Nikunj M. Shukla, Cole A. Mutz, Subbalakshmi S. Malladi, Hemamli J. Warshakoon, Rajalakshmi Balakrishna, and Sunil A. David, "Regioisomerism-dependent TLR7 agonism and antagonism in an imidazoquinoline; Structure-Activity Relationships in Human Toll-Like Receptor 7-Active Imidazoquinoline Analogues," J Med Chem. 2012 Feb. 9; 55(3): 1106-1116.

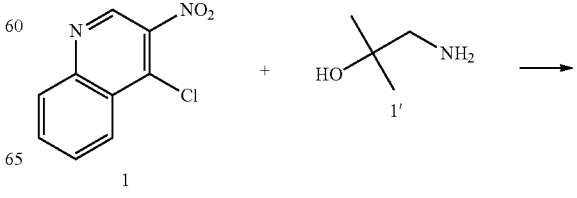

Scheme 1

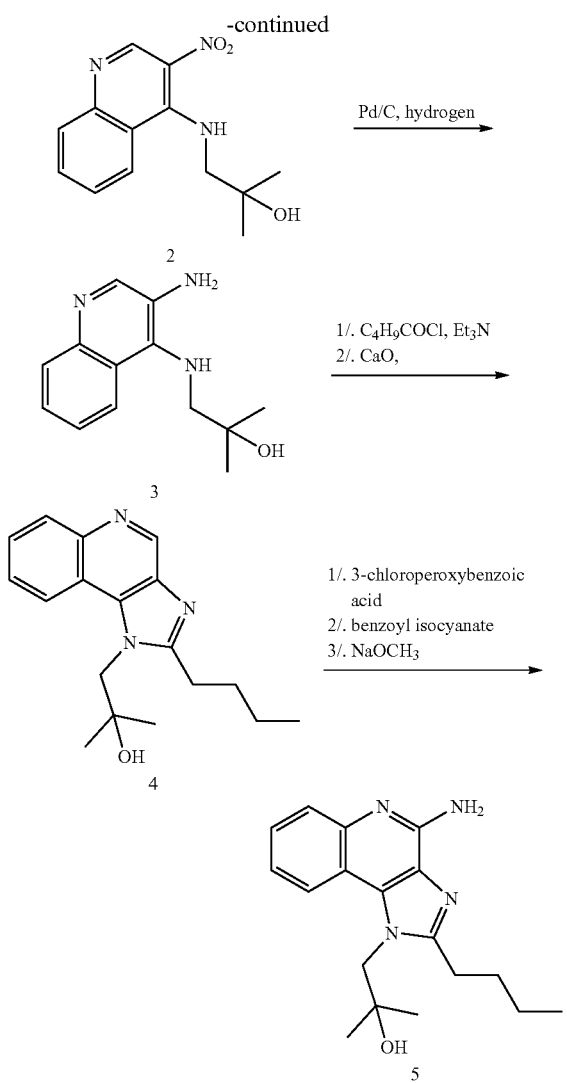

Step 1: Synthesis of 1-amino-2-methylpropan-2-ol (Compound)

2,2-dimethyloxirane (0.1 g, 1.388 mmol) was added dropwise to 20 mL ice cooled solution of ammonium hydroxide. The reaction mixture was stirred for 12 hours at room temperature. The solvent was removed under vacuum and the residue was dissolved in methanol. Di-tert-butyl dicarbonate (0.75 g, 3.47 mmol) was added to the reaction mixture and stirred for 4 hours. The mixture was purified using column chromatography (24% ethyl acetate (EtOAc)/hexane) to obtain tert-butyl 2-hydroxy-2-methylpropylcarbamate. The pure tert-butyl 2-hydroxy-2-methylpropylcarbamate was dissolved in 5 mL of trifluoroacetic acid and stirred for 35 minutes. The solvent was removed under reduced pressure to afford 1-amino-2-methylpropan-2-ol as the trifluoroacetate salt 1'. 1H NMR 500 MHz (500 MHz, CDCl3, δ in ppm): δ 8.62 (s, 2H), 3.02 (d, 2H), 2.06-2.04 (m, 2H), 1.37-1.34 (s, 6H).

Step 2: Synthesis of 2-methyl-1-(3-nitroquinolin-4-ylamino)propan-2-ol (compound 2)

The trifluoroacetate salt of 1-amino-2-methylpropan-2-ol (compound) (450 mg, 2.4 mmol) was added to the solution of 4-chloro-3-nitroquinoline (compound 1) (250 mg, 1.2 mmol) and Et3N (0.5 ml, 3 mmol) in 4:1 mixture of toluene and 2-propanol. The mixture was heated to 70° C. for half an hour until a solid started precipitating. The reaction mixture was then cooled, filtered, washed with toluene/2-propanol (7:3), ether and cold water. The residue was dried at 80° C. to obtain 2-methyl-1-(3-nitroquinolin-4-ylamino)propan-2-ol (compound 2). Liquid chromatography-mass spectrometry (LCMS) analysis: [M+H]+ m/z=261.

Step 3: Synthesis of 1-(3-aminoquinolin-4-ylamino)-2-methylpropan-2-ol (compound 3)

2-Methyl-1-(3-nitroquinolin-4-ylamino)propan-2-ol (compound 2) (450 mg, 1.72 mmol) was dissolved in methanol and hydrogenated over Pd/C as catalyst with hydrogen balloon for 4 hours. The solution was then filtered using celite, followed by evaporation of solvent under reduced pressure to afford 1-(3-aminoquinolin-4-ylamino)-2-ethylpropan-2-ol (compound 3). LCMS: [M+1-1]+ m/z=231. H NMR 500 MHz (CDCl3, δ in ppm): δ 8.12 (s, 1H), 7.61-7.58 (m, 1H), 7.48-7.40 (m, 2H), 4.90 (s, 2H), 3.47 (2H), 1.35-1.21 (s, 6H).

Step 4: Synthesis of 1-(4-Amino-2-butyl-1H-imidazo[4,5-c]quinolin-1-yl)-2-methylpropan-2-ol (Compound 5, TLR7A)

To a solution of compound 3 (100 mg, 0.43 mmol) in anhydrous THF were added triethylamine (66 mg, 0.65 mmol) and valeryl chloride (62 mg, 0.52 mmol). The reaction mixture was then stirred for 6-8 hours, followed by removal of the solvent under vacuum. The residue was dissolved in EtOAc, washed with water and brine, and then dried over Na2SO4 to obtain the intermediate amide compound. This was dissolved in methanol (MeOH), followed by the addition of calcium oxide, and was heated in microwave at 110° C. for 1 hour. The solvent was then removed and the residue was purified using column chromatography (9% MeOH/dichloromethane) to obtain the compound 4 (58 mg). To a solution of compound 4 in a solvent mixture of MeOH:dichloromethane:chloroform (0.1:1:1) was added 3-chloroperoxybenzoic acid (84 mg, 0.49 mmol), and the solution was refluxed at 45-50° C. for 40 min. The solvent was then removed and the residue was purified using column chromatography (20% MeOH/dichloromethane) to obtain the oxide derivative (55 mg). This was then dissolved in anhydrous dichloromethane, followed by the addition of benzoyl isocyanate (39 mg, 0.26 mmol) and heated at 45° C. for 15 min. The solvent was then removed under vacuum, and the residue was dissolved in anhydrous MeOH, followed by the addition of excess sodium methoxide. The reaction mixture was then heated at 80° C. for an hour. The solvent was removed under vacuum, and the residue was purified using column chromatography (11% MeOH/dichloromethane) to obtain the compound 5. LCMS: [M+H]+ m/z=312. H NMR 500 MHz (CDCl3, δ in ppm): δ 8.16-8.15 (d, 1H), 7.77-7.46 (d, 1H), 7.46-7.43 (m, 1H), 7.33-7.26 (m, 1H), 3.00-2.97 (m, 2H), 1.84-1.78 (m, 2H), 1.47-1.41 (m, 2H), 1.36 (s, 6H), 0.98-0.95 (m, 3H).

Example B: Synthesis of Compound 1B

Compound 1A can thereafter be used to synthesize Compound 1B according to scheme 2 below.

Scheme 2

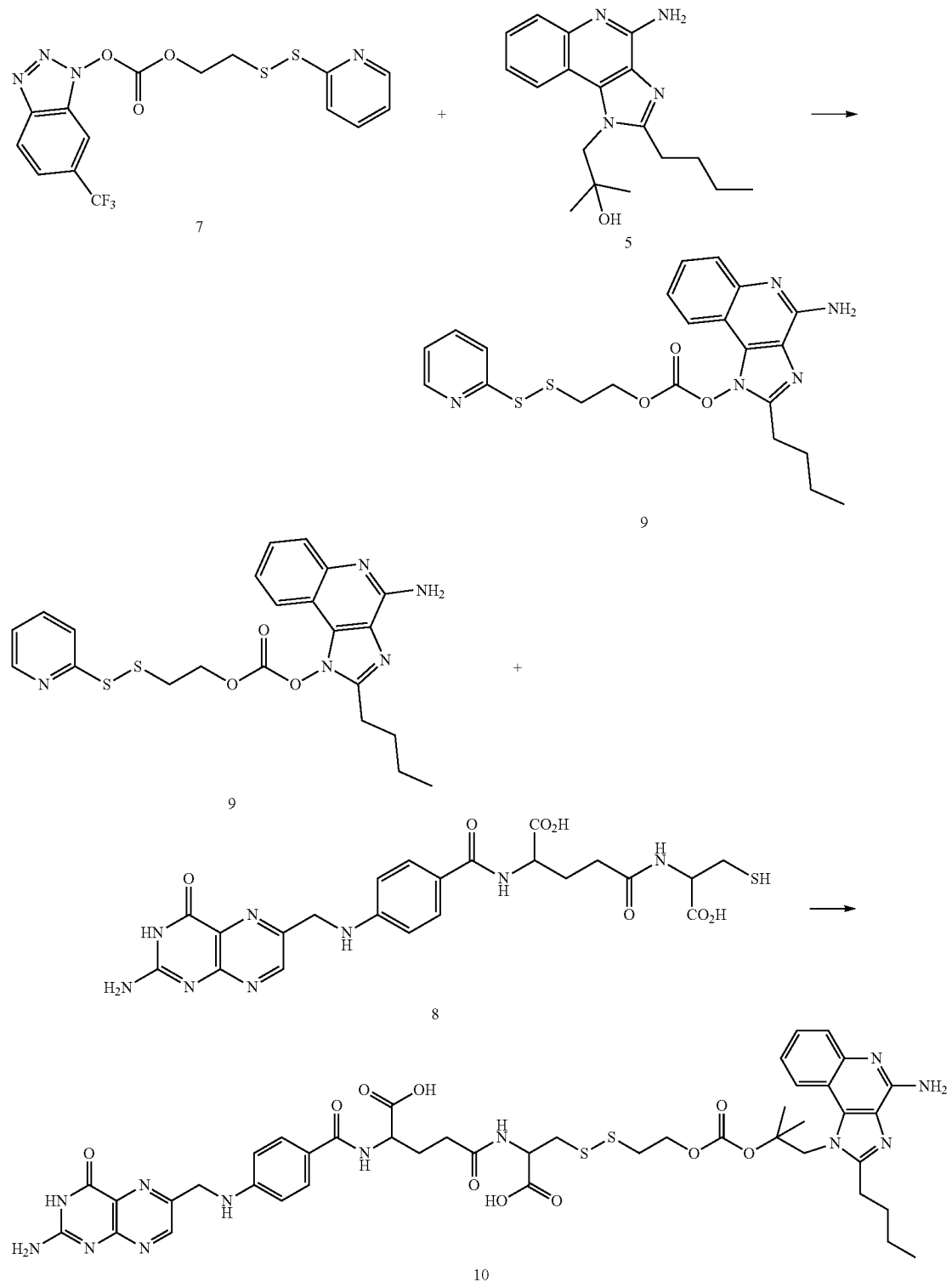

Compound 1A, folate, and linker are commercially available or can be prepared according to methods known to the person skilled in the art.

Heterobifunctional linker 7 (88 mg, 0.213 mmol) was added to a solution of compound 5 (33 mg, 0.106 mmol) and dimethylaminopyridine (39 mg, 0.319 mmol) in 4 mL of methylene chloride at room temperature under nitrogen atmosphere and the mixture was stirred at reflux temperature for 7 hours at which time thin layer chromatography (TLC) analysis of the mixture indicated >80% conversion. The mixture was concentrated and purified by column chromatography using 10% acetonitrile in methylene chloride as eluant. The pure product compound 9 was obtained as a light yellow solid. A solution of compound 8 (1 eq.) in dimethyl sulfoxide (DMSO) was added in 3 portions at 20 min intervals to a solution of drug-linker intermediates compound 9 (1.0 eq.-1.5 eq.) in DMSO with dimethylaminopyridine (1 eq.). After 1-2 hours of stirring at room temperature under argon, LCMS analysis of the mixture indicated formation of the desired folate-drug conjugate (compound 10) as the major product. The mixture was purified by preparative high-performance liquid chromatography (HPLC). LCMS: [M+H]$^+$ m/z=959. $^1$H NMR (500 MHz, DMSO-d6) δ 8.58 (s, 1H), 8.49 (d, J=8.8 Hz, 1H), 7.90 (d, J=8.3 Hz, 1H), 7.83-7.74 (m, 1H), 7.54 (d, J=8.0 Hz, 2H), 7.48 (t, J=7.6 Hz, 1H), 7.41 (s, 1H), 7.06 (s, 1H), 6.81 (d, J=6.2 Hz, 1H), 6.61 (d, J=8.3 Hz, 2H), 6.27 (s, 1H), 4.43 (d, J=5.9 Hz, 2H), 4.28 (t, J=6.6 Hz, 2H), 4.00 (d, J=25.7 Hz, 3H), 3.03 (t, J=7.5 Hz, 2H), 2.97 (dd, J=13.0, 6.5 Hz, 1H), 2.09 (s, 2H), 1.81 (s, 7H), 1.40 (q, J=7.4 Hz, 2H), 1.22 (s, 2H), 1.13 (s, 2H), 0.91 (t, J=7.4 Hz, 3H).

Example C: Synthesis of Compound 2A

Compound 2A can be synthesized according to Scheme 3 and Scheme 4.

Scheme 3

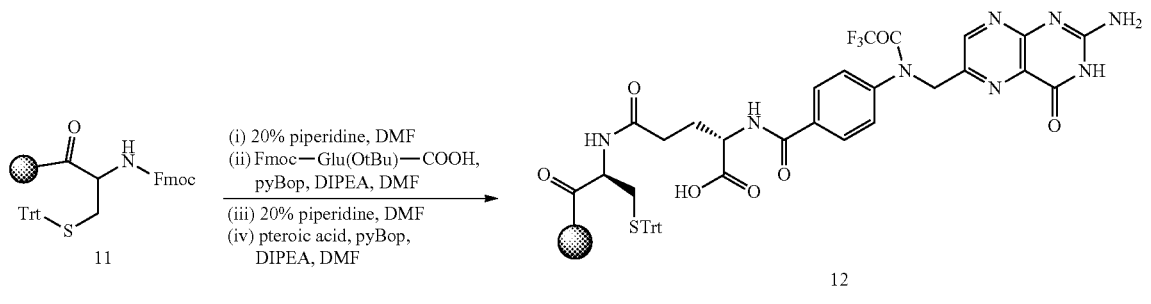

(i) 50% NH$_3$:DMF
(ii) TFA:TIPS:H$_2$O:TCEP

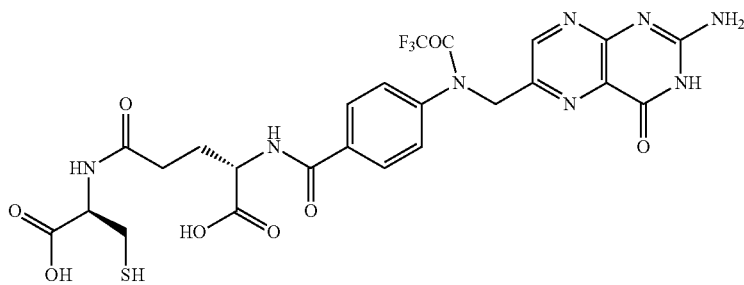

Schme 4
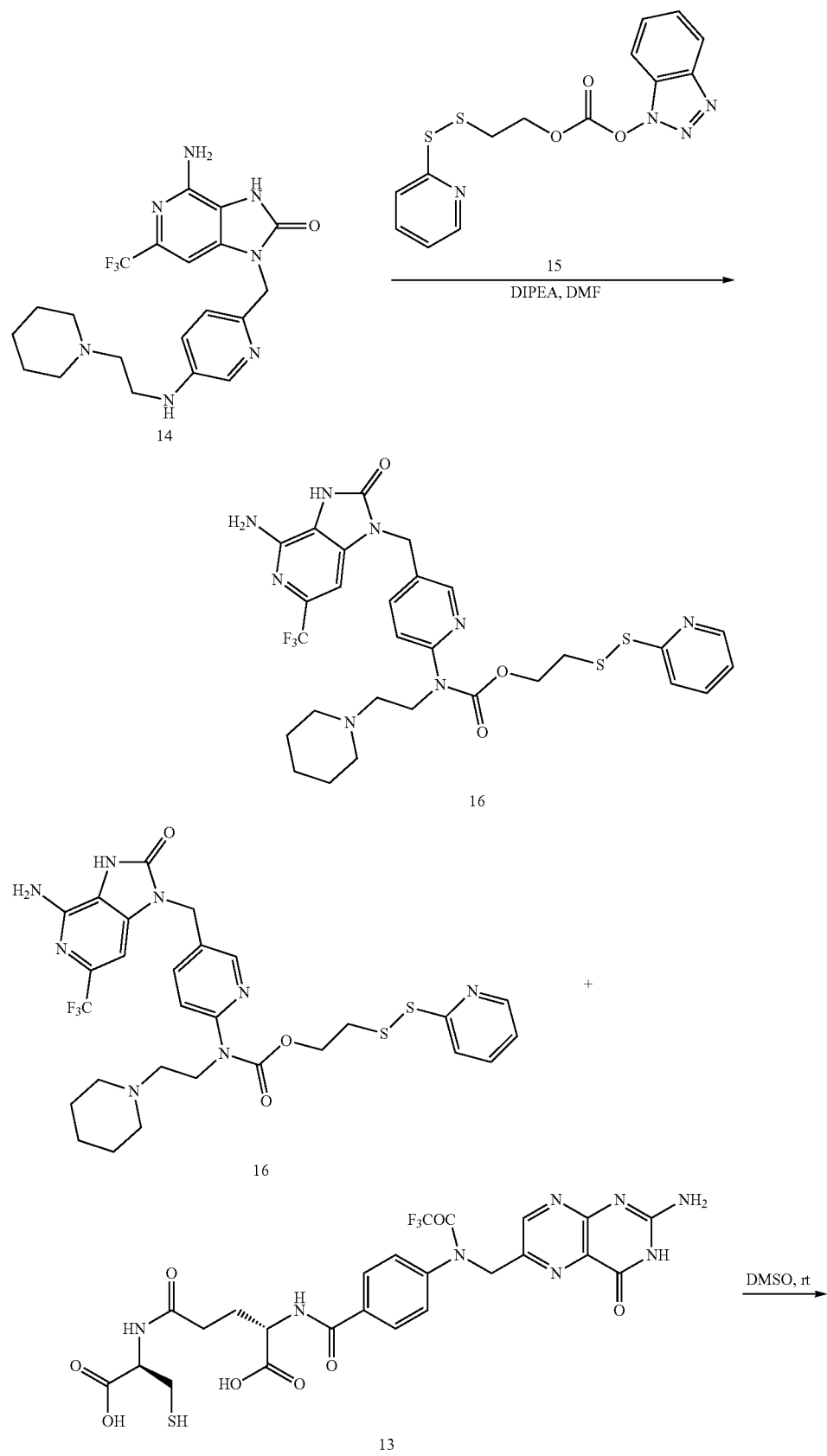

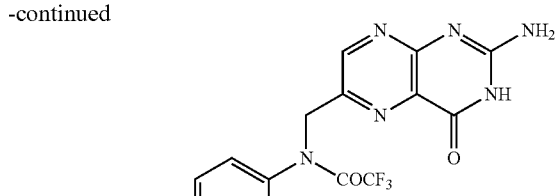
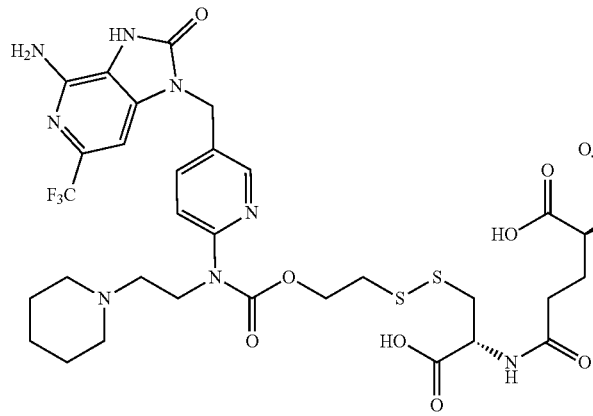

17

Cysteine loaded Wang resin (11) was initially deprotected using 20% piperidine in dimethylformamide (DMF). The free amine was treated with Fmoc-Glu(OtBu)-COOH in presence of benzotriazole-1-yl-oxytripyrrolidinophosphonium hexafluorophosphate (PyBop), N,N-Diisopropylethylamine (DIPEA) and DMF. The coupled product was deprotected using 20% piperidine in DMF and treated with pteroic acid in presence of PyBop, DIPEA and DMF, producing compound 12. The trifluoroacetyl group was deprotected with 50% ammonia-DMF solution. Finally, the resin was cleaved using a trifluoracetic acid:triisopropyl silane:water: tris(2-carboxyethyl)phosphine cocktail solution and purified using HPLC to get the folate-cysteine (13) as a yellow color solid.

Compound 14 was initially treated with a heterobifunctional linker reagent (15) to get the folate-cystine disulfide intermediate (16). This was then reacted with folate-cysteine (13) in DMSO and was purified using HPLC to produce compound 17 (e.g., Compound 2A). Characterization of all compounds was with LCMS using ammonium bicarbonate and acetonitrile as the buffer system. Observed mass from LCMS for Compound 2A was [M+H]+=1082.2.

In conjunction with the current state of the relevant arts, especially in view of Schemes 1, 2, and 3 set forth above, the present disclosure provides sufficient detail such that one of ordinary skill in the art can leverage the concepts set forth herein to synthesize all other compounds of the present disclosure.

Methods for Treatment

In addition to the compounds described herein, methods for providing treatment for and/or preventing a fibrotic disease or cancer are also provided.

In some embodiments, provided herein is a method of treating a subject suffering from a fibrotic disease state or a cancer, the method comprising contacting a cell of the subject with any compound provided herein, or a pharmaceutically acceptable salt thereof, or a (e.g., pharmaceutical) composition comprising any compound provided herein, or a pharmaceutically acceptable salt thereof, such as a compound having the structure of any one of Formula I, Formula II, Formula III, Formula IV, Formula V, Formula VI, Formula VII, Formula VIII, Formula IX, Formula X, Formula XI, Formula XII, Formula XIII, Formula XIV, Formula XV, Formula XVI, Formula XVII, Formula XVIII, Formula XX, or Formula XXX. In some embodiments, the immune modulator comprises an agonist of TLR 7, 8, or 9.

In some embodiments, provided herein is a method of treating an oncological, an inflammatory, an auto-immune, or a fibrotic disease or disorder in an individual in need thereof, comprising administering to the individual any compound provided herein, or a pharmaceutically acceptable salt thereof, or a (e.g., pharmaceutical) composition comprising any compound provided herein, or a pharmaceutically acceptable salt thereof, such as a compound having the structure of any one of Formula I, Formula II, Formula III, Formula IV, Formula V, Formula VI, Formula VII, Formula VIII, Formula IX, Formula X, Formula XI, Formula XII, Formula XIII, Formula XIV, Formula XV, Formula XVI, Formula XVII, Formula XVIII, Formula XX, or Formula XXX.

In some embodiments, provided herein is a method of treating an oncological disease or disorder in an individual in need thereof, comprising administering to the individual any compound provided herein, or a pharmaceutically acceptable salt thereof, or a (e.g., pharmaceutical) composition comprising any compound provided herein, or a pharmaceutically acceptable salt thereof, such as a compound having the structure of any one of Formula I, Formula II, Formula III, Formula IV, Formula V, Formula VI, Formula VII, Formula VIII, Formula IX, Formula X, Formula XI, Formula XII, Formula XIII, Formula XIV, Formula XV, Formula XVI, Formula XVII, Formula XVIII, Formula XX, or Formula XXX. In some embodiments, the oncological disease or disorder is cancer. In some embodiments, the cancer is selected from bladder cancer, brain cancer, liver cancer, renal cancer, skin cancer, thymus carcinoma, gastrointestinal stromal tumor (GIST), esophageal cancer, pancreatic cancer, and breast cancer.

In some embodiments, provided herein is a method of treating a fibrotic disease or disorder in an individual in need thereof, comprising administering to the individual any compound provided herein, or a pharmaceutically acceptable salt thereof, or a (e.g., pharmaceutical) composition comprising any compound provided herein, or a pharmaceutically acceptable salt thereof, such as a compound having the structure of any one of Formula I, Formula II, Formula III, Formula IV, Formula V, Formula VI, Formula VII, Formula VIII, Formula IX, Formula X, Formula XI, Formula XII, Formula XIII, Formula XIV, Formula XV, Formula XVI, Formula XVII, Formula XVIII, Formula XX, or Formula XXX. In some embodiments, the fibrotic disease or disorder is fibrosis. In some embodiments, the fibrosis is selected from IPF, fatty liver disease, cirrhosis, colitis, chronic liver disease, cardiac fibrosis, and scleroderma.

In certain embodiments, provided herein is a method of preventing or treating a fibrotic disease state comprising contacting a cell with at least one compound comprising an immune modulator or pharmaceutically acceptable salt thereof attached, via a linker, to a folate ligand or functional fragment or analog thereof, wherein the immune modulator or pharmaceutically acceptable salt thereof targets a pattern recognition receptor.

In some embodiments of the compounds, compositions, and/or methods provided herein, the immune modulator comprises a TLR agonist and is of a structure represented by Formula X or XX, or is a pharmaceutically acceptable salt of Formula X or XX:

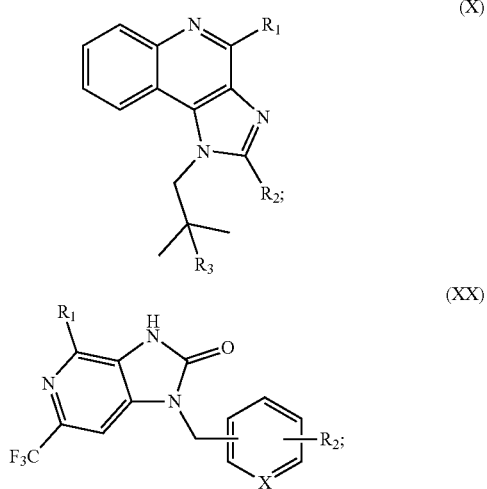

wherein, in Formulas X and XX:
$R_1$ is —$NH_2$ or —NH—$R_{1X}$,
$R_2$ is an H, an alkyl, an alkenyl, an alkynyl, an alicyclic, an aryl, a biaryl, a heteroaryl, —NH—$R_{2X}$, —O—$R_{2X}$, —S—$R_{2X}$,

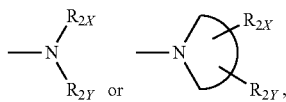

and

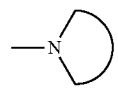

is a 3-10 membered N-containing non-aromatic mono- or bicyclic heterocycle;
wherein, in Formula X, $R_3$ is —OH, —SH, —$NH_2$ or —NH—$R_{1X}$,
wherein, in Formula XX, X is a CH, $CR_2$, or an N; and each of $R_{1X}$, $R_{2X}$, and RY are independently selected from the group consisting of an H, an alkyl, an alkenyl, an alkynyl, an alicyclic, an aryl, a biaryl, and a heteroaryl.

In some embodiments, the cell comprises a cell of a subject experiencing, or at risk for experiencing, a fibrotic disease state and contacting the cell with at least one compound further comprising administering or applying to the subject a therapeutically effective amount of the at least one compound. In some embodiments, the subject is a patient experiencing IPF and the at least one compound is administered to the subject intravenously, intramuscularly, intraperitoneally, topically or by inhalation. In some embodiments, the fibrotic disease state comprises IPF or a fibrotic disease of a liver, skin, bladder, heart, pancreas, prostate, or kidneys.

In some embodiments, the method further comprises obtaining, or having obtained, a sample from the subject; quantifying a level of expression of one or more biomarkers in the sample, each of the one or more biomarkers selected from the group consisting of CCL18, arginase 1 (Arg1), matrix metallopeptidase 9 (MMP9), metalloproteinase 3 (TIMP 3), IL-1β, hydroxyproline, collagen, PDGF, TGFβ, FRβ, TNFα, IFN-γ, anti-mannose receptor (CD206), cluster of differentiation 86 (CD86), cluster of differentiation 163 (CD163), IL-6, chemokine 10 (CXCL10), immune interferon (IFNα); comparing the level of expression of each of the one or more biomarkers in the sample to an expression level of such biomarker in a control; and administering or having administered to the subject a therapeutically effective amount of an unconjugated agonist or inhibitor if CCL18, Arg1, MMP9, TIMP 3, IL-1β, PDGF, TGFβ, FRβ, CD206, CD163, hydroxyproline, or collagen are unregulated relative to the expression level of the control or TNFα, IFN-γ, IL-6, CXCL10, IFNα or CD86 are downregulated or not expressed relative to the expression level of the control. In some embodiments, the folate ligand or functional fragment or analog thereof is specific for FRβ and binds to a FRβ on the cell.

In at least one embodiment, a method is provided for treating and/or preventing a fibrotic disease (such as IPF, for example). The method comprises administering to the subject a therapeutically effective amount of one or more compounds comprising a targeting moiety (such as a folate receptor binding ligand) attached to a drug (via a linker or otherwise) for reprogramming the M2-like macrophages in the fibrotic tissue or organ to a M1-like phenotype. For example, the drug may be a toll-like receptor agonist (for example, having formula I, III, or IV) or any other molecule or compound that is effective to reprogram a macrophage from the M2 phenotype to the M1 phenotype conjugated to folate. In at least one embodiment, the drug may be selected from a TLR 3 agonist, a TLR7 agonist, a TLR 7/8 agonist, a TLR8 agonist, and a TLR9 agonist. In some embodiments, the drug can reprogram M2-like macrophages to a M1 phenotype, thereby reducing profibrotic cytokine and growth factor production.

In at least one embodiment, a method is provided for treating a subject suffering from, or at risk for experiencing, a disease state, wherein the disease state comprises a fibrotic disease state or a cancer and the method comprises contacting a cell of the subject with at least one compound. The at least one compound may comprise any of the compounds of the present disclosure and, in at least one exemplary embodiment, comprises a targeting moiety specific for FRβ. In some instances, contacting a cell may be achieved through administering the at least one compound to the subject intravenously, intramuscularly, intraperitoneally, topically, orally, or through inhalation or any of the other administration modalities described herein. Additionally or alternatively, the at least one compound may comprise a composition containing one or more pharmaceutically-acceptable carriers, adjuvants, diluents, excipients, and/or vehicles, or combinations thereof. The dosage of the at least one compound administered may be modified as appropriate by the clinician; however, the at least one compound is preferably dosed in an amount that is therapeutically effective or prophylactically effective and, in at least one embodiment, the dosage is in a range of between 1 nmol/kg body weight of the subject and 50 nmol/kg body weight of the subject.

Figure 2:
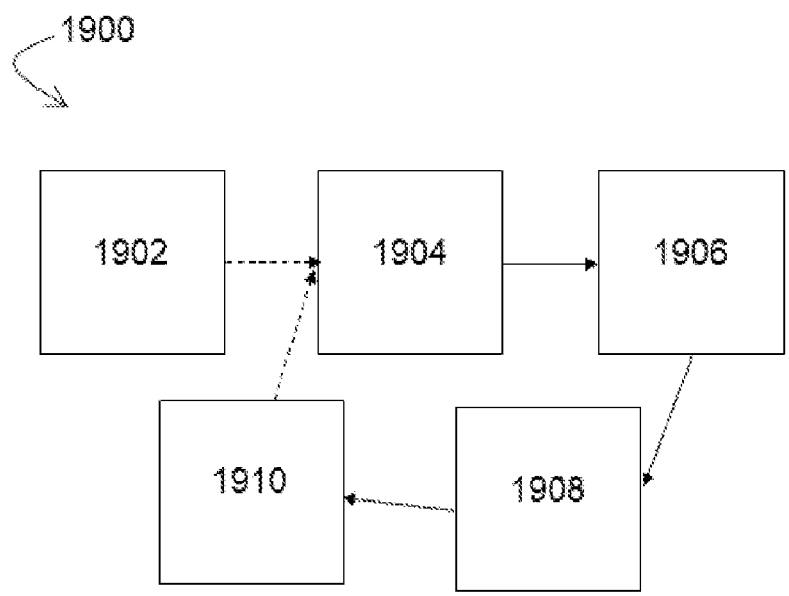
FIG. 2 shows a flow chart representative of methods for treating a subject experiencing, or at risk for experiencing, a fibrotic disease or a cancer.

Now referring to FIG. 2, a flow chart representative of a method 1900 for preventing or treating a fibrotic disease state or cancer is shown using one or more of the compounds of the present disclosure. In at least one instance, method 1900 comprises the steps of contacting a cell of a subject with at least one compound comprising an immune modulator (or pharmaceutically acceptable salt thereof) attached, via a linker, to a folate ligand or a functional fragment or analog thereof (step 1902). In at least one exemplary embodiment, the immune modulator or pharmaceutically acceptable salt thereof targets a pattern recognition receptor. The cell may comprise, for example, a cell of a subject experiencing, or at risk for experiencing, a fibrotic disease state and the at least one compound may comprise any of the compounds provided herein.

In at least one embodiment, the step 1902 of contacting a cell with at least one compound further comprises administering or applying to the subject a therapeutically effective amount of the at least one compound. Additionally or alternatively, the at least one compound may comprise a composition containing one or more pharmaceutically-acceptable carriers, adjuvants, diluents, excipients, and/or vehicles, or combinations thereof.

In at least one embodiment, the disease state comprises IPF or a fibrotic disease of a liver, skin, heart, or kidney. Further, the subject may comprise a mouse, a human, or any other mammal.

In addition to step 1902, method 1900 may optionally comprise steps 1904-1910. At step 1904, a biological sample is obtained from the subject and, at step 1906, the level of expression of one or more biomarkers in the sample is quantified. For example, the sample may be obtained from an amount of peripheral blood drawn from the subject.

The quantification step 1906 may be performed using any appropriate method known in the art and may include, for example, qPCR, mass spectrometry, ELISA, and/or any other modality that is capable to measure/quantify biomarker expression. In at least one exemplary embodiment, the one or more biomarkers are selected from the group consisting of CCL18, Arg1, MMP9, TIMP 3, IL-1β, PDGF, TGFβ, FRβ, hydroxyproline, collagen, TNFα, IFN-γ, CD206, CD163, IL-6, CXCL10, IFNα and CD86.

At step 1908, the level of expression of each of the one or more biomarkers in the sample is compared to an expression level of such biomarker in a control. The control may be a healthy individual or simply an individual that is not experiencing the disease state at issue. In at least one embodiment, a clinical difference between the expression level(s) of the one or more biomarkers in the sample and the expression level of the related biomarker(s) in the control can be indicative that the subject suffers from the disease state at issue. For example, and without limitation, if the comparison step 1908 indicates that expression of one or more of the biomarkers CCL18, Arg1, CD163, MMP9, TIMP3, IL-1β, PDGF, TGFβ, FRβ, hydroxyproline, collagen, and/or CD206 (i.e. the "profibrotic biomarkers") are upregulated as compared to the control, it is indicative of the subject experiencing a profibrotic immune response, which is linked to the M2-like macrophage phenotype. Accordingly, in at least one embodiment, such result is indicative of the need to administer one or more compounds of the present disclosure to reprogram such M2-like macrophages to the M1 phenotype.

In contrast, if the comparison step 1908 indicates that expression of the aforementioned biomarkers are downregulated as compared to the control, or if the expression of one or more of TNFα, IFN-γ, and/or CD86 (the "antifibrotic biomarkers") are upregulated as compared to the control, this, in certain embodiments, is indicative of the subject either showing a positive response to a previously administered compound (if applicable) and/or that the subject is experiencing an antifibrotic immune response, which is linked to the M1 phenotype.

Optionally, at step 1910, if expression of one or more of the profibrotic biomarkers in the sample are upregulated as compared to the respective expression level(s) in the control, or if the expression of one or more antifibrotic biomarkers are downregulated in the sample as compared to the respective expression level(s) in the control, an alternative therapy may be administered. In at least one embodiment, the alternative therapy may comprise administering a therapeutically effective amount of a derivative of the at least one compound previously administered at step 1902, where the derivative comprises the previously administered at least one compound modified with respect to either employing a different targeting moiety, a different linker size, and/or a different immune modulator in an attempt to better optimize the efficacy of the at least one compound for the subject. Additionally or alternatively, other treatments may be employed, including those conventionally known for treatment of the fibrotic disease at issue. Steps 1904-1910 can be repeated as necessary or desired.

Additional embodiments may provide a method for treating and/or preventing a cancer (whether folate receptor-positive or folate receptor-negative). For example, in certain instances, such a method comprises administering to the host subject a therapeutically effective amount and/or a prophylactically effective amount of one or more compounds comprising a targeting moiety attached to a drug (via a linker or otherwise) to reprogram the M2-like macrophages in the cancerous and/or tumor cells to a M1-like phenotype. Where the cancer is folate receptor-negative, such administration may additionally act to deplete or inhibit the MDSCs present in such tissue/tumor. For example, and without limitation, the drug may be selected from a PI3k inhibitor, a signal transducer and activator of transcription 6 (STAT6) inhibitor, a mitogen-activated protein kinase (MAPK) inhibitor, an inducible nitric oxide synthase (iNOS) inhibitor, and an anti-inflammatory drug (e.g., methotrexate). In at least one embodiment, the drug can inactivate MDSCs.

In describing representative embodiments, the disclosure may have presented a method and/or process as a particular sequence of steps. To the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps disclosed herein should not be construed as limitations on the claims. In addition, the claims directed to a method and/or process should not be limited to the performance of their steps in the order written, and one skilled in the art can readily appreciate that the sequences may be varied and still remain within the spirit and scope of the present disclosure.

EXAMPLES

Human monocytic THP-1 cells were obtained from American Type Culture Collection and cultured in folate-deficient RPMI 1640 medium (Invitrogen, Carlsbad, CA) containing 10% of heat inactivated fetal bovine serum and 1% Penicillin/streptomycin (Invitrogen, Carlsbad, CA). THP-1 cells were initially selected as a model system because this human monocytic cell line is known to acquire an M2-like phenotype and produce significant quantities of pro-fibrotic cytokines upon stimulation with IL-4, IL-6 plus IL-13.

IFN-γ, IL-4, interleukin-6 (IL-6), and interleukin-13 (IL-13) were obtained from Biolegend. Phorbol 12-myristate 13-acetate (PMA), lipopolysaccharide (LPS), all other reagents and solvents were purchased from Sigma.

Example 1: Differentiation and Polarization of THP-1 Cells into M2-Like Macrophages In Vitro THP-1 cells were seeded into 96-well plates at a density of 60,000 cells/well. Cells were differentiated into unpolarized macrophages by 48 hours incubation with 200 nM PMA followed by 24 hours incubation in fresh RPMI medium. The resulting macrophages were polarized to an M2-like phenotype by incubation with 20 ng/ml IL-4, 20 ng/ml IL-13, and 5 ng/mL IL-6 for 3 days and then reprogrammed with different concentrations of Compound 1A and Compound 1B for 48 hours and harvested for gene analysis by quantitative polymerase chain reaction (qPCR). Cultures were maintained at 37° C. in a humidified 5% $CO_2$ incubator.

To evaluate whether a potent TLR7 agonist (e.g., Compound 1A; e.g., of formula III) could reprogram the profibrotic macrophages into a less fibrotic phenotype, IL-4, IL-6 plus IL-13 stimulated THP-1 cells were incubated with different concentrations of nontargeted Compound 1A and the mRNA levels of several profibrotic markers were examined—namely, CCL18, CD206, IL-1β, and PDGFα and β.

Figure 3:
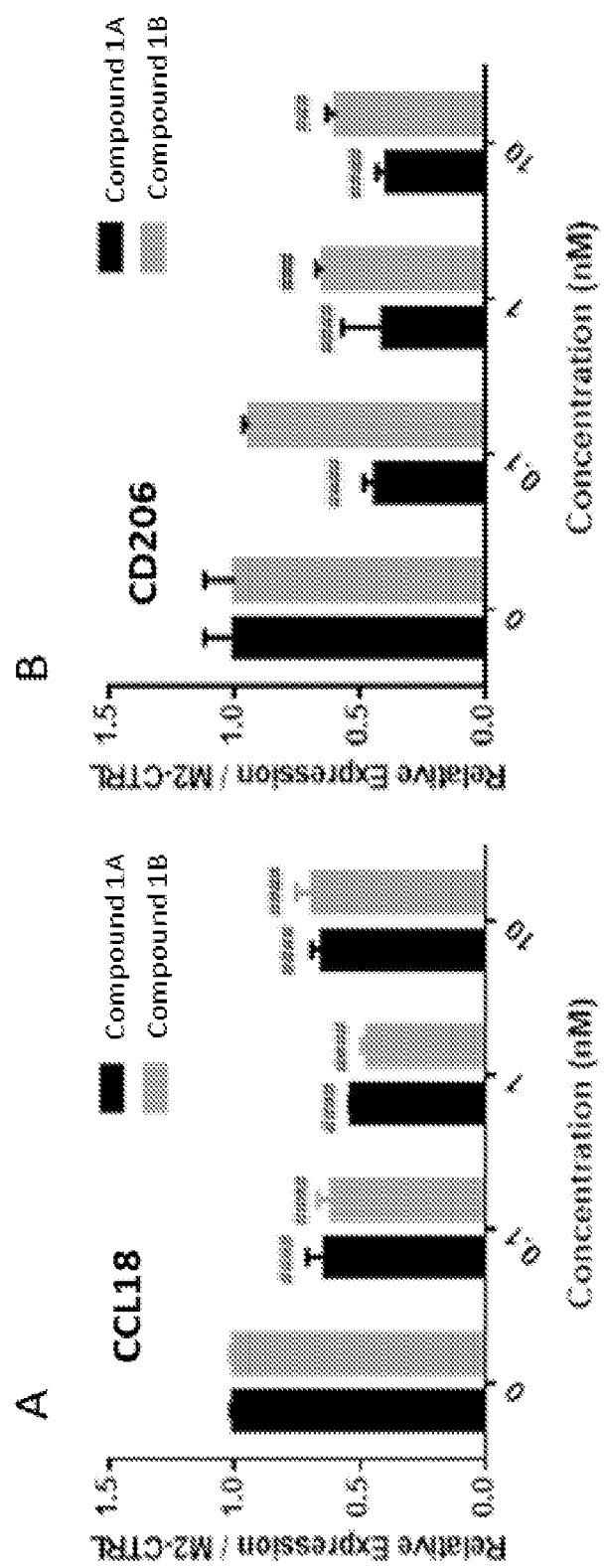
FIGS. 3A-3F show graphical data of various marker levels measured from human M2-type macrophages when contacted with an exemplary free (non-targeted) TLR7 agonist or an exemplary targeted (e.g., with a folate receptor binding ligand) TLR7 agonist at various concentrations for each compound. Data shown in FIGS. 3A-3C support that administration of either the non-targeted TLR7 agonist or the targeted TLR7 agonist successfully reprogrammed M2-type macrophages to M1-type macrophages (i.e., downregulated the M2-type profibrotic macrophages) and the data shown in FIGS. 3D-3F support that administration of the tested compounds upregulated the M1-type macrophages; each value represents the mean±S.D. for each group; #P<0.05, ##P<0.01, ###P<0.005, ####P<0.0001; treated groups versus M2-untreated group by Dunnett's multiple comparison test.

As shown in FIG. 3A-3C, incubation with the Compound 1A for 48 hours induced a decrease in CCL18, CD206 and IL-1β expression, suggesting that the TLR7 agonist can indeed promote a shift in these profibrotically polarized THP-1 cells towards a less fibrotic phenotype. Moreover, when expression of TNFα, a marker of an antifibrotic phenotype was examined, an increase in its expression was observed (FIG. 3D), confirming that the THP-1 shift from pro- to anti-fibrotic properties had occurred.

Example 2: Evaluation of the Macrophage Reprogramming

To confirm that folate-conjugated TLR7 agonist can cause the same THP-1 reprogramming seen in Example 1, Compound 1B was prepared in which a releasable linker connecting folate to Compound 1A was constructed with a disulfide, self-immolative bond to allow for release of Compound 1A following internalization of Compound 1B into the reducing environment of intracellular endosomes.

Different concentrations of either Compound 1A or Compound 1B were incubated with the above polarized THP-1 macrophages for the indicated times, after which the culture medium was harvested for analysis of secreted cytokines and the collection of cells for qPCR analysis.

Total RNA was isolated from $1 \times 10^5$ —$2 \times 10^5$ macrophages using a Quick-RNA™ MicroPrep kit (Zymo Research, Irvine, CA) according to the manufacturer-recommended protocol. The RNA samples were then reverse-transcribed into cDNA using high-capacity cDNA reverse transcription kits (Applied Biosystems, Foster City, CA; #4368814). qPCR analyses were performed using the iTaq™ Universal SYBR Green SuperMix (Bio-Rad Laboratories GmbH, Hercules, CA; #1725121), iCycler thermocycler, and iCycler iQ 3.0 software (Bio-Rad Laboratories GmbH, Hercules, CA) to track the expression of markers characteristic of macrophage polarization states. IL-6, CXCL10, IFNα, IFN-γ and CD86 were used as markers for an M1 phenotype, while CCL18, CD206, CD163 and Arg1 were employed as markers for the M2 phenotype. IL-1β, PDGFβ, MMP9 and TIMP 3 were measured as indicators of a profibrotic phenotype. IRAK-4 was used as an indicator of TLR7 stimulation. To control for specificity of the amplification products, a melting curve analysis was performed. No amplification of nonspecific products was observed in any of the reactions. Each sample was analyzed independently in triplicate for each marker.

Upon repeating the studies described above (see grey bars, FIGS. 3A-3F), the same qualitative changes were observed, only the magnitude of the impact of Compound 1B was somewhat reduced. This reduction in potency was expected because the nontargeted TLR7 agonist enters the cultured cells immediately, whereas its folate-targeted counterpart is designed to enter cells only after folate receptor binding and receptor-mediated endocytosis.

Figure 4:
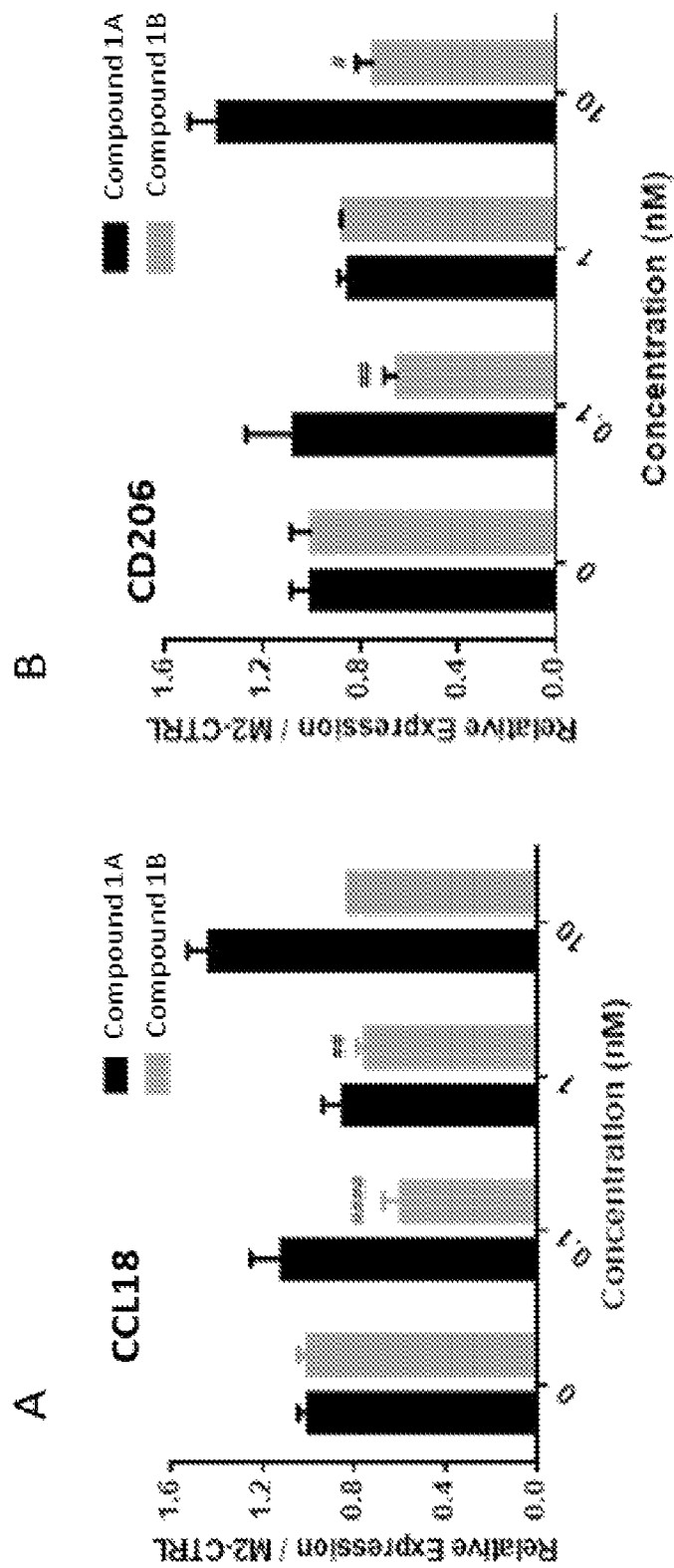
FIGS. 4A-4E and FIGS. 5A-5D show graphical data representative of various marker levels measured from M2 macrophages that were incubated with various concentrations of exemplary free or targeted TLR7 agonists for 2 hours (FIGS. 4A-4E), or 46 hours (FIGS. 5A-5D).
Figure 5:
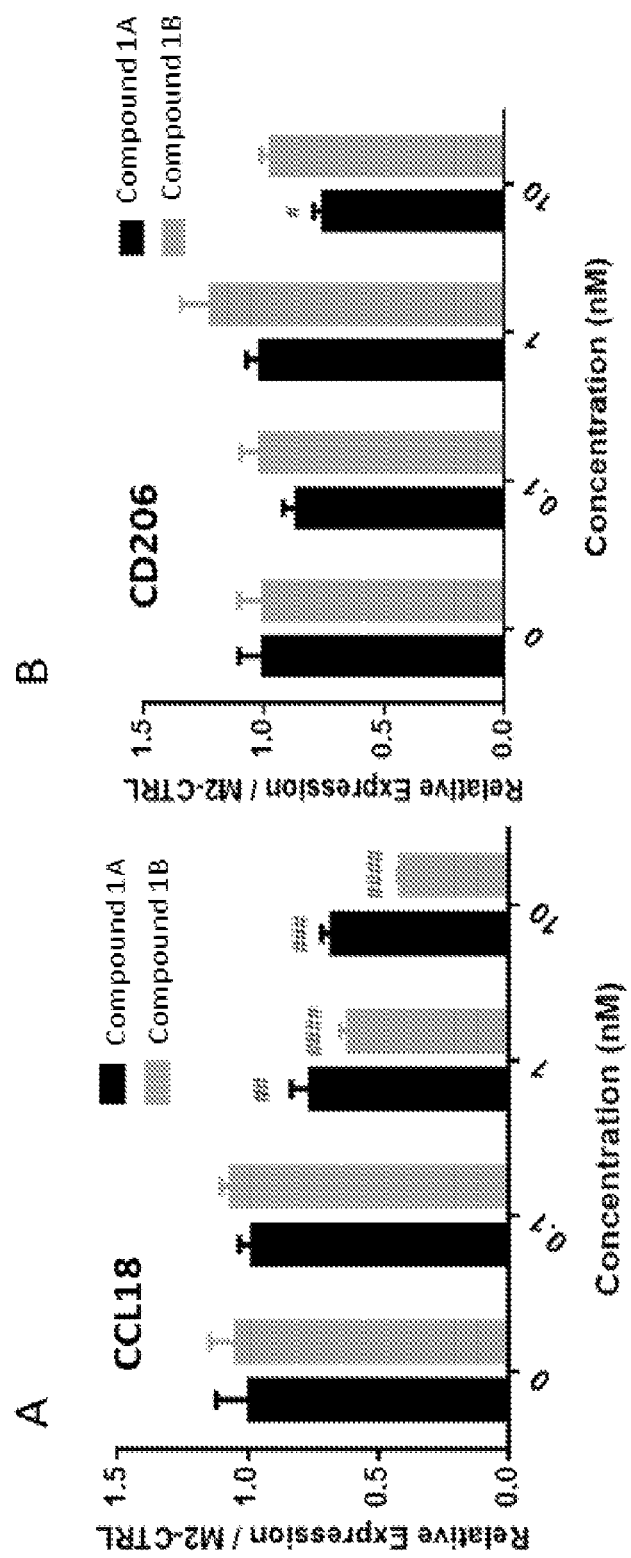

FIGS. 4A-4E and FIGS. 5A-5D show graphical data representative of various marker levels measured from THP-1 cells induced to M2 macrophages that were subsequently incubated with different concentrations of Compound 1B or Compound 1A for 2 hours, washed with PBS, for the data shown in FIG. 5A-5D, again incubated for 46 hours (for the data shown in FIG. 4A-4E, the cells were harvested immediately after the initial 2 hours of incubation). In both data sets, the cells were harvested for gene analysis by qPCR. FIG. 4A-4C shows CCL18 mRNA levels (FIG. 4A and FIG. 5A), CD206 mRNA levels (FIG. 4B and FIG. 5B), IL-1β mRNA levels (FIG. 4C and FIG. 5C), and PDGFβ mRNA levels (FIG. 4E). The data supports that the M2-type profibrotic phenotype was downregulated following administration of the tested compounds. In particular, Compound 1B downregulated profibrotic/M2-type markers of macrophages more than Compound 1A. Furthermore, FIG. 4D shows CD86 mRNA levels and FIG. 5D shows TNFα levels, which data supports that the M1-like phenotype was upregulated following administration of the tested compounds. While collected, data is not shown for PDGFα as no significant difference following treatment was observed.

Because low molecular weight water-soluble drugs like Compound 1A and Compound 1B are often excreted from the body within 2 hours of injection, a more physiologically relevant in vitro model of drug exposure in vivo is to limit incubation of a cell with drug for only two hours and then examine drug efficacy after an additional 46 hours of incubation in the absence of the drug. As shown in FIGS. 4A-4E, when THP-1 cells were incubated with the TLR7 agonists for 2 hours prior to replacement of the drug-containing medium with drug-free medium, Compound 1B was observed to have superior potency relative to Compound 1A, especially in the case of TNFα induction where the folate-targeted conjugate was dramatically improved. This is most likely because the folate-targeted TLR7 agonist was captured by the folate receptor positive cells, whereas Compound 1A was not retained by the same cells.

These data support that Compound 1B should be more effective in reprogramming profibrotic macrophages in vivo, with the added advantage that the folate-conjugated drug (e.g., Compound 1B) should also cause less systemic toxicity because it is concentrated in the FRβ-expressing macrophages and unable to enter folate receptor negative cells that predominate throughout the body (e.g., Compound 1B is designed to be impermeable to folate receptor negative cells).

FIGS. 6A-6D show graphical data representative of various marker levels measured from M2-induced THP-1 macrophages treated with different concentrations of drugs for 48 hours (FIGS. 6A and 6B) or for 2 hours, then displaced with fresh medium and cultured for the remaining 46 hours (FIGS. 6C and 6D). In both cases, cell supernatants were collected and secreted CCL18 protein and IL-1β was detected by ELISA. The data supports that administration of the TLR7 compound or the folate-targeted TLR7 compound downregulates the secretion of CCL18 and IL-1β at low concentration ranges (0.1-10 nM).

Further, to ensure that the above mRNA analyses accurately reflected the levels of profibrotic cytokines produced by IL-4, IL-6 plus IL-13 stimulated THP-1 cells, the concentrations of CCL18 and IL-1β polypeptides in the THP-1 supernatants were quantitated by ELISA assay. As shown in FIGS. 6A and 6B, both Compound 1A and Compound 1B induced reductions in CCL18 and IL-1β when incubated continuously with agonist for 48 hours, however, Compound 1B again was found to be superior when drug exposure was limited to only 2 hours (see FIGS. 6C and 6D).

Example 3: Characterization of FRβ Expression by Flow Cytometry

To measure the expression of FRβ on THP-1 derived macrophages, fluorescence-activated cell sorter (FACS) analysis was performed. Cells were detached using Accutase® Cell Detachment Solution (Biolegend, San Diego, CA; #423201) and gently lifted with a cell scraper. Cells were washed with PBS and nonspecific binding was blocked by incubation with Fc receptor blocking solution (Biolegend, San Diego, CA; #422301) at room temperature for 10 min. Biotinylated anti-human FRβ monoclonal antibody (m909) was then added and the cells were incubated for an additional 30 min on ice prior to washing in staining buffer (PBS supplemented with 2% FBS). Cells were then incubated on ice for 20 min in fluorescein-labeled streptavidin (BD Biosciences, Franklin Lakes, NJ; #554060), washed twice in PBS, stained with 7AAD (viability stain) for 15 min and analyzed by flow cytometry using BD Accuri C6 Software (BD Biosciences, Franklin Lakes, NJ). FIG. 6E shows the flow cytometry data, supporting that the THP-1 macrophages and were FRβ+ and, thus, suitable for the in vitro study of Compound 1B and other studies described herein.

FIG. 6F confirms that Compound 1B remained stable during the incubation period, which was 37° C. in the culture media. Indeed, Compound 1B retained the original structure after 48 hours incubation.

Example 4: Bleomycin Induced Pulmonary Fibrosis and Profibrotic Macrophage Reprogramming In Vivo Studies were also performed to determine if macrophages in pulmonary fibrotic lungs might be specifically targeted with folate-linked drugs in vivo. After testing multiple protocols for induction of pulmonary fibrosis in mice, a protocol was selected where 0.75 mg/kg bleomycin (BM) is instilled into the lungs of C57BL/6 mice via an incision in the trachea and the mice are allowed to progress through both inflammatory and fibrotic stages of fibrosis prior to initiation of therapy. (The BM model is widely regarded to be helpful in terms of enabling mechanistic investigations relevant to fibrogenesis in an in vivo context.)

As shown in FIGS. 7A-7D, mice treated using this protocol typically display fibrosis by day 7 post-BM treatment and this nascent fibrosis develops into severe fibrosis by day 14. Progress of the pathology then continues for 2-5 additional days before it begins to spontaneously resolve by day 21.

More specifically, eight-week-old C57BL6 male mice from Charles River (average weight 22 g to 25 g) were housed under pathogen-free conditions at room temperature (22° C.) under a 12 hours light-dark cycle. Mice were placed on a folate deficient chow (Envigo Teklad Global Rat Food Pellets) for 1 week prior to the BM or PBS instillation. Fresh water and folate-deficient diet were freely available. All animal procedures were approved by the Purdue Animal Care and Use Committee in accordance with National Institute of Health guidelines.

Thereafter, the mice were anesthetized with ketamine/xylazine and the necks of the mice were shaved using hair remover lotion and then sterilized with 70% alcohol. A small incision was made on the neck to visualize the trachea. Mice were positioned at a 75-degree angle and injected intratracheally with 100 μL sterile PBS or BM (Cayman Chemicals, Ann Arbor, MI; #13877) dissolved in PBS (0.75 mg/kg) using a 1 cc syringe with 26 G needle. Body weights were monitored every other day throughout the experiment.

To evaluate if profibrotic lung macrophages in these mice can be specifically targeted with folate-linked drugs, 10 days after the instillation, 10 nmol (for in vivo imaging) or 100 nmol (for in vivo labeling) of a folate-linked, near infrared fluorescent dye (OTL38) with or without 200-fold excess of FA-glucosamine (a competitor of OTL38) was injected into the tail veins of BM-treated mice and the dye uptake in the major organs was evaluated.

After 2 hours, mice were sacrificed using $CO_2$ asphyxiation and an incision in the skin from the abdomen to neck was immediately made to expose the lungs and trachea. A small cut in the upper trachea was then introduced for insertion of a blunted, 22-gauge needle, and a nylon string was tied around the trachea to seal the trachea around the needle. The trachea (containing the inserted needle), lungs and heart were then removed en masse by carefully cutting the connective tissue beneath the lungs, and the bronchus of left lung was clipped with a Dieffenbach vessel clip. The right lung was injected with PBS and aspirated 3 times using a 1 ml syringe, and the recovered lavage fluid was saved on ice.

Bronchoalveolar lavage fluid (BALF) was then analyzed to determine how the targeted TLR7 agonist works. BALF samples were centrifuged at 1500 rpm for 5 min at 4° C. and the supernatant was aliquoted and stored at −80° C. for cytokine/chemokine analyses. Cell pellets were resuspended and cultured in pre-warmed RPMI 1640 medium for 2 hours and then washed 3× with pre-warmed PBS prior to harvesting for qPCR assay. The right lung was then tied with a nylon string and used for subsequent analysis of hydroxyproline content. The left lung was inflated with 1 ml PBS using the inserted syringe and transferred to 10% formalin solution for subsequent histological analyses.

Lobes of the right lung collected above were weighed, placed in a pressure-tight vial (Supelco Inc., Bellefonte, PA; #27003), and hydrolyzed with 6N HCl (10 ml/g, v/w) in a sand bath at 120° C. for 3.5 hours. The hydrolyzed solution was cooled at 4° C. for 15 min and transferred to a 1.5 ml Eppendorf tube prior to centrifugation at 12,000 rcf for 15 min at 4° C. Supernatant was carefully collected, aliquoted and used for hydroxyproline (HYP) analysis.

For the subsequent HYP analysis, 10 µl of sample was transferred into a 96-well plate and neutralized with 10 µl of 5.3 M sodium hydroxide solution. Isopropanol (40 µl) was then added to each well followed by 20 µl of oxidation buffer and the mixture was incubated on a shaker at room temperature for 5 min. Analytical reagent (260 µl) was added, and the plate was incubated on a shaker at room temperature for 30 seconds and incubated immediately at 60° C. for 25 min. The absorbance was measured at 560 nm (A560) within 15 min. All reagents were prepared according to a previously reported protocol.

For histological analysis of the lung sections, fixed lungs (see above) were embedded in paraffin, sectioned and stained with hematoxylin-eosin (H&E), Masson's trichrome or F3 (anti-mouse FRβ antibody). Tissue sections were examined in a blinded manner by a licensed pathologist. More than 90×10$^6$ cells were quantified per section using Aperio-Image Scope (Leica Biosystems, Wetzlar, DE).

CCL18 and IL-1β were quantified in induced THP-1 cell supernatants using a human DuoSet ELISA Development System (R&D Systems Europe, Abingdon, UK; #DY394-05) and an IL-1 beta Human ELISA Kit (Thermo Fisher Scientific, Waltham, MA; #BMS224-2) as described by manufactures. BALF samples were analyzed for mouse IFN-γ using ELISA MAX™ Deluxe (Biolegend, San Diego, CA; #430804).

Finally, for the in vivo folate imaging studies, major organs (heart, lung, spleen, liver, small intestine, large intestine, and kidney) were resected and imaged using an AMI live imager (Spectral Instruments Imaging, Tucson, AZ). For in vivo folate receptor labeling studies, lungs of the mice were harvested immediately following euthanasia, digested with a lung dissociation kit (Miltenyi Biotec, Bergisch Gladbach, DE; #130-098-427) as described by gentleMACS Octo Dissociator with Heathers (Miltenyi Biotec, Bergisch Gladbach, DE; #130-096-427) as described by manual and filtered through a 70 µm cell strainer (Miltenyi Biotec, Bergisch Gladbach, DE; #130-098-462). Cells collected in the filtrate were depleted of erythrocytes by ammonium sulfate lysis, washed 2× in cold PBS and labeled for 30 min on ice with antibodies to desired macrophage markers (FITC-CD11b, Biolegend, San Diego, CA; #101205; FE-F4/80, Biolegend, San Diego, CA; #123109). Labeled macrophages were then washed twice in PBS, stained with 7AAD (viability stain) for 15 min and analyzed by flow cytometry using BD Accuri C6 Software (BD Biosciences, San Jose, CA).

As shown in FIG. 7A (top panel) untreated lungs (PBS control column) and BM-treated lungs on day 7 display a similar high density of alveoli interconnected by minimal extracellular matrix. In contrast, at day 14 post-BM instillation, the sizes and frequencies of air sacs were significantly decreased and the density of extracellular matrix is visibly increased, suggesting the development of significant fibrosis in the treated mice. By day 21, the pathology in this model had already begun to spontaneously resolve, with many mice eventually recovering from the BM-induced trauma by day 35.

Evidence for development of inflammation by day 7 is seen from the infiltration of FRβ-expressing macrophages (see lower panel of FIG. 7A and quantitation in FIG. 7B) that are almost completely absent from the healthy lungs but continue to accumulate through day 14 in the BM-exposed lungs. Further, staining with F3 showed significant expression of FRβ in the IPF lung (majorly in the interstitial space) as previously reported in the literature (FIG. 7A). Expression of FRβ was restricted to the inflamed lung (either IPF patient or BM-induced PF, but not in healthy lung). Moreover, FRβ-expressing macrophages were observed in mouse lungs on day 7 after the administration of BM with a maximum expression on day 14 (FIG. 7B). These results corroborated with previously reported FRβ expression on the activated macrophages in the inflamed lung.

That these FRβ-expressing macrophages can be targeted with folate-linked molecules was then demonstrated by the accumulation of OTL38, a folate-targeted fluorescent dye, in the lungs of BM-treated but not healthy mice following tail vein injection. As shown in FIG. 7B, OTL38 fluorescence was only observed in the kidneys of healthy mice (i.e. its major site of excretion), with little or no uptake in other tissues.

FIGS. 7C and 7D show FRβ IHC staining of human IPF lung tissue (FIG. 7C) and healthy human lung tissue (FIG. 7D). Eight-week-old C57BL/6 male mice were placed on a folate deficient chow for 1 week prior to the BM or PBS instillation, 10 days after the instillation, mice were injected via tail vein with 10 nmol (for in vivo imaging) or 100 nmol (for in vivo labeling) of OTL38 with or without 200-fold excess of FA-glucosamine. After 2 hours, mice were sacrificed prior to analysis. For in vivo folate imaging studies, major organs (heart, lung, spleen, liver, small intestine, large intestine and kidney) were resected and imaged using an AMI live imager (Spectral Instruments Imaging, Tucson, AZ). For in vivo folate receptor labeling studies, lungs of the mice were harvested immediately following euthanasia, digested and then labeled with antibodies to desired macrophages markers (FITC-CD11b, PE-F4/80) and 7AAD (live/dead staining) and analyzed by flow cytometry.

FIG. 7E shows images of various mice tissues/organs taken from mice with (BM) or without (PBS control) BM-induced experimental fibrosis and imaged with a folate receptor-targeted fluorescent dye, OTL38, with healthy (column a) or BM-treated mice (columns b and c) tail vein injected with 10 nmol OTL38 in the absence (b) or presence (c) of 200-fold excess of a folate-targeted glucosamine (competitive reagent of FRβ, which blocks the binding of OTL38) on day 10 post induction of fibrosis and euthanized 2 h later for tissue resection and fluorescence imaging, supporting that the inventive FA-targeting conjugates of the present disclosure exhibit FRβ-specific binding without uptake in other healthy tissue.

Tail vein injection of OTL38 into BM-treated mice yielded not only the aforementioned fluorescence in the kidneys, but also pronounced accumulation in the fibrotic lungs (see FIG. 7E). That this lung uptake was largely mediated by folate receptors could be demonstrated by the nearly quantitative blockade of lung accumulation when the BM-treated mice were simultaneously injected with 200-fold excess folate-glucosamine (i.e. a competitive inhibitor of FRβ-binding (see FIG. 7E)). These data demonstrate that a folate-targeted molecule binds selectively to folate receptor expressing cells in fibrotic tissue without accumulating to any significant extent in other tissues of the body. In other words, the FRβ-expressing macrophages can in fact be targeted with folate-linked molecules and, in clinical application, localize almost exclusively to the fibrotic tissue. As such, when a targeted moiety is used in the compounds of the present disclosure, any TLR7 agonist that is not captured by the targeted fibrotic (or cancerous) tissue will be minimal.

Next, to determine what cell type is capturing the folate-dye conjugates in the lungs of BM-treated mice, lungs from the above animals were digested with collagenase and examined by flow cytometry for cell-specific dye uptake. FIG. 7F shows data from a FACS analysis resulting from the in vivo labeling of such mice experiencing BM-induced experimental fibrosis that were tail vein injected with PBS (row 1) or 100 nmol OTL38 in the absence (row 2) or presence (row 3) of 200-fold excess of the folate-targeted [glucosamine]. As shown in FIG. 7F, no macrophage-like cells displayed any fluorescence when isolated from BM-treated mice not injected with OTL38 (see row 1). In contrast, about 22% of the macrophage-like cells from OLT38-injected fibrotic mice showed significant folate-targeted dye retention (row 2), which supports that OTL38 targets the FRβ positive macrophages in the inflamed lung. Indeed, the dye uptake was specifically folate receptor-mediated, as demonstrated by the observation that concurrent tail vein injection of 200-fold excess folate-glucosamine blocked essentially all folate-dye retention, demonstrating that accumulation of the dye required unoccupied folate receptors. Importantly, this conclusion is further supported by data showing that FRβ expression is essentially nondetectable in untreated lungs (see FIG. 7A), but increases dramatically during the development of fibrosis in BM-treated lungs (see FIGS. 7A-7D). FRβ expression is also prominently expressed in the lungs of human IPF patients.

Example 5

With an ability to target attached drugs to FRβ expressing fibrotic macrophages established, it was then investigated whether a folate targeted TLR7 agonist might be capable of suppressing the signs and symptoms of fibrosis in BM-treated mice. For this, BM-treated mice were intravenously injected every other day beginning on day 10 with either vehicle (3% DMSO in PBS) or Compound 1B (see FIG. 8A). Because the TLR7-54 agonist caused rapid body weight loss followed by death (see FIGS. 9A and 9B), Compound 1A could not be similarly evaluated in vivo. In BM-induced experimental pulmonary fibrosis in mice, inflammation is known to persist for about 9-10 days after BM installation. Because, inflammation to fibrosis switch happens in this model approximately day 9 to day 14, and profibrotic markers start appearing at about day 10, dosing began on day 10 (FIG. 8A).

Two doses were given every other day till day 21. The individual doses on a day are separated by 6 hours to prevent any "tolerance" to TLR agonists. Mice were then sacrificed on day 21 and subjected immediately to bronchoalveolar lavage followed by resection of the lungs for immunohistochemistry and quantitation of collagen and hydroxyproline.

Figure 8:
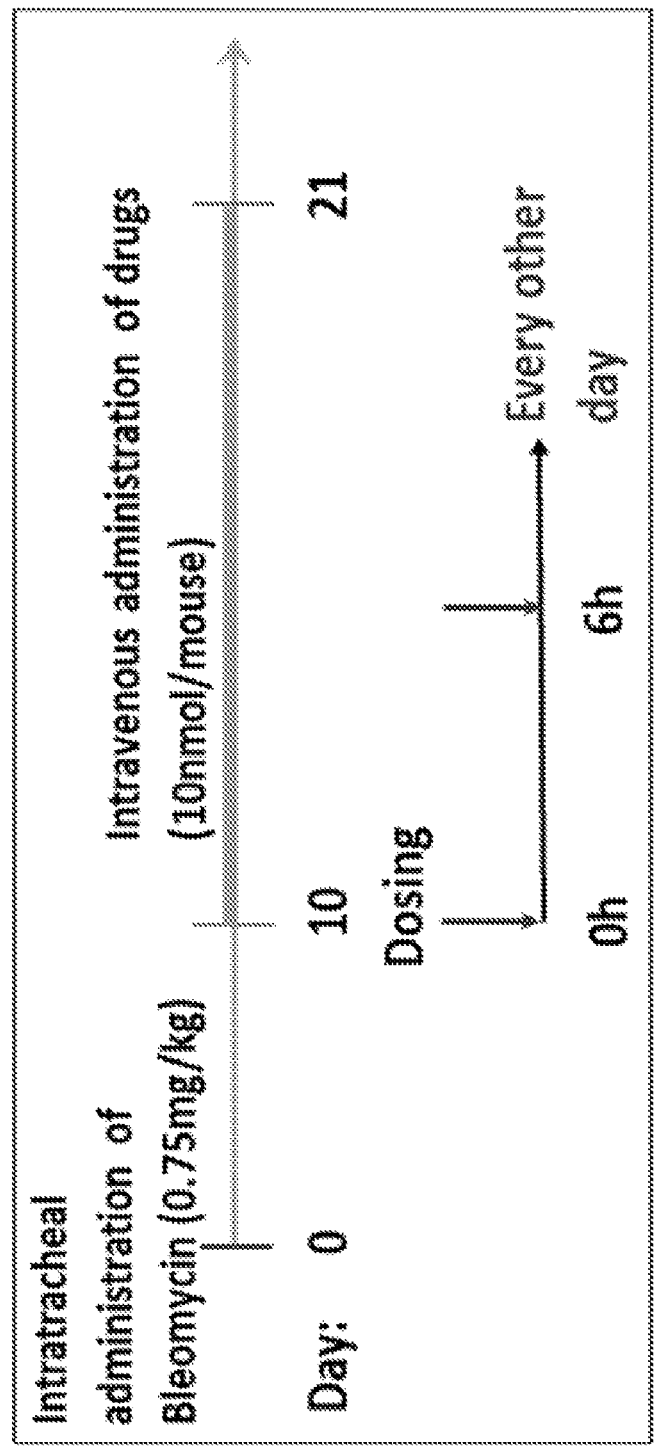
FIG. 8A illustrates the treatment plan of free and targeted TLR7 agonists in a BM model.
FIGS. 8B-8G show pro-fibrotic marker levels (FIGS. 8B-8D) and antifibrotic marker levels (FIGS. 8E-8G) measured from mice treated with the BM model of FIG. 8A.
FIG. 8H shows the number of cells in the bronchoalveolar lavage fluid (BALF) from mice treated with the BM model of FIG. 8A.

FIGS. 8B-8G show graphical data representative of various marker levels measured from mice treated with the BM model of FIG. 8A, with BALF collected on day 21 and centrifuged at 4° C., the resulting pellet resuspended in the medium and seeded into 96-well plates, cultured for 2 hours, washed with pre-warmed PBS 3 times, and cells harvested for qPCR; the data showing that Arg1 (FIG. 8B), MMP9 (FIG. 8C), TIMP 3 (FIG. 8D) (e.g., profibrotic markers) were all downregulated. CD86 (FIG. 8E) and IFN-γ (FIG. 8F) (e.g., antifibrotic markers) were both upregulated. Further, the negative regulator of TLR7 signaling IRAK-4 was upregulated (FIG. 8G), as were the number of BALF cells present (FIG. 8H). Indeed, the total number of mice BALF cells decreased in a dose-dependent manner following treatment with different doses of the Compound 1B. Each value shown in FIGS. 8B-8G represents the mean±S.D. for each group; *P<0.05, P<0.005, *<0.0005; for the saline versus vehicle group, Compound 1A and Compound 1B-treated groups versus vehicle group calculated by Student's t test, except for the BALF cell count and protein concentration measurements, in which the Compound 1B treated and vehicle group were calculated by Dunnett's multiple comparison test; and vehicle=3% DMSO in PBS.

As shown in FIGS. 8B-8D, qPCR analysis of the profibrotic markers in the macrophage subpopulation of bronchioalveolar lavage cells revealed that Arg1, MMP9, and tissue inhibitor of TIMP 3 were all elevated in BM-induced mice relative to the control mice. More importantly, parallel studies demonstrated that the same profibrotic markers were all suppressed when BM-induced mice were treated with Compound 1B, yielding levels of the fibrotic markers similar to those seen in healthy mice. Consistent with these data, quantitation of anti-fibrotic markers revealed that transcripts of CD86 (qPCR) and concentrations of IFN-γ (ELISA of lavage fluid) were both elevated following treatment with Compound 1B (see FIGS. 7E and 7F). Taken together with the observed upregulation of IRAK-4 (i.e. a marker of TLR activation; results shown in FIG. 7G) and the total number of BALF cells present being decreased in a dose-dependent manner after treatment with different doses of Compound 1B (FIG. 7H), these data demonstrate that administration of a folate-targeted TLR7 agonist can reprogram macrophages from a profibrotic M2-like phenotype to an anti-fibrotic M1-like phenotype in the lungs of BM-treated mice in vivo.

Example 6

An additional study was conducted to determine if the above-described reprogramming of fibrotic lung macrophages resulted in actual improvement of the fibrotic condition in the fibrotic mice. Lung tissue from the above mice was embedded in paraffin, and sectioned and stained with H&E and Masson's trichrome for evaluation of tissue density and extracellular collagen deposition, respectively.

FIGS. 9A and 9B show survival curves (FIG. 9A) and body weight change (FIG. 9B) of mice having experimental pulmonary fibrosis treated with non-targeted and targeted TLR7 agonists. The data supports that administration of the compounds of the present disclosure (here, for example, Compound 1B) increases survival of BM-treated mice without causing significant body weight loss. Each value represents the mean±S.D. for each group.

FIG. 10A shows the hydroxyproline content (μg/lung) of lung tissue to utilize collagen deposition as a measure of fibrosis. Tissue at day 21 for each of the following are shown: a healthy control (saline) (●), a disease control (vehicle) (■), treated with free drug TLR7 agonist (Compound 1A) (▼), and treated with a folate-targeted TLR7 agonist (Compound 1B) (▲). BM-induced mice treated with 10 nmol of either Compound 1B (1) and Compound 1A (T) showed a significant decrease in the total hydroxyproline content per lung as compared with the vehicle control (■). Each value shown in FIG. 9A represents the mean±S.D. for each group; *p<0.05, p<0.005, *<0.0005; saline versus vehicle group, Compound 1A and Compound 1B-treated groups versus vehicle group by Student's t test.

FIGS. 10B and 10C show stained images of the lung tissue represented in FIG. 10A with H&E staining (FIG. 10B) and Masson's trichrome (collagen) staining (FIG. 10C).

As shown in the H&E stains of the panel of FIG. 10B, healthy lungs contain an abundance of air sacs surrounded by thin reticular membranes. In contrast, BM-induced lungs display far fewer alveoli with pronounced deposition of extracellular matrix where air sacs once existed. Most importantly, BM-instilled mice treated beginning on day 10 with Compound 1B exhibited a lung architecture that resembles that of healthy mice (FIG. 10B), suggesting that targeting of Compound 1A to the fibrotic lung macrophages is effective to suppress the major hallmarks of pulmonary fibrosis. That this prevention of fibrosis indeed involves the blockade of collagen deposition is documented by Masson's trichome staining of parallel lunch sections (FIG. 10C), where the collagen stain is strongly suppressed in mice injected via tail vein with the Compound 1B (FIG. 10B). Accordingly, the data supports the IPF mice treated with at least Compound 1B (▲) demonstrate suppression of the IPF pathology (e.g., fibrosis).

Finally, to confirm that Compound 1B did indeed impact the production of collagen in vivo, hydroxyproline (a major component of collagen) was quantitated in total hydrolysates of the affected lungs. More specifically, lung tissue from the above mice was perfused with PBS, hydrolyzed with acid, and analyzed for hydroxyproline content. As shown in FIG. 10A, induction of fibrosis induces a large increase in the hydroxyproline content and this increase was suppressed upon treatment with Compound 1B. Accordingly, the data supports that treatment with the targeted TLR7 agonist compounds of the present disclosure reduces (and even counters) the deposition of collagen, and thus fibrosis, in vivo.

Figure 7:
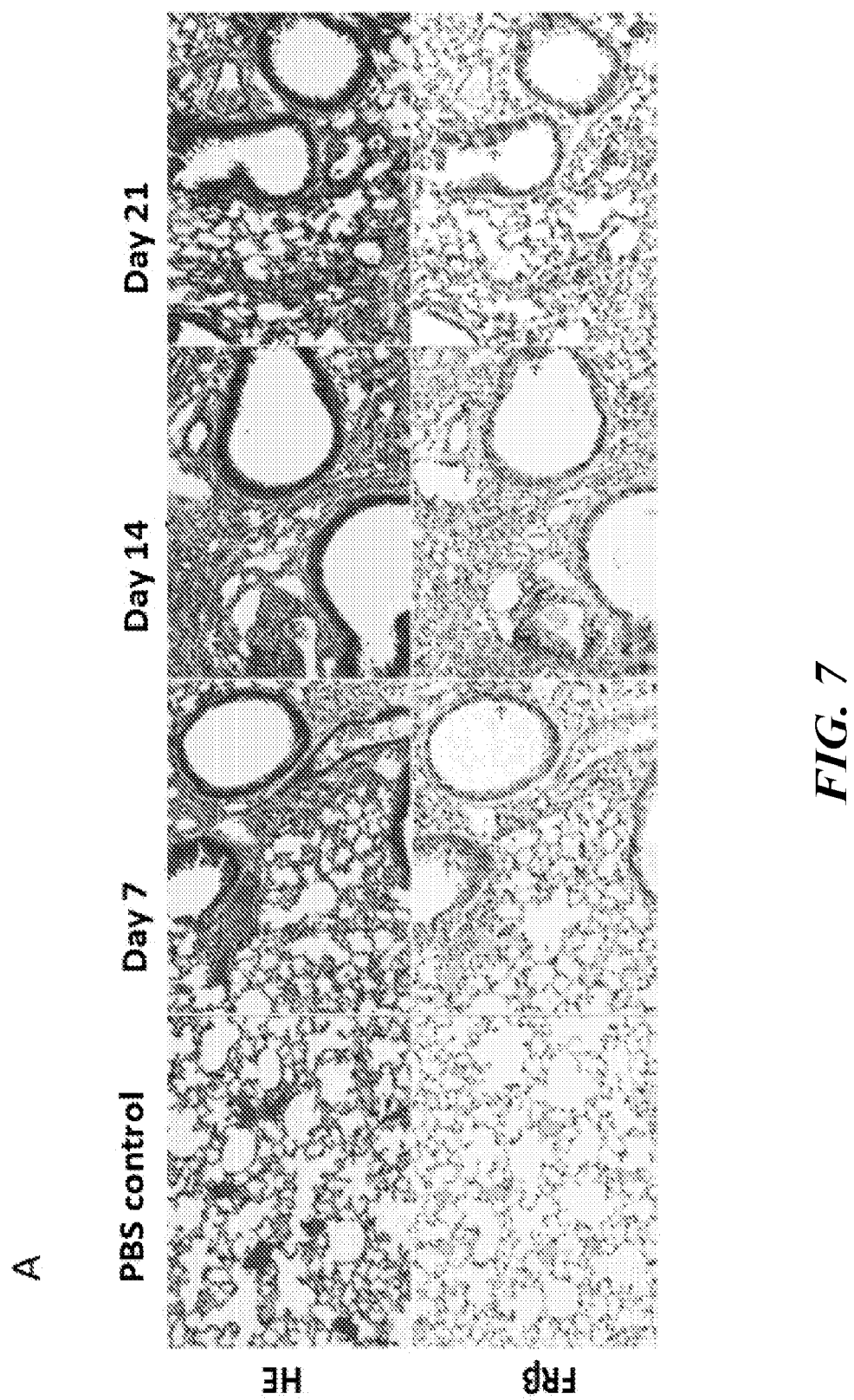
FIG. 7A shows stained images of lungs taken from mice with bleomycin (BM)-induced experimental fibrosis and stained using anti-mouse FRβ antibody, with the hematoxylin-eosin (H&E) staining performed on days 7, 14, and 21 post-BM-induced lung injury.
FIG. 7B shows quantification of FRβ staining in the panels of FIG. 7A.
FIGS. 7C and 7D show FRβ immunohistochemistry (IHC) staining of human idiopathic pulmonary fibrosis (IPF) lung tissue (FIG. 7C) and healthy human lung tissue (FIG. 7D).
FIG. 7E shows images of mice tissues/organs taken from mice with BM or without (phosphate-buffered saline (PBS) control) BM-induced experimental fibrosis and imaged with a folate receptor-targeted fluorescent dye.
FIG. 7F shows a fluorescence-activated cell sorter (FACS) analysis of mice with BM-induced experimental fibrosis.

In sum, overall survival of mice injected with optimized BM dose (0.75 mg/kg) was significantly improved by treatment with Compound 1B, whereas there was no survival benefit with Compound 1A except for showing significant weight loss (>25%, FIG. 7). While free drug performed better in the reduction of hydroxyproline content, the poor survival seen can be attributed to overall toxicity (i.e. weight loss, see FIG. 7B). This was not surprising as the systemic administration of TLR7 agonists has been known to cause toxicity.

Example 7

Because use of the nontargeted TLR7 agonist to treat IPF (or other fibrotic diseases) has been prevented by its systemic activation of the immune system and resulting toxicity, it was assessed whether any obvious toxicities might have accompanied systemic administration of Compound 1B in mice. To this end, BM-induced mice were treated every other day beginning on day 10 with 0, 1, 3, or 10 nmoles of Compound 1B and body weight, lung hydroxyproline content, and histological analyses were performed on day 21. Unlike conventional systemic administration, the targeted drug not only improved the survival, but also reduced the weight loss underlining the significance of targeting approach (FIGS. 11A and 11B).

Figure 12:
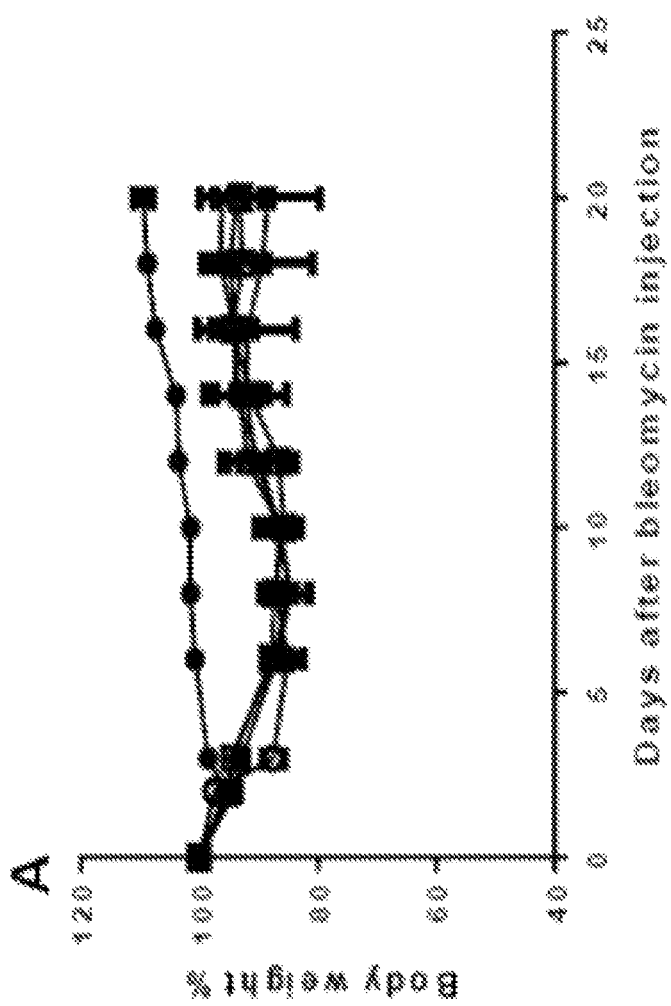
FIG. 12 shows the dose-dependent effect of an exemplary targeted TLR7 agonist of the present disclosure on the suppression of fibrosis in BM-induced mice.

FIG. 12 shows data relating to the dose-dependent effect of a folate-targeted TLR7 agonist on the suppression of fibrosis in BM-induced mice, using collagen deposition as a measure of fibrosis. The data are represented by: healthy control (PBS, ●), BM-induced mice with the treatment vehicle (■), 1 nmol Compound 1B (○), 3 nmol Compound 1B (□), or 10 nmol Compound 1B (▲)), with subpart A showing graphical data related to the body weight of the BM-induced mice over time, subpart B showing measurement of hydroxyproline content of the lung tissue (μg/lung) treated with different doses (10 nmol, 3 nmol, or 1 nmol of the Compound 1B), and subpart C showing images for histological analysis of the right lung tissue with H&E staining and Trichrome staining.

Figure 11:
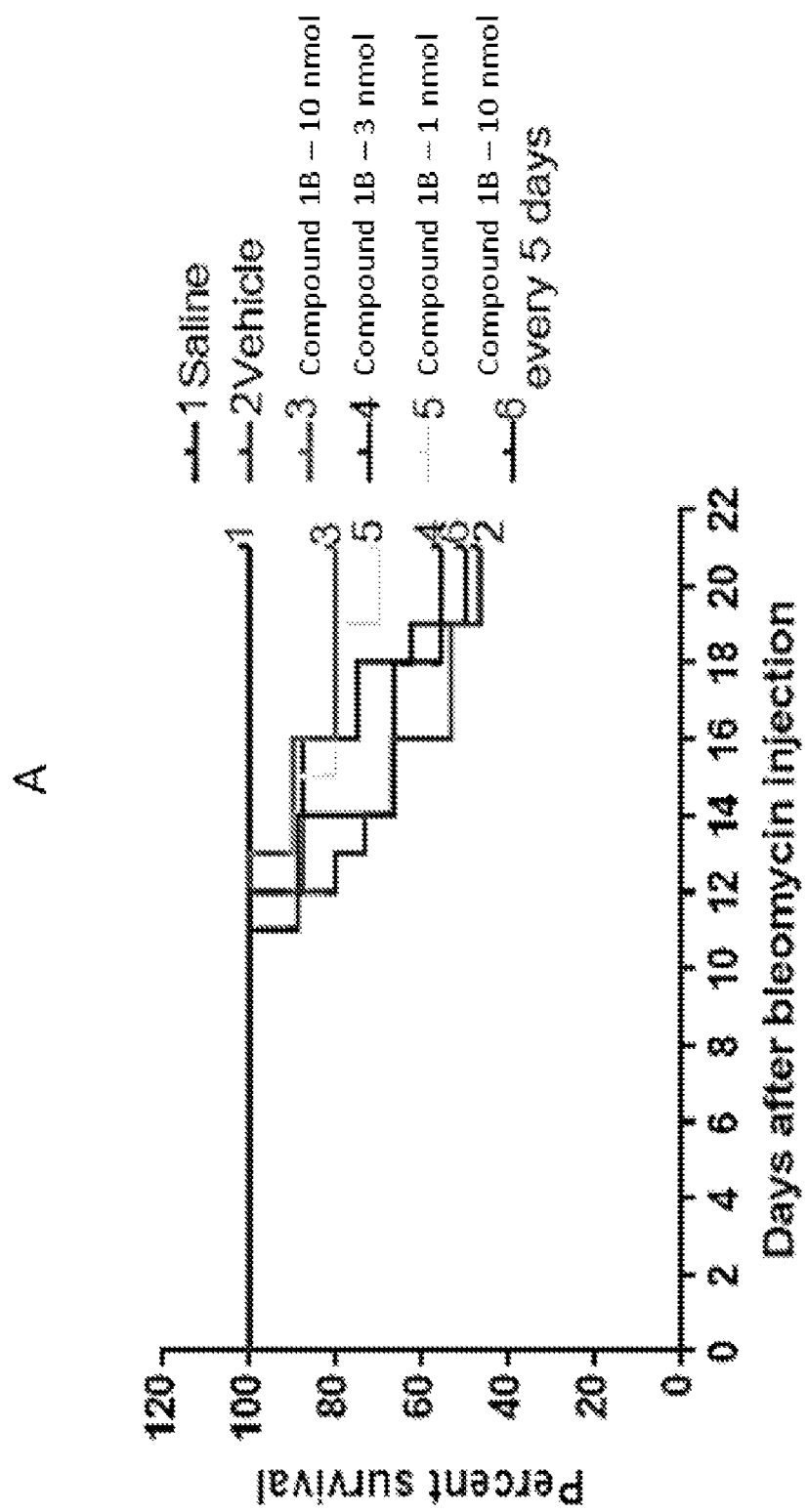
FIGS. 11A and 11B show survival curves (FIG. 11A) and body weight change (FIG. 11B) of mice with pulmonary fibrosis treated with exemplary targeted TLR7 agonists, with each value representing the mean±S.D. for each group.

As seen in FIG. 11B and subpart A of FIG. 12, no difference in weight loss was observed between mice treated with 0, 1, 3, or 10 nmoles of Compound 1B, suggesting that no gross toxicity was caused by repeated dosing with the compound. That these treatments were still having the anticipated effects on lung fibrosis could nevertheless be seen from comparison of the hydroxyproline contents of the various lung hydrolysates, where the order of efficacy was 10 nmol/mouse>3 nmol/mouse>1 nmol/mouse>0 nmol/mouse (subparts B and C of FIG. 12). More importantly, detailed analyses of the lung histology demonstrated that as the dose of Compound 1B increased, lung histology improved, which suggests that the tissue in which the TLR7 agonist was most strongly concentrated was in fact the tissue in which the microscopic morphology was most normal. Taken together, these data support that the targeting of the TLR7 agonist FRβ+ macrophages in fibrotic tissue can effectively prevent fibrosis without systemic activation of the immune system that otherwise limits TLR7 agonist use in humans.

Figure 9:
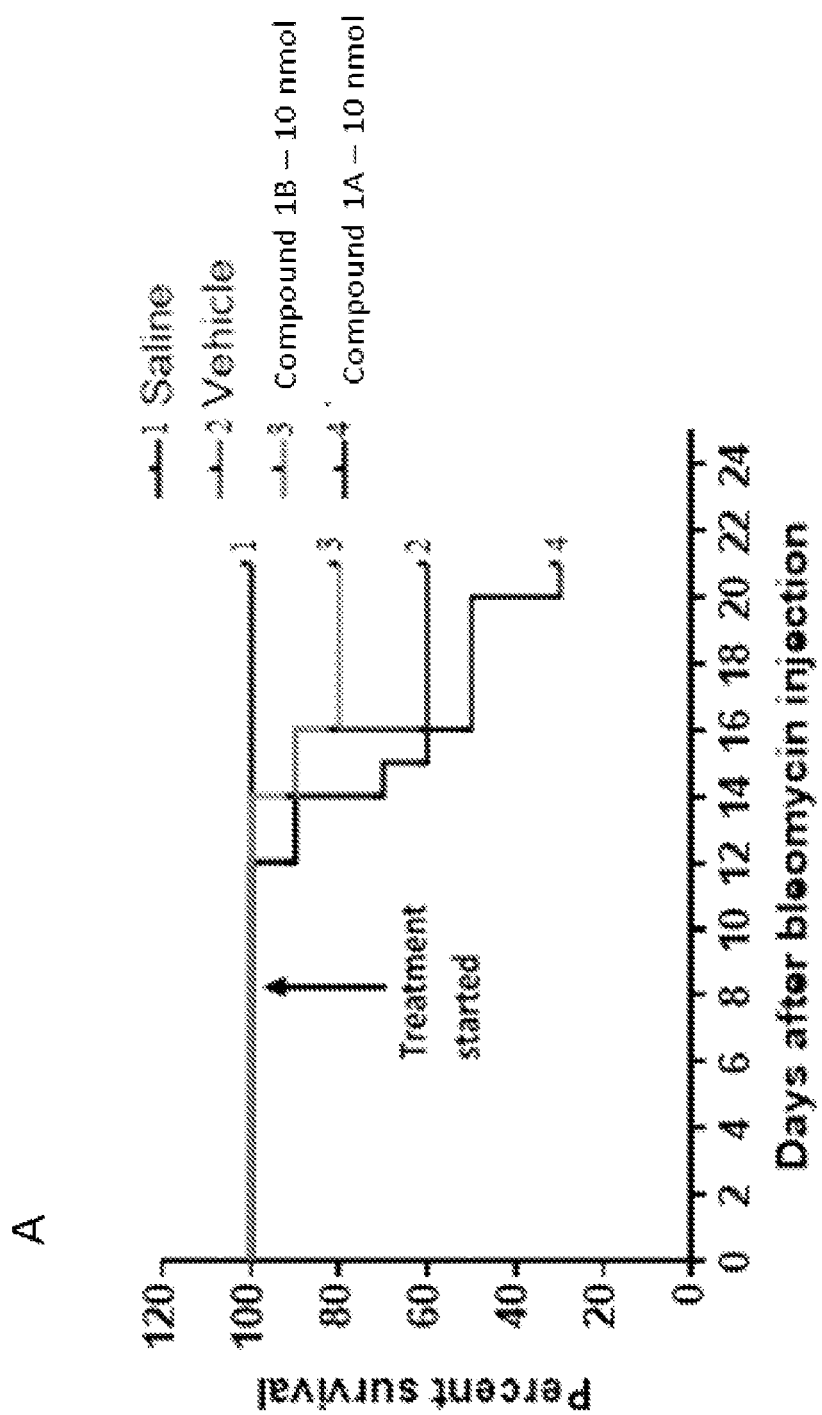
FIGS. 9A and 9B show survival curves (FIG. 9A) and body weight change (FIG. 9B) of mice with pulmonary fibrosis treated with non-targeted and targeted TLR7 drugs.
Figure 10:
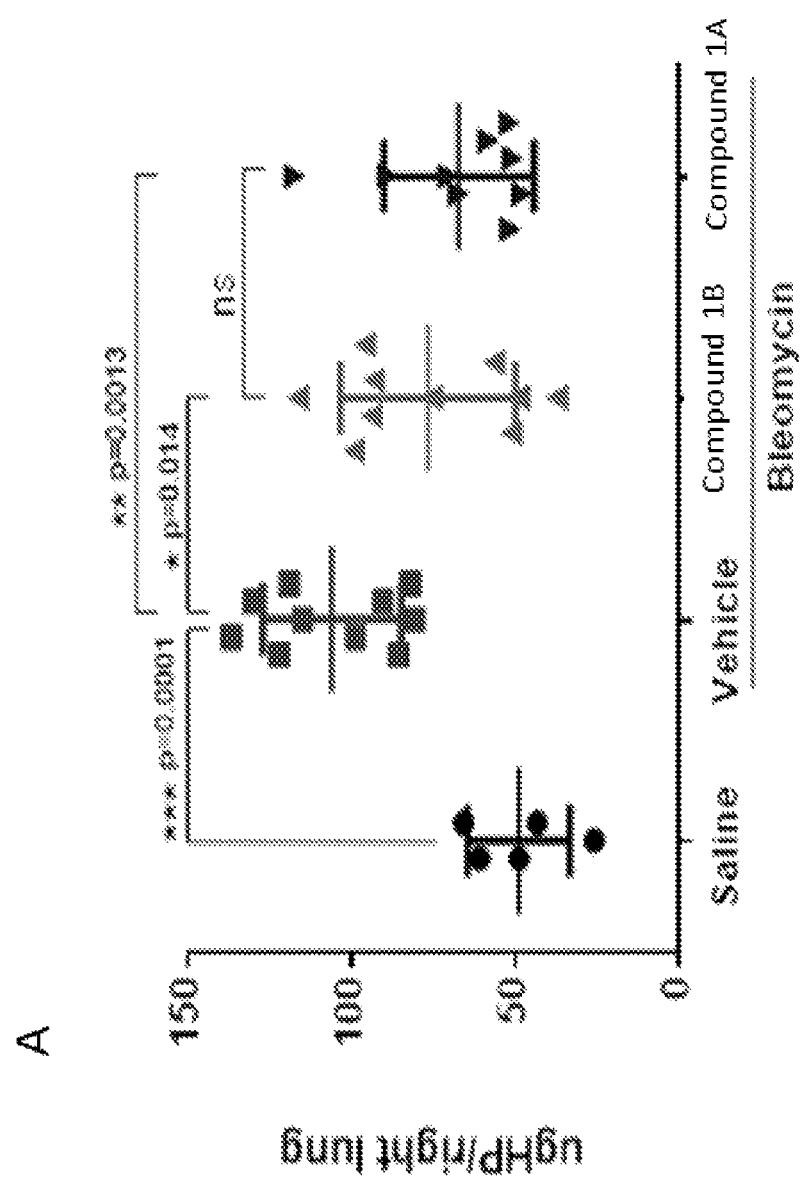
FIG. 10A shows the hydroxyproline content (μg/lung) of lung tissue as a measure of fibrosis.
FIGS. 10B and 10C show lung tissue in FIG. 9A with H&E staining (FIG. 10B) and Masson's trichrome (collagen) staining (FIG. 10C).

Finally, to determine if this antifibrotic effect can be achieved with lower doses, a therapeutic study with two lower doses (3 nmol/kg and 1 nmol/kg) was undertaken (FIGS. 9 and 10). Interestingly, while the low doses showed significant reduction in hydroxyproline content and collagen deposition levels, the 10 nmol dose provided the best survival rates.

Example 8

To support that embodiments of the compounds of the present disclosure other than Compound 1A and Compound 1B perform similarly in application, other representative embodiments of the compounds hereof were examined in in vitro studies.

Figure 13:
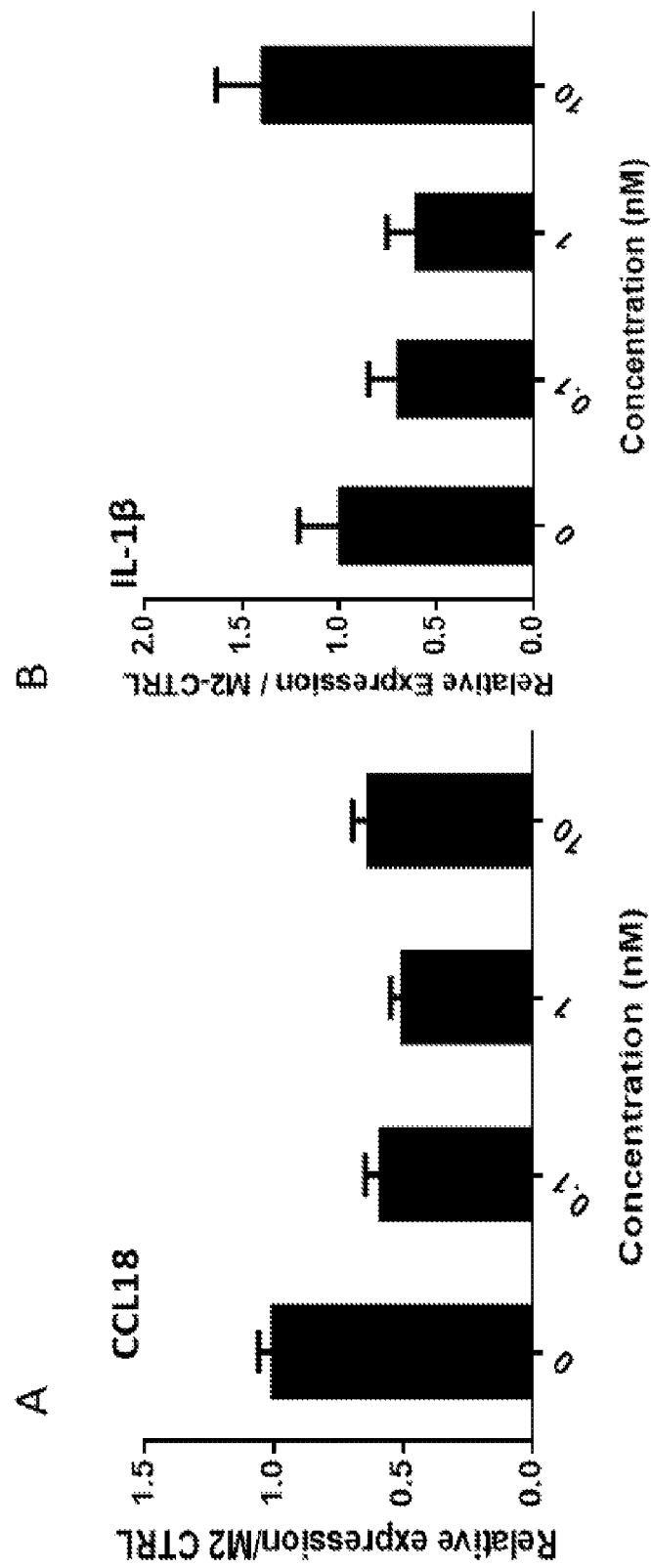
FIGS. 13A-13D show various marker levels measured from M2-type macrophages reprogrammed pursuant to methods of the present disclosure with various concentrations of an exemplary targeted TLR7 agonist for 48 hours and each value representing the mean±S.D. for each group.

FIGS. 13A-13D show graphical data representative of various marker levels measured from human THP-1 cells that were induced to M2 macrophages with 20 ng/mL IL-4, 20 ng/mL IL-13, 5 ng/mL IL-6. The cells were subsequently reprogrammed with different nM concentrations of a TLR7 agonist having formula IV (e.g., Compound 2A) for 48 hours and harvested for gene analysis by qPCR. mRNA levels of the following markers relative to the expression of a M2-like macrophage control: CCL18 mRNA levels (FIG. 12A), IL-1β mRNA levels (FIG. 13B), and TNFα levels (FIG. 13C), and FIG. 13D show protein analysis results after cell supernatants were collected. Secreted CCL18 protein was detected by ELISA.

In FIGS. 13A-13D, an agonist compound of the present disclosure having formula IV (e.g., Compound 2A) was evaluated with respect to its ability to reprogram M2-like macrophages to M1-like macrophages.

Primarily, human monocytic (THP-1) cells were induced to the M2-like phenotype using the methods and materials previously described. In particular, THP-1 cells were seeded into 96-well plates at a density of 60,000 cells/well. Cells were differentiated into unpolarized macrophages by 48 h incubation with 200 nM PMA followed by 24 hours incubation in fresh RPMI medium. The resulting macrophages were polarized to an M2-like phenotype by incubation with 20 ng/ml IL-4, 20 ng/ml IL-13, and 5 ng/mL IL-6 for 48 h. Cultures were maintained at 37° C. in a humidified 5% $CO_2$ incubator.

To evaluate whether Compound 2A could reprogram the profibrotic macrophages into a less fibrotic phenotype, IL-4, IL-6 plus IL-13 stimulated THP-1 cells were incubated with different concentrations of Compound 2A and the mRNA levels of several profibrotic markers were examined using qPCR and ELISA—namely, CCL18, IL-1$\beta$, and TNF$\alpha$.

As shown in FIGS. 13A and 13B, incubation with Compound 2A (free drug) for 48 hours induced a decrease in CCL18 and IL-1$\beta$ expression, suggesting that the TLR7 agonist can indeed promote a shift in these profibrotically polarized THP-1 cells towards a less fibrotic phenotype. (Note FIG. 13B shows a bell-shaped curve indicative of Compound 2A having an inhibitory response at lower concentrations and a stimulatory response at high concentrations, which is a common response curve with certain drugs.) Moreover, when expression of TNF$\alpha$ (an antifibrotic phenotype marker) was examined, an increase in its expression was observed (FIG. 13C), confirming that the THP-1 shift from pro- to anti-fibrotic properties occurred.

In addition to the nonconjugated TLR7 agonist, conjugated compounds of the present disclosure were likewise evaluated. Human THP-1 cells were induced to macrophages having the M2-like phenotype per the methods set forth herein (e.g., using 20 ng/mL IL-4, 20 ng/mL IL-13, 5 ng/mL IL-6), then reprogrammed with different nM concentrations of various compounds of the present disclosure for 2 hours; namely, a nonconjugated (free drug) TLR7 agonist compound having formula I and/or II (data shown collectively as Compound 3A), a folate-conjugated TLR7 agonist compound having formula XV (having a releasable linker) (e.g., Compound 3B), a folate-conjugated TLR7 agonist compound having formula XVII (having a non-releasable linker) (e.g., Compound 3C), and a folate-conjugated TLR7 agonist compound having formula XVI (having a non-releasable linker) (e.g., Compound 3D). The cells were subsequently harvested for gene analysis by qPCR and the relative expression of CCL18 (FIG. 14A), CD206 (FIG. 14B), and IL-1$\beta$ (FIG. 14C) analyzed.

Figure 14:
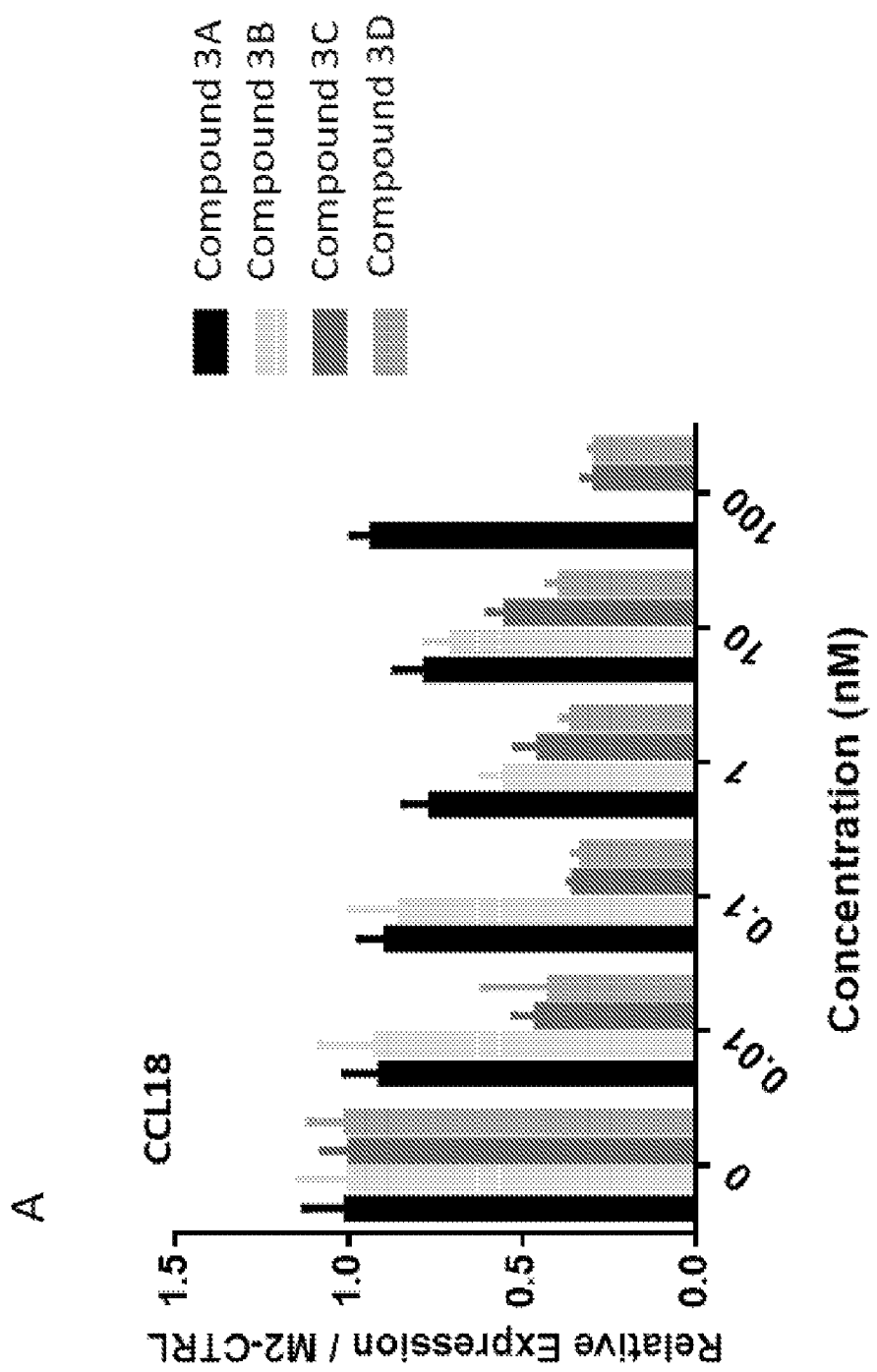
FIGS. 14A-14C show various marker levels measured from M2-type macrophages reprogrammed pursuant to methods of the present disclosure with various concentrations of exemplary free and targeted TLR7 agonists. Each value shown in FIGS. 14A-14C represents the mean±S.D. for each group; #P<0.05, ##P<0.005, ###P<0.0005; ####P<0.0001; Compound 3A, Compound 3B-treated, and Compound 3C-treated groups versus M2-untreated group by Dunnett's multiple comparison test.

Expression of the various profibrotic (M2 phenotype) markers CCL18, IL-1$\beta$, and CD206 markers were quantified. As shown in FIGS. 14A-14C, expression of each of these profibrotic markers were reduced after administration of each of Compound 3B, Compound 3D, and Compound 3C, with Compound 3D and Compound 3C compound (both with non-releasable linkers) most effective relative to the other compounds.

Figure 15:
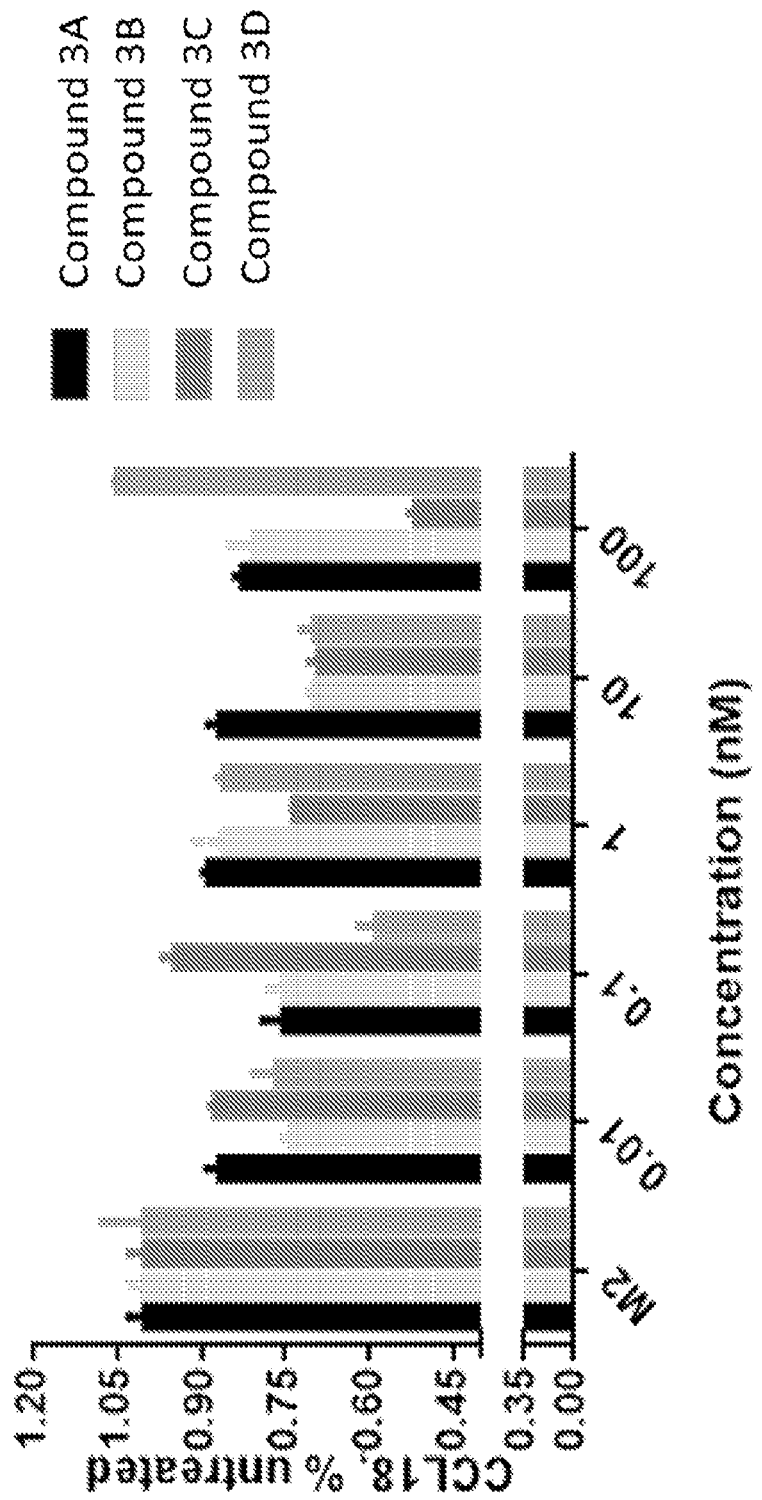
FIG. 15 shows secreted chemokine (C—C motif) ligand 18 (CCL18) protein levels in each group of cells of FIGS. 14A-14C after treatment with exemplary free and targeted TLR7 agonists.

FIG. 15 shows secreted CCL18 protein levels in each of the groups of THP-1 cells of FIGS. 14A-14C after treatment with the Compound 3A, Compound 3B, Compound 3C, or Compound 3D. Compound 3A and the folate-targeted TLR7 compounds (e.g., Compound 3B, Compound 3C, and Compound 3D) downregulate the secretion of CCL18 at a low concentration range (0.1-10 nM).

Additionally, cell supernatants were collected and secreted CCL18 protein was detected by ELISA. FIG. 15 confirms that Compound 3A (free drug) and the folate-targeted compounds (Compound 3B, Compound 3C, and Compound 3D) all downregulated the secretion of CCL18 at a low concentration range (0.1-10 nM), further supporting that, akin to the examples described in connection with Compound 1A and Compound 1B, these compounds can similarly reprogram M2-like profibrotic macrophages to M1-like antifibrotic macrophages through like mechanisms.

Example 9

Upon repeating the studies described above (see grey bars, FIGS. 3A-3F), the same qualitative changes were observed, only the magnitude of the impact of Compound 1B was somewhat reduced. This reduction in potency was expected because the nontargeted TLR7 agonist enters the cultured cells immediately, whereas its folate-targeted counterpart is designed to enter cells only after folate receptor binding and receptor-mediated endocytosis. Because low molecular weight water-soluble drugs like Compound 1A and Compound 1B are often excreted from the body within 2 hours of injection, a more physiologically relevant in vitro model of drug exposure in vivo is to limit incubation of a cell with drug for only two hours and then examine drug efficacy after an additional 46 hours of incubation in the absence of the drug. As shown in FIGS. 4A-4E, when THP-1 cells were incubated with the TLR7 agonists for 2 hours prior to replacement of the drug-containing medium with drug-free medium, Compound 1B was observed to have superior potency relative to Compound 1A, especially in the case of TNF$\alpha$ induction where the folate-targeted conjugate was dramatically improved. This is most likely because the folate-targeted TLR7 agonist was captured by the folate receptor positive cells, whereas Compound 1A was not retained by the same cells.

These data support that Compound 1B should be more effective in reprogramming profibrotic macrophages in vivo, with the added advantage that the folate-conjugated drug (e.g., Compound 1B) should also cause less systemic toxicity because it is concentrated in the FR$\beta$-expressing macrophages and unable to enter folate receptor negative cells that predominate throughout the body (e.g., Compound 1B is designed to be impermeable to folate receptor negative cells).

Further, to ensure that the above mRNA analyses accurately reflected the levels of profibrotic cytokines produced by IL-4, IL-6 plus IL-13 stimulated THP-1 cells, the concentrations of CCL18 and IL-1$\beta$ polypeptides in the THP-1 supernatants were quantitated by ELISA assay. As shown in FIGS. 6A and 6B, both Compound 1A and Compound 1B induced reductions in CCL18 and IL-1$\beta$ when incubated continuously with agonist for 48 hours; however, Compound 1B again was found to be superior when drug exposure was limited to only 2 hours (see FIGS. 6C and 6D).

Example 10

Figure 16:
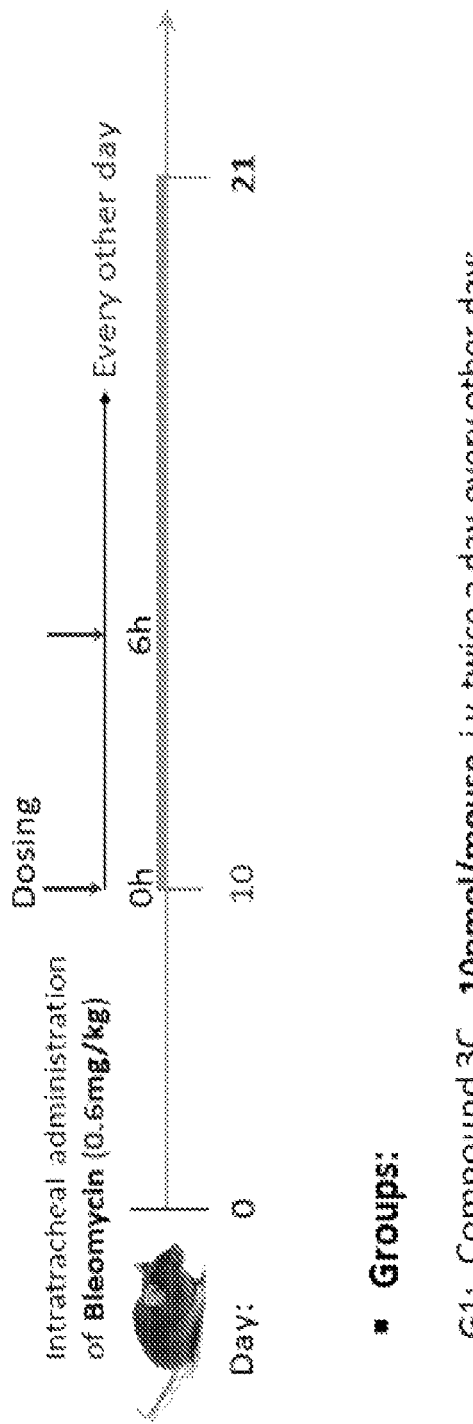
FIG. 16 illustrates a methodology for a BM murine model.
Figure 17:
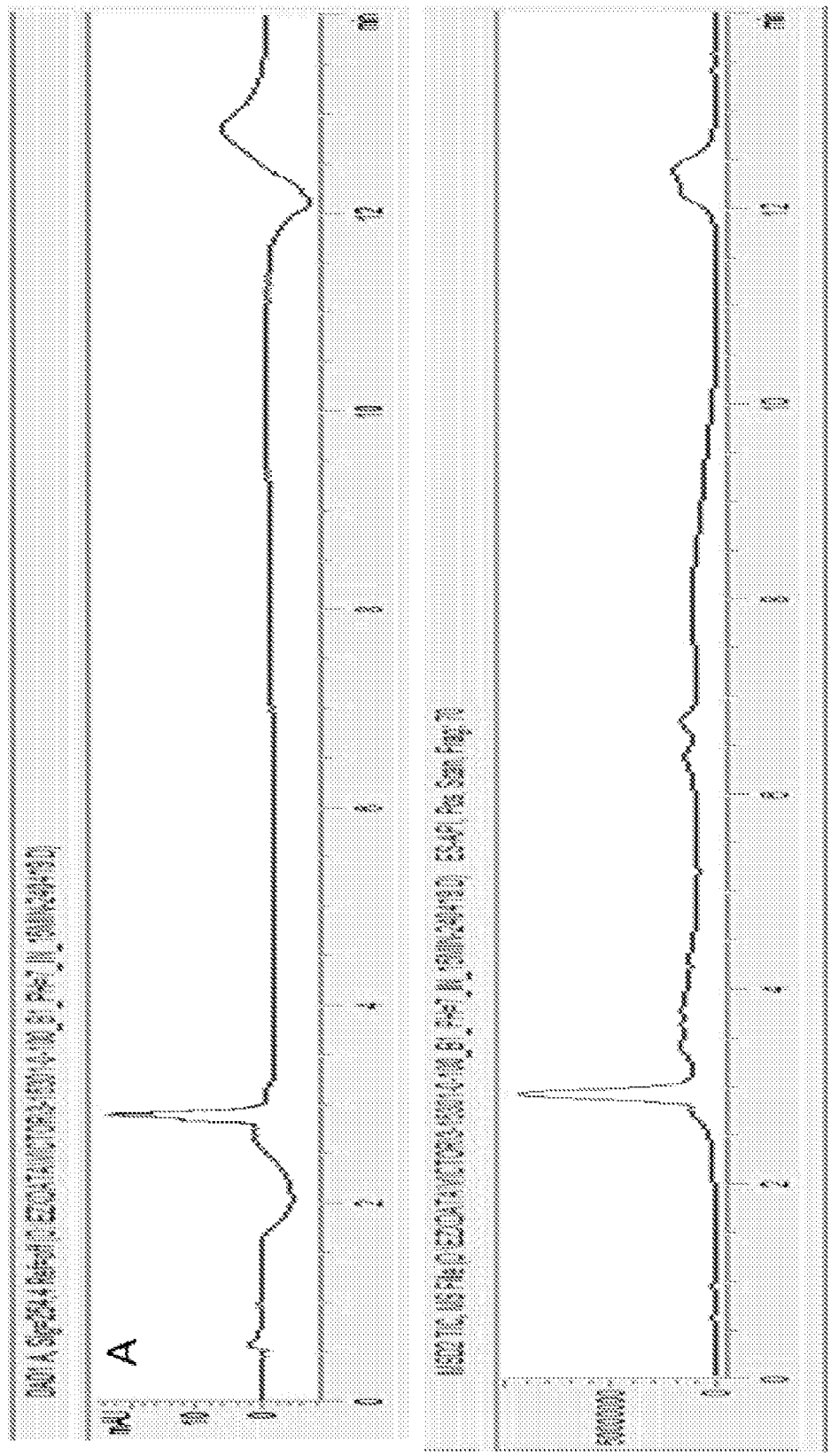
FIGS. 17A and 17B show the purity of an exemplary targeted TLR7 agonist provided herein.

FIG. 16 illustrates the in vivo study methodology of at least one embodiment of a compound of the present disclosure in a BM murine model, the compound having formula XVII (e.g., Compound 3C). FIGS. 17A and 17B are the LC-MS spectrum of Compound 3C and support the high purity of the conjugate and no free drug was detected.

Figure 18:
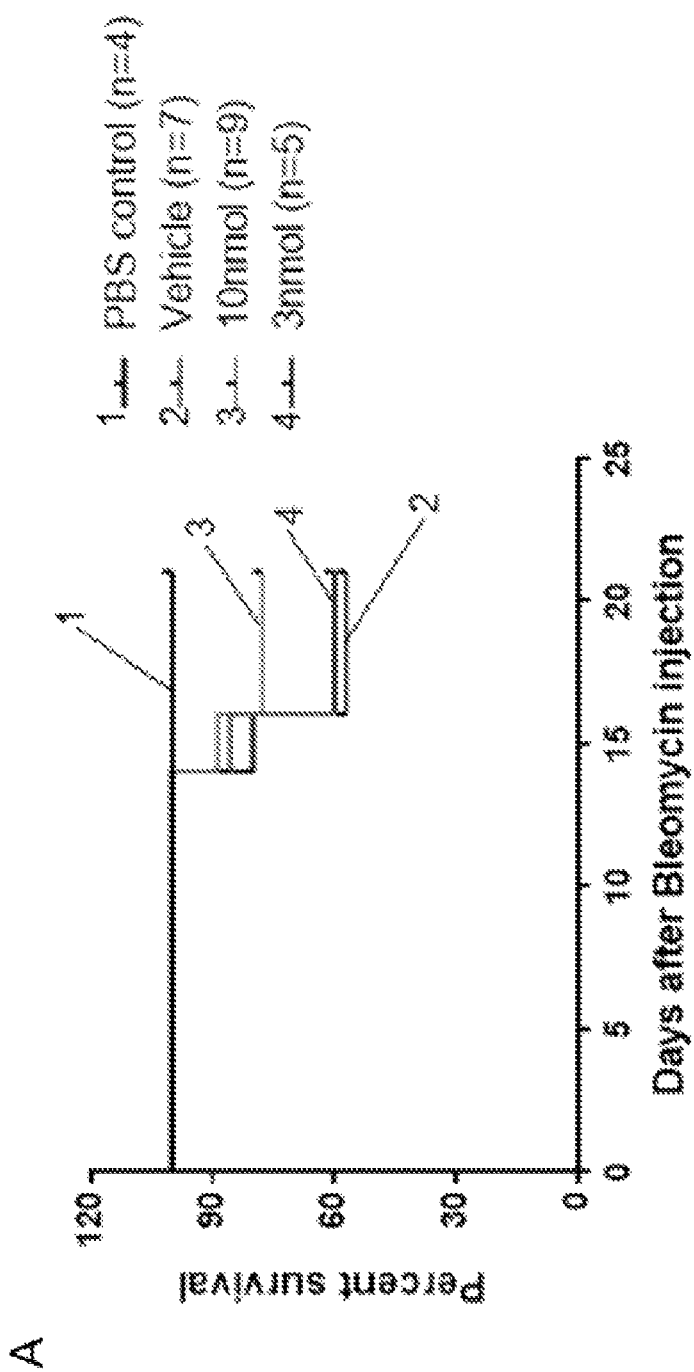
FIGS. 18A-18F show data from the in vivo study methodology of FIG. 16, including survival curves (FIG. 18A), body weight changes (FIGS. 18B and 18D), concentration of cells with BALF present (FIG. 18C), hydroxyproline concentration (μg HP/lobe) in live mice (FIG. 18E) and in all mice (i.e. inclusive of both live mice and those that died before day 21) (FIG. 18F).

FIGS. 18A-18F shows results from the subject mice of the in vivo study methodology of FIG. 16, including survival curves (FIG. 18A), body weight changes (FIGS. 18B and 18D), concentration of cells with BALF (FIG. 17C), hydroxyproline concentration ($\mu$g HP/lobe) in live mice (FIG. 18E) and in all mice (e.g., inclusive of both live mice and those that died before day 21) (FIG. 18F). The 10 nmol concentration dosage of the compound having formula XVII (e.g., Compound 3C) increased the survival rates of the subject mice, while concurrently decreasing the HP and number of BALF cells. Also, the 3 nmol concentration dosage did not show measurable benefit to the subject mice.

Example 11

Figure 19:
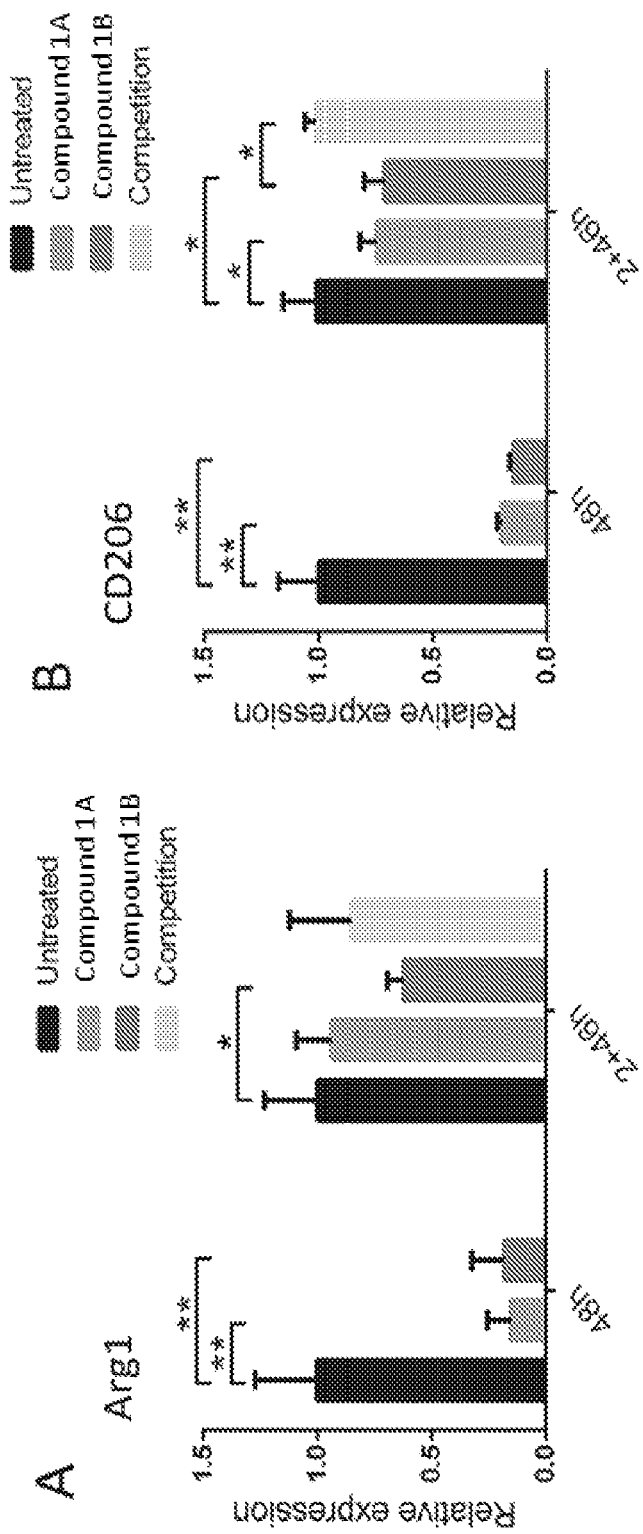
FIG. 19 shows that both targeted and nontargeted TLR7 agonists reprogram human monocyte-derived profibrotic macrophages to an anti-fibrotic phenotype (FIGS. 19A-19F). Mean±SD. Statistical significance between groups was determined using unpaired two-tailed t-test (*P<0.05, P<0.01, *P<0.001, ****P<0.0001).

M2-induced human monocyte-derived macrophages were treated with 100 nM of Compound 1A or Compound 1B either continuously for 48 hours, or initially for 2 hours in the presence or absence of FA-glucosamine (competition) followed by 46 hours in the absence of drug (2+46 h). As shown in FIG. 19, mRNA levels of profibrotic markers, Arg1 (FIG. 19A), CD206 (FIG. 19B) and CD163 (FIG. 19C), and protein levels of secreted profibrotic CCL18 (FIG. 19D) and antifibrotic cytokines, CXCL10 (FIG. 19E) and IL-6 (FIG. 19F) (n=3, technical replicates) were then determined. Changes in both sets of cytokines were inhibited by blockade of unoccupied folate receptors with excess FA-glucosamine (2+46 h, competition). This data supports that Compound 1B binds to folate receptor since the downregulation of biomarkers was blocked with excess FA-glucosamine (competitor).

Example 12

Figure 20:
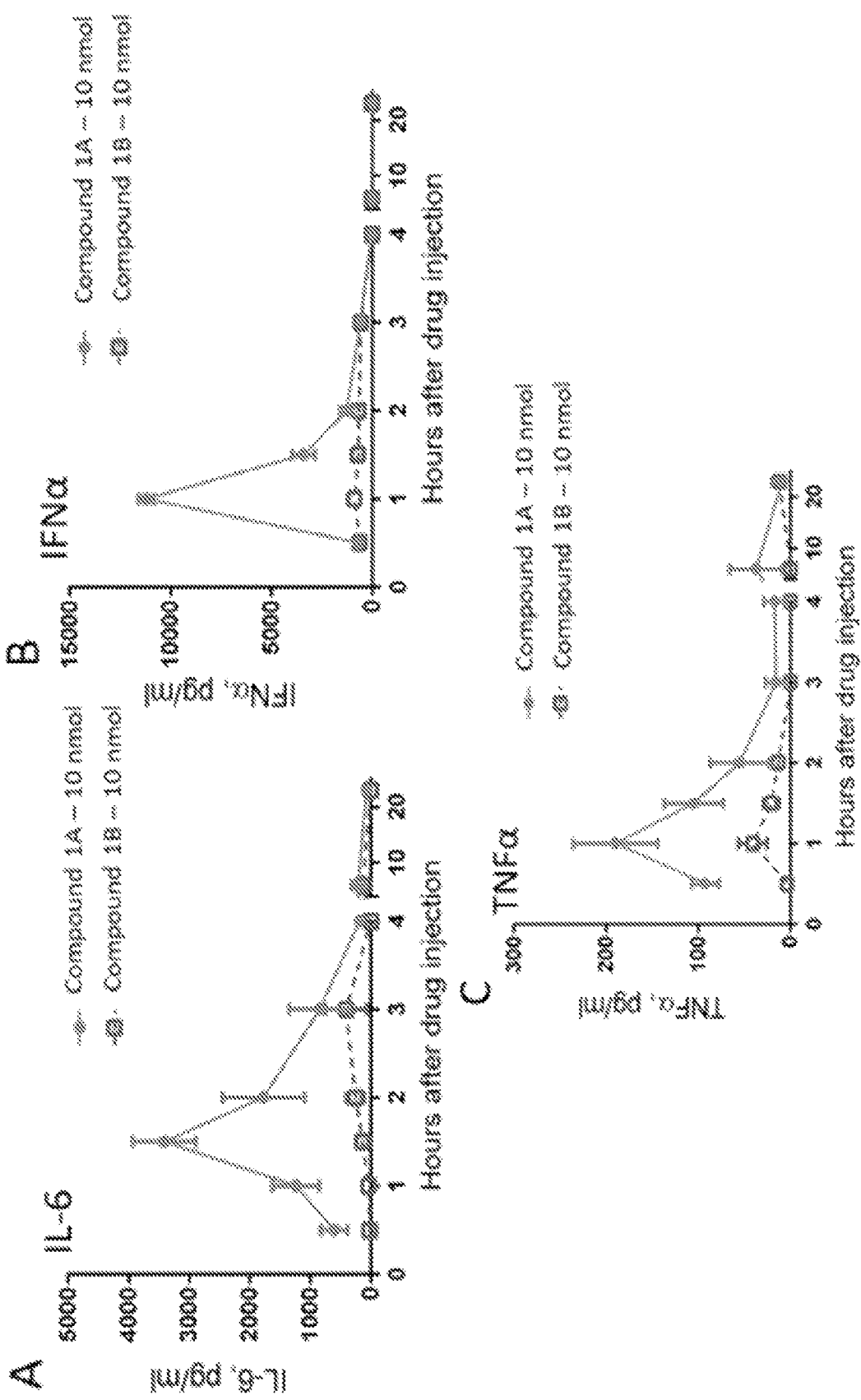
FIG. 20 shows comparison of plasma cytokine levels in healthy mice following treatment with Compound 1A versus Compound 1B (FIGS. 20A-20F).
Figure 21:
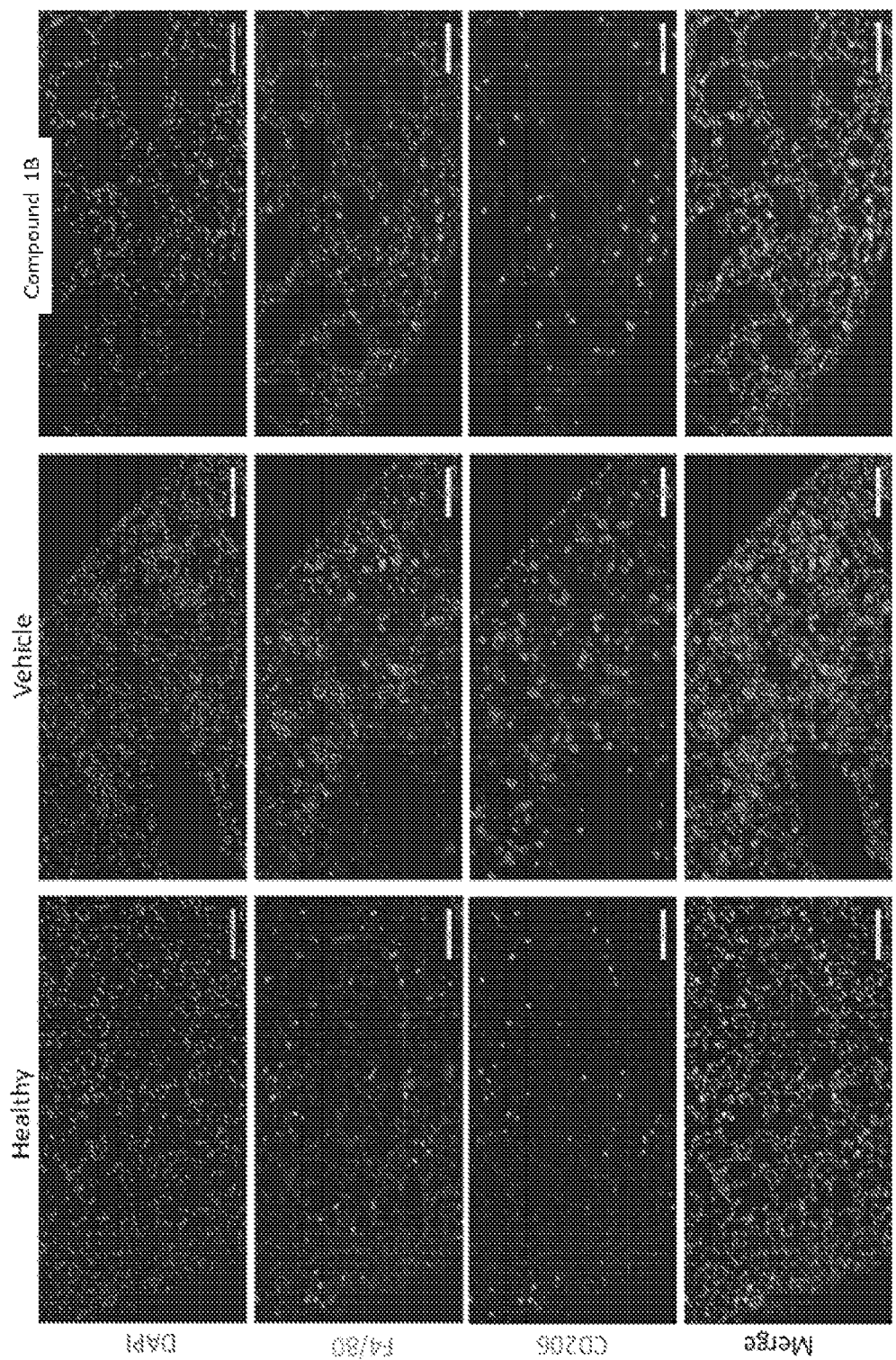
FIG. 21 shows healthy and fibrotic lungs described in FIG. 6 stained with 4',6-diamidino-2-phenylindole (DAPI) (nuclei; blue), anti-F4/80 (macrophages; red), and anti-mannose receptor (CD206).

Healthy mice were tail vein injected with 10 nmol Compound 1A (circles) or Compound 1B (squares), and peripheral blood was collected at indicated time points after drug injection. (FIGS. 20A-C) Measurement of plasma IL-6 (FIG. 20A), IFNα (FIG. 20B) and TNFα (FIG. 20C) (n=3). (FIGS. 20D-F). The effect of drug concentration on plasma levels of IL-6 (FIG. 20D), IFNα (FIG. 20E), and TNFα (FIG. 20F) was determined at 1.5 h, 1 h, or 1 h after treatment, respectively (n=2) (FIG. 20G). Compound 1A stimulates systemic cytokine release in healthy mice, while Compound 1B does not. Furthermore, Compound 1B stimulates less inflammatory cytokine release than half the dose of Compound 1A. These data suggest that TLR7 agonists can be safely employed to reprogram fibrotic lung macrophages to an anti-fibrotic state if they are targeted to the pulmonary macrophages with a folate receptor targeting ligand.

Example 13

Figure 6:
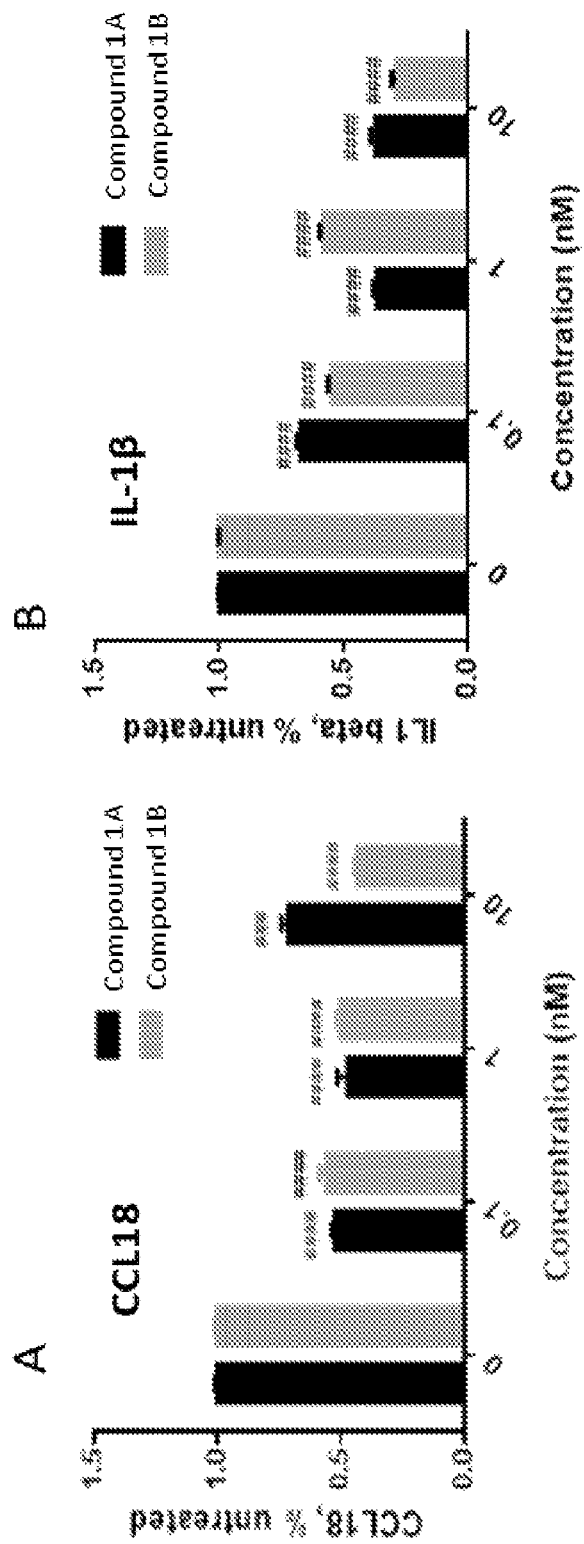
FIGS. 6A-6D show graphical data representative of various marker levels measured from M2 macrophages treated with various concentrations of exemplary free and targeted TLR7 agonists for: (i) 48 hours (FIGS. 6A and 6B); or (ii) 2 hours, then displaced with fresh medium and cultured for the remaining 46 hours (FIGS. 6C and 6D). Each value represents the mean±S.D. for each group; #P<0.05, ##P<0.01, ###P<0.005, ####P<0.0001; Compound 1A and Compound 1B treated groups versus M2-untreated group by Dunnett's multiple comparison test.
FIG. 6E shows flow cytometry data supporting that the THP-1 (a human monocytic cell line derived from an acute monocytic leukemia patient) induced macrophages were folate receptor beta (FRβ)-positive (FRβ+).
FIG. 6F show that exemplary targeted TLR7 agonists are stable.

Sections from the same healthy and fibrotic lungs described in FIG. 6 were stained with DAPI (nuclei; blue), anti-F4/80 (macrophages; red), and anti-CD206 (M2 macrophage marker; green), and images were obtained with a Leica Versa 8 whole-slide scanner as described in Methods (n=2). Scale bars, 100 μm. Differences between treated groups indicate that Compound 1B produces a robust anti-fibrotic response in vivo.

While various embodiments of compounds, compositions, and methods have been described in considerable detail herein, the embodiments are merely offered by way of non-limiting examples. Many variations and modifications of the embodiments described herein will be apparent to one of ordinary skill in the art in light of the disclosure. It will therefore be understood by those skilled in the art that various changes and modifications may be made, and equivalents may be substituted for elements thereof, without departing from the scope of the disclosure. Indeed, this disclosure is not intended to be exhaustive or too limiting. The scope of the disclosure is to be defined by the appended claims, and by their equivalents.

Additionally, while many of the examples provided herein use mouse models, it will be appreciated by one of ordinary skill in the art that gene expression patterns in mouse models show extraordinarily significant correlations with those of the human conditions and many pathways are commonly regulated by multiple conditions in humans and mice. Accordingly, gene expression patterns and disease progression in mouse models closely recapitulate those in human conditions—particularly with respect to inflammatory diseases and cancers—and, as such, support that the working examples set forth herein correlate with the human data, specified conditions, and applications.

It is therefore intended that this description and the appended claims will encompass, all modifications and changes apparent to those of ordinary skill in the art based on this disclosure.

The invention claimed is:

1. A compound represented by the formula:

Q-L-T wherein,
Q is a radical of a folate receptor binding ligand;
L is a non-releasable linker; and
T is a radical of a toll-like receptor (TLR) agonist,
or a pharmaceutically acceptable salt thereof.

2. The compound of claim 1, wherein the linker is a non-releasable linker.

3. The compound of claim 1, wherein the non-releasable linker comprises a formula:

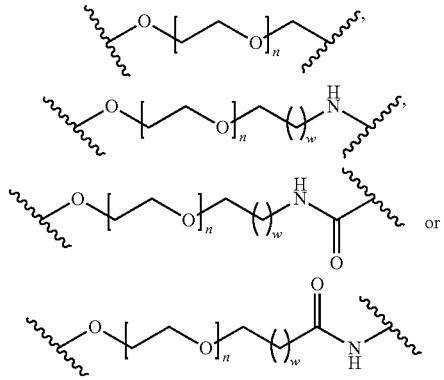

wherein:
n is 1-30; and
w is 0-5.

4. The compound of claim 1, wherein the TLR agonist is a toll-like receptor 7 (TLR7) agonist.

5. The compound of claim 1, wherein the radical of the TLR agonist is a radical of a structure represented by Formula X:

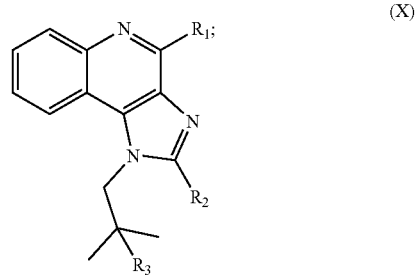

wherein, $R_1$ is —$NH_2$ or —NH—$R_{1X}$, $R_2$ is an H, an alkyl, an alkenyl, an alkynyl, an alicyclic, an aryl, a biaryl, a heteroaryl, —NH—$R_{2X}$, —O—$R_{2X}$, —S—$R_{2X}$,

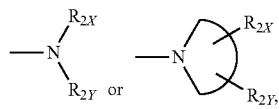

each of $R_{1X}$, $R_{2X}$, and $R_{2Y}$ are independently selected from the group consisting of an H, an alkyl, an alkenyl, an alkynyl, an alicyclic, an aryl, a biaryl, and a heteroaryl,

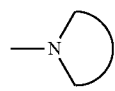

is a 3-10 membered N-containing non-aromatic mono- or bicyclic heterocycle; and $R_3$ is —OH, —SH, —$NH_2$ or —NH—$R_{1X}$.

6. The compound of claim 1, wherein the radical of the TLR agonist is a radical of a structure represented by Formula XX:

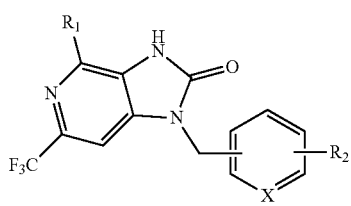

wherein, $R_1$ is —$NH_2$ or —NH—$R_{1X}$, $R_2$ is an H, an alkyl, an alkenyl, an alkynyl, an alicyclic, an aryl, a biaryl, a heteroaryl, —NH—$R_{2X}$, —O—$R_{2X}$, —S—$R_{2X}$,

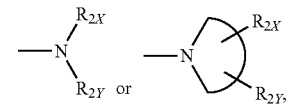

each of $R_{1X}$, $R_{2X}$, and $R_{2Y}$ are independently selected from the group consisting of an H, an alkyl, an alkenyl, an alkynyl, an alicyclic, an aryl, a biaryl, and a heteroaryl,

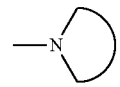

is a 3-10 membered N-containing non-aromatic mono- or bicyclic heterocycle; and

X is CH, $CR_2$, or N.

7. The compound of claim 6, wherein the radical of the TLR agonist is a radical of a toll-like receptor 7 (TLR7) agonist having a structure represented by Formula XXX:

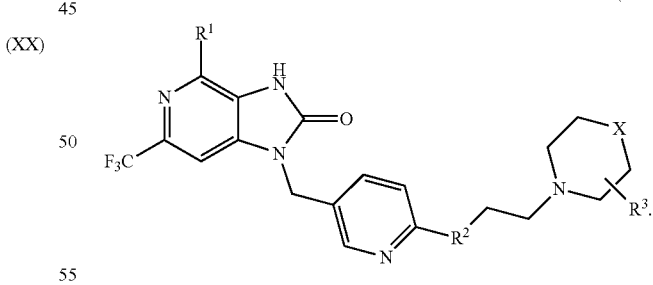

8. The compound of claim 1, wherein the linker $L_n$ comprises polyethylene glycol (PEG) or a PEG derivative, and the radical of folate receptor binding ligand is a folate receptor β binding ligand.

9. The compound of claim 1, which has a structure represented by:

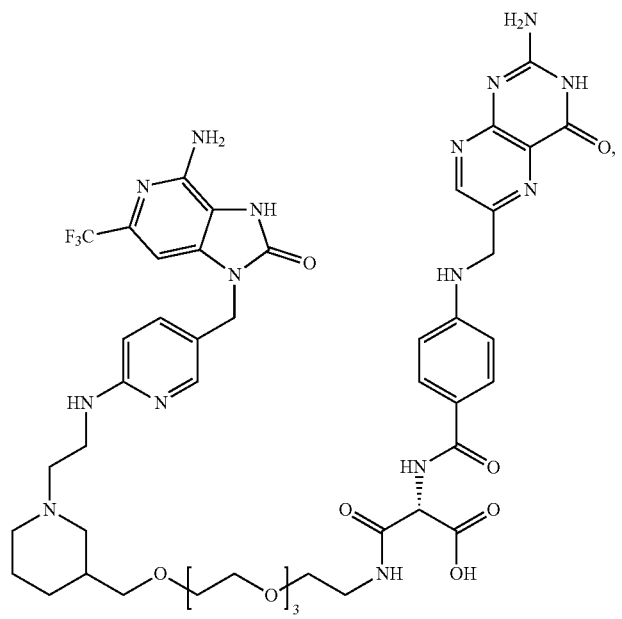
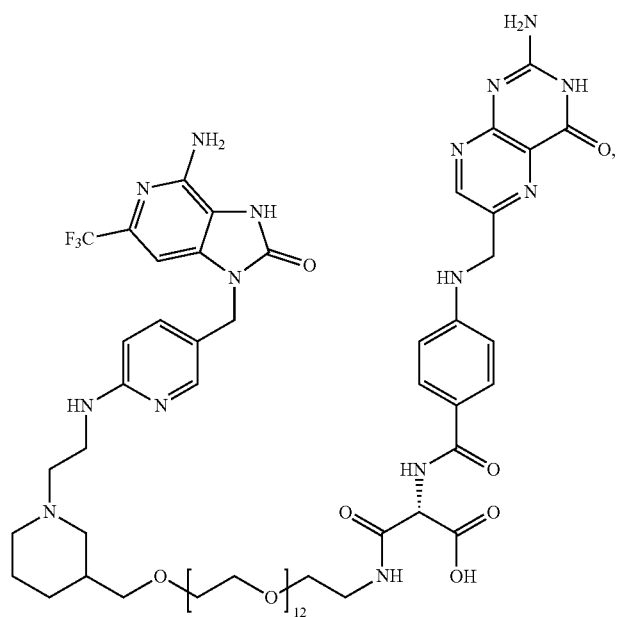

-continued

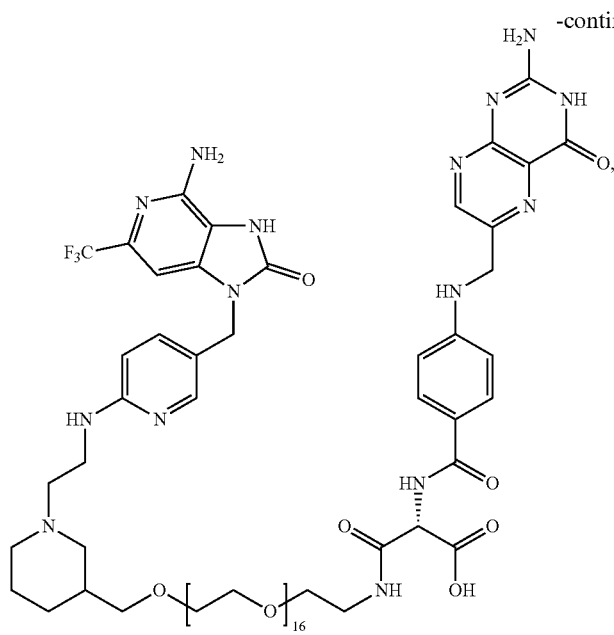

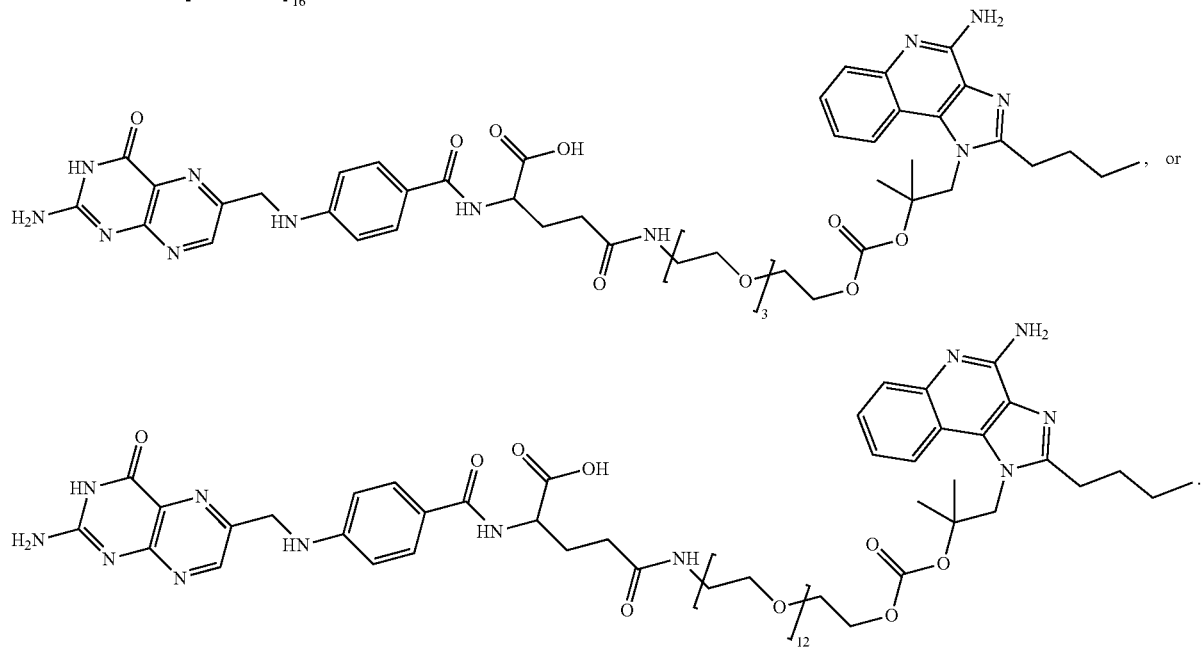

10. A pharmaceutical composition comprising (a) the compound of claim 1, and (b) a pharmaceutically acceptable excipient.

11. The compound of claim 1, wherein Q is a radical of a compound represented by:

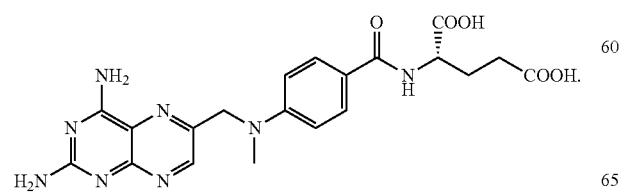

12. The compound of claim 1, wherein the non-releasable linker comprises

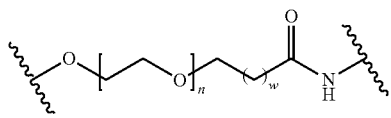

wherein n is 1-30 and w is 0-5.

13. The compound of claim 5, wherein the radical of the TLR agonist is a radical of a compound represented by:

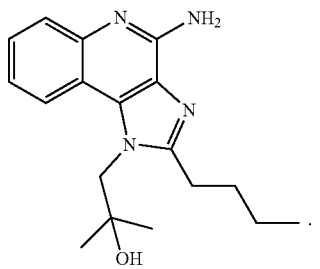
14. The compound of claim 7, wherein the radical of the TLR agonist is a radical of a compound represented by:
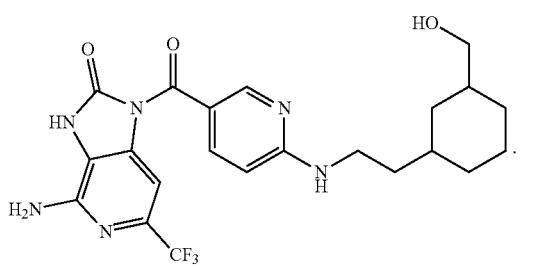
* * * * *